(12) United States Patent
Calabrese

(10) Patent No.: US 10,570,165 B2
(45) Date of Patent: Feb. 25, 2020

(54) AZIRIDINE SPINOSYN DERIVATIVES AND METHODS OF MAKING

(71) Applicant: AgriMetis, LLC, Lutherville, MD (US)

(72) Inventor: Andrew A. Calabrese, Cockeysville, MD (US)

(73) Assignee: AgriMetis, LLC, Lutherville, MD (US)

( * ) Notice: Subject to any disclaimer, the term of this patent is extended or adjusted under 35 U.S.C. 154(b) by 0 days.

(21) Appl. No.: 15/861,368

(22) Filed: Jan. 3, 2018

(65) Prior Publication Data

US 2018/0291053 A1 Oct. 11, 2018

Related U.S. Application Data

(60) Provisional application No. 62/446,177, filed on Jan. 13, 2017.

(51) Int. Cl.
*C07H 17/00* (2006.01)
*A01N 43/90* (2006.01)

(52) U.S. Cl.
CPC ............. *C07H 17/00* (2013.01); *A01N 43/90* (2013.01)

(58) Field of Classification Search
None
See application file for complete search history.

(56) References Cited

U.S. PATENT DOCUMENTS

| | | | |
|---|---|---|---|
| 6,001,981 | A | 12/1999 | DeAmicis et al. |
| 6,063,771 | A | 5/2000 | Snyder |
| 6,342,482 | B1 | 1/2002 | Snyder |
| 6,927,210 | B1 | 8/2005 | Thompson et al. |
| 7,015,001 | B2 | 3/2006 | Baltz et al. |
| 7,709,447 | B2 | 5/2010 | Hacket et al. |
| 8,470,381 | B2 | 6/2013 | Kritikou |
| 8,536,142 | B2 | 9/2013 | Lowe et al. |
| 8,697,661 | B2 | 4/2014 | Kritikou |
| 9,253,979 | B2 | 2/2016 | Sparks et al. |
| 2012/0172322 | A1 | 7/2012 | Sparks et al. |
| 2012/0252746 | A1 | 10/2012 | Snyder |
| 2013/0210755 | A1 | 8/2013 | Marr et al. |
| 2015/0111743 | A1 | 4/2015 | Gomez et al. |

FOREIGN PATENT DOCUMENTS

| | | |
|---|---|---|
| EP | 1207757 B1 | 2/2005 |
| EP | 2654757 A1 | 10/2013 |
| WO | 97/00265 A1 | 1/1997 |
| WO | 02/077004 A1 | 10/2002 |
| WO | 2017/040769 A1 | 3/2017 |
| WO | WO 2017/040882 A1 * | 9/2017 |

OTHER PUBLICATIONS

Daxin, S. et al., Chinese Journal of Chemistry, "Study of Synthesis and Biological Activities of a Novel Macrolide Derivatives", 2014, vol. 34, pp. 2543-2550 (Year: 2014).*
Kirst, Herbert, The Journal of Antibiotics, "The spinosyn family of insecticides: realizing the potential of natural products research", 2010, vol. 63, pp. 101-111 (Year: 2010).*
Orr, N. et al., Pesticide Biochemistry and Physiology, "Novel mode of action of spinosad: Receptor binding studies demonstrating lack of interaction with known insecticidal target sites", 2009, vol. 95, pp. 1-5 (Year: 2009).*
Sparks, T. et al., Pest Management Science, "Natural products as insecticides: the biology, biochemistry and quantitative structure-activity relationships of spinosyns and spinosoids", 2001, vol. 57, pp. 896-905 (Year: 2001).*
PCT/US2018/012220, "International Search Report and Written Opinion", dated Mar. 22, 2018, 13 pages.
PCT/US2018/012220 , "International Preliminary Report on Patentability", dated Jul. 25, 2019, 8 pages.

* cited by examiner

*Primary Examiner* — Shaojia A Jiang
*Assistant Examiner* — Bahar Craigo
(74) *Attorney, Agent, or Firm* — Kilpatrick Townsend & Stockton LLP

(57) ABSTRACT

Compositions including derivatives of spinosyns and methods for the production of derivatives of spinosyns are provided. The spinosyn derivatives described herein include those functionalized on the C-5,6 double bond to provide an aziridine ring system. The method produces spinosyn derivatives that exhibit activity towards insects, arachnids, and nematodes and are useful in the agricultural and animal health markets.

38 Claims, No Drawings

AZIRIDINE SPINOSYN DERIVATIVES AND METHODS OF MAKING

CROSS-REFERENCE TO RELATED APPLICATIONS

The present application claims the benefit of priority of U.S. Provisional Application No. 62/446,177, filed on Jan. 13, 2017, which is hereby incorporated by reference as though set forth in its entirety.

FIELD

Described herein are spinosyn derivatives for use as agrichemicals.

BACKGROUND

Spinosyn refers to a large family of compounds produced from the fermentation of soil actinomycetes species of *Saccharopolyspora*. The individual components from the fermentation broth were subsequently given the generic name of spinosyn to connect these compounds with their producing microorganism, *Saccharopolyspora spinose*. Members of the spinosyn family share a core structure having a polyketide-derived tetracyclic macrolide appended with two saccharides. There are many naturally occurring variants, which exhibit potent insecticidal activities against many commercially significant species that cause extensive damage to crops and other plants. Some of these variants also exhibit activity against important external parasites of livestock, companion animals and humans.

Fermentation of *S. spinosa* produces a natural mixture containing spinosyn A as the major component and spinosyn D as the minor component and named spinosad. The structure of spinosyn A was determined by NMR, MS, and X-ray analyses and comprises a tetracyclic polyketide aglycone to which is attached a neutral saccharide substituent (2,3,4-tri-O-methyl-α-L-rhamnosyl) on the C-9 hydroxyl group and an aminosugar moiety (β-D-forosaminyl) on the C-17 hydroxyl group. This spinosyn tetracyclic ring system composed of a cis-anti-trans-5,6,5-tricyclic moiety fused to a 12-membered lactone is a unique ring system.

The second most abundant fermentation component is spinosyn D, which is 6-methyl-spinosyn A. Spinosyn D is likely formed by incorporation of propionate instead of acetate at the appropriate stage during polyketide assembly.

Numerous structurally related compounds from various spinosyn fermentations have now been isolated and identified. Their structures fall into several general categories of single-type changes in the aglycone or saccharides of spinosyn A.

Spinosyns have a unique mechanism of action (MOA) involving disruption of nicotinic acetylcholine receptors. When compared with many other insecticides, spinosyns generally show greater selectivity toward target insects and lesser activity against many beneficial predators. Structure-activity relationships (SARs) have been extensively studied, leading to development of a semisynthetic second-generation derivative, spinetoram (Kirst (2010) *J. Antibiotics* 63:101-111).

Studies to date have concluded that the mechanism(s) by which spinosyn exerts its insecticidal action is different from those of any other known agents, and thus cross-resistance between spinosyn and other agents was initially absent or low. However, as well known for other insecticides, continued usage is likely to exert selective pressures on insects and to eventually provoke resistance.

The unique and highly complex core structure of the spinosyns has provided challenging opportunities for synthesis. Additionally, with the increase of insect resistance, new spinosyn compounds and methods for their synthesis are needed.

SUMMARY

Spinosyn compounds and methods for making and using the spinosyn compounds are provided. The spinosyn compounds described herein exhibit activity towards insects, arachnids, and nematodes and are useful in the agricultural and animal health markets. The spinosyn compounds described herein exhibit activity comparable to or greater than the spinosyn-type natural products, often with an improved resistance profile over the natural products.

A spinosyn compound as described herein includes a compound of Formula I.

Formula I or a salt thereof, wherein $\rlap{=}{=}$ is a single bond or a double bond; A is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl; B is selected from the group consisting of substituted or unsubstituted cycloalkyl, substituted or unsubstituted heterocycloalkyl, substituted or unsubstituted aryl, and substituted or unsubstituted heteroaryl; C is O or NH; $X^1$, $X^2$, $X^3$, $X^4$ and $X^5$ are each independently selected from N, NR, CR, and CR2, wherein $X^5$ may alternatively be a direct bond and when $X^5$ is a direct bond, one of $X^1$, $X^2$, $X^3$, and $X^4$ may be further selected from O or S, wherein each R is selected from hydrogen, hydroxyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl.

Optionally, when $X^1$ and $X^2$ are selected from NR, CR, and CR2, the R groups of $X^1$ and $X^2$ can combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl. Optionally, when $X^2$ and $X^3$ are selected from NR, CR, and $CR_2$, the R groups of $X^2$ and $X^3$ can combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

Optionally, A comprises forosamine. Optionally, B comprises rhamnose or (2R,5S)-4-ethoxy-3,5-dimethoxy-6-methyloxan-2-yl group. In some examples, A is forosamine, B is rhamnose, C is O, $X_1$ is N, $X_2$ is $C(CH_3)$, and $X_3$ is S. Optionally, the spinosyn compound is (1S,2R,8R,10S,12S, 13R,17R,18S,22S)-18-{[(2R,5S,6R)-5-(dimethylamino)-6-methyloxan-2-yl]oxy}-22-ethyl-5,17-dimethyl-10-{[(2R, 3R,4R,5S,6S)-3,4,5-trimethoxy-6-methyloxan-2-yl]oxy}-23-oxa-6-thia-4-azapentacyclo[13.10.0.0$^2$,$^{13}$.0$^3$,$^7$.0$^8$,$^{12}$] pentacosa-3 (7),4,14-triene-16,24-dione.

Also described herein are formulations. A formulation as described herein comprises at least one spinosyn compound as described herein and an acceptable carrier. Optionally, the formulation can further comprise at least one additional active ingredient and/or at least one plant or plant product treatment compound. The at least one additional active ingredient can comprise, for example, an insecticide or a miticide (e.g., a contact-acting insecticide or contact-acting miticide).

Further described herein is a method for controlling pests. A method for controlling pests as described herein comprises contacting a pest with an effective amount of a spinosyn compound or a formulation as described herein. Optionally, the pest is an insect, an arachnid, or a nematode.

Also described herein are methods for making a spinosyn compound. A method for making a spinosyn compound comprises reacting the C-5, 6 double bond of spinosyn A to form a spinosyn compound as described herein, wherein the spinosyn compound forms via an α-halo ketone intermediate.

The details of one or more embodiments are set forth in the drawings and the description below. Other features, objects, and advantages will be apparent from the description and drawings, and from the claims.

DETAILED DESCRIPTION

Provided herein are spinosyn compounds. The compositions are useful in the agricultural and animal health markets having activity towards pests such as insects, arachnids, nematodes and the like. Methods for making the compounds are also provided.

I. Compounds

A class of spinosyn compounds described herein is represented by Formula I:

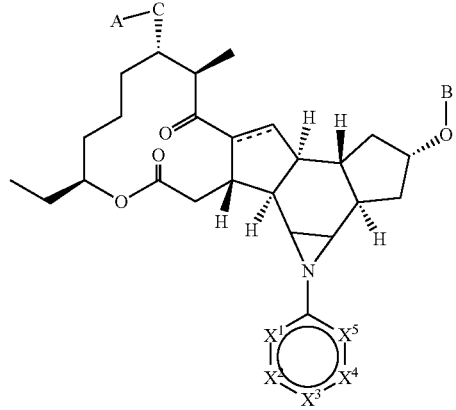

and salts thereof.

In Formula I, ⚌ is a single bond or a double bond.

Also, in Formula I, A is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl. Optionally, A can be a substituted or unsubstituted saccharide. For example, A can be forosamine or a forosamine derivative.

Additionally, in Formula I, B is selected from the group consisting of substituted or unsubstituted cycloalkyl, substituted or unsubstituted heterocycloalkyl, substituted or unsubstituted aryl, and substituted or unsubstituted heteroaryl. Optionally, B can be a substituted or unsubstituted saccharide. For example, B can be rhamnose. Optionally, B can include a (2R,5S)-4-ethoxy-3,5-dimethoxy-6-methyl-oxan-2-yl group.

Further, in Formula I, C is O or NH.

Also, in Formula I, $X^1$, $X^2$, $X^3$, $X^4$ and $X^5$ are each independently selected from N, NR, CR, and $CR_2$, wherein $X^5$ may alternatively be a direct bond and when $X^5$ is a direct bond, one of $X^1$, $X^2$, $X^3$, and $X^4$ may be further selected from O or S, wherein each R is selected from hydrogen, hydroxyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl.

Optionally, when $X^1$ and $X^2$ are selected from NR, CR, and $CR_2$, the R groups of $X^1$ and $X^2$ can be combined to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl. Optionally, when $X^2$ and $X^3$ are selected from NR, CR, and $CR_2$, the R groups of $X^2$ and $X^3$ can be combined to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

Optionally, the C-13, 14 bond of the compound of Formula I is a double bond. In these examples, Formula I can be represented by Structure I-A:

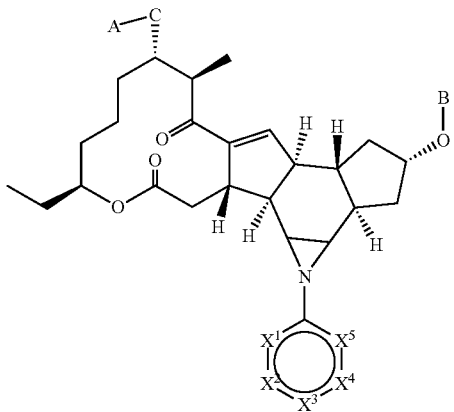

In Structure I-A, A, B, C, $X^1$, $X^2$, $X^3$, $X^4$ and $X^5$ are as defined above.

Optionally, $X^5$ is a direct bond. In these examples, Formula I can be represented by Structure I-B:

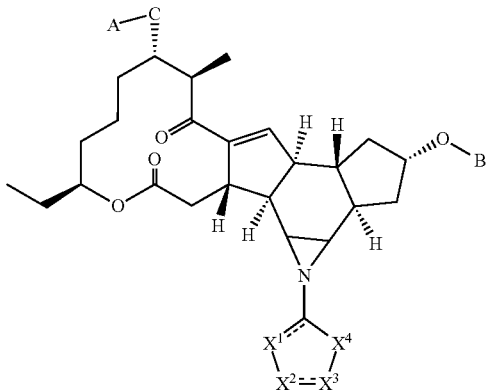

In Structure I-B, ═══, A, B, C, are as defined above, and $X^1$, $X^2$, $X^3$, and $X^4$ are each independently selected from O, S, N, NR, CR, and $CR_2$, wherein R is as defined above.

Optionally, $X^5$ is not a direct bond. In these examples, Formula I can be represented by Structure I-C:

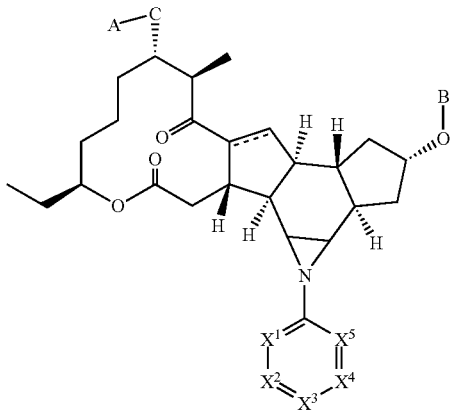

In Structure I-C, ═══, A, B, C, are as defined above, and $X^1$, $X^2$, $X^3$, $X^4$ and $X^5$ are each independently selected from N, NR, CR, and $CR_2$, wherein R is as defined above.

Where substituent groups are specified by their conventional chemical formulae, written from left to right, the structures optionally also encompass the chemically identical substituents, which would result from writing the structure from right to left, e.g., —$CH_2O$— is intended to also optionally recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above.

Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to optionally include both substituted and unsubstituted forms of the indicated radical.

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The compounds described herein can be prepared using spinosyn precursor, spinosyn, or spinosyn analogue starting materials, such as those set forth in U.S. Pat. No. 5,362,634. As used herein, spinosyn precursors, spinosyns, or spinosyn analogue starting materials used in the synthetic methods include any tetracyclic spinosyn molecule comprising a polyketide-derived tetracyclic macrolide appended with two saccharides.

The methods of making the compounds described herein can include from one to five chemical steps performed on spinosyns, often without need for purification of thus formed intermediates.

Compounds described by Formula I and pharmaceutically acceptable salts thereof can be made using the methods shown in Scheme 1, which depicts the synthesis of compounds of Formula I wherein C=O, $X^1$, $X^2$, $X^3$, $X^4$ and $X^5$=CR and R=H.

Scheme 1:

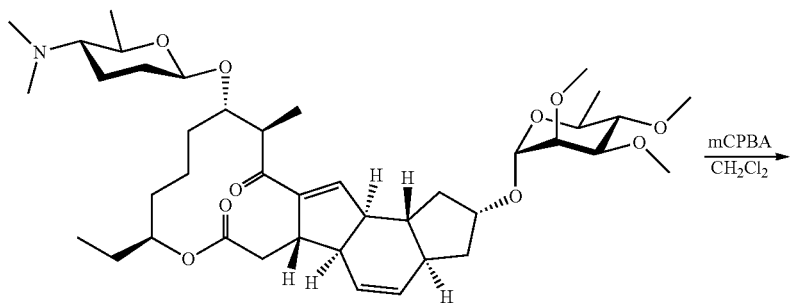

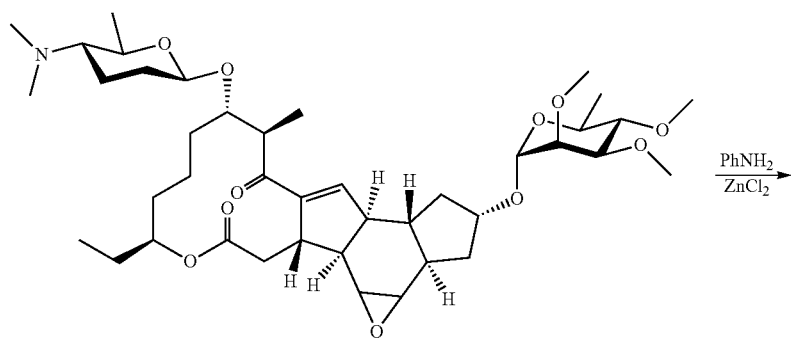

In the synthetic method shown above in Scheme 1, the olefin of spinosyn A can be oxidized using reagents such as m-CPBA. The epoxide intermediate can then be opened with an amine (in this case aniline), followed by treatment of the amino alcohol intermediate with DAST. Another method would be to dibrominate the olefin, aminate one of the bromides with an amine and then close with a reagent like DAST.

Alternatively, compounds described herein can be made by those skilled in the art using synthetic chemistry transformations known to convert C, C double bonds to aziridines, either directly or in multiple chemical steps. See, for example, Rakesh K. Parashar in *Chemistry of Heterocyclic Compounds*, CRC Press, 2014, ISBN-13 978-1466517 and John A. Joule and Keith Mills, *Heterocyclic Chemistry*, Wiley, 2010, ISBN-13 978-1405133005.

Additional modifications can be made to compounds according to Formula I while retaining the desired activity of the compounds. For example, the saccharide groups optionally present as A and B in the compounds according to Formula I (e.g., forosamine and rhamnose) can be modified by methods in the art and retain pesticidal activity. Forosamine can be replaced by certain nitrogen-containing sugars and non-sugar substituents with retention of some degree of activity. See, Gaisser et al. (2002) *Chem. Comm.* 6:618-619; and Gaisser et a. (2009) *Org. Biomol. Chem.* 7:1705-1708, herein incorporated by reference. Likewise, rhamnose replacement analogs may be produced. See, Creemer et al. (2000) *J. Antibiotics*, 53:171-178; Sparks et al. (2001) *Pest Manag. Sci.*, 57:896-905, herein incorporated by reference. Activity of the spinosyn derivative can be retained after changes in the structure of the rhamnose, especially certain modifications at C-2' and C-3' of the tri-O-methylrhamnose moiety.

Other methods of sugar modification can be made and are well known in the art. See, Kirst et al. (2002) *Curr. Top. Med. Chem.* 2:675-699. In some embodiments, one or more of the saccharide moieties is replaced with another natural or a synthetic sugar. Synthetic sugars include modified sugars. As used herein, a "modified sugar" is covalently functionalized with a "modifying group." Useful modifying groups include, but are not limited to, water-soluble polymers, therapeutic moieties, diagnostic moieties, biomolecules and the like. Addition or removal of any saccharide moieties present on the precursor or substrate is accomplished either chemically or enzymatically.

In some embodiments, chemical deglycosylation can be used by exposure of the spinosyn compounds described herein to the compound trifluoromethanesulfonic acid, or an equivalent compound. This treatment results in the cleavage of most or all sugars except the linking sugar (N-acetylglucosamine or N-acetylgalactosamine), while leaving the remainder of the molecule intact. See, Hakimuddin et al. (1987) *Arch. Biochem. Biophys.* 259:52 and Edge et al. (1981) *Anal. Biochem.* 118:131. Enzymatic cleavage of carbohydrate moieties on peptide variants can be achieved by the use of a variety of endo- and exo-glycosidases as described by Thotakura et al. (1987) *Meth. Enzymol.* 138:350. Chemical addition of glycosyl moieties is carried out by any art-recognized method. See, for example, U.S. Pat. Nos. 5,876,980; 6,030,815; 5,728,554; 5,922,577; and WO 2004/99231.

1. Synthesis of Compound 1: (1aS,1bR,3S,4aS,4bR,7R,8S,12S,15aS,15bR,15cR)-8-(((2R,5S,6R)-5-(dimethylamino)-6-methyltetrahydro-2H-pyran-2-yl)oxy)-12-ethyl-7-methyl-1-phenyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
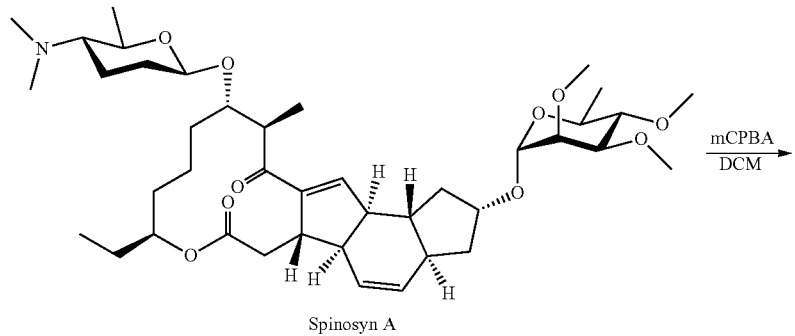
Spinosyn A
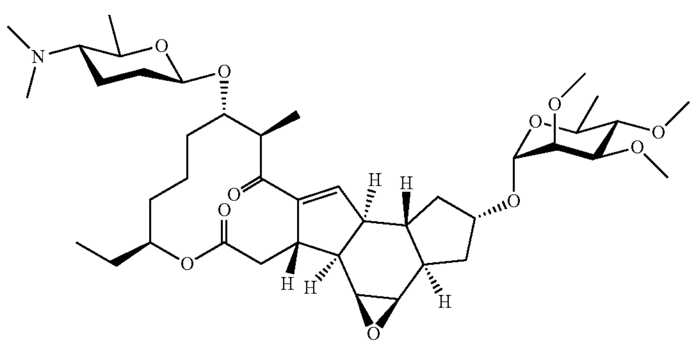
+
A1
(ratio: A1/A2 = 5/1)
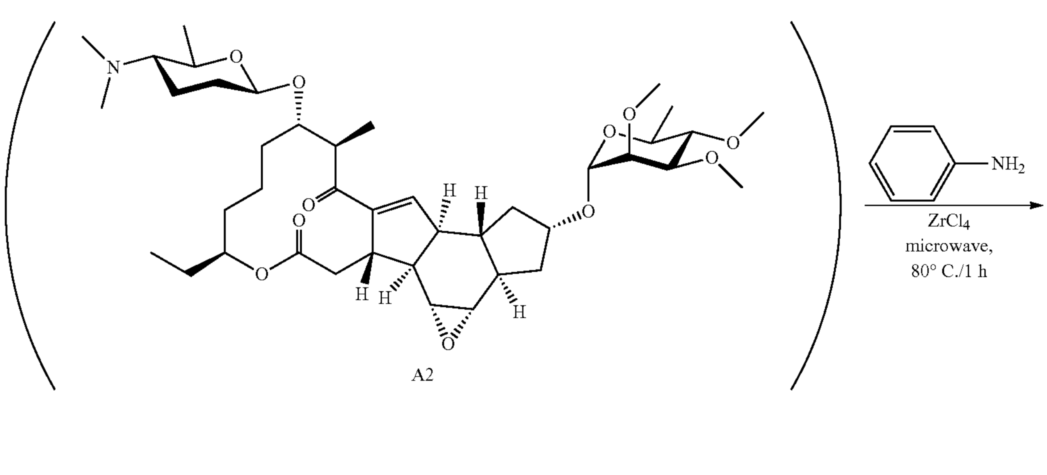
A2

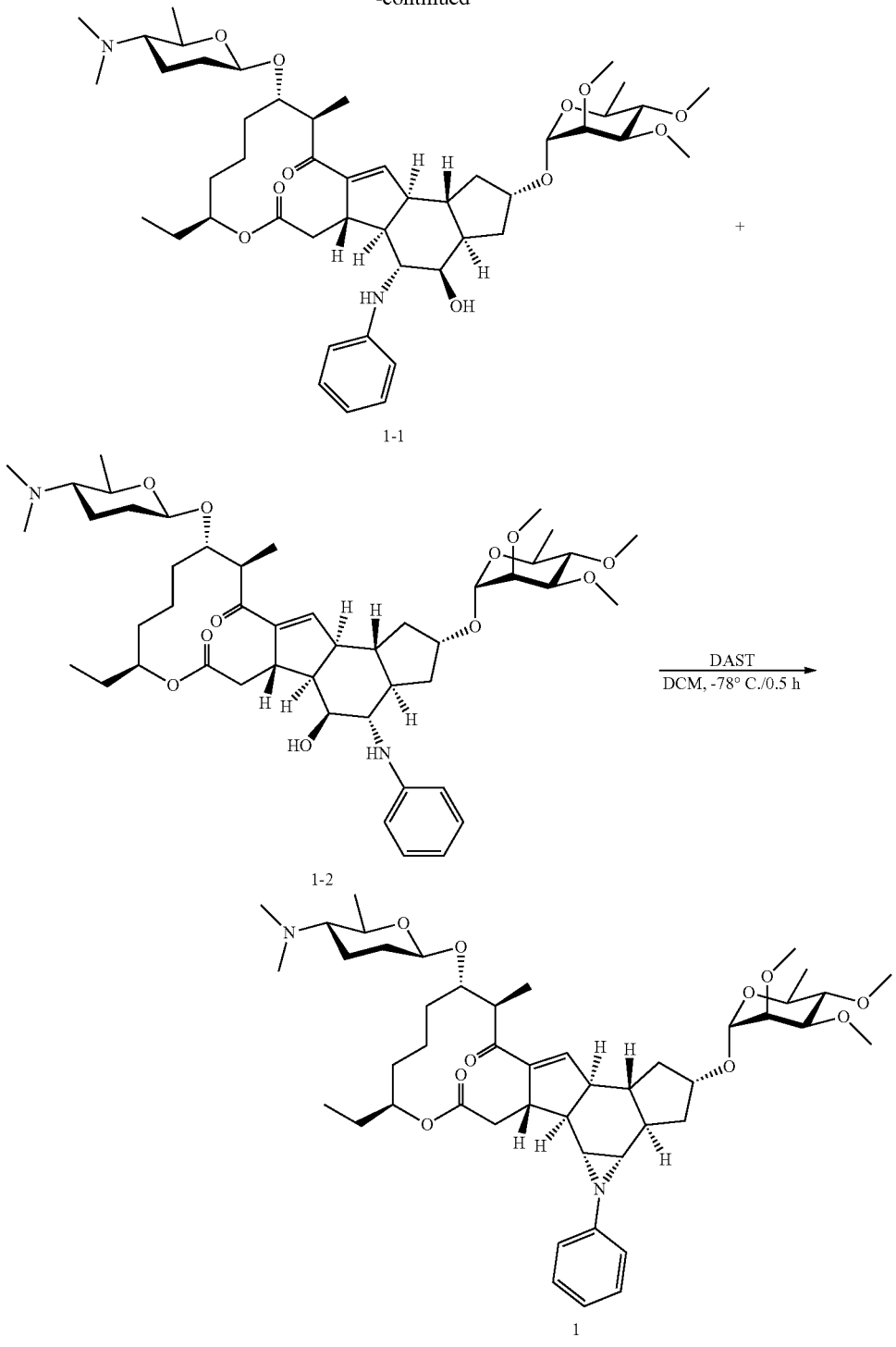

To a solution of Spinosyn A (20.0 g, 27.3 mmol) in DCM (200 mL) was added mCPBA (12.8 mg, 74.5 mmol) at 0° C. The mixture was allowed to warm to r.t and stirred for 6 h. Saturated $Na_2SO_3$ solution (300 mL) was added and the mixture was stirred at r.t for overnight. The resulted mixture was extracted with DCM (500 mL×2). The combined organic layer was washed by brine and dried over $Na_2SO_4$, filtered and concentrated. The residue was purified by column chromatography on silica gel (DCM/MeOH=20/1) to give the crude product A1 (13.0 g, containing ~15% of A2 from HNMR and LC-MS) which was used for next step without further purification. 300 mg of crude A1 was further purified by prep-HPLC to afford the pure compounds A1 (120 mg) and A2 (20 mg) as white solid.

A1: Partial $^1$H NMR (CDCl$_3$, 400 MHz): δ 6.58 (s, 1H), 4.85 (s, 1H), 4.67 (m, 1H), 4.41 (d, J=7.2 Hz, 1H), 4.23 (m, 1H), 3.25-3.10 (m, 3H), 2.61-2.54 (m, 1H), 2.44 (dd, J=13.6, 3.2 Hz, 1H), 0.82 (t, J=7.2 Hz, 3H); LC-MS: m/z 748.4 [M+H]$^+$.

A2: Partial $^1$H NMR (CDCl$_3$, 400 MHz): δ 6.70 (s, 1H), 4.84 (s, 1H), 4.70 (m, 1H), 4.42 (d, J=8.4 Hz, 1H), 4.28 (m, 1H), 3.63-3.42 (m, 16H), 3.27-3.06 (m, 6H), 2.57-2.42 (m, 2H), 2.24-2.07 (m, 6H), 0.82 (t, J=14.8 Hz, 3H); LC-MS: m/z 748.4 [M+H]$^+$ To a solution of crude compound A1 (0.5 g, 0.65 mmol) in aniline (3 mL) was added ZrCl$_4$ (7.5 mg, 0.033 mmol). The mixture was stirred at 80° C. under microwave for 1 h. The mixture was purified by silica gel column (DCM/MeOH=20:1-10:1) and then prep-HPLC to give a mixture of compounds 1-1 and 1-2 (165 mg, 30.3% yield) as white solid. Small amount of compounds 1-1 (20 mg) and 1-2 (12 mg) has been separated by Chiral-prep-HPLC. LCMS: m/z 841.2 [M+H]$^+$.

To a solution of the mixture of compounds 1-1 and 1-2 (50 mg, 0.059 mmol) in DCM (5 mL) was added DAST (28.7 mg, 0.18 mmol) at −78° C. under N$_2$. The mixture was stirred at −78° C. under N$_2$ pressure for 0.5 h. The reaction mixture was diluted with saturated NaHCO$_3$ solution (5 mL) and extracted with DCM (5 mL×2). The combined organic phase was dried over anhydrous Na$_2$SO$_4$, filtered and concentrated. The residue was purified by Prep-HPLC to afford compound 1 (20 mg, yield 40.8%) as a white solid. Partial $^1$H NMR (CDCl$_3$, 400 MHz): δ 7.22 (d, J=7.6 Hz, 2H), 7.03 (d, J=7.2 Hz, 1H), 6.96 (t, J=7.2 Hz, 1H), 6.75 (s, 1H), 4.89 (d, J=0.8 Hz, 1H), 4.73-4.68 (m, 1H), 4.42-4.40 (m, 1H), 4.33-4.32 (m, 1H), 3.67-3.44 (m, 16H), 3.32-3.26 (m, 2H), 3.14-3.09 (m, 2H), 2.58-2.49 (m, 2H), 2.41-2.39 (m, 1H), 2.24 (brs, 10H), 2.00-1.97 (m, 1H), 0.80 (t, J=7.2 Hz, 3H). LCMS: m/z 823.2 [M+H]$^+$.

2. Synthesis of Compound 2: (1aS,1bR,3S,4aS,4bR, 7R,8S,12S,15aS,15bR,15cR)-1-(2-chlorophenyl)-8-(((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione

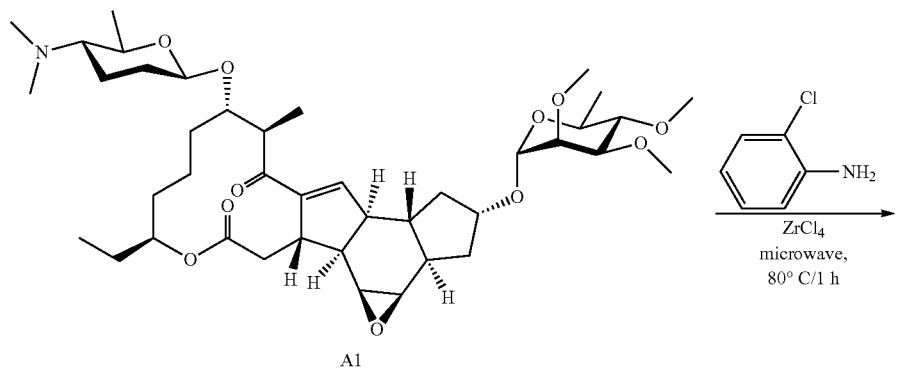

A1

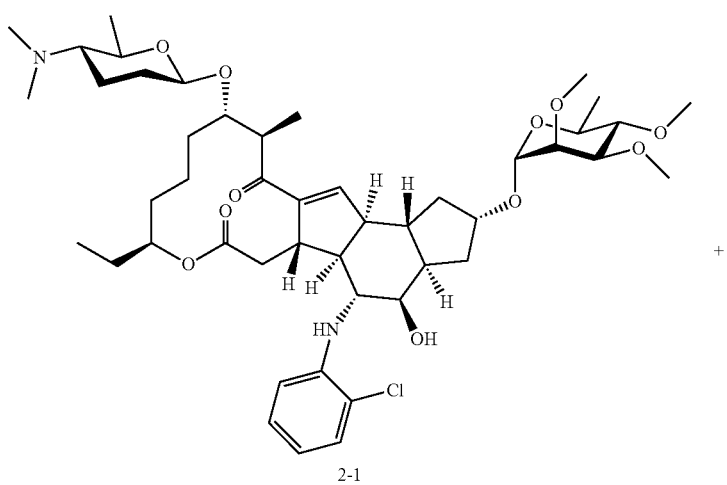

2-1

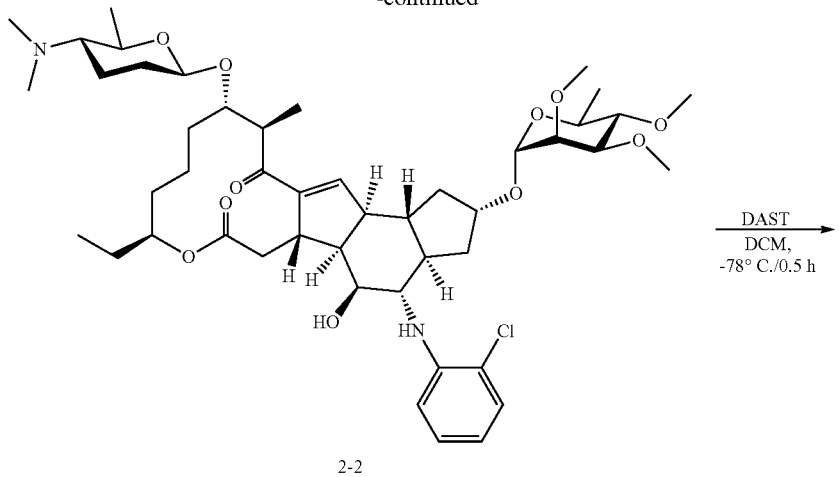

2-2

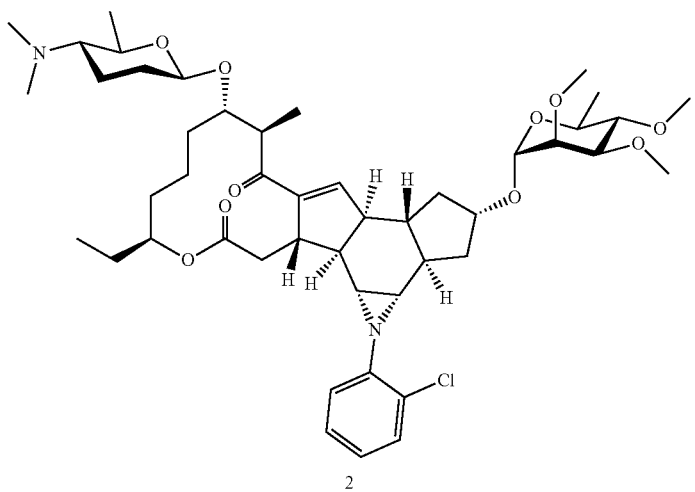

2

To a solution of compound A1 (0.5 g, 0.65 mmol) in 2-chloroaniline (3 mL) was added $ZrCl_4$ (7.5 mg, 0.033 mmol). The mixture was stirred at 80° C. under microwave for 0.5 h. The mixture was purified by silica gel column (DCM/MeOH=20:1-10:1) and then prep-HPLC to give a mixture of compounds 2-1 and 2-2 (132 mg, 24.2% yield) as white solid. LCMS: m/z 875.1 [M+H]+.

To a solution of a mixture of compounds 2-1 and 2-2 (50 mg, 0.057 mmol) in DCM (5 mL) was added DAST (28.0 mg, 0.17 mmol) at −78° C. under $N_2$. The mixture was stirred at −78° C. under $N_2$ pressure for 0.5 h. The reaction mixture was diluted with saturated $NaHCO_3$ solution (15 mL) and extracted with DCM (15 mL×2). The combined organic phase was dried over anhydrous $Na_2SO_4$, filtered and concentrated. The residue was purified by Prep-HPLC to afford compound 2 (15 mg, yield 30.7%) as a white solid. Partial $^1H$ NMR (CDCl$_3$, 400 MHz): δ 7.31 (d, J=6.8 Hz, 1H), 7.17-7.13 (m, 1H), 6.97-6.90 (m, 2H), 6.76 (s, 1H), 4.88 (s, 1H), 4.71-4.69 (m, 1H), 4.44-4.42 (m, 1H), 4.34-4.32 (m, 1H), 3.30-3.22 (m, 2H), 3.17-3.09 (m, 2H), 2.61-2.58 (m, 1H), 2.46-2.44 (m, 1H), 1.99-1.97 (m, 1H), 0.84 (t, J=7.6 Hz, 3H). LCMS: m/z 857.1 [M+H]+.

3. Synthesis of Compound 3: (1aS,1bR,3S,4aS,4bR,7R,8S,12S,15aS,15bR,15cR)-1-(4-chlorophenyl)-8-(((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
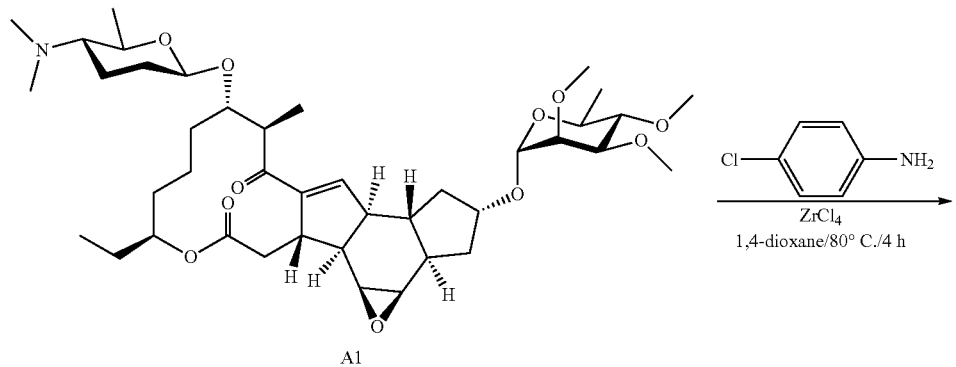
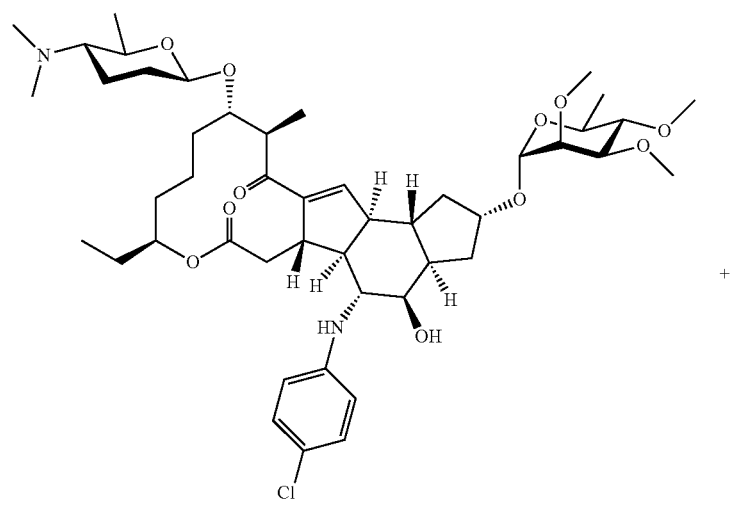
3-1

-continued

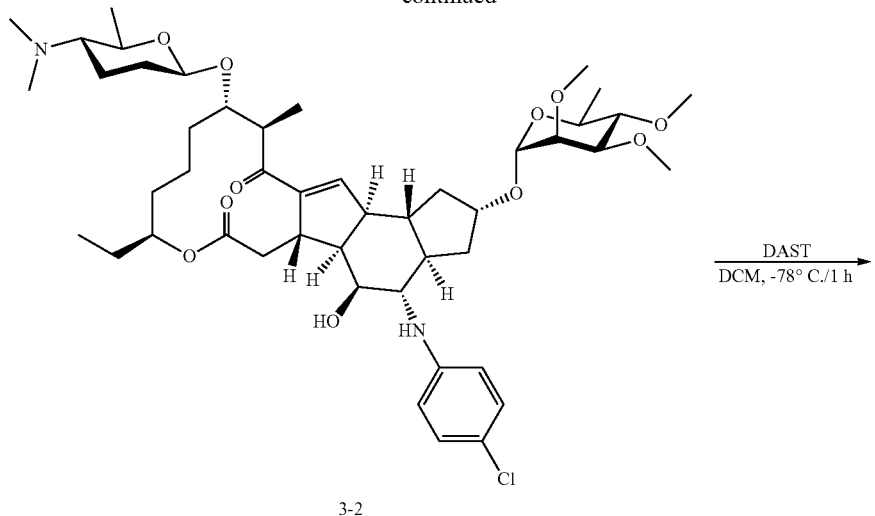

3-2

$\xrightarrow{\text{DAST}}{\text{DCM, -78° C./1 h}}$

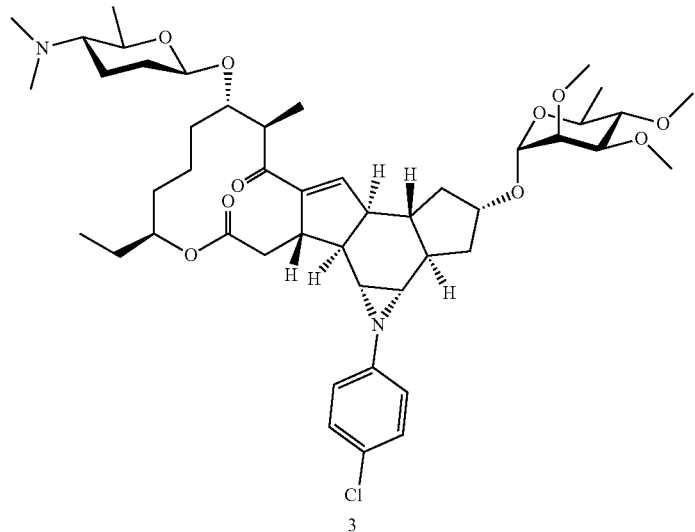

3

To a solution of compound A1 (500 mg, 0.65 mmol) and 4-Chloro-phenylamine (340 mg, 2.68 mmol) in 1,4-dioxane (5 mL) was added ZrCl₄ (156 mg, 0.65 mmol). The mixture was stirred at 80° C. for 4 h under N₂. The mixture was quenched with H₂O and was extracted with DCM (30 mL×3), The combined organic layer was dried over potassium carbonate, filtered and concentrated. The residue was purified by silica gel column (DCM/MeOH=20:1-10:1) and then prep-HPLC to give a mixture of compounds 3-1 and 3-2 (150 mg, 27.5% yield) as yellow solid.

LCMS: m/z 875.1 [M+H]⁺.

To a solution of a mixture of compounds 3-1 and 3-2 (150 mg, 0.17 mmol) in DCM (5 mL) was added DAST (0.2 mL) at −78° C. under N₂ pressure. The mixture was stirred at −78° C. under N₂ pressure for 1 h. The mixture was quenched with aqueous NaHCO₃ and was extracted with DCM (30 mL×3). The combined organic layer was dried over Na₂SO₄, filtered and concentrated. The residue was purified by Prep-HPLC to afford compound 3 (20 mg, yield 13.7%) as yellow solid. Partial ¹H NMR (CDCl₃, 300 MHz): δ 7.23 (d, J=20.4 Hz, 2H), 6.95 (d, J=8.4 Hz, 2H), 6.76 (s, 1H), 4.89 (s, 1H), 4.75-4.65 (m, 1H), 4.48-4.41 (m, 1H), 4.36-4.29 (m, 1H), 3.68-3.41 (m, 15H), 3.34-3.25 (m, 2H), 3.17-3.08 (m, 2H), 2.58-2.45 (m, 2H), 2.40-2.35 (m, 1H), 0.86 (t, J=7.5 Hz, 3H); LC-MS: m/z 857.1 [M+H]⁺.

4. Synthesis of Compound 4: (1aS,1bR,3S,4aS,4bR,7R,8S,12S,15aS,15bR,15cR)-8-(((2R,5S,6R)-5-(dimethylamino)-6-methyltetrahydro-2H-pyran-2-yl)oxy)-12-ethyl-1-(2-fluoro-6-methylphenyl)-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
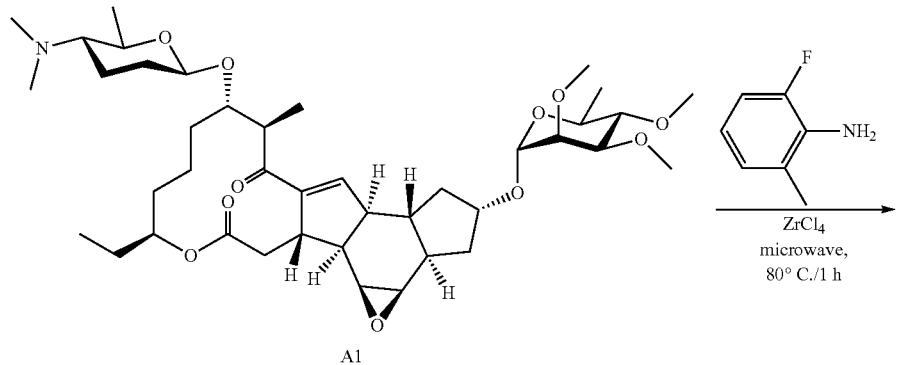
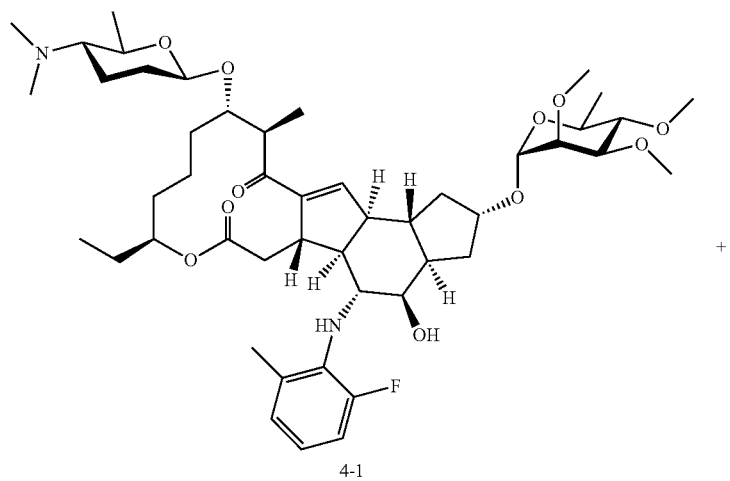
4-1

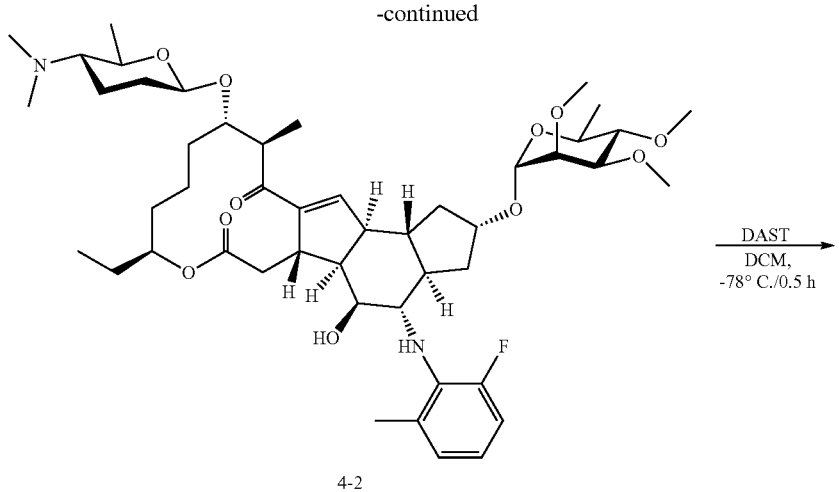

4-2

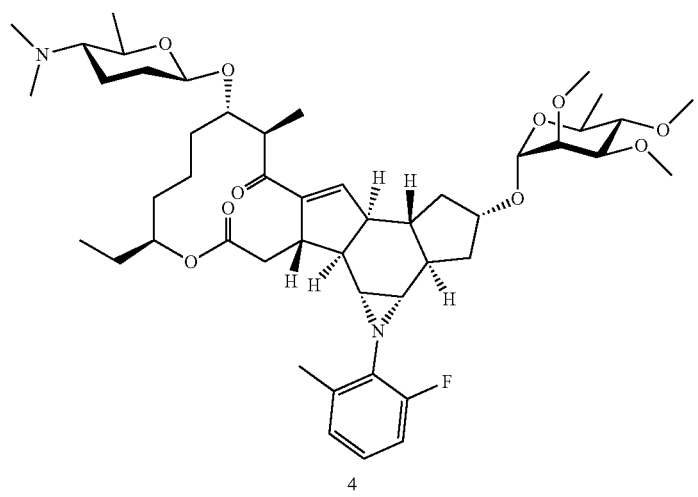

4

To a solution of compound A1 (400 mg, 0.53 mmol) in 2-Fluoro-6-methylaniline (3 mL) was added ZrCl₄ (6.0 mg, 0.026 mmol). The mixture was stirred at 80° C. under microwave for 1 h. The mixture was purified by silica gel column (DCM/MeOH=20:1-10:1) and then prep-HPLC to give a mixture of compound 4-1 and 4-2 (210 mg, 45.3% yield) as white solid. Small amount of compounds 4-1 (25 mg) and 4-2 (10 mg) has been separated by Chiral-prep-HPLC.

LCMS: m/z 874.2 [M+H]⁺.

To a solution of a mixture of compounds 4-1 and 4-2 (88 mg, 0.1 mmol) in DCM (5 mL) was added DAST (50.0 mg, 0.3 mmol) at −78° C. under N₂ pressure. The mixture was stirred at −78° C. under N₂ pressure for 0.5 h. The reaction mixture was diluted with saturated NaHCO₃ solution (10 mL) and extracted with DCM (15 mL×2). The combined organic phase was dried over anhydrous Na₂SO₄, filtered and concentrated. The residue was purified by Prep-HPLC to afford compound 4 (20 mg, yield 22.6%) as a white solid. Partial ¹H NMR (CDCl₃, 400 MHz): δ6.90-6.74 (m, 4H), 4.88 (s, 1H), 4.75-4.66 (m, 1H), 4.44-4.40 (m, 1H), 4.33-4.29 (m, 1H), 3.31-3.21 (m, 2H), 3.17-3.11 (m, 2H), 2.61-2.51 (m, 2H), 0.84 (t, J=7.2 Hz, 3H). LCMS: m/z 856.2[M+H]⁺.

5. Synthesis of Compound 5
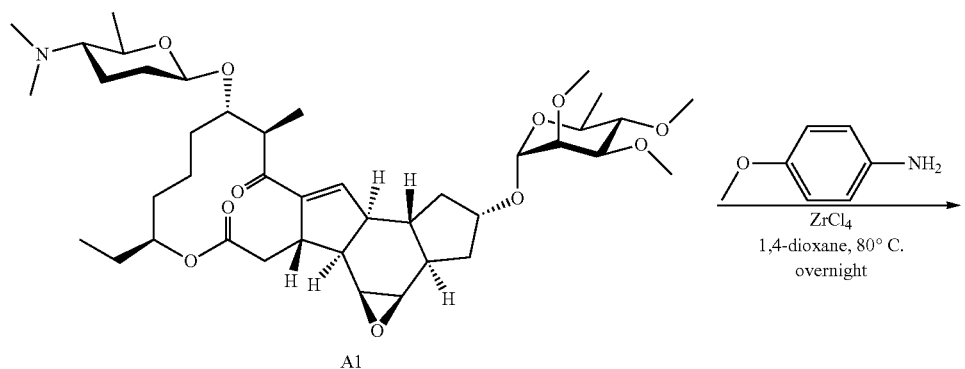
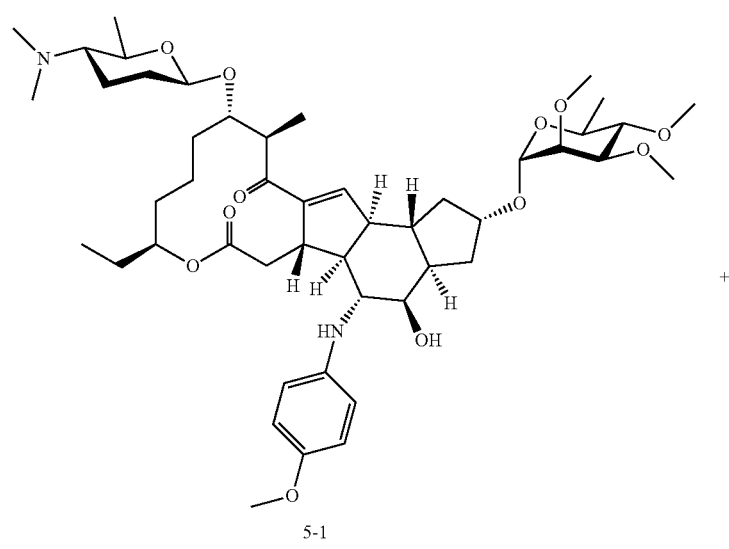

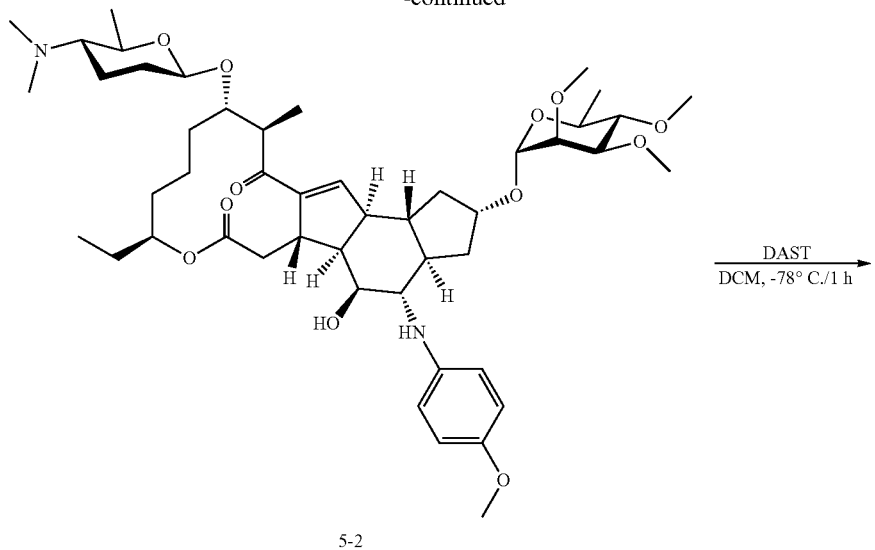

5-2

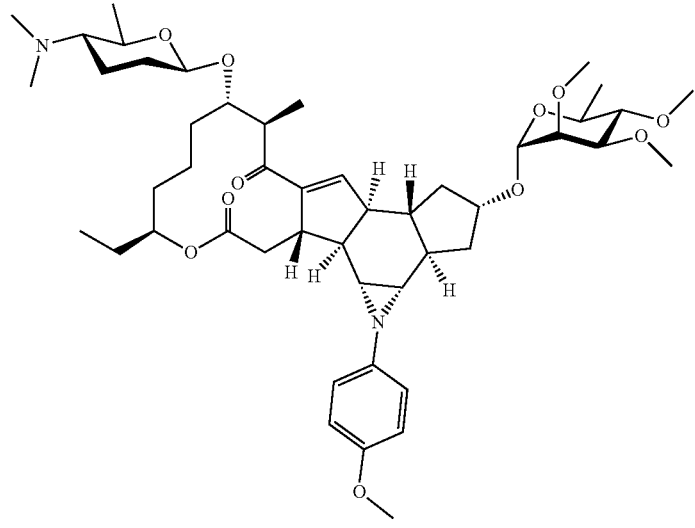

5

To a solution of compound A1 (500 mg, 0.65 mmol) and 4-Methoxy-phenylamine (95.9 mg, 0.78 mmol) in 1,4-dioxane (3 mL) was added $ZrCl_4$ (60.6 mg, 0.26 mmol). The mixture was stirred at 80° C. for overnight under $N_2$. The mixture was quenched with $H_2O$ and was extracted with DCM (30 mL×3). The combined organic layer was dried over $Na_2SO_4$, filtered and concentrated. The residue was purified by prep-HPLC to give the mixture of products 5-1 and 5-2 (125 mg, 22.9% yield) as yellow solid. LC-MS: m/z 871.2 [M+H]$^+$.

To a solution of a mixture of compounds 5-1 and 5-2 (125 mg, 0.14 mmol) in DCM (5 mL) was added DAST (0.1 mL) at −78° C. under $N_2$ pressure. The mixture was stirred at −78° C. under $N_2$ pressure for 1 h. The mixture was quenched with aqueous $NaHCO_3$ and $H_2O$. The mixture was extracted with DCM (30 mL×3). The combined organic layer was dried over $Na_2SO_4$, filtered and concentrated. The residue was purified by Prep-HPLC to afford compound 5 (30 mg, yield 20.7%) as yellow solid. Partial $^1H$ NMR ($CDCl_3$, 300 MHz): δ 7.01-6.82 (m, 4H), 6.75 (s, 1H), 4.90 (s, 1H), 4.79-4.68 (m, 1H), 4.48-4.26 (m, 1H), 3.91 (s, 3H), 3.70-3.44 (m, 16H), 3.35-3.06 (m, 4H), 2.67-2.51 (m, 2H), 2.43-2.36 (m, 1H), 2.26-2.14 (m, 10H), 2.10-1.94 (m, 2H), 0.85 (t, J=7.2 Hz, 3H); LC-MS: m/z 853.2 [M+H]$^+$.

6. Synthesis of Compound 6
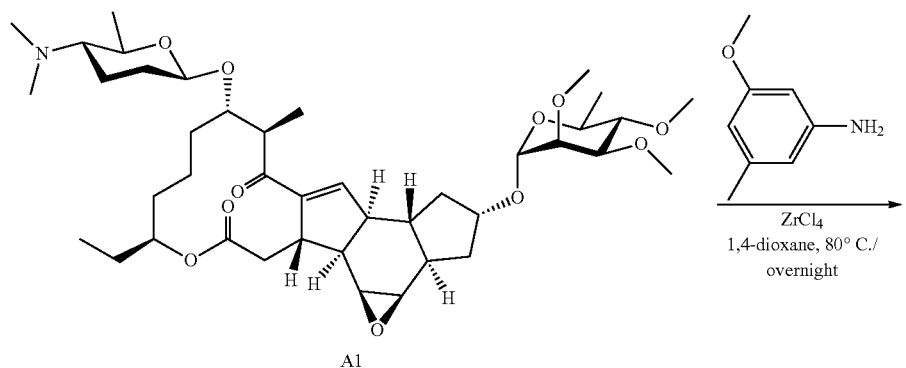
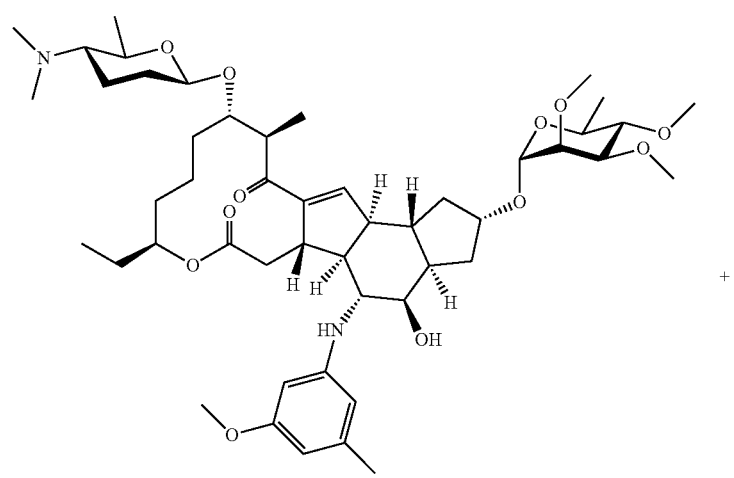

-continued

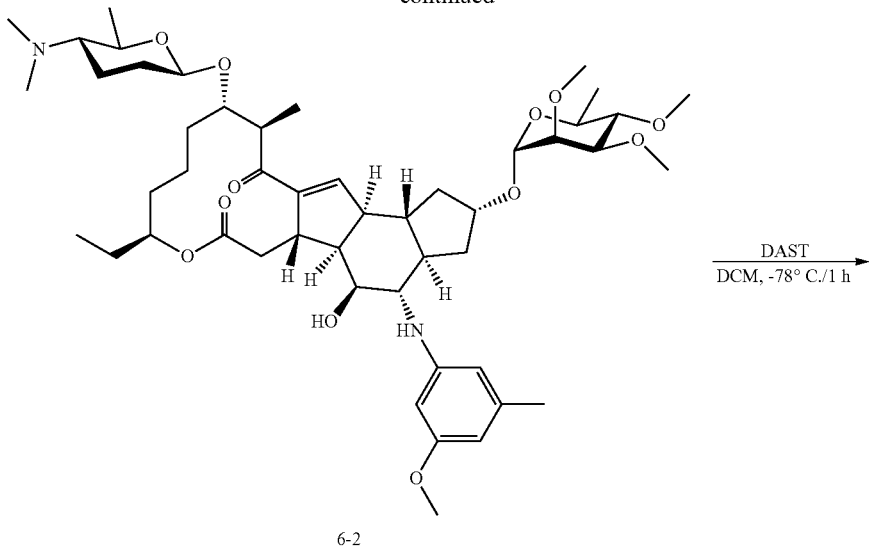

6-2

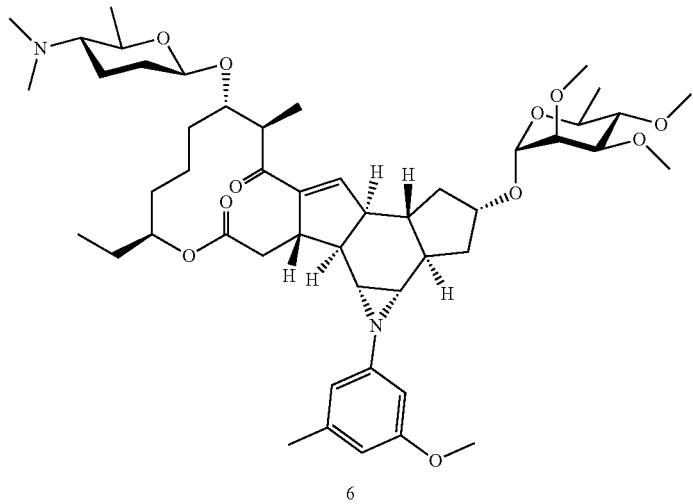

6

To a solution of compound A1 (300 mg, 0.4 mmol) and 2-Methoxy-4-methyl-phenylamine (164.6 mg, 1.2 mmol) in 1,4-dioxane (5 mL) was added ZrCl$_4$ (93.2 mg, 0.4 mmol). The mixture was stirred at 80° C. overnight under N$_2$. The mixture was quenched with H$_2$O and was extracted with DCM (30 mL×3). The combined organic layer was dried over Na$_2$SO$_4$, filtered and concentrated. The residue was purified by prep-HPLC to give the crude mixture of products 6-1 and 6-2 (200 mg) as yellow solid. LC-MS: m/z 886.2 [M+H]$^+$.

To a solution of a mixture of compounds 6-1 and 6-2 (100 mg, 0.11 mmol) in DCM (5 mL) was added DAST (87.3 mg, 0.54 mmol) at −78° C. under N$_2$ pressure. The mixture was stirred at −78° C. under N$_2$ pressure for 1 h. The mixture was quenched with aqueous NaHCO$_3$ and H$_2$O. The mixture was extracted with DCM (30 mL×3). The combined organic layer was dried over Na$_2$SO$_4$, filtered and concentrated. The residue was purified by Prep-HPLC to afford compound 6 (14.3 mg, yield 16.4%) as yellow solid. Partial $^1$H NMR (CDCl$_3$, 300 MHz): δ 6.82-6.74 (m, 2H), 6.68-6.62 (m, 2H), 4.90 (s, 1H), 4.78-4.69 (m, 1H), 4.46-4.41 (m, 1H), 4.36-4.29 (m, 1H), 3.89 (s, 3H), 3.68-3.43 (m, 15H), 3.33-3.07 (m, 4H), 2.64-2.49 (m, 2H), 0.85 (t, J=7.8 Hz, 3H); LC-MS: m/z 868.2 [M+H]$^+$.

7. Synthesis of Compound 7: (1aS,1bR,3S,4aS,4bR, 7R,8S,12S,15aS,15bR,15cR)-8-(((2R,5S,6R)-5-(dimethylamino)-6-methyltetrahydro-2H-pyran-2-yl)oxy)-12-ethyl-1-(3-fluorophenyl)-7-methyl-3-(((2R, 3R,4R,5S,6S)-3,4,5-trimethoxy-6-methyltetrahydro-2H-pyran-2-yl)oxy)-1,1a, 1b,2,3,4,4a,4b,7,8,9,10,11, 12,15,15a,15b,15c-octadecahydro-[1]oxacyclododecino[5',4':2,3]-as-indaceno[4,5-b]azirine-6,14-dione
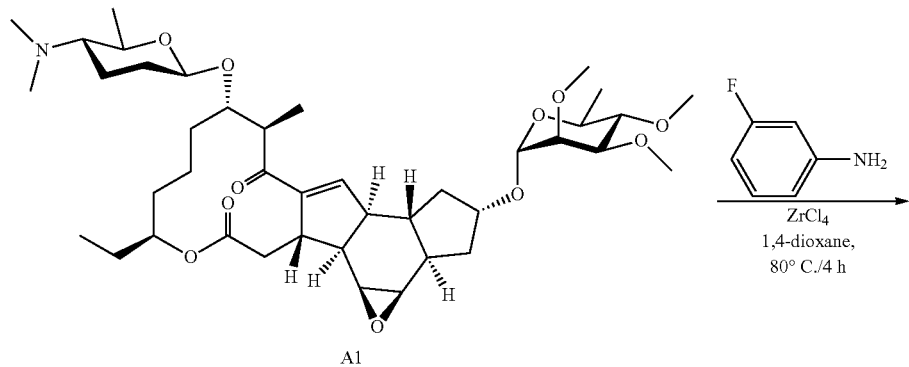
A1
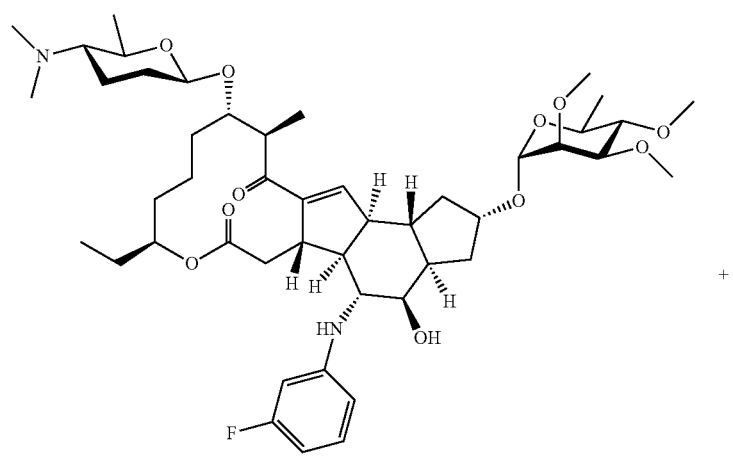
7-1

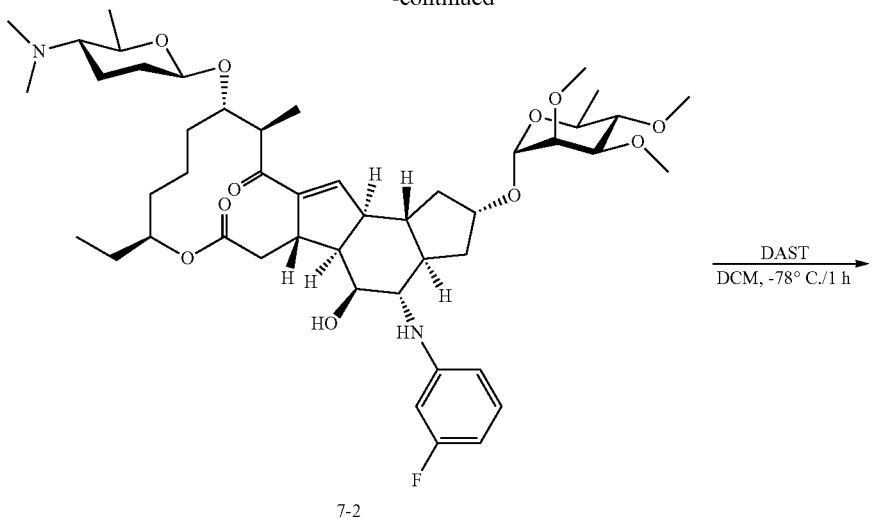

7-2

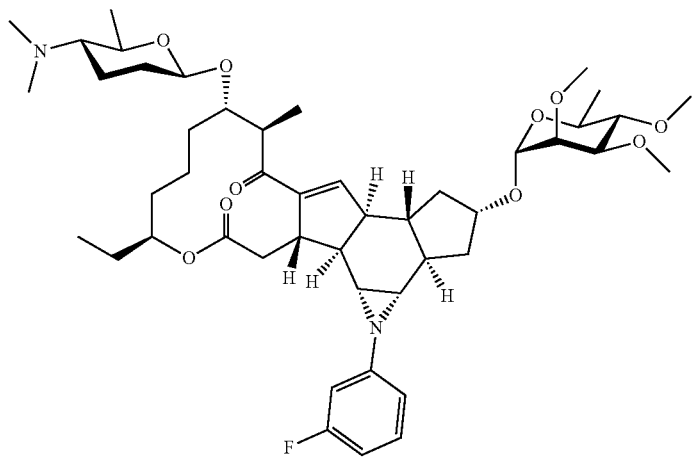

7

To a solution of compound A1 (500 mg, 0.65 mmol) and 3-Fluoro-phenylamine (222.8 mg, 2.0 mmol) in 1,4-dioxane (5 mL) was added ZrCl$_4$ (156.1 mg, 0.65 mmol). The mixture was stirred at 80° C. for 4 h under N$_2$. The mixture was quenched with H$_2$O and was extracted with DCM (30 mL×3). The combined organic layer was dried over Na$_2$SO$_4$, filtered and concentrated. The residue was purified by prep-HPLC to give the crude mixture of products 7-1 and 7-2 (150 mg) as yellow solid. LC-MS: m/z 886.2 [M+H]$^+$.

To a solution of a mixture of compounds 7-1 and 7-2 (150 mg, 0.17 mmol) in DCM (5 mL) was added DAST (0.1 mL) at −78° C. under N$_2$ pressure. The mixture was stirred at −78° C. under N$_2$ pressure for 1 h. The mixture was quenched with aqueous NaHCO$_3$ and H$_2$O and was extracted with DCM (30 mL×3). The combined organic layer was dried over Na$_2$SO$_4$, filtered and concentrated. The residue was purified by Prep-HPLC to afford compound 7 (40 mg, yield 28%) as yellow solid. Partial $^1$H NMR (CDCl$_3$, 300 MHz): δ 7.22-7.14 (m, 1H), 6.64-6.62 (m, 4H), 4.89 (s, 1H), 4.75-4.64 (m, 1H), 4.46-4.40 (m, 1H), 4.37-4.29 (m, 1H), 3.68-3.42 (m, 16H), 3.34-3.07 (m, 4H), 2.59-2.39 (m, 3H), 0.90-0.75 (m, 4H); LC-MS: m/z 841.2 [M+H]$^+$.

8. Synthesis of Compound 8
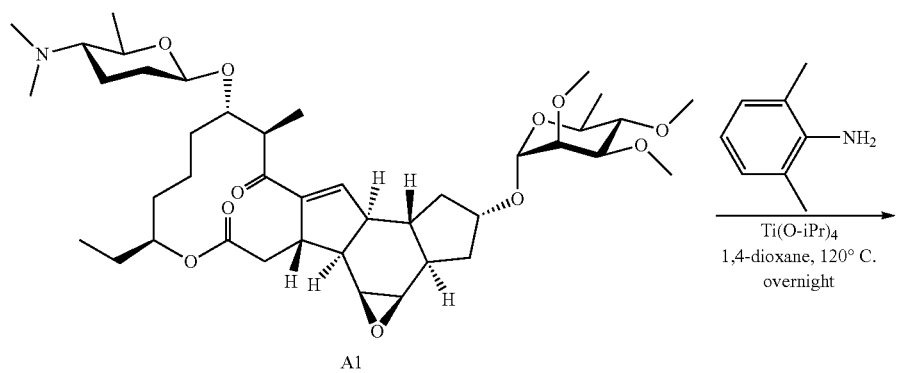
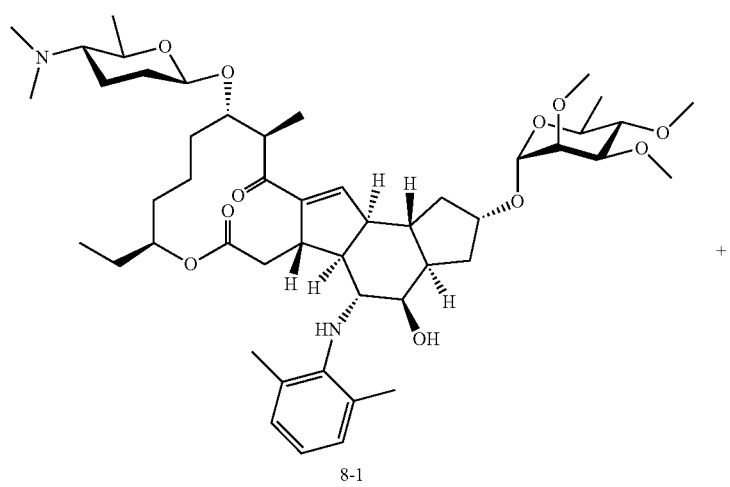

-continued

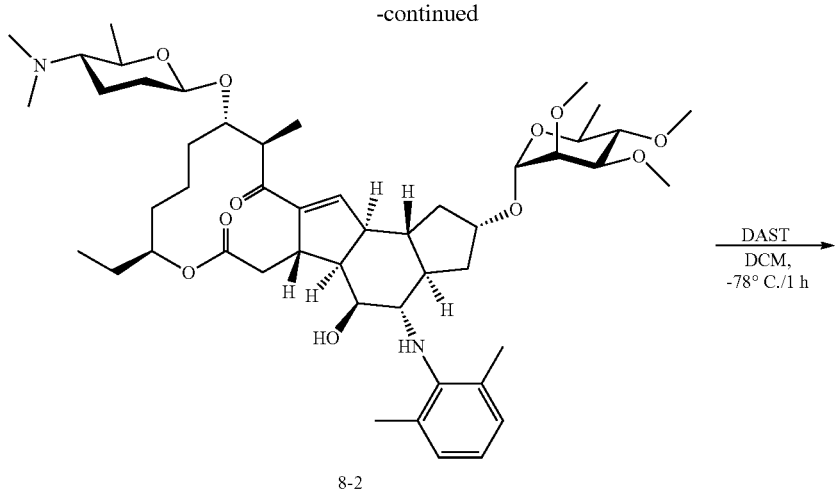

8-2

$\xrightarrow{\text{DAST}}_{\substack{\text{DCM,} \\ -78°\text{C./1 h}}}$

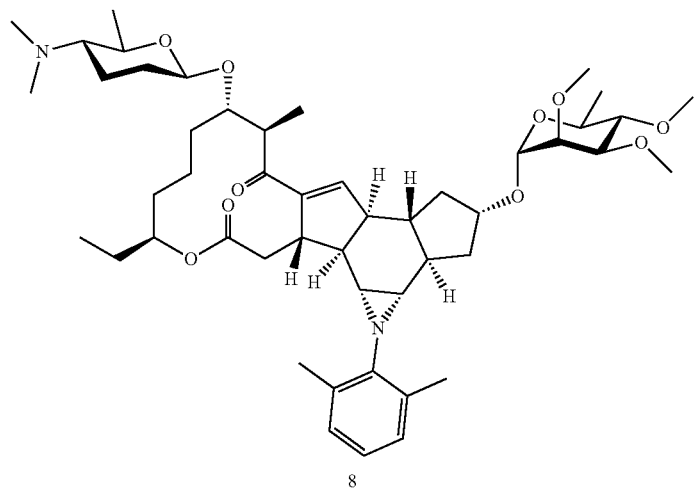

8

To a solution of compound A1 (400 mg, 0.53 mmol) and 2,6-Dimethyl-phenylamine (129 mg, 1.07 mmol) in 1,4-dioxane (10 mL) was added Ti(O-iPr)$_4$ (156 mg, 0.67 mmol). The mixture was stirred at 120° C. overnight under N$_2$. The mixture was quenched with H$_2$O and extracted with DCM (30 mL×3). The combined organic layer was dried over potassium carbonate, filtered and concentrated. The residue was purified by prep-HPLC to give the crude products 8-1 and 8-2 (200 mg) as yellow solid. LC-MS: m/z 869.5 [M+H]$^+$.

To a solution of the mixture of compounds 8-1 and 8-2 (200 mg, 0.23 mmol) in DCM (10 mL) was added DAST (74 mg, 0.46 mmol) at −78° C. under N$_2$ pressure. The mixture was stirred at −78° C. under N$_2$ pressure for 1 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 8 (40 mg, yield 20.5%) as yellow solid. Partial $^1$H NMR (CDCl$_3$, 400 MHz): δ 6.98-6.92 (m, 2H), 6.83-6.75 (m, 2H), 4.88 (s, 1H), 4.75-4.65 (m, 1H), 4.44-4.40 (m, 1H), 4.37-4.29 (m, 1H), 3.31-3.08 (m, 4H), 2.65-2.60 (m, 1H), 2.56-2.50 (m, 1H), 2.42-2.33 (m, 7H), 1.64 (s, 3H), 1.29-1.16 (m, 12H), 0.89-0.80 (m, 4H); LC-MS: m/z 851.5 [M+H]$^+$.

9. Synthesis of Compound 9
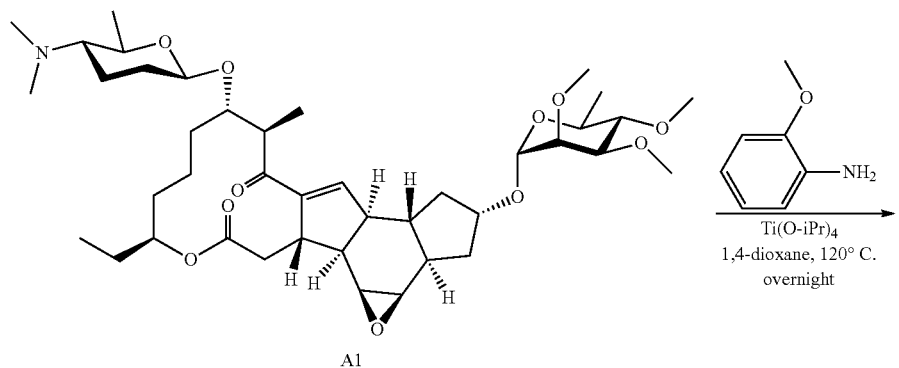
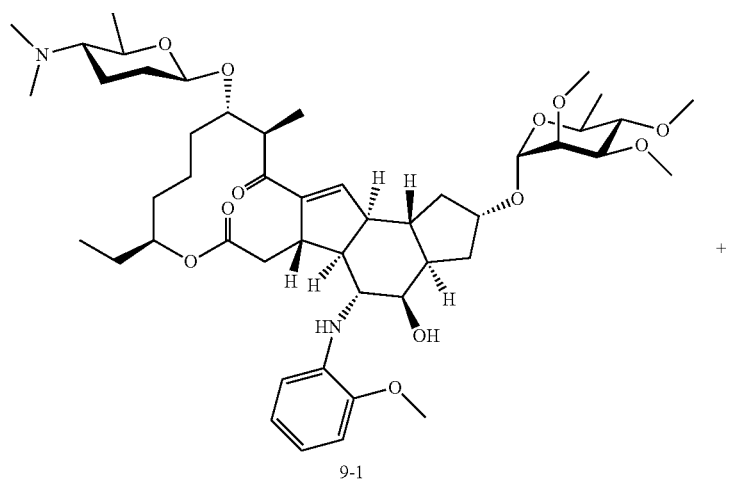

-continued

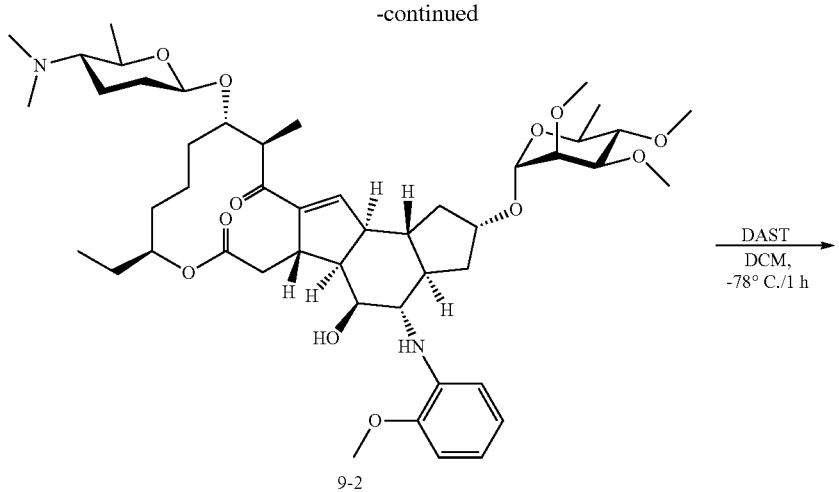

9-2

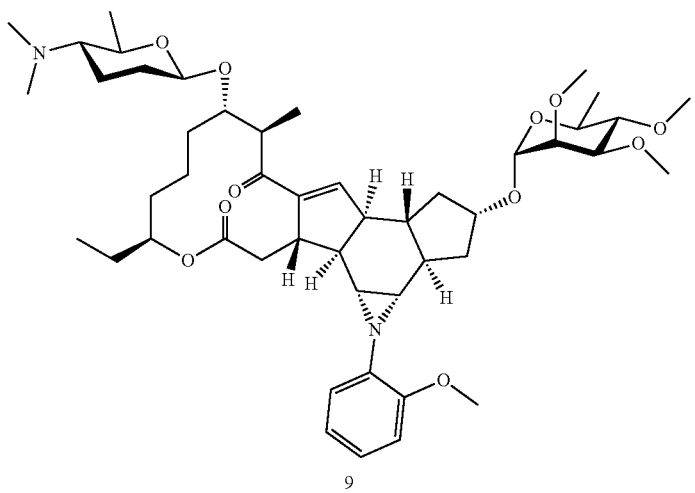

9

To a solution of compound A1 (300 mg, 0.4 mmol) and 2-Methoxy-phenylamine (117.6 mg, 0.8 mmol) in 1,4-dioxane (10 mL) was added Ti(O-iPr)$_4$ (113.6 mg, 0.4 mmol). The mixture was stirred at 120° C. overnight under N$_2$. The mixture was quenched with H$_2$O and extracted with DCM (30 mL×3). The combined organic layer was dried over potassium carbonate, filtered and concentrated. The residue was purified by prep-HPLC to give the crude products 9-1 and 9-2 (100 mg) as yellow solid. LC-MS: m/z 871.2 [M+H]$^+$.

To a solution of the mixture of compounds 9-1 and 9-2 (100 mg, 0.11 mmol) in DCM (10 mL) was added DAST (37 mg, 0.22 mmol) at −78° C. under N$_2$ pressure. The mixture was stirred at −78° C. under N$_2$ pressure for 1 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 9 (40 mg, yield 46%) as yellow solid. Partial $^1$H NMR (CDCl$_3$, 400 MHz): δ 6.97-6.81 (m, 4H), 6.75 (s, 1H), 4.89 (s, 1H), 4.76-4.68 (m, 1H), 4.46-4.39 (m, 1H), 4.35-4.27 (m, 1H), 3.90 (s, 3H), 3.67-3.40 (m, 17H), 3.32-3.18 (m, 2H), 3.14-3.07 (m, 2H), 2.63-2.50 (m, 2H), 2.40-2.36 (m, 1H), 0.87-0.78 (m, 4H); LC-MS: m/z 853.2 [M+H]$^+$.

10. Synthesis of Compound 10
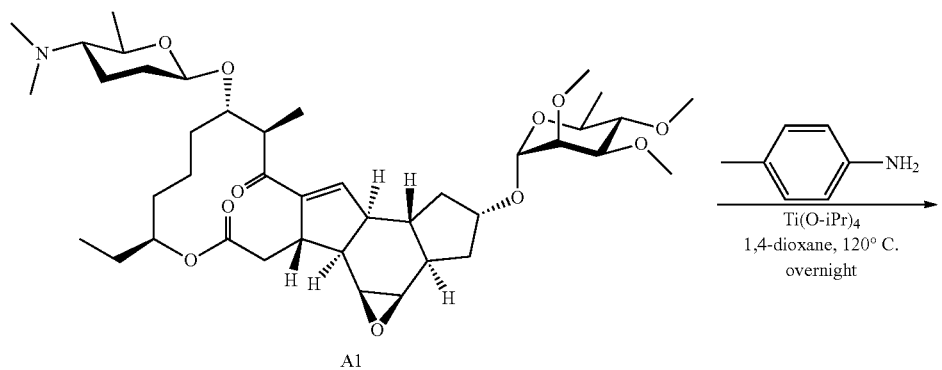
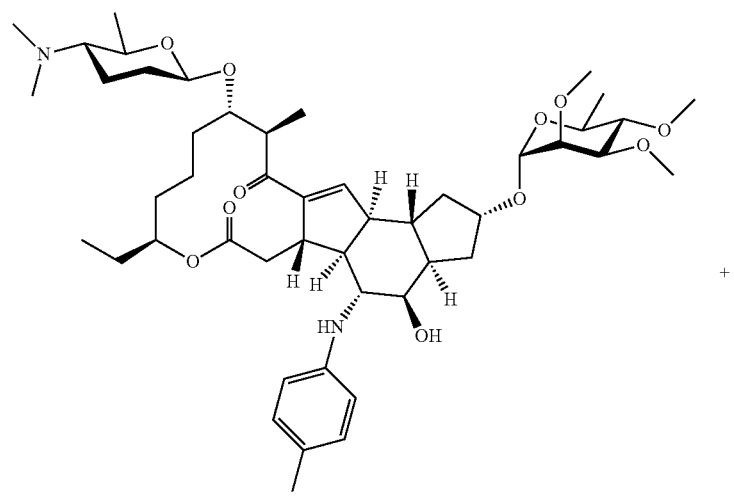
10-1

-continued

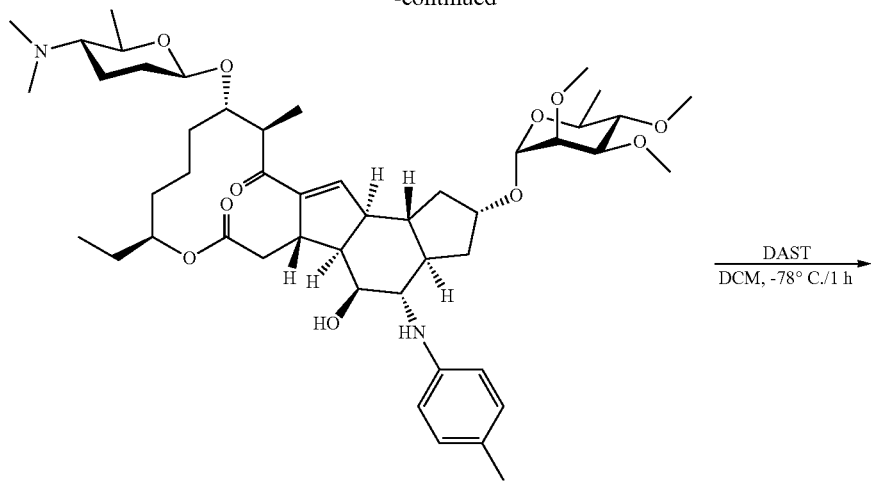

10-2

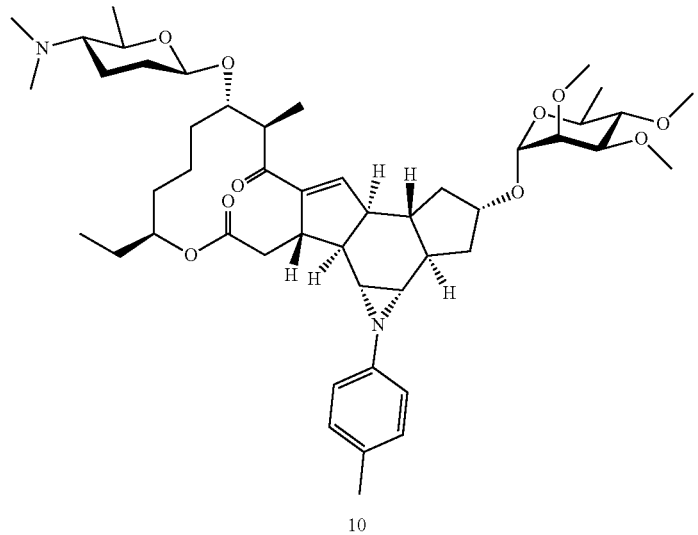

10

To a solution of compound A1 (400 mg, 0.53 mmol) and p-Tolylamine (114.4 mg, 1.06 mmol) in 1,4-dioxane (10 mL) was added Ti(O-iPr)$_4$ (150.5 mg, 0.53 mmol). The mixture was stirred at 120° C. overnight under N$_2$. The mixture was quenched with H$_2$O and extracted with DCM (30 mL×3). The combined organic layer was dried over potassium carbonate, filtered and concentrated. The residue was purified by prep-HPLC to give the crude products 10-1 and 10-2 (100 mg) as yellow solid. LC-MS: m/z 855.2 [M+H]$^+$.

To a solution of the mixture of compounds 10-1 and 10-2 (100 mg, 0.11 mmol) in DCM (10 mL) was added DAST (32 mg, 0.19 mmol) at −78° C. under N$_2$ pressure. The mixture was stirred at −78° C. under N$_2$ pressure for 1 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 10 (15 mg, yield 16.2%) as white solid. Partial $^1$H NMR (CDCl$_3$, 400 MHz): δ 6.97-6.81 (m, 4H), 6.75 (s, 1H), 4.89 (s, 1H), 4.76-4.68 (m, 1H), 4.46-4.39 (m, 1H), 4.35-4.27 (m, 1H), 3.00 (s, 3H), 3.32-3.18 (m, 2H), 3.14-3.07 (m, 2H), 2.63-2.50 (m, 2H), 2.40-2.36 (m, 1H), 2.28-2.13 (m, 10H), 0.87-0.78 (m, 4H); LC-MS: m/z 853.2 [M+H]$^+$.

11. Synthesis of Compound 11
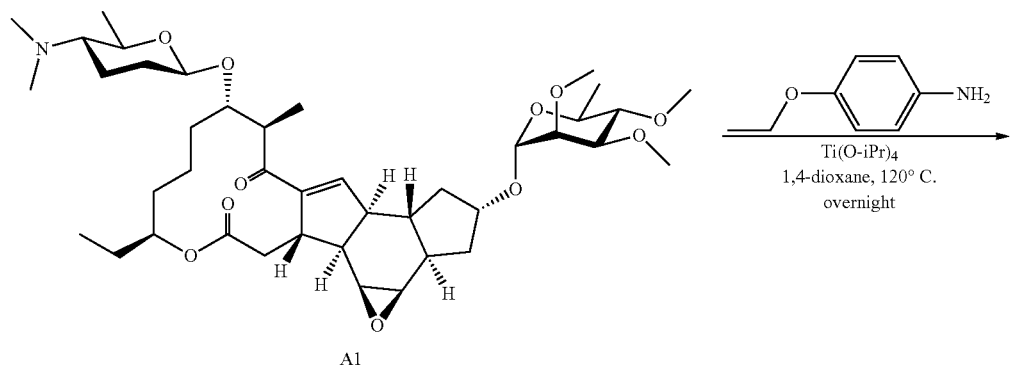
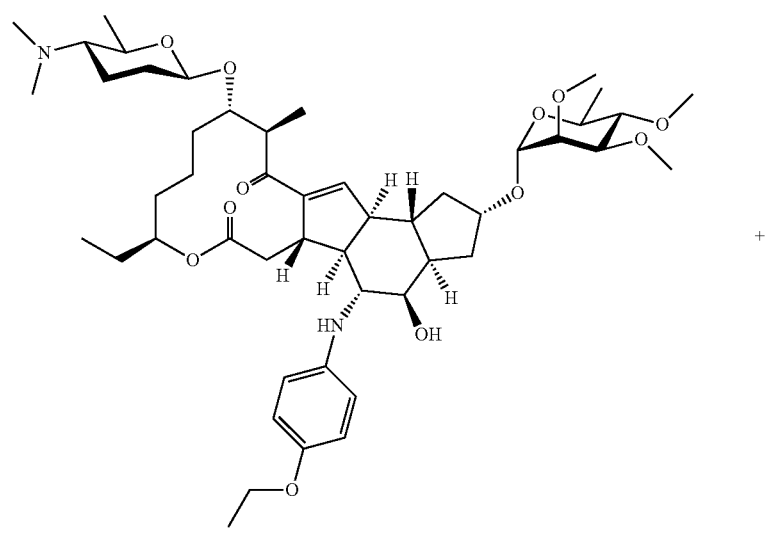
11-1

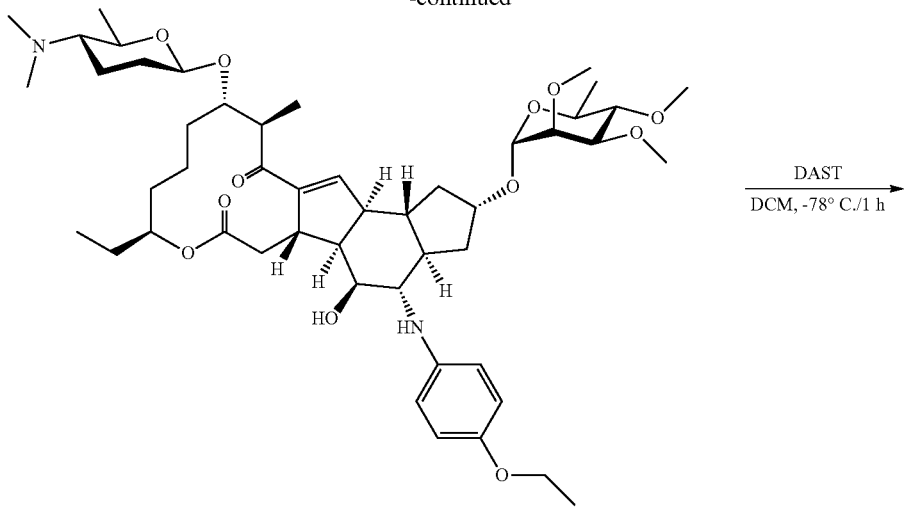

11-2

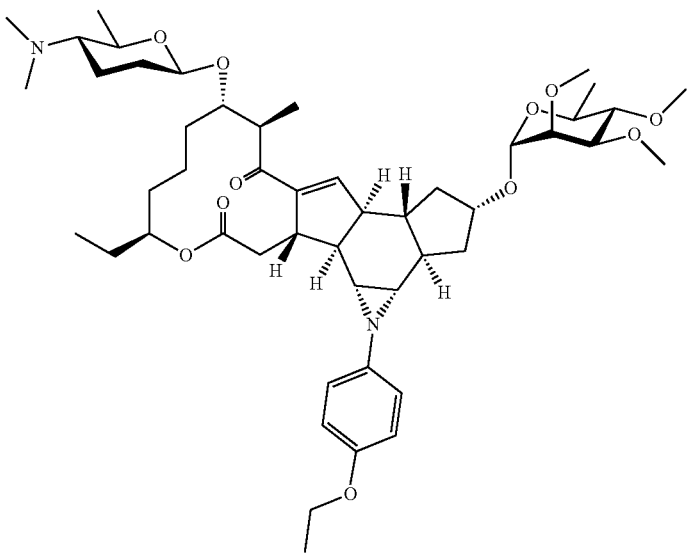

11

To a solution of compound A1 (500 mg, 0.65 mmol) and 4-Ethoxy-phenylamine (184 mg, 1.33 mmol) in 1,4-dioxane (10 mL) was added Ti(O-iPr)$_4$ (190.3 mg, 0.65 mmol). The mixture was stirred at 120° C. overnight under N$_2$. The mixture was quenched with H$_2$O and extracted with DCM (30 mL×3). The combined organic layer was dried over potassium carbonate, filtered and concentrated. The residue was purified by prep-HPLC to give the crude products 11-1 and 11-2 (250 mg) as yellow solid. LC-MS: m/z 885.2 [M+H]$^+$.

To a solution of the mixture of compounds 11-1 and 11-2 (250 mg, 0.28 mmol) in DCM (10 mL) was added DAST (45 mg, 0.28 mmol) at −78° C. under N$_2$ pressure. The mixture was stirred at −78° C. under N$_2$ pressure for 1 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 11 (25 mg, yield 10.3%) as white solid. Partial $^1$H NMR (CDCl$_3$, 400 MHz): δ 6.98-6.92 (m, 2H), 6.81-6.73 (m, 2H), 4.89 (s, 1H), 4.76-4.64 (m, 1H), 4.48-4.40 (m, 1H), 4.36-4.28 (m, 1H), 3.96 (q, J=6.9 Hz, 2H), 3.35-3.24 (m, 2H), 3.17-3.08 (m, 2H), 2.61-2.47 (m, 2H), 0.90-0.72 (m, 4H); LC-MS: m/z 867.2 [M+H]$^+$.

12. Synthesis of Compound 12: (1aS,1bR,3S,4aS, 4bR,7R,8S,12S,15aS,15bR,15cR)-1-(2,4-dichlorophenyl)-8-(((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
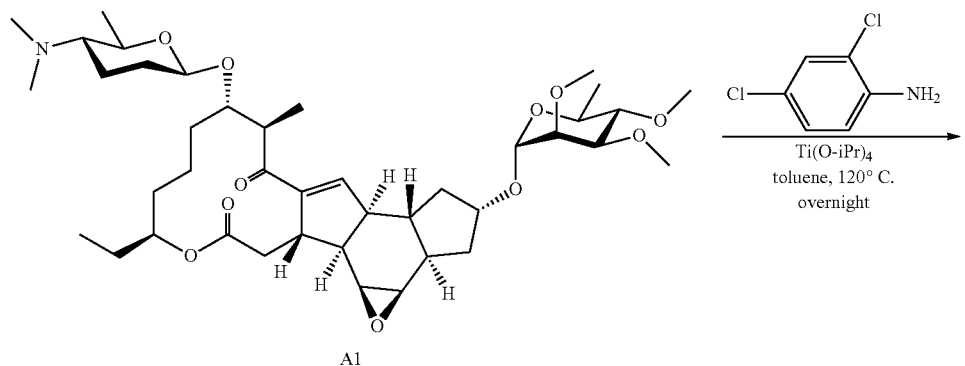

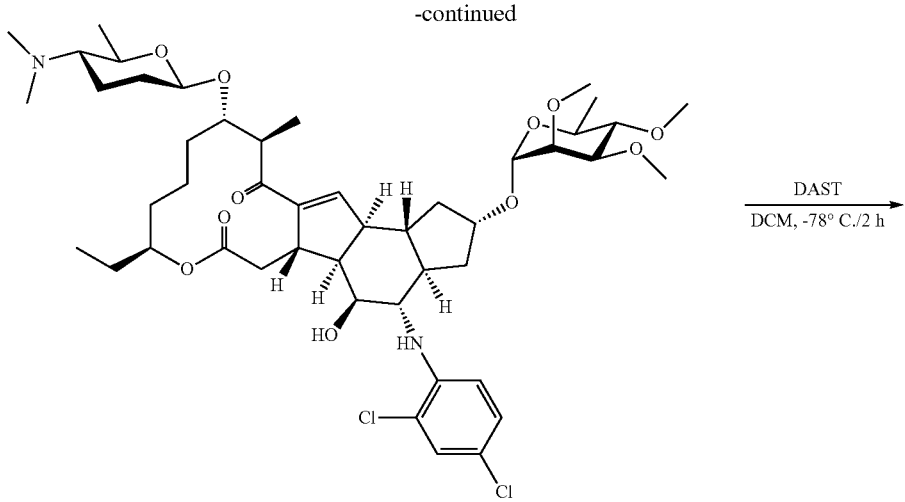

12-2

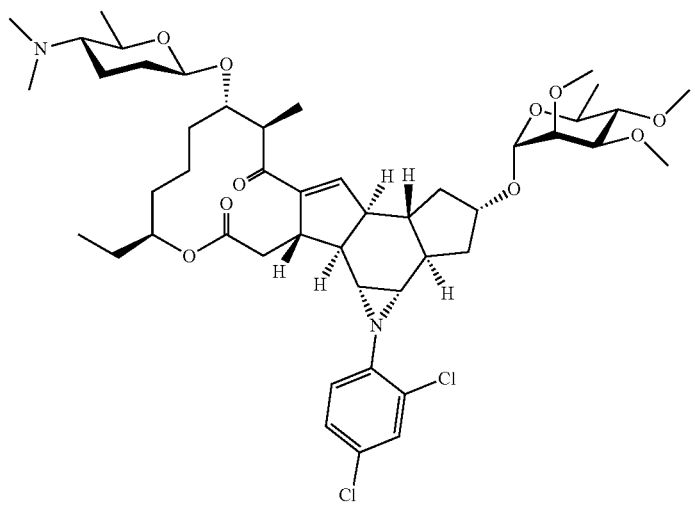

12

To a solution of compound A1 (400 mg, 0.53 mmol) and 2,4-Dichloro-phenylamine (172 mg, 1.06 mmol) in toluene (10 mL) was added Ti(O-iPr)$_4$ (152 mg, 0.53 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 12-1 and 12-2 (350 mg) as yellow solid. LC-MS: m/z 909.1 [M+H]$^+$.

To a solution of the mixture of compounds 12-1 and 12-2 (300 mg, 0.4 mmol) in DCM (15 mL) was added DAST (96.8 mg, 0.6 mmol) at −78° C. under N$_2$. The mixture was stirred at −78° C. for 2 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 12 (20 mg, yield 5.6%) as white solid.

Partial $^1$H NMR (CDCl$_3$, 400 MHz): δ 7.34-7.31 (m, 1H), 7.15-7.09 (m, 1H), 6.92-6.87 (m, 2H), 6.76 (s, 1H), 4.73-4.65 (m, 1H), 4.47-4.41 (m, 1H), 4.36-4.28 (m, 1H), 3.33-3.22 (m, 2H), 3.18-3.08 (m, 2H), 2.65-2.53 (m, 2H), 2.46-2.41 (m, 1H), 2.28-2.16 (m, 10H); LC-MS: m/z 891.1 [M+H]$^+$.

13. Synthesis of Compound 13
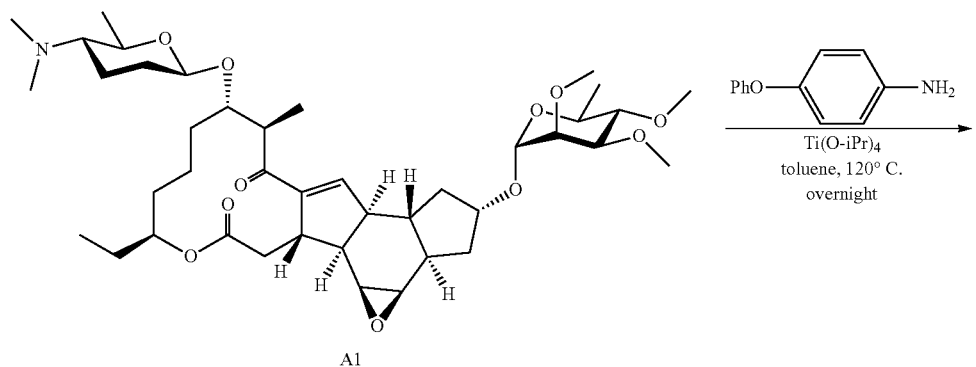
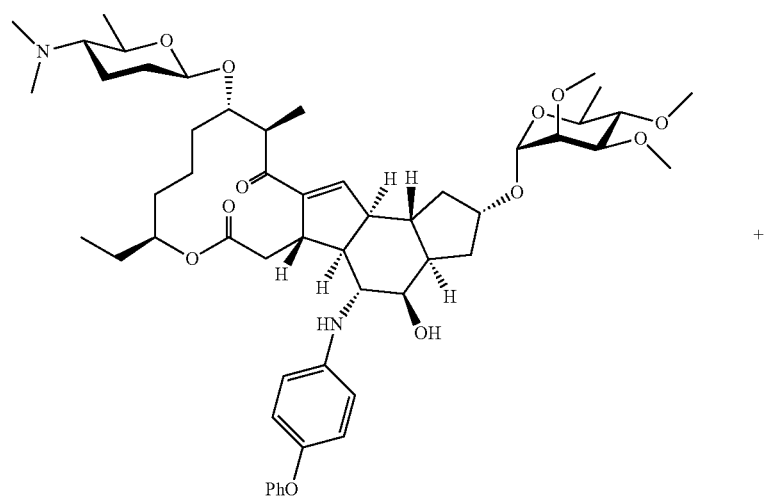
13-1

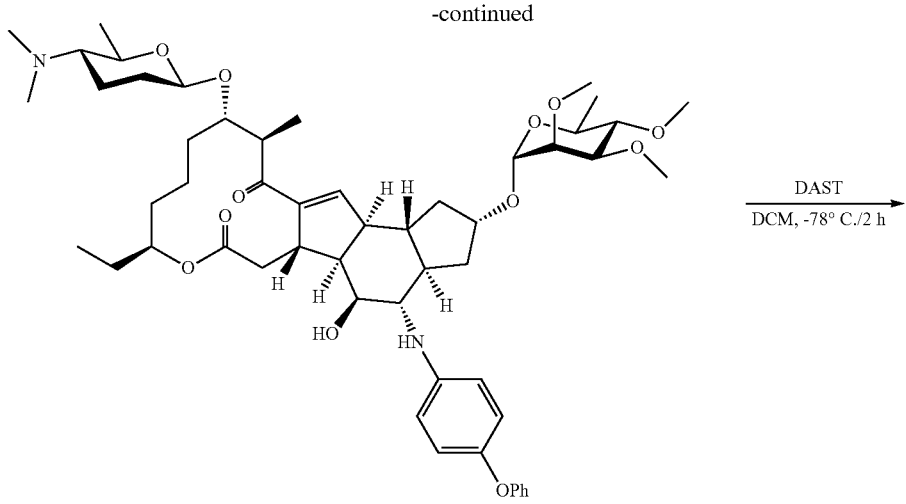

13-2

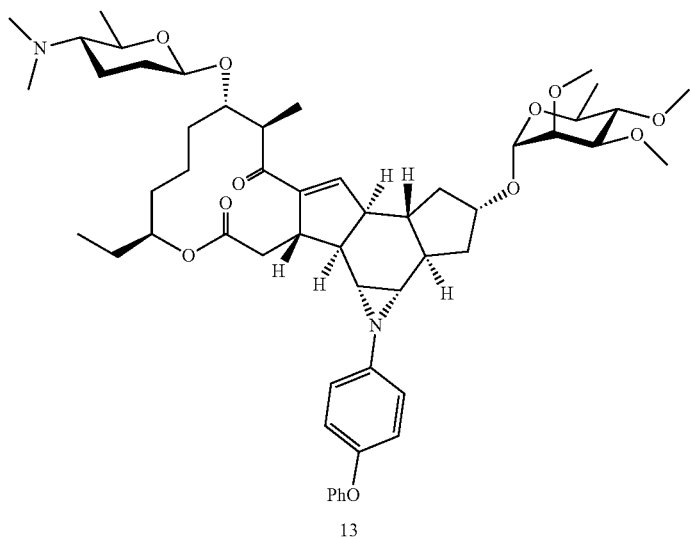

13

To a solution of compound A1 (400 mg, 0.53 mmol) and 4-Phenoxy-phenylamine (197.8 mg, 1.07 mmol) in toluene (10 mL) was added Ti(O-iPr)$_4$ (150.5 mg, 0.53 mmol). The mixture was quenched with H$_2$O (100 mL) and extracted with DCM (30 mL×3). The combined organic layer was dried over potassium carbonate, filtered and concentrated. The residue was purified by prep-HPLC to give the crude products 13-1 and 13-2 (300 mg) as yellow solid. LC-MS: m/z 933.2 [M+H]$^+$.

To a solution of the mixture of compounds 13-1 and 13-2 (300 mg, 0.32 mmol) in DCM (15 mL) was added DAST (51.7 mg, 0.32 mmol) at −78° C. under N$_2$. The mixture was stirred at −78° C. for 2 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 13 (20 mg, yield 6.8%) as yellow solid.

Partial $^1$H NMR (CDCl$_3$, 300 MHz): δ 7.33-7.28 (m, 2H), 7.08-6.99 (m, 3H), 6.95-6.91 (m, 4H), 6.76 (s, 1H), 4.89 (s, 1H), 4.73-4.65 (m, 1H), 4.47-4.41 (m, 1H), 4.37-4.29 (m, 1H), 3.70-3.62 (m, 1H), 3.35-3.24 (m, 2H), 2.60-2.47 (m, 2H), 2.42-2.38 (m, 1H), 0.85 (t, J=7.5 Hz, 3H); LC-MS: m/z 915.2 [M+H]$^+$.

14. Synthesis of Compound 14: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl)oxy)-12-ethyl-1-(4-fluorophenyl)-7-methyl-3-(((2R, 3R,4R,5S,6S)-3,4,5-trimethoxy-6-methyltetrahydro-2H-pyran-2-yl)oxy)-1,1a,1b,2,3,4,4a,4b,7,8,9,10,11, 12,15,15a,15b,15c-octadecahydro-[1]oxacyclododecino[5',4':2,3]-as-indaceno[4,5-b]azirine-6,14-dione

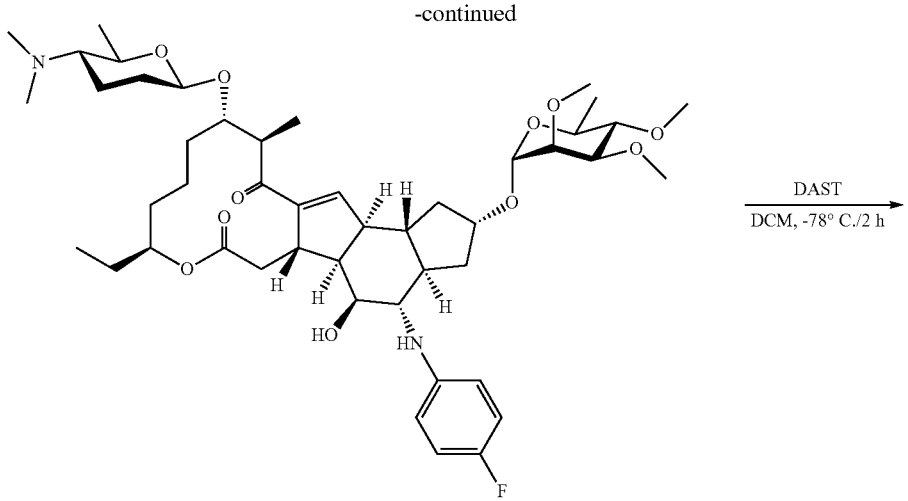

14-2

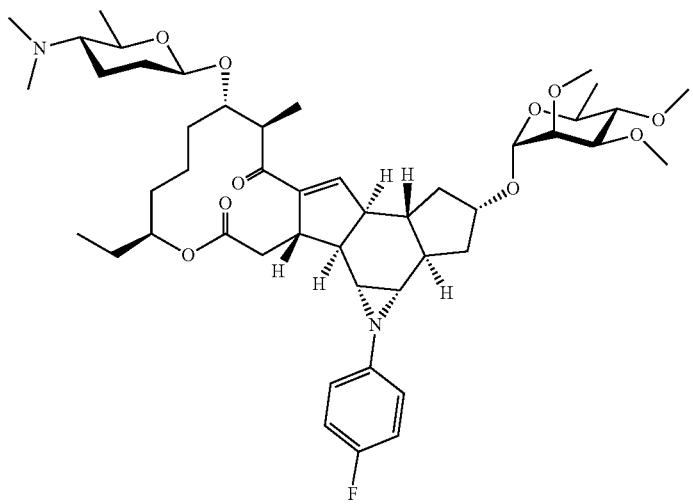

14

To a solution of compound A1 (500 mg, 0.65 mmol) and 4-Fluoro-phenylamine (168 mg, 1.33 mmol) in toluene (20 mL) was added Ti(O-iPr)$_4$ (189.8 mg, 0.66 mmol). The mixture was quenched with H$_2$O (100 mL) and extracted with DCM (30 mL×3). The combined organic layer was dried over potassium carbonate, filtered and concentrated. The residue was purified by prep-HPLC to give the crude products 14-1 and 14-2 (250 mg) as yellow solid. LC-MS: m/z 860.2 [M+H]+.

To a solution of the mixture of compounds 14-1 and 14-2 (250 mg, 0.28 mmol) in DCM (10 mL) was added DAST (46 mg, 0.28 mmol) at −78° C. under N$_2$. The mixture was stirred at −78° C. for 2 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 14 (20 mg, yield 8.5%) as yellow solid. Partial $^1$H NMR (CDCl$_3$, 400 MHz): δ 7.01-6.88 (m, 4H), 6.75 (s, 1H), 4.89 (s, 1H), 4.73-4.65 (m, 1H), 4.45-4.40 (m, 1H), 4.35-4.29 (m, 1H), 3.67-3.61 (m, 1H), 3.32-3.24 (m, 2H), 3.16-3.08 (m, 2H), 2.58-2.46 (m, 2H), 2.39-2.35 (m, 1H), 2.02-1.96 (m, 1H), 1.87-1.78 (m, 2H); LC-MS: m/z 842.2 [M+H]+.

15. Synthesis of Compound 15
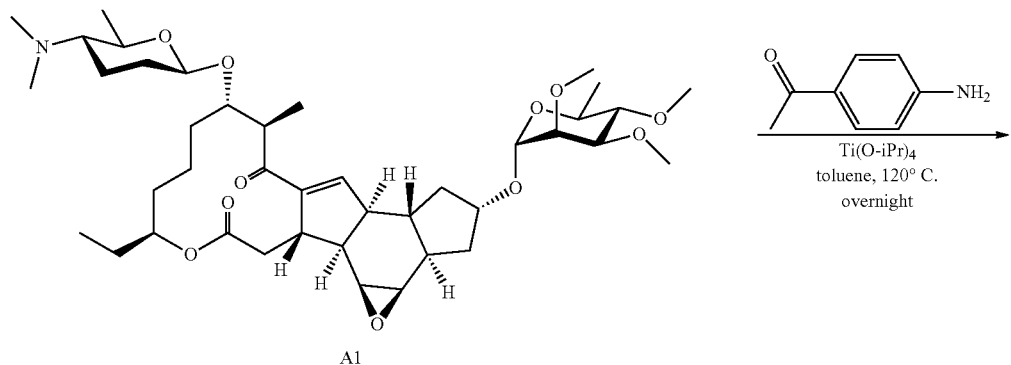
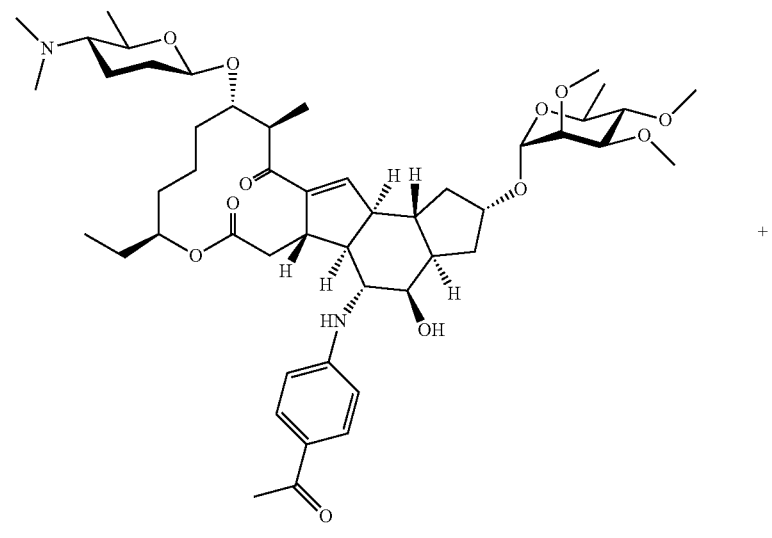

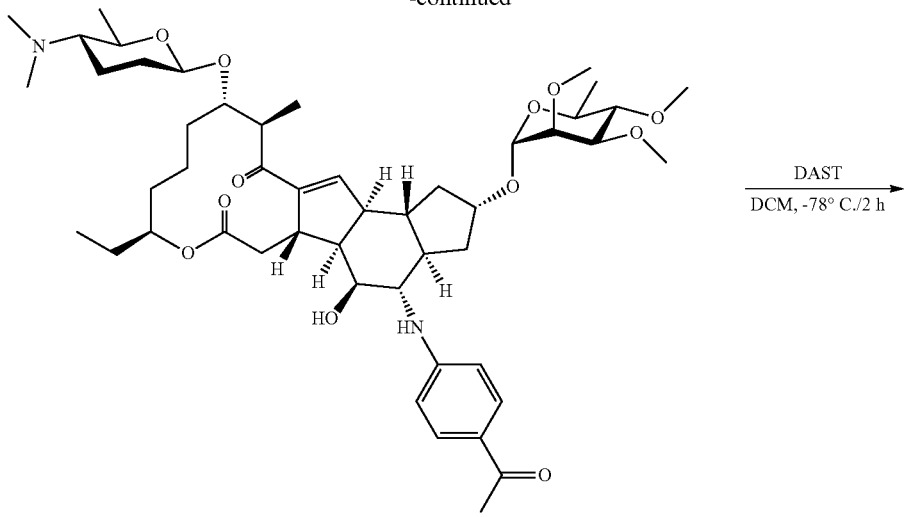

15-2

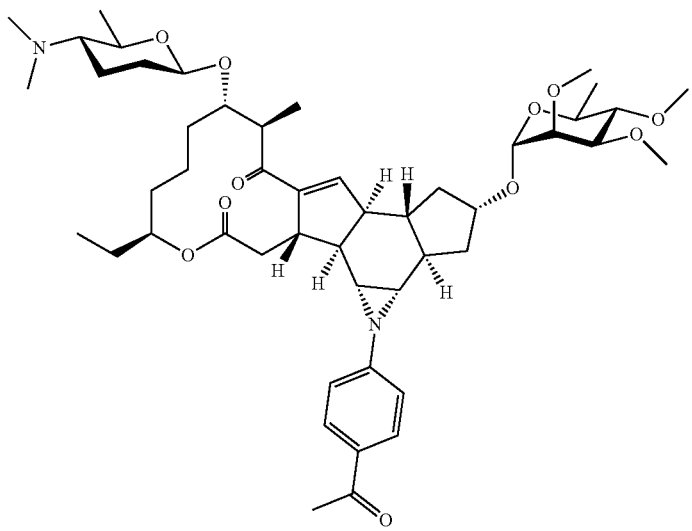

15

To a solution of compound A1 (400 mg, 0.53 mmol) and 1-(4-Amino-phenyl)-ethanone (197.8 mg, 1.07 mmol) in Toluene (20 mL) was added Ti(O-iPr)$_4$ (150.5 mg, 0.53 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 15-1 and 15-2 (250 mg) as yellow solid. LC-MS: m/z 983.5 [M+H]$^+$.

To a solution of the mixture of compounds 15-1 and 15-2 (200 mg, 0.22 mmol) in DCM (10 mL) was added DAST (36.4 mg, 0.22 mmol) at −78° C. under N$_2$. The mixture was stirred at −60° C. under N$_2$. The mixture was stirred at −78° C. for 2 h. The mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 15 (30 mg, yield 15.7%) as white solid. Partial $^1$H NMR (CDCl$_3$, 300 MHz): δ 7.91-7.86 (m, 2H), 7.09-7.05 (m, 2H), 6.76 (s, 1H), 4.89 (s, 1H), 4.75-4.65 (m, 1H), 4.47-4.41 (m, 1H), 4.38-4.32 (m, 1H), 3.69-3.62 (m, 1H), 3.58-3.45 (m, 16H), 3.34-3.27 (m, 2H), 3.18-3.12 (m, 2H), 2.57-2.53 (m, 4H); LC-MS: m/z 865.5 [M+H]+.

16. Synthesis of Compound 16
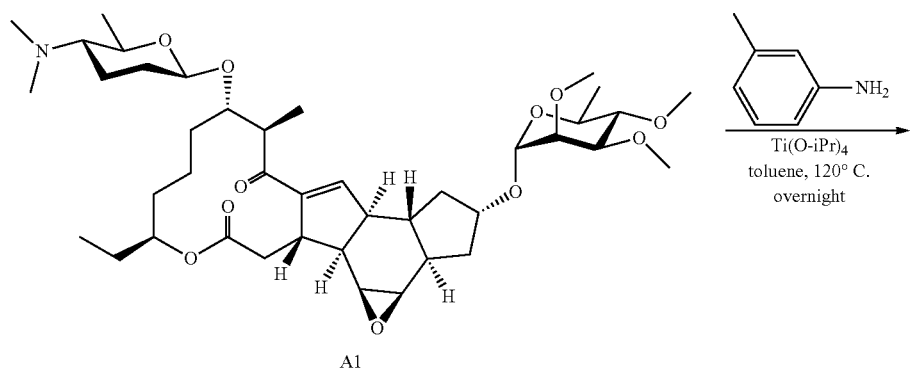
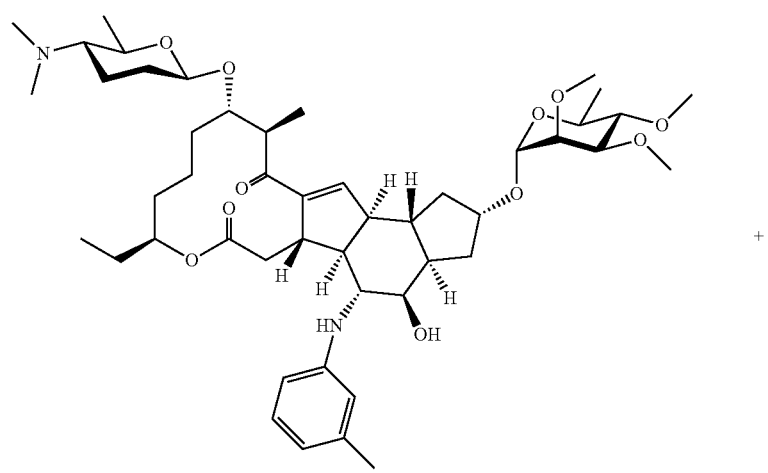
16-1

-continued

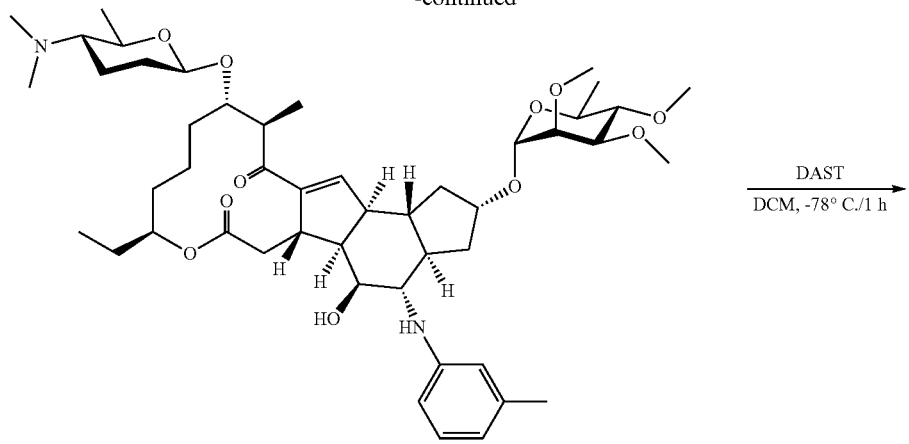

16-2

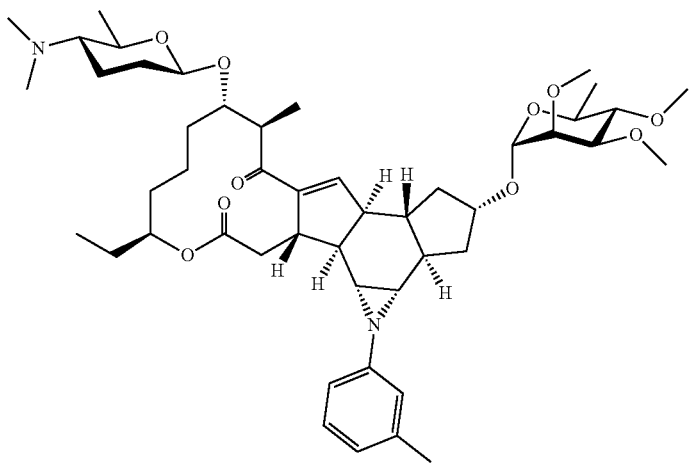

16

To a solution of compound A1 (500 mg, 0.65 mmol) and m-Tolylamine (143 mg, 1.33 mmol) in Toluene (10 mL) was added Ti(O-iPr)$_4$ (190 mg, 0.66 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 16-1 and 16-2 (180 mg) as yellow solid. LC-MS: m/z 855.2 [M+H]$^+$.

To a solution of the mixture of compounds 16-1 and 16-2 (170 mg, 0.19 mmol) in DCM (10 mL) was added DAST (32 mg, 0.20 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 16 (30 mg, yield 18.8%) as yellow solid. Partial $^1$H NMR (CDCl$_3$, 300 MHz): δ 7.17-7.09 (m, 1H), 6.87-6.75 (m, 4H), 4.90 (s, 1H), 4.75-4.67 (m, 1H), 4.74-4.41 (m, 1H), 4.37-4.30 (m, 1H), 3.69-3.62 (m, 1H), 3.59-3.44 (m, 14H), 3.33-3.25 (m, 2H), 2.41-2.15 (m, 14H), 2.03-1.97 (m, 1H), 1.32-1.16 (m, 13H), 0.90-0.79 (m, 4H); LC-MS: m/z 837.2 [M+H]+.

17. Synthesis of Compound 17: (1aS,1bR,3S,4aS, 4bR,7R,8S,12S,15aS,15bR,15cR)-1-(3-chlorophenyl)-8-(((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
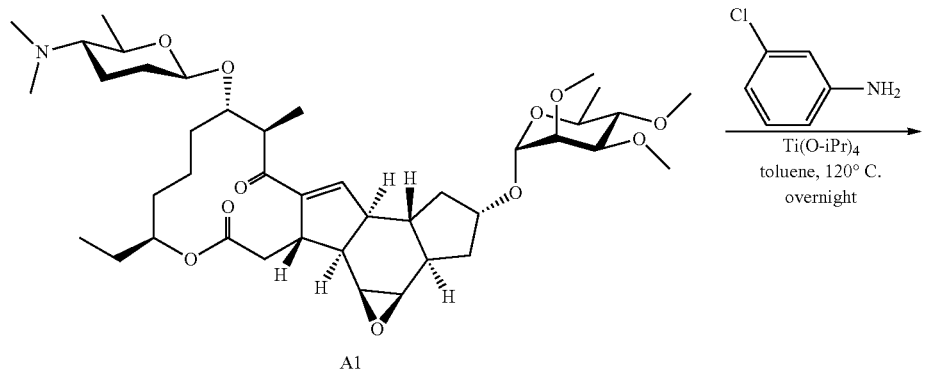
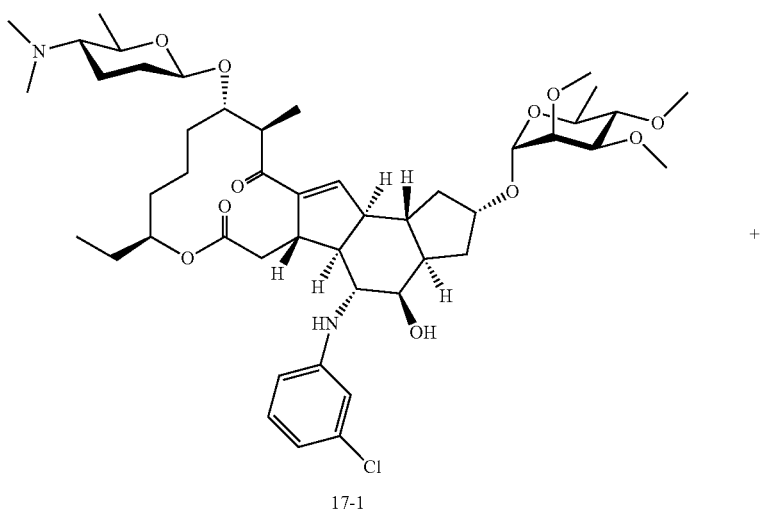
17-1

-continued

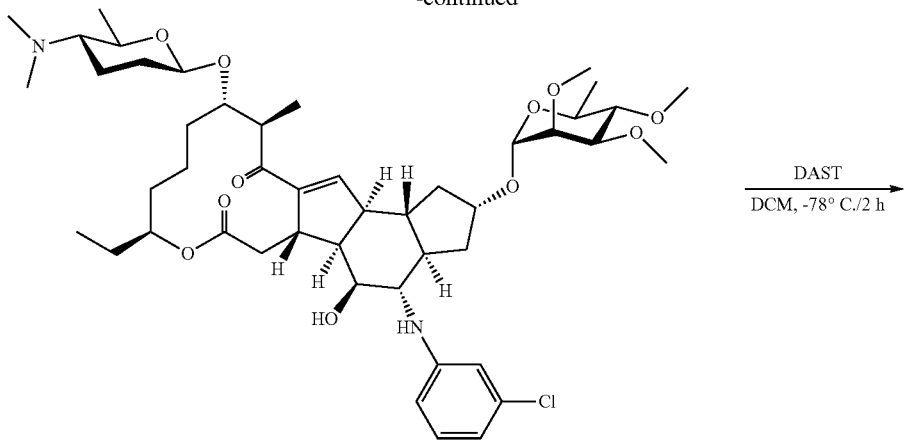

17-2

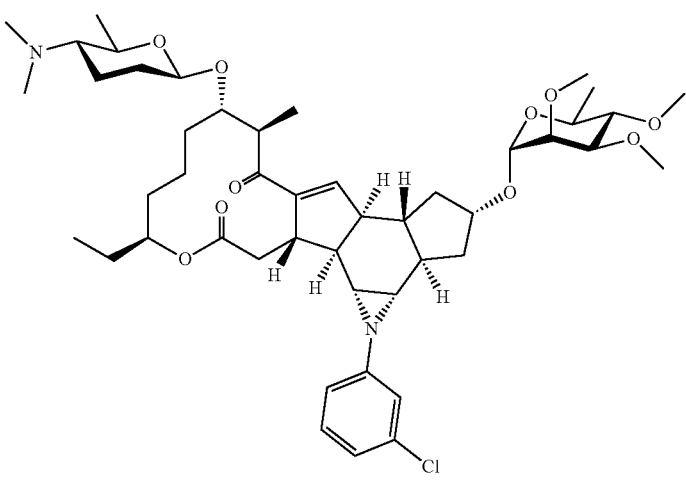

17

To a solution of compound A1 (500 mg, 0.65 mmol) and 3-Chloro-phenylamine (170.5 mg, 1.33 mmol) in toluene (10 mL) was added Ti(O-iPr)$_4$ (190 mg, 0.66 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 17-1 and 17-2 (120 mg) as yellow solid. LC-MS: m/z 875.1 [M+H]$^+$.

To a solution of the mixture of compounds 17-1 and 17-2 (120 mg, 0.14 mmol) in DCM (10 mL) was added DAST (32 mg, 0.20 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 17 (40 mg, yield 34.1%) as white solid. Partial $^1$H NMR (CDCl$_3$, 300 MHz): δ 7.18-7.12 (m, 1H), 6.99-6.92 (m, 3H), 6.75 (s, 1H), 4.89 (s, 1H), 4.73-4.65 (m, 1H), 4.44-4.41 (m, 1H), 4.36-4.29 (m, 1H), 3.68-3.61 (m, 1H), 3.31-3.24 (m, 2H), 2.58-2.47 (m, 2H), 2.41-2.39 (m, 1H), 2.28-2.15 (m, 10H), 2.01-1.96 (m, 1H), 0.89-0.76 (m, 4H); LC-MS: m/z 857.1 [M+H]+.

18. Synthesis of Compound 18
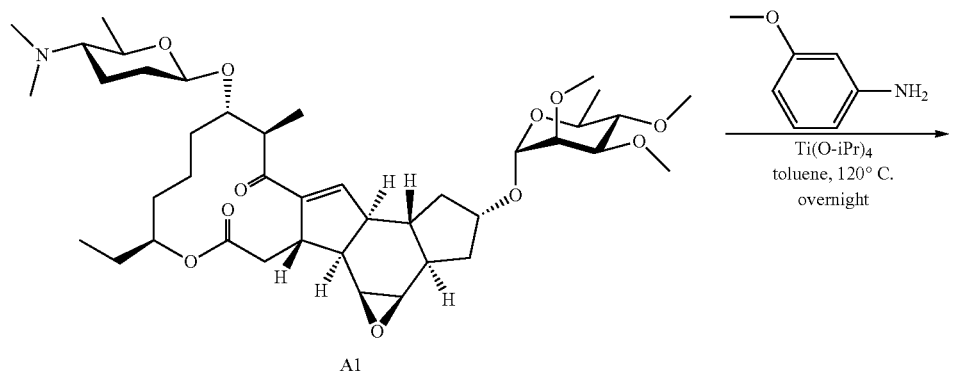
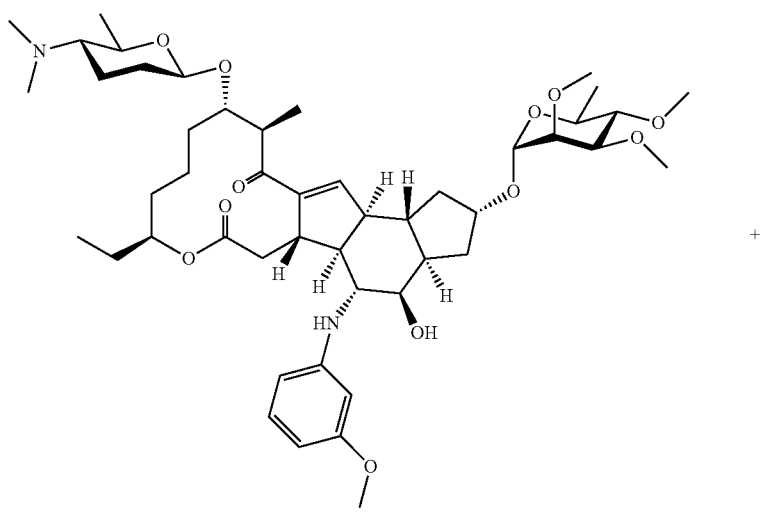
18-1

-continued

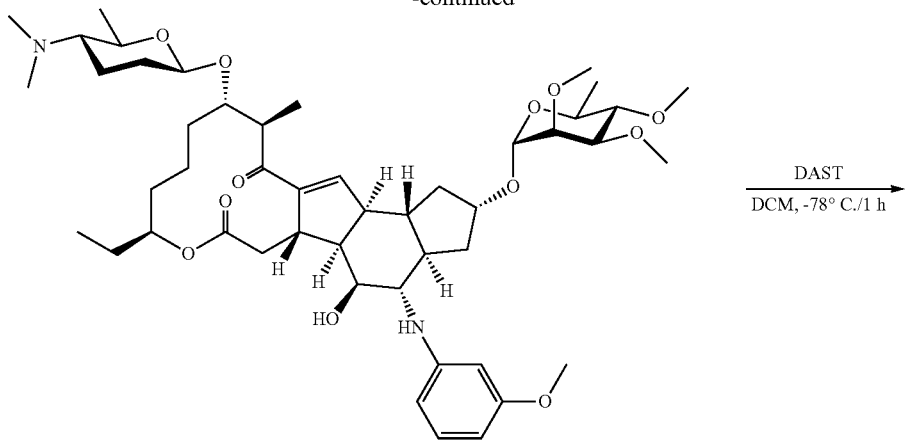

18-2

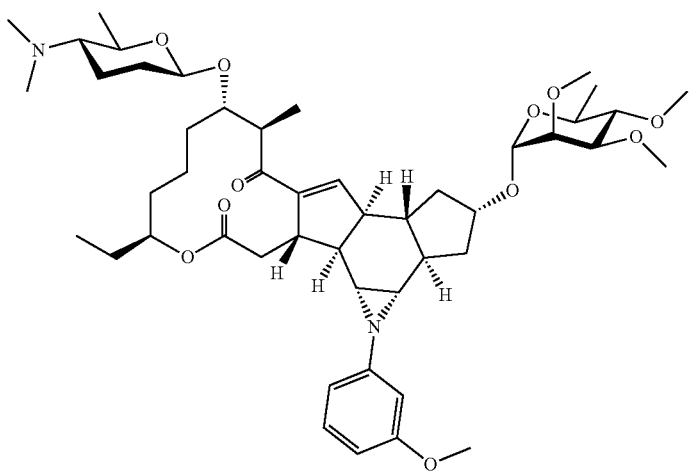

18

To a solution of compound A1 (500 mg, 0.65 mmol) and 3-Methoxy-phenylamine (164 mg, 1.31 mmol) in toluene (10 mL) was added Ti(O-iPr)$_4$ (190 mg, 0.66 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 18-1 and 18-2 (120 mg) as yellow solid. LC-MS: m/z 871.2 [M+H]$^+$.

To a solution of the mixture of compounds 18-1 and 18-2 (120 mg, 0.13 mmol) in DCM (10 mL) was added DAST (32 mg, 0.20 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 18 (30 mg, yield 27%) as yellow solid. Partial $^1$H NMR (CDCl$_3$, 400 MHz): δ 7.15 (d, J=8.0 Hz, 1H), 6.75 (s, 1H), 6.66 (d, J=7.2 Hz, 1H), 6.59 (s, 1H), 6.52 (dd, J=8.0, 1.6 Hz, 1H), 4.89 (s, 1H), 4.73-4.65 (m, 1H), 4.46-4.40 (m, 1H), 4.36-4.28 (m, 1H), 3.78 (s, 3H), 3.67-3.60 (m, 1H), 3.32-3.24 (m, 2H), 3.14-3.08 (m, 2H), 2.59-2.47 (m, 2H), 2.41-2.37 (m, 1H), 2.02-1.96 (m, 1H), 0.89-0.75 (m, 4H); LC-MS: m/z 853.2 [M+H]$^+$.

19. Synthesis of Compound 19
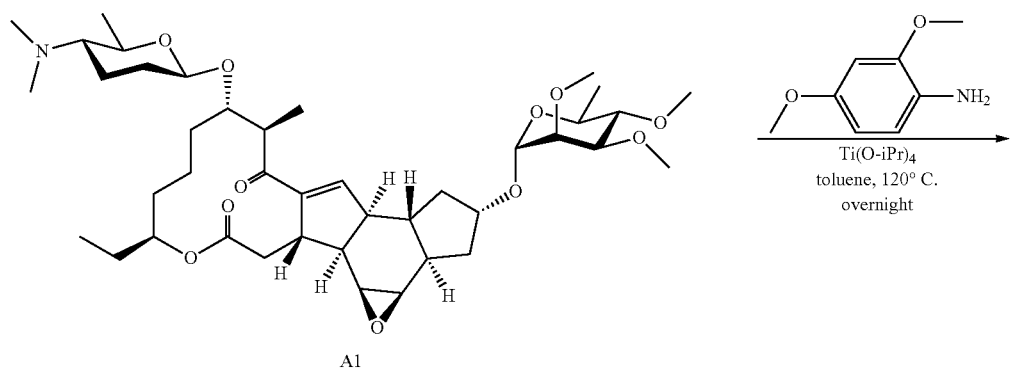
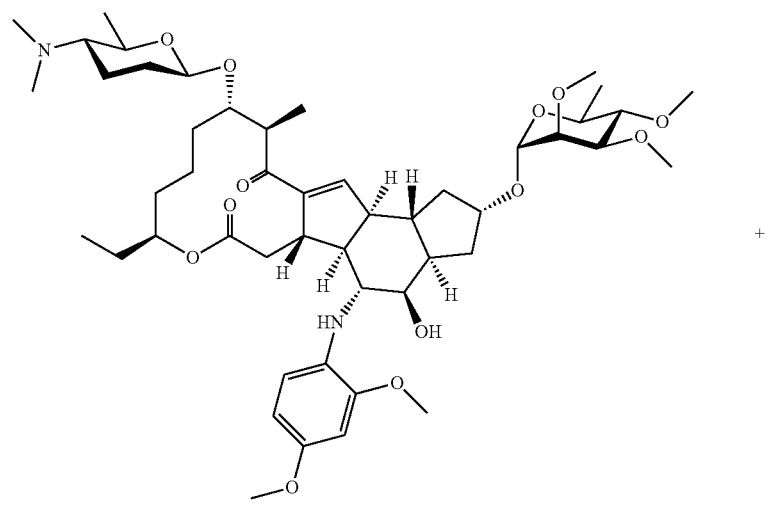

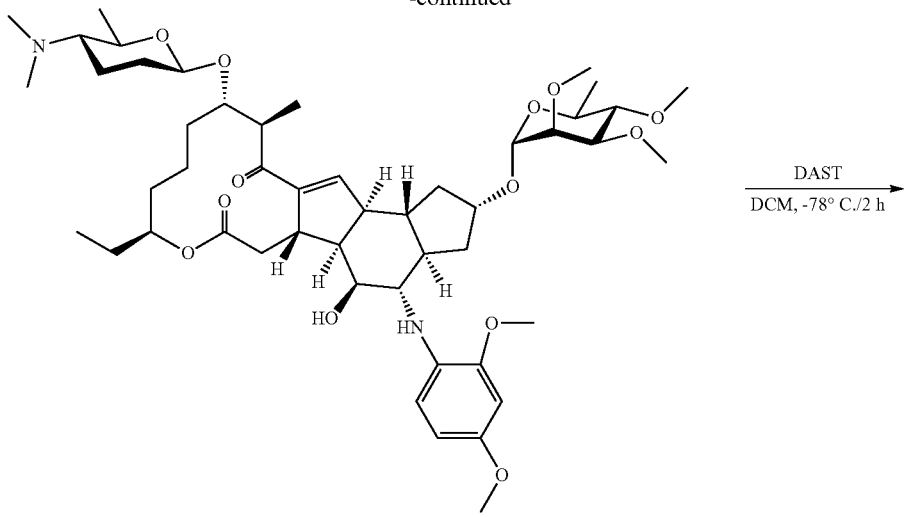

19-2

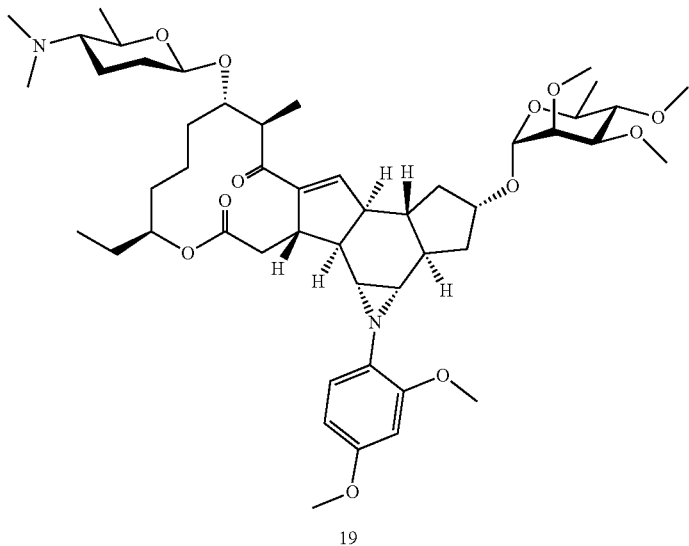

19

To a solution of compound A1 (500 mg, 0.65 mmol) and 2,4-Dimethoxy-phenylamine (203.5 mg, 1.33 mmol) in toluene (10 mL) was added Ti(O-iPr)$_4$ (190 mg, 0.66 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 19-1 and 19-2 (200 mg) as yellow solid. LC-MS: m/z 901.2 [M+H]$^+$.

To a solution of the mixture of compounds 19-1 and 19-2 (200 mg, 0.22 mmol) in DCM (10 mL) was added DAST (53.6 mg, 0.33 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 19 (15 mg, yield 7.7%) as yellow solid. Partial $^1$H NMR (CDCl$_3$, 300 MHz): δ 6.85-6.72 (m, 1H), 6.45 (s, 1H), 6.39-6.32 (m, 2H), 4.89 (s, 1H), 4.78-4.68 (m, 1H), 4.47-4.39 (m, 1H), 4.36-4.26 (m, 1H), 3.88 (s, 3H), 3.77 (s, 3H), 3.56-3.43 (m, 15H), 3.35-3.04 (m, 4H), 2.64-2.46 (m, 3H), 2.36-2.13 (m, 10H), 2.05-1.93 (m, 2H), 0.91-0.73 (m, 4H); LC-MS: m/z 883.2 [M+H]$^+$.

20. Synthesis of Compound 20
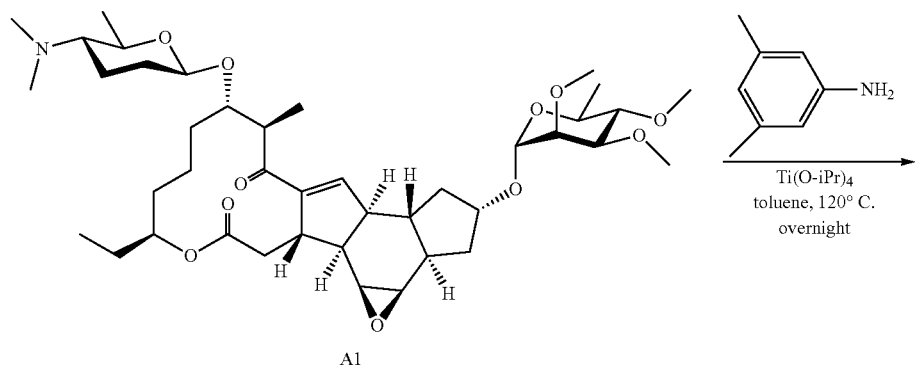
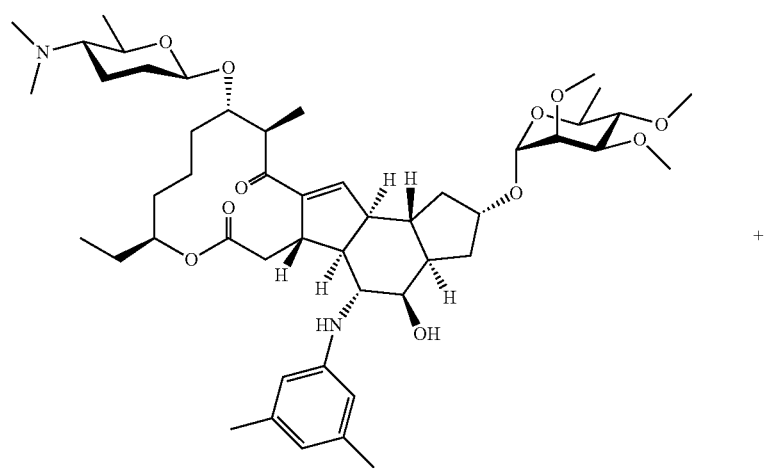
20-1

-continued

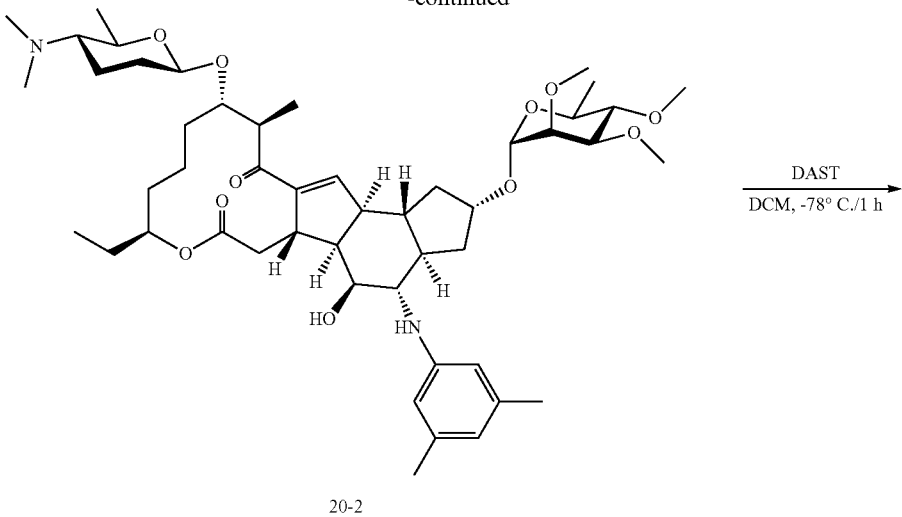

20-2

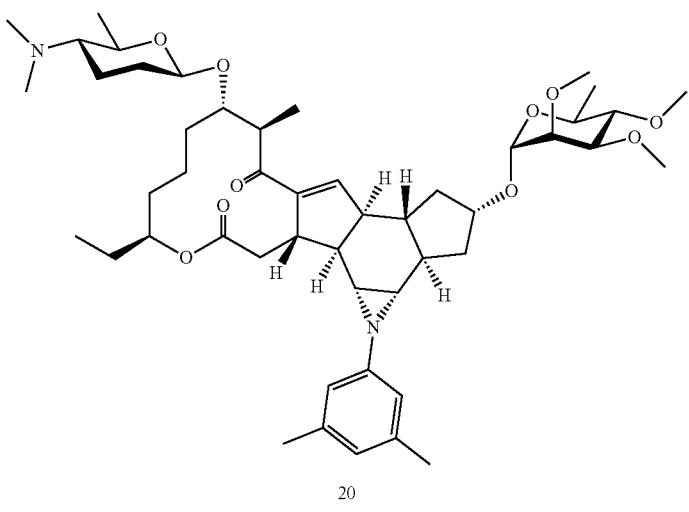

20

To a solution of compound A1 (500 mg, 0.65 mmol) and 2,4-Dimethoxy-phenylamine (203.5 mg, 1.33 mmol) in Toluene (10 mL) was added Ti(O-iPr)$_4$ (190 mg, 0.66 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 20-1 and 20-2 (200 mg) as yellow solid. LC-MS: m/z 869.2 [M+H]$^+$.

To a solution of the mixture of compounds 20-1 and 20-2 (200 mg, 0.23 mmol) in DCM (10 mL) was added DAST (53.6 mg, 0.33 mmol) at −78° C. under N$_2$. After stirred at −78° C. for 2 h, the mixture was quenched with aqueous NaHCO$_3$ and H$_2$O and then extracted with DCM. The organic layer was dried over K$_2$CO$_3$, filtered and concentrated. The residue was purified by Prep-HPLC to afford compound 20 (16 mg, yield 8.2%) as yellow solid. Partial $^1$H NMR (CDCl$_3$, 300 MHz): δ 6.76 (s, 1H), 6.63 (s, 2H), 6.61 (s, 1H), 4.89 (s, 1H), 4.74-4.66 (m, 1H), 4.46-4.38 (m, 1H), 4.36-4.29 (m, 1H), 3.69-3.63 (m, 1H), 3.32-3.24 (m, 2H), 2.29-2.13 (m, 18H), 2.01-1.96 (m, 1H), 0.89-0.75 (m, 4H); LC-MS: m/z 851.2 [M+H]$^+$.

21. Synthesis of Compound 21
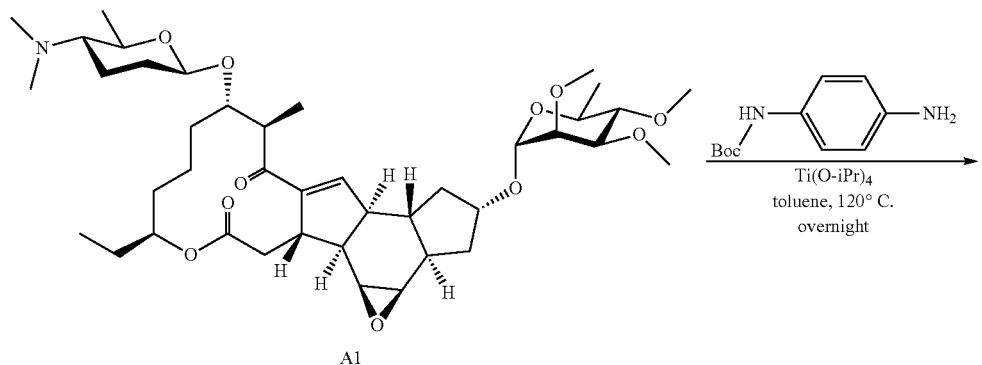
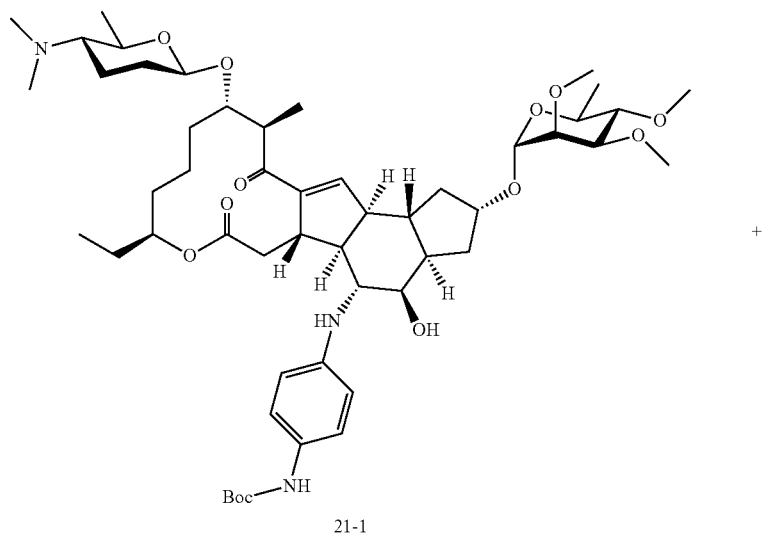
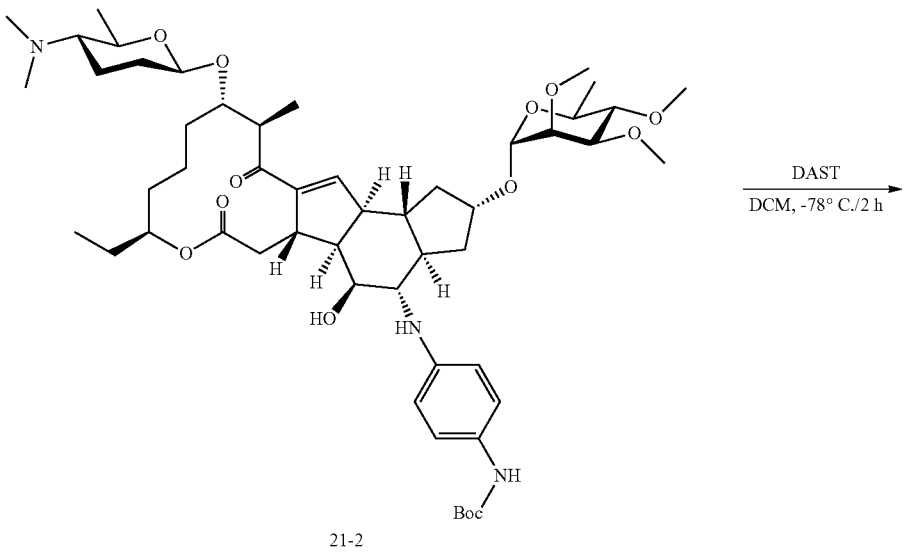

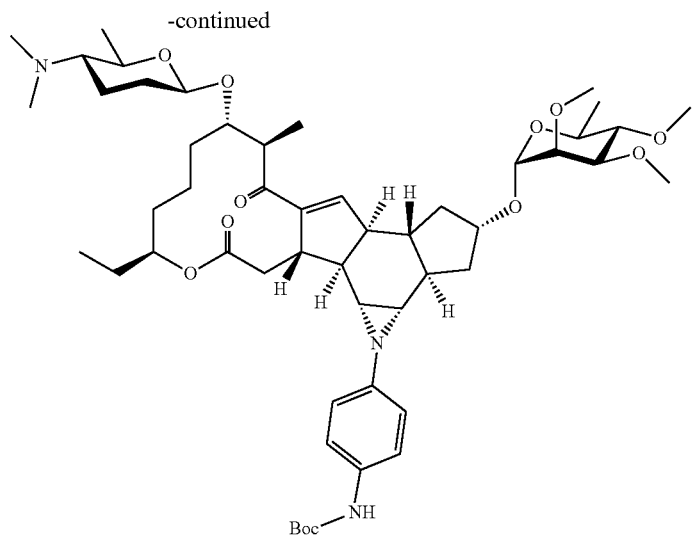

To a solution of compound A1 (0.5 g, 0.65 mmol) and (4-Amino-phenyl)-carbamic acid tert-butyl ester (278 mg, 1.33 mmol) in toluene (10 mL) was added Ti(O-iPr)$_4$ (190 mg, 0.66 mmol). The mixture was stirred at 120° C. overnight under N$_2$. The mixture was quenched with H$_2$O (100 mL) and extracted with DCM (30 mL×3). The combined organic layer was dried over potassium carbonate, filtered and concentrated. The residue was purified by prep-HPLC to give the crude products 21-1 and 21-2 (300 mg) as yellow solid. LC-MS: m/z 956.6 [M+H]$^+$.

To a solution of the mixture of compounds 21-1 and 21-2 (220 mg, 0.22 mmol) in DCM (10 mL) was added DAST (52 mg, 0.32 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 21 (12 mg, yield 5.9%) as white solid. Partial $^1$H NMR (CDCl$_3$, 400 MHz): δ 7.23-7.19 (m, 2H), 6.94 (d, J=8.4 Hz, 2H), 6.75 (s, 1H), 6.34 (s, 1H), 4.88 (s, 1H), 4.72-4.66 (m, 1H), 4.48-4.43 (m, 1H), 4.34-4.29 (m, 1H), 3.68-3.62 (m, 1H), 3.56-3.42 (m, 17H), 3.30-3.24 (m, 2H), 3.14-3.07 (m, 1H), 0.85 (t, J=7.6 Hz, 3H); LC-MS: m/z 938.6 [M+H]$^+$.

22. Synthesis of Compound 22: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl)oxy)-12-ethyl-1-(3-fluoro-2-methylphenyl)-7-methyl-3-(((2R,3R,4R,5S,6S)-3,4,5-trimethoxy-6-methyltetrahydro-2H-pyran-2-yl)oxy)-1,1a,1b,2,3,4, 4a,4b,7,8,9,10,11,12,15,15a,15b,15c-octadecahydro-[1]oxacyclododecino[5',4':2,3]-as-indaceno[4,5-b]azirine-6,14-dione

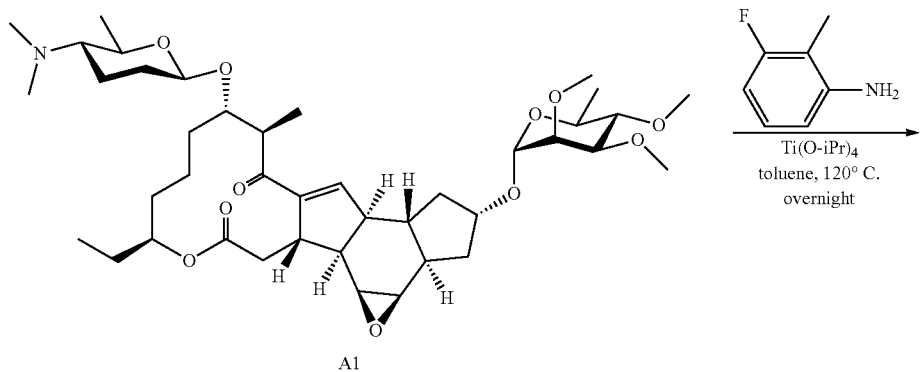

-continued
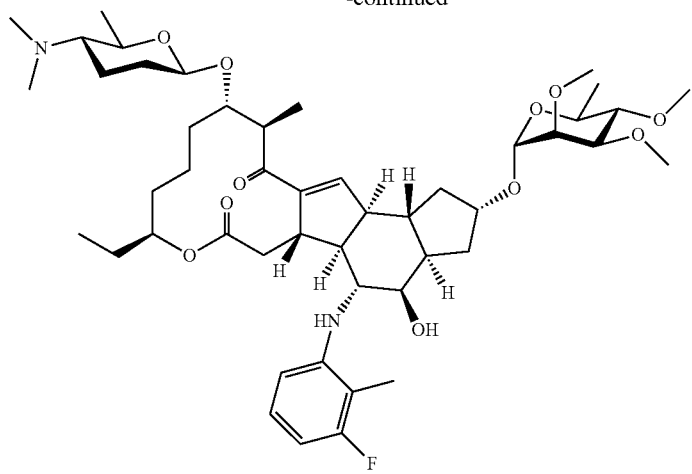
22-1
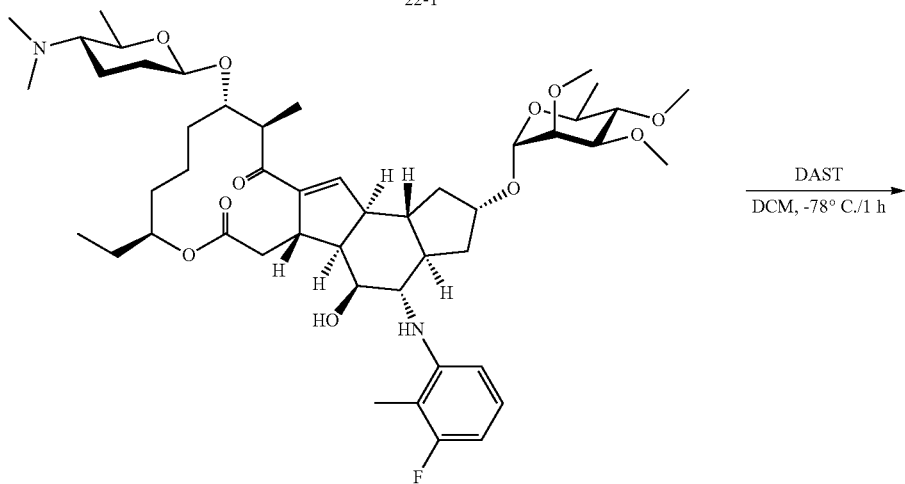
22-2
DAST
―――――――→
DCM, -78° C./1 h
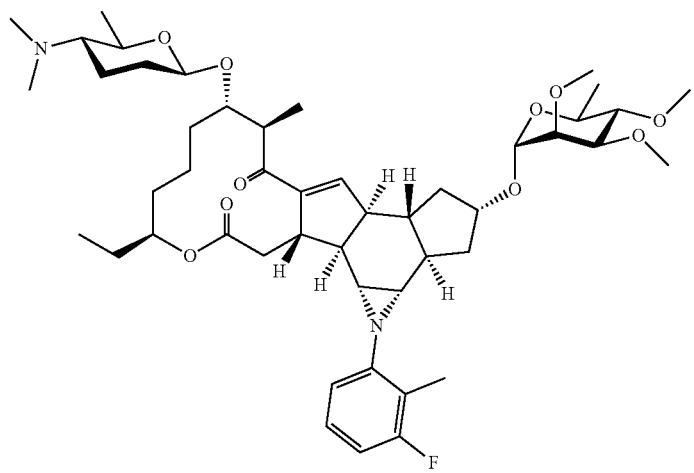
22

To a solution of compound A1 (500 mg, 0.65 mmol) and 3-Fluoro-2-methyl-phenylamine (166 mg, 1.33 mmol) in toluene (10 mL) was added Ti(O-iPr)$_4$ (190 mg, 0.66 mmol). The mixture was stirred at 120° C. over night under N$_2$. The mixture was quenched with H$_2$O and extracted with DCM (30 mL×3). The combined organic layer was dried over potassium carbonate, filtered and concentrated. The residue was purified by column chromatography on silica gel (DCM/MeOH=20/1) to give the crude products 22-1 and 22-2 (350 mg) as yellow solid which was used in next step without further purification. LC-MS: m/z 873.5 [M+H]$^+$.

To a solution of the mixture of compounds 22-1 and 22-2 (350 mg, 0.4 mmol) in DCM (10 mL) was added DAST (64.5 mg, 0.4 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 22 (100 mg, yield 29.2%) as yellow solid. Partial $^1$H NMR (CDCl$_3$, 400 MHz): δ 7.05-6.99 (m, 1H), 6.76 (s, 1H), 6.71-6.64 (m, 2H), 4.88 (s, 1H), 4.73-4.67 (m, 1H), 4.45-4.41 (m, 1H), 4.35-4.31 (m, 1H), 3.67-3.62 (m, 1H), 3.30-3.25 (m, 2H), 3.18-3.09 (m, 2H), 2.62-2.55 (m, 1H), 2.51-2.47 (m, 1H), 2.39-2.35 (m, 1H), 2.29 (s, 3H), 0.88-0.80 (m, 4H); LC-MS: m/z 855.2 [M+H]+.

23. Synthesis of Compound 23

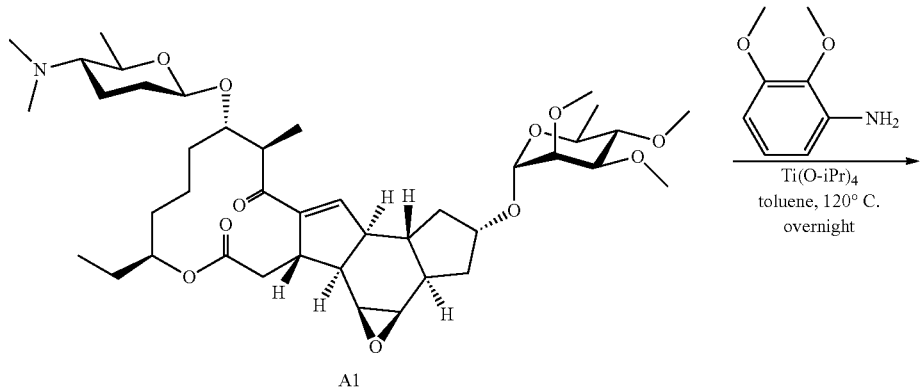

A1

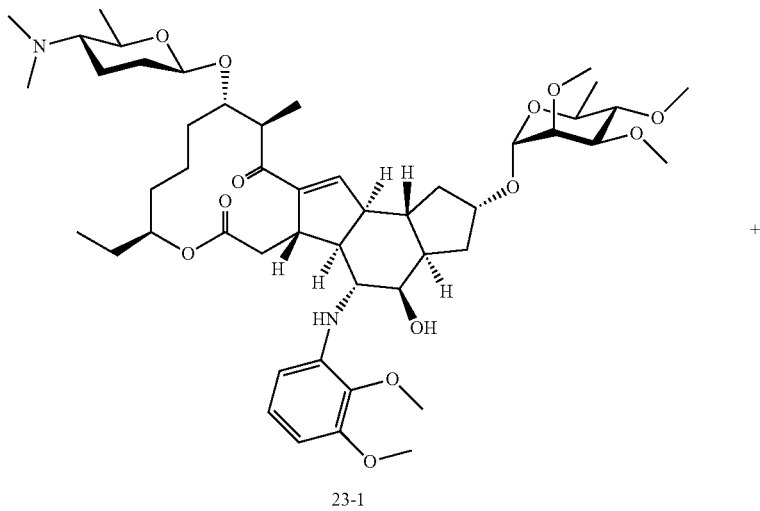

23-1

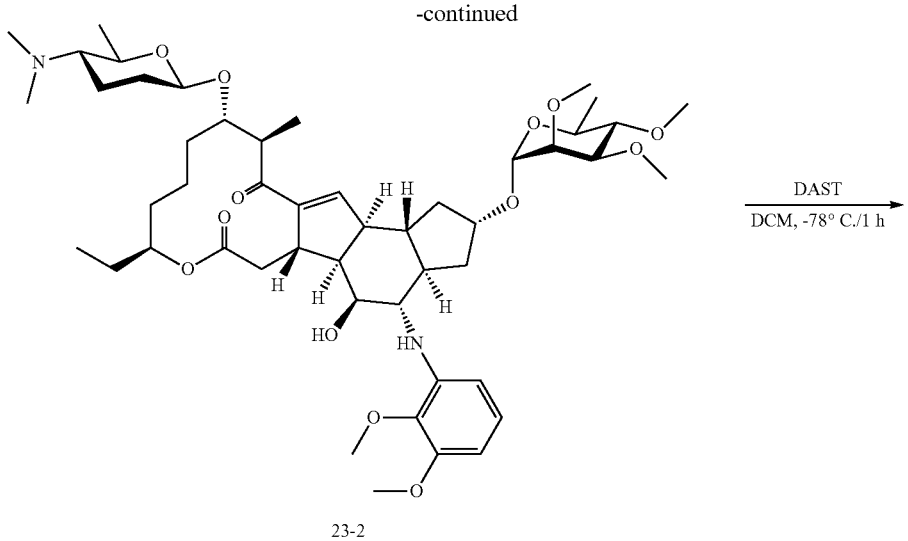

23-2

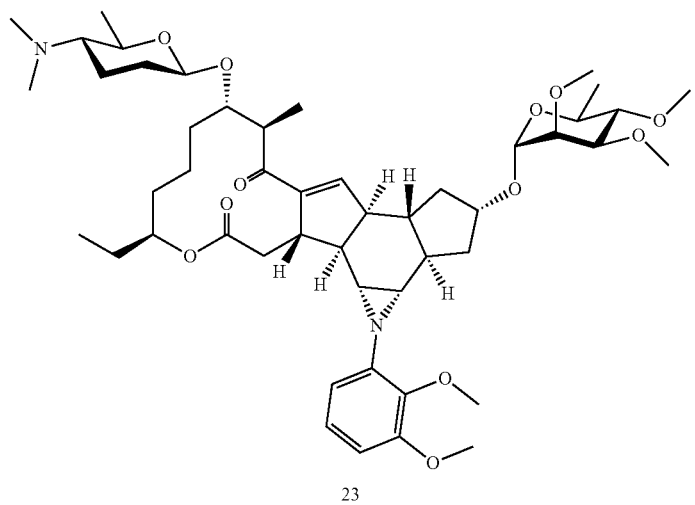

23

To a solution of compound A1 (500 mg, 0.65 mmol) and 2,3-Dimethoxy-phenylamine (203.5 mg, 1.33 mmol) in toluene (10 mL) was added Ti(O-iPr)$_4$ (190 mg, 0.66 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by column chromatography on silica gel (DCM/MeOH=20/1) to give the crude products 23-1 and 23-2 (300 mg) as yellow solid which was used in next step without further purification. LC-MS: m/z 901.2 [M+H]$^+$.

To a solution of the mixture of compounds 23-1 and 23-2 (300 mg, 0.33 mmol) in DCM (10 mL) was added DAST (107.2 mg, 0.66 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 23 (40 mg, yield 13.7%) as white solid. Partial $^1$H NMR (CDCl$_3$, 400 MHz): δ 6.92 (d, J=8.0 Hz, 1H), 6.75 (s, 1H), 6.59-6.54 (m, 2H), 4.89 (s, 1H), 4.77-4.68 (m, 1H), 4.45-4.39 (m, 1H), 4.36-4.28 (m, 1H), 3.93 (s, 3H), 3.85 (s, 3H), 3.71-3.59 (m, 1H), 3.31-3.08 (m, 4H), 2.74-2.68 (m, 1H), 2.64-2.56 (m, 1H), 2.39-2.34 (m, 1H), 2.01-1.94 (m, 1H); LC-MS: m/z 883.2 [M+H]+.

24. Synthesis of Compound 24: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl)oxy)-12-ethyl-7-methyl-1-(3,4,5-trifluorophenyl)-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
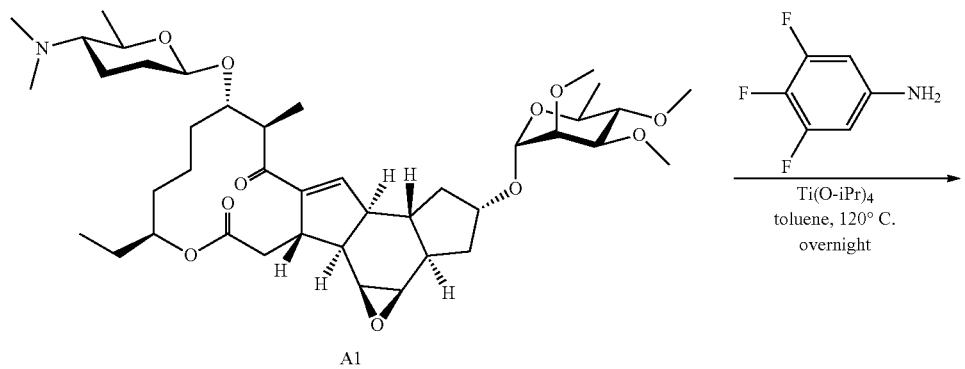
A1
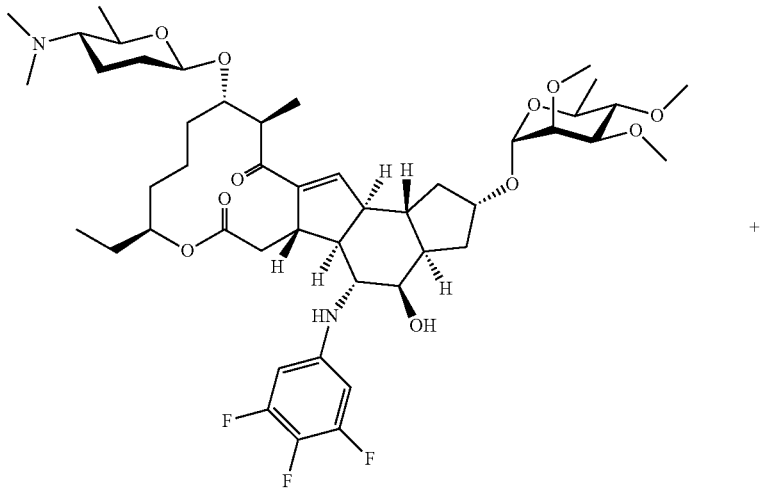
24-1
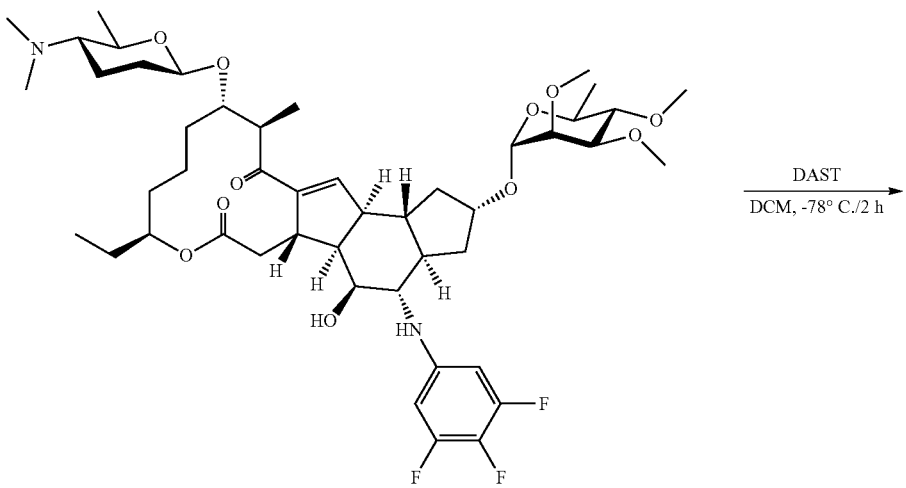
24-2

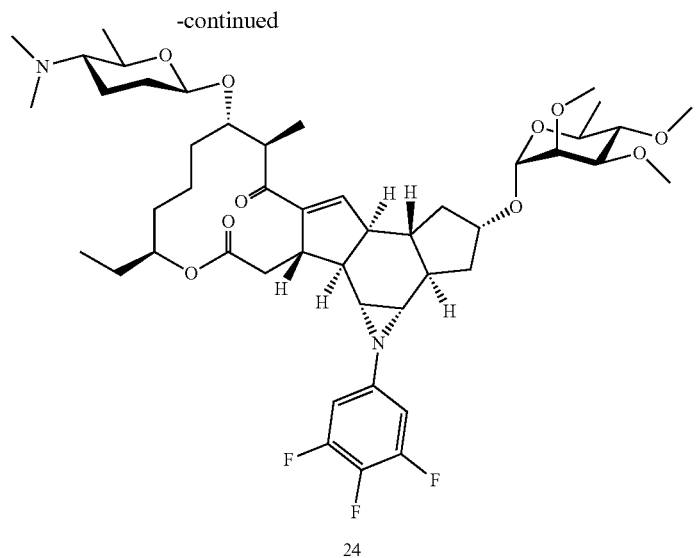

24

To a solution of compound A1 (500 mg, 0.65 mmol) and 3,4,5-Trifluoro-phenylamine (196.5 mg, 1.33 mmol) in Toluene (10 mL) was added Ti(O-iPr)$_4$ (190 mg, 0.66 mmol). The mixture was stirred at 120° C. over night under N$_2$. The mixture was quenched with H$_2$O (100 mL) and extracted with DCM (30 mL×3). The combined organic layer was dried over potassium carbonate, filtered and concentrated. The residue was purified by column chromatography on silica gel (DCM/MeOH=20/1) to afford the crude products 24-1 and 24-2 (300 mg) as yellow solid which was used in next step without further purification. LC-MS: m/z 895.5 [M+H]+.

To a solution of compounds 24-1 and 24-2 (300 mg, 0.33 mmol) in DCM (10 mL) was added DAST (54 mg, 0.33 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by Prep-HPLC to afford compound 24 (30 mg, yield 10.3%) as white solid. Partial $^1$H NMR (CDCl$_3$, 400 MHz): δ 6.73 (s, 1H), 6.63-6.59 (m, 2H), 4.88 (s, 1H), 4.71-4.64 (m, 1H), 4.47-4.41 (m, 1H), 4.35-4.29 (m, 1H), 3.67-3.61 (m, 1H), 3.57-3.40 (m, 1H), 3.67-3.61 (m, 1H), 3.57-3.40 (m, 14H), 3.33-3.23 (m, 2H), 3.15-3.08 (m, 2H), 0.90-0.75 (m, 4H); LC-MS: m/z 877.5 [M+H]$^+$.

25. Synthesis of Compound 25: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl)oxy)-12-ethyl-1-(3-fluoro-2-methoxyphenyl)-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4l:2,3]-as-indaceno[4,5-b]azirine-6,14-dione

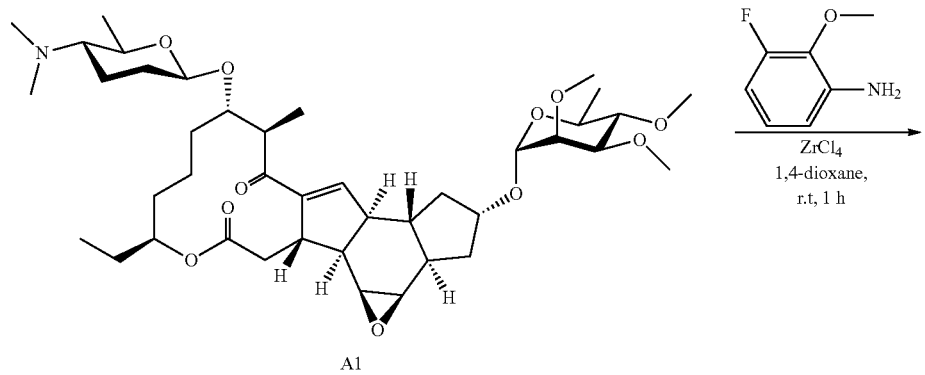

A1

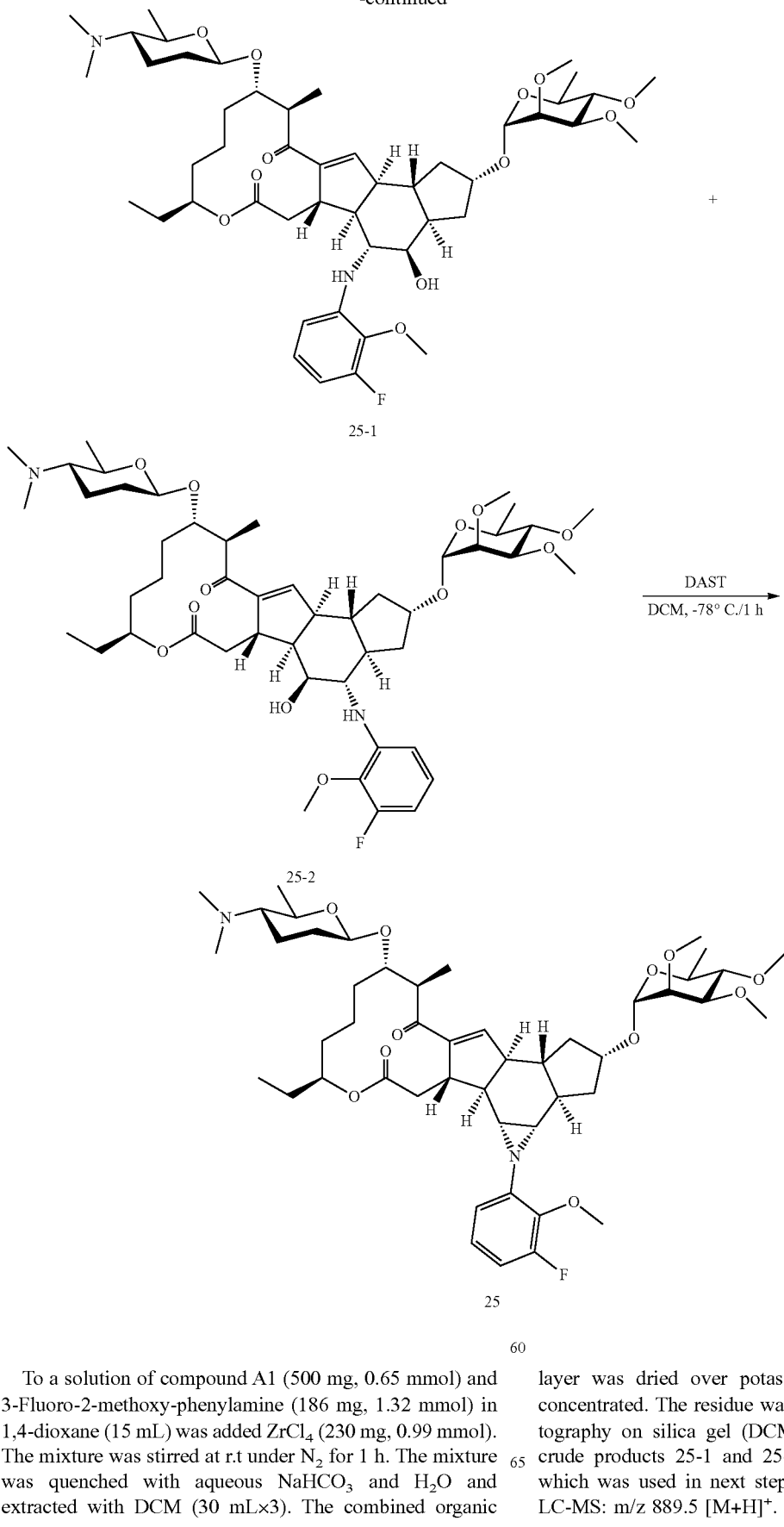

To a solution of compound A1 (500 mg, 0.65 mmol) and 3-Fluoro-2-methoxy-phenylamine (186 mg, 1.32 mmol) in 1,4-dioxane (15 mL) was added ZrCl$_4$ (230 mg, 0.99 mmol). The mixture was stirred at r.t under N$_2$ for 1 h. The mixture was quenched with aqueous NaHCO$_3$ and H$_2$O and extracted with DCM (30 mL×3). The combined organic layer was dried over potassium carbonate, filtered and concentrated. The residue was purified by column chromatography on silica gel (DCM/MeOH=20/1) to afford the crude products 25-1 and 25-2 (350 mg) as yellow solid which was used in next step without further purification. LC-MS: m/z 889.5 [M+H]$^+$.

To a solution of compounds 25-1 and 25-2 (350 mg, 0.39 mmol) in DCM (10 mL) was added DAST (95 mg, 0.59 mmol) at −78° C. under N₂. After stirred at −78° C. for 2 h, the mixture was quenched with aqueous NaHCO₃ and H₂O and then extracted with DCM (30 mL×3). The combined organic layer was dried over potassium carbonate, filtered and concentrated. The residue was purified by Prep-HPLC to afford compound 25 (40 mg, yield 11.7%) as white solid. Partial ¹H NMR (CDCl₃, 400 MHz): δ 6.92-6.83 (m, 1H), 6.77-6.67 (m, 3H), 4.89 (s, 1H), 4.76-4.70 (m, 1H), 4.49-4.44 (m, 1H), 4.36-4.29 (m, 1H), 3.99 (s, 3H), 3.67-3.61 (m, 1H), 3.59-3.44 (m, 18H), 3.30-3.09 (m, 4H), 0.89-0.78 (m, 4H); LC-MS: m/z 871.5 [M+H]⁺.

26. Synthesis of Compound 26: (1aS,1bR,3S,4aS, 4bR,7R,8S,12S,15aS,15bR,15cR)-1-(3,5-difluorophenyl)-8-(((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione

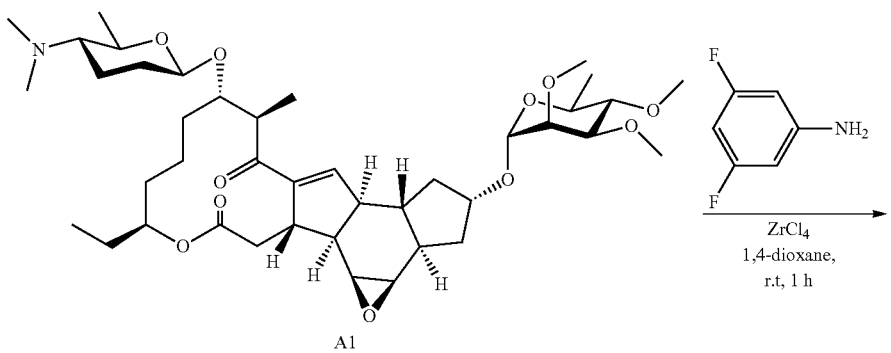

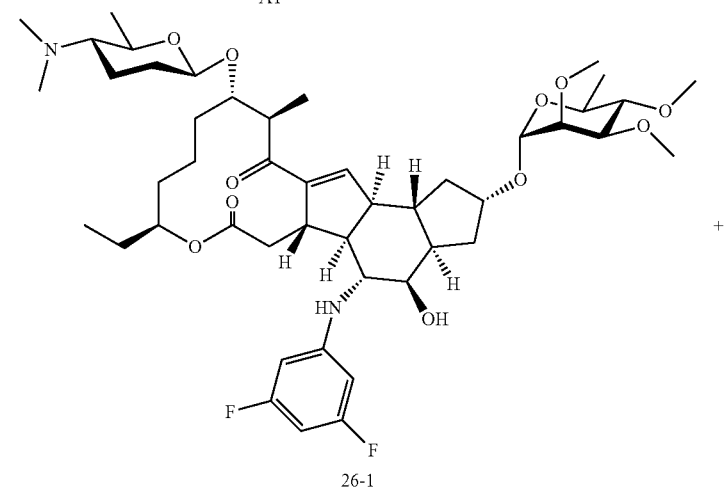

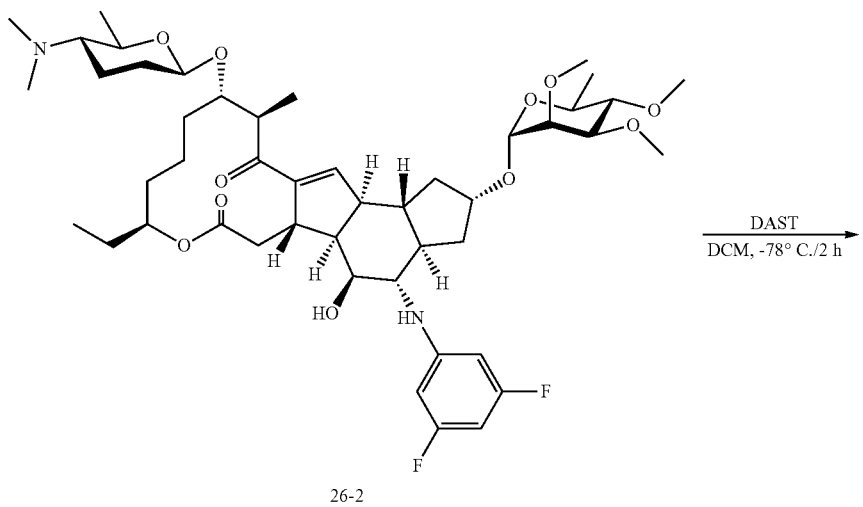

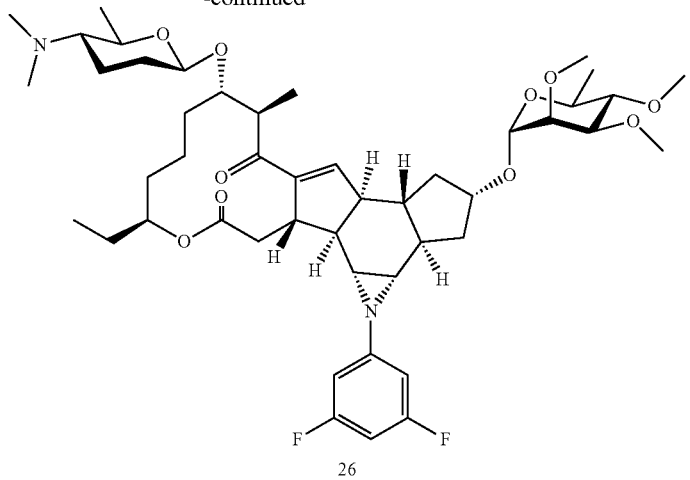

To a solution of compound A1 (500 mg, 0.65 mmol) and 3,5-Difluoro-phenylamine (172 mg, 1.33 mmol) in 1,4-dioxane (15 mL) was added $ZrCl_4$ (230 mg, 0.99 mmol). The mixture was stirred at r.t under $N_2$ for 1 h. The mixture was quenched with aqueous $NaHCO_3$ and $H_2O$ and extracted with DCM (30 mL×3). The combined organic layer was dried over $K_2CO_3$, filtered and concentrated. The residue was purified by column chromatography on silica gel (DCM/MeOH=20/1), give the crude products 26-1 and 26-2 (300 mg) as yellow solid which was used in next step without further purification. LC-MS: m/z 889.5 [M+H]$^+$.

To a solution of compounds 26-1 and 26-2 (300 mg, 0.34 mmol) in DCM (10 mL) was added DAST (82.6 mg, 0.5 mmol) at −78° C. under $N_2$. After stirred at −78° C. for 2 h, the mixture was quenched with aqueous $NaHCO_3$ and $H_2O$ and then extracted with DCM (30 mL×3). The combined organic layer was dried over potassium carbonate, filtered and concentrated. The residue was purified by Prep-HPLC to afford compound 26 (15 mg, yield 5.1%) as white solid. Partial $^1H$ NMR (CDCl$_3$, 400 MHz): δ 6.74 (s, 1H), 6.54-6.51 (m, 2H), 6.44-6.37 (m, 1H), 4.88 (s, 1H), 4.73-4.65 (m, 1H), 4.48-4.34 (m, 1H), 4.35-4.28 (m, 1H), 3.67-3.612 (m, 1H), 3.56-3.41 (m, 19H), 3.32-3.23 (m, 2H), 3.14-3.09 (m, 2H), 0.91-0.77 (m, 4H); LC-MS: m/z 860.1 [M+H]$^+$.

27. Synthesis of Compound 27: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl) oxy)-12-ethyl-1-(5-fluoro-2-methylphenyl)-7-methyl-3-(((2R,3R,4R,5S,6S)-3,4,5-trimethoxy-6-methyltetrahydro-2H-pyran-2-yl)oxy)-1,1a, 1b,2,3,4, 4a,4b,7,8,9,10,11,12,15,15a,15b,15c-octadecahydro-[1]oxacyclododecino[5',4':2,3]-as-indaceno[4,5-b] azirine-6,14-dione

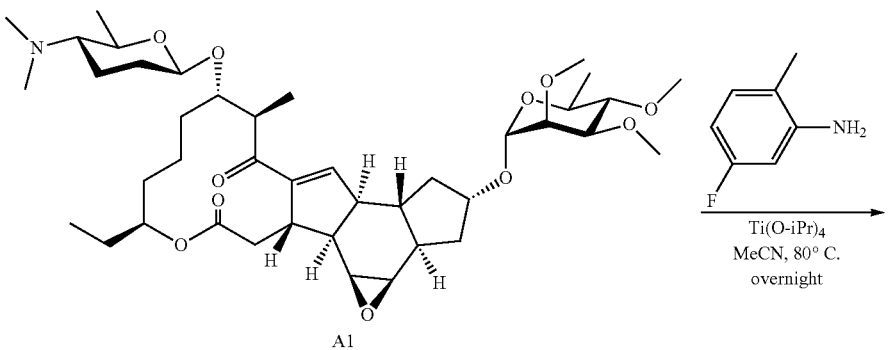

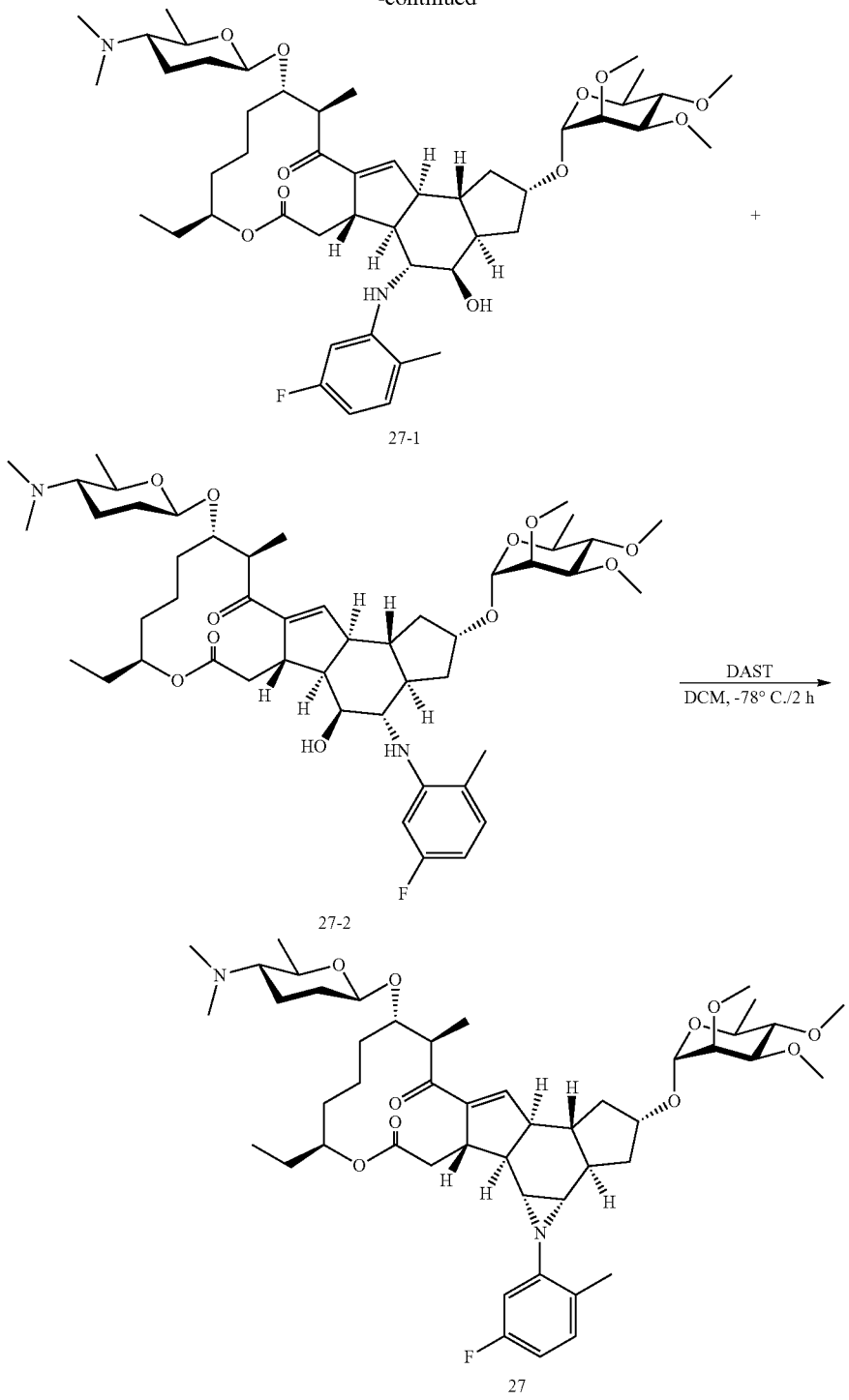

To a solution of compound A1 (500 mg, 0.65 mmol) and 5-fluoro-2-methylaniline (167 mg, 1.32 mmol) in MeCN (10 mL) was added Ti(O-iPr)$_4$ (190 mg, 0.66 mmol). The mixture was stirred at 80° C. over night under N$_2$. The mixture was quenched with H$_2$O (50 mL) and extracted with DCM (20 mL×3). The combined organic layer was dried over potassium carbonate, filtered and concentrated. The residue was purified by silica gel column chromatography (DCM/MeOH=20/1) to afford the crude products 27-1 and 27-2 (300 mg) as a yellow solid.

LC-MS: m/z 873.2 [M+H]$^+$.

To a solution of compounds 27-1 and 27-2 (250 mg, 0.29 mmol) in DCM (10 mL) was added DAST (82.6 mg, 0.5 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 27 (79 mg, yield 32.4%) as white solid.

Partial $^1$H NMR (CDCl$_3$, 400 MHz): δ7.04 (t, J=8 Hz, 1H), 6.76 (s, 1H), 6.63-6.55 (m, 2H), 4.88 (s, 1H), 4.70 (d, J=4 Hz, 1H), 4.43 (d, J=8 Hz, 1H), 4.36-4.31 (m, 1H), 3.67-3.62 (m, 1H), 3.30-3.24 (m, 2H), 3.16-3.09 (m, 2H), 2.59 (m, 1H), 2.50 (m, 1H), 2.34 (s, 3H), 2.24-2.12 (m, 12H), 1.99 (d, J=9.6 Hz, 1H), 1.87-1.43 (m, 18H), 1.31-1.18 (m, 17H), 0.89-0.79 (m, 3H).
LC-MS: m/z 855.2 [M+H]$^+$.
28. Synthesis of Compound 28
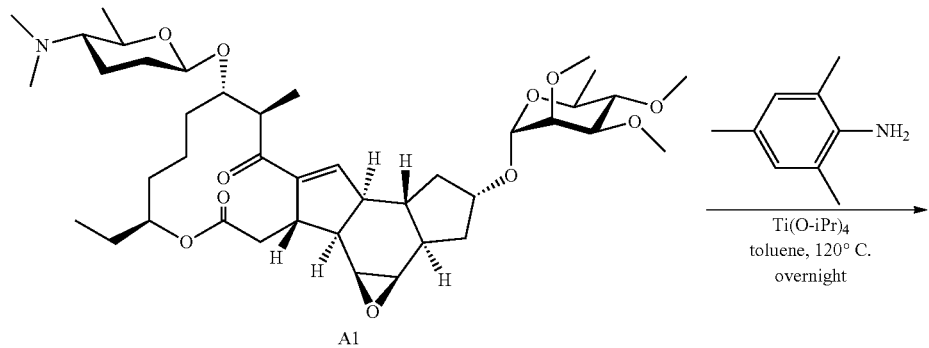
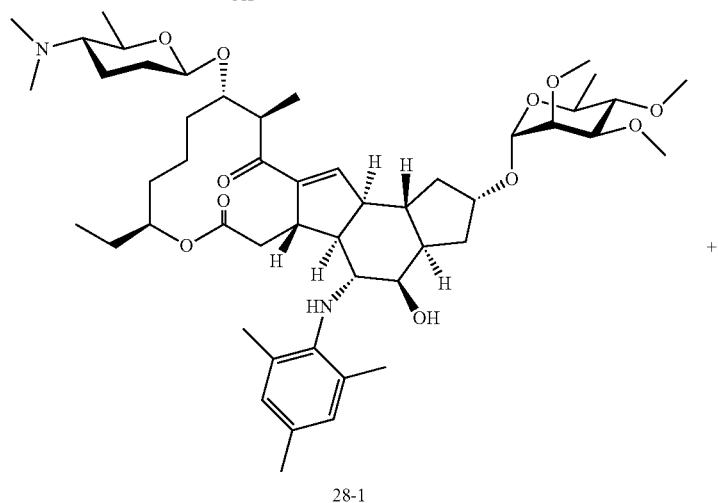
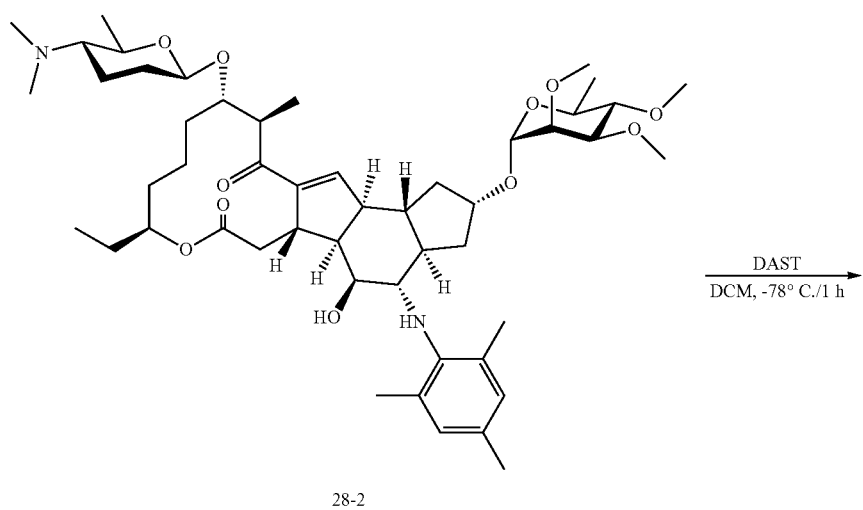

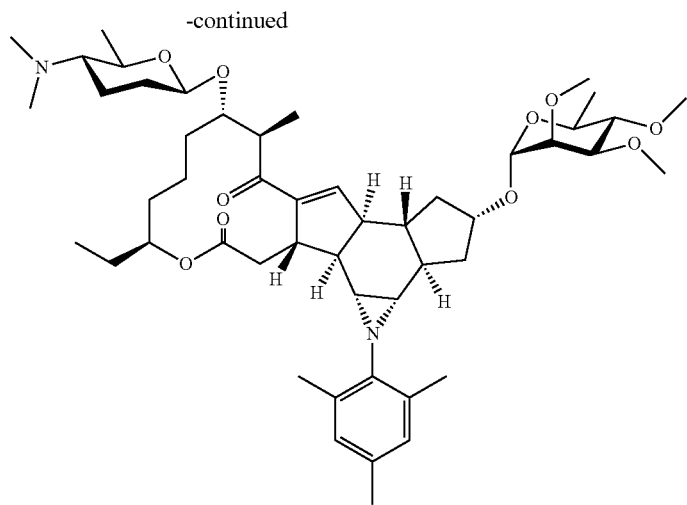

28

To a solution of compound A1 (400 mg, 0.53 mmol) and 2,4,6-trimethylaniline (144 mg, 1.07 mmol) in toluene (10 mL) was added Ti(O-iPr)$_4$ (151.6 mg, 0.53 mmol). The mixture was stirred at 120° C. over night under N$_2$. The mixture was quenched with H$_2$O (50 mL) and extracted with DCM (20 mL×3). The combined organic layer was dried over potassium carbonate, filtered and concentrated. The residue was purified by silica gel column chromatography (DCM/MeOH=15/1) to afford the crude products 28-1 and 28-2 (280 mg) as a yellow solid. LC-MS: m/z 883.6 [M+H]$^+$.

To a solution of compounds 28-1 and 28-2 (280 mg, 0.32 mmol) in DCM (5 mL) was added DAST (51 mg, 0.32 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 28 (65 mg, yield 23%) as yellow solid. Partial $^1$H NMR (CDCl$_3$, 400 MHz): δ6.77 (m, 3H), 4.87 (s, 1H), 4.87 (s, 1H), 4.75-7.70 (m, 1H), 4.43 (d, J=7.6 Hz, 1H), 4.34-4.29 (m, 1H), 3.30-3.21 (m, 2H), 3.16-3.09 (m, 2H), 2.65-2.60 (m, 1H), 2.55-2.50 (m, 1H), 2.36 (s, 6H), 2.02-1.95 (m, 1H), LC-MS: m/z 865.6 [M+H]$^+$.

29. Synthesis of Compound 29: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl) oxy)-12-ethyl-1-(5-fluoro-2-methoxyphenyl)-7-methyl-3-(((2R,3R,4R,5S,6S)-3,4,5-trimethoxy-6-methyltetrahydro-2H-pyran-2-yl)oxy)-1,1a,1b,2,3,4, 4a,4b,7,8,9,10,11,12,15,15a,15b,15c-octadecahydro-[1]oxacyclododecino[5',4':2,3]-as-indaceno[4,5-b] azirine-6,14-dione

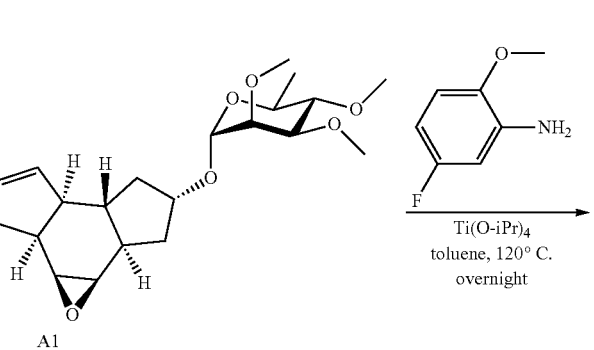

A1

-continued
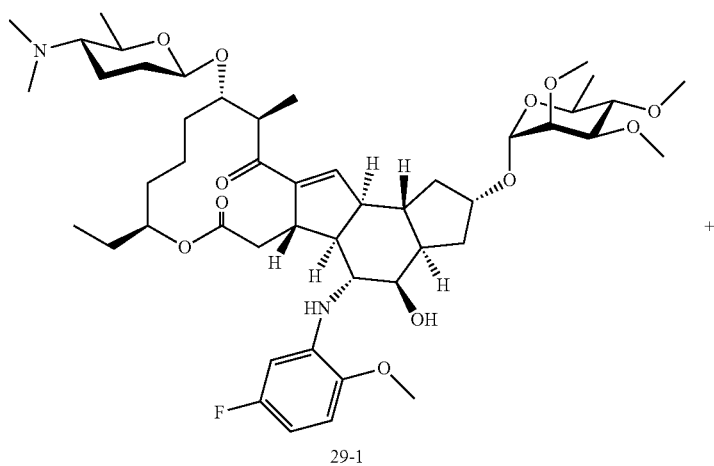
29-1
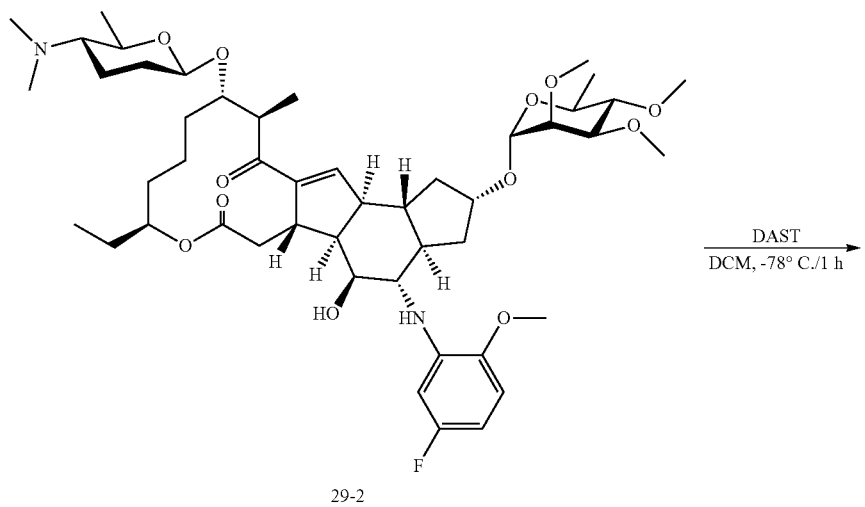
29-2
$\xrightarrow{\text{DAST}}{\text{DCM, -78° C./1 h}}$
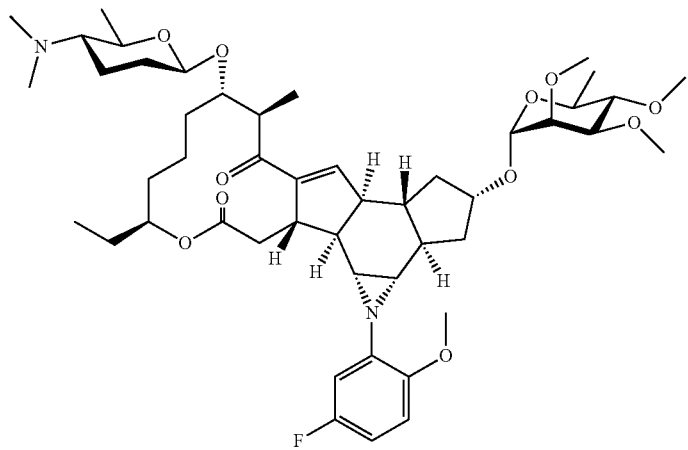
29

To a solution of compound A1 (400 mg, 0.53 mmol) and 5-fluoro-2-methoxyaniline (150.7 mg, 1.07 mmol) in toluene (10 mL) was added Ti(O-iPr)$_4$ (151.6 mg, 0.53 mmol). The mixture was stirred at 120° C. over night under N$_2$. The mixture was quenched with H$_2$O (50 mL) and extracted with DCM (20 mL×3). The combined organic layer was dried over potassium carbonate, filtered and concentrated. The residue was purified by silica gel column chromatography (DCM/MeOH=15/1) to afford the crude products 29-1 and 29-2 (320 mg) as a yellow solid. LC-MS: m/z 889.4 [M+H]$^+$.

To a solution of compounds 29-1 and 29-2 (310 mg, 0.35 mmol) in DCM (5 mL) was added DAST (56.2 mg, 0.35 mmol) at −78° C. under N$_2$. After stirred at −78° C. for 2 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 29 (53 mg, yield 17.5%) as white solid. Partial $^1$H NMR (CDCl$_3$, 400 MHz): δ6.75-6.71 (m, 2H), 6.64-6.59 (m, 2H), 4.89 (s, 1H), 4.76-4.72 (m, 1H), 4.43 (d, J=8.0 Hz, 1H), 4.34-4.30 (m, 1H), 3.87 (s, 3H), 2.59-2.50 (m, 2H), LC-MS: m/z 871.4 [M+H]$^+$.

30. Synthesis of Compound 30

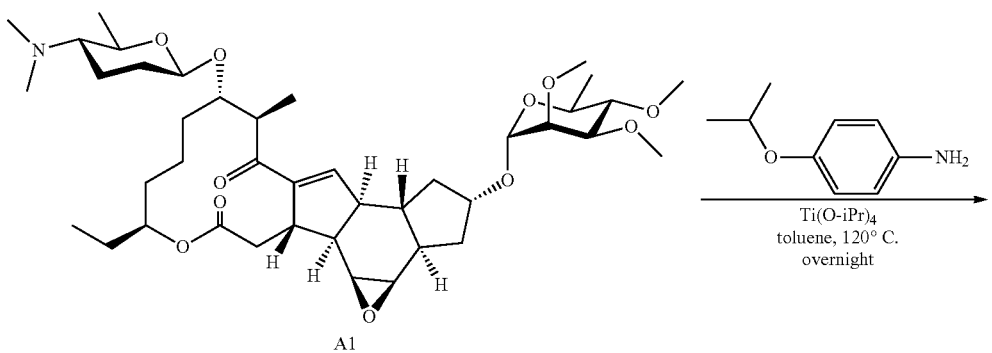

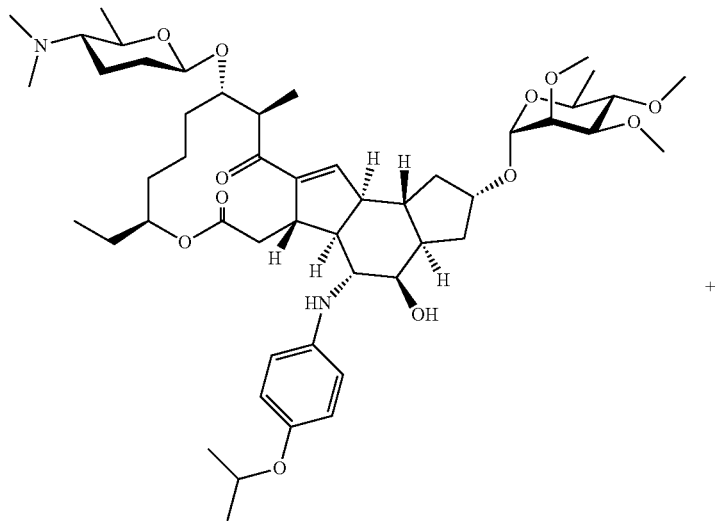

30-1

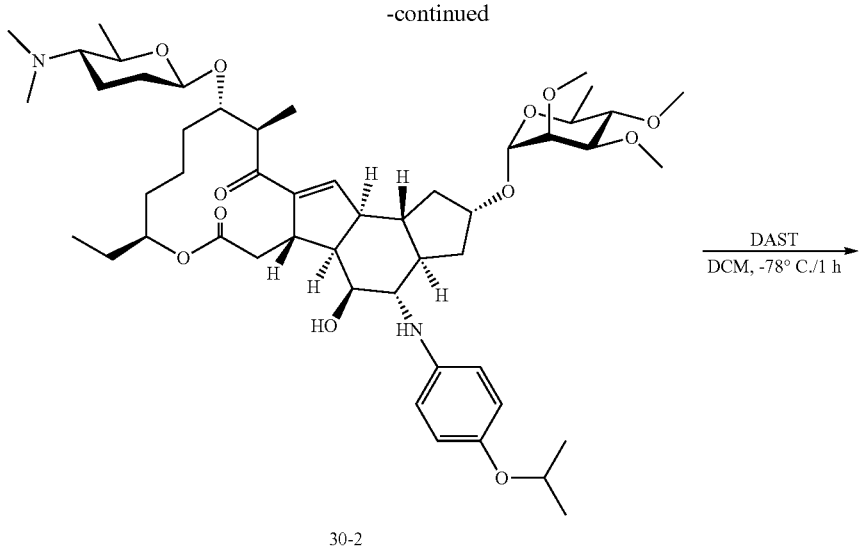

30-2

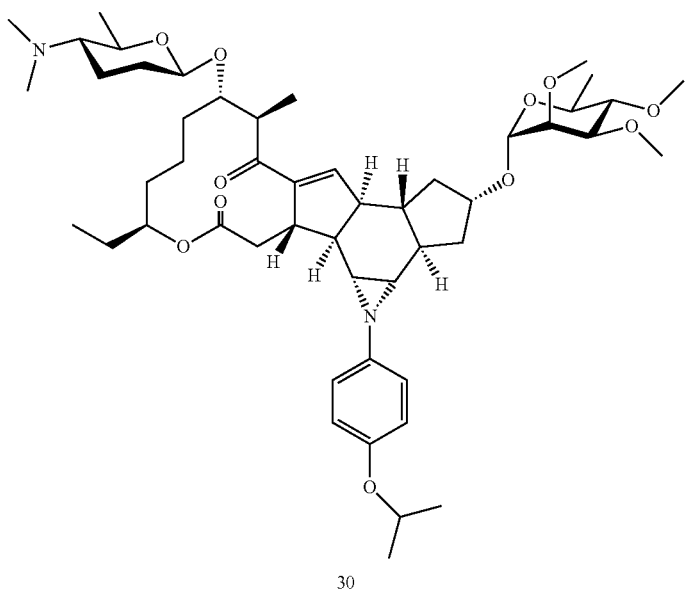

30

To a solution of compound A1 (0.5 g, 0.65 mmol) in toluene (10 mL) and 4-Isopropoxyaniline (202 mg, 1.34 mmol) was added Ti(O-iPr)$_4$ (190 mg, 0.66 mmol). The mixture was stirred at 120° C. overnight. The mixture was quenched with H$_2$O (50 mL) and extracted with DCM (20 mL×3). The combined organic layer was dried over potassium carbonate, filtered and concentrated. The residue was purified by silica gel column chromatography (DCM/MeOH=15/1) to afford the crude products 30-1 and 30-2 (140 mg) as a brown solid. LC-MS: m/z 899.2 [M+H]$^+$.

To a solution of compounds 30-1 and 30-2 (137 mg, 0.15 mmol) in DCM (5 mL) was added DAST (24.5 mg, 0.15 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 30 (19 mg, yield 14%) as yellow solid. Partial $^1$H NMR (CDCl$_3$, 400 MHz): δ 6.93 (d, J=8.8 Hz, 2H), 6.78-6.75 (m, 3H), 4.88 (s, 1H), 4.71-4.66 (m, 1H), 4.46-4.33 (m, 2H), 4.32-4.29 (m, 1H), 3.66-3.63 (m, 1H), 3.29-3.26 (m, 2H), 3.13-3.09 (m, 2H), 3.56-2.33 (m, 3H); LC-MS: m/z 881.2 [M+H]$^+$.

31. Synthesis of Compound 31: (1aS,1bR,3S,4aS,4bR,7R,8S,12S,15aS,15bR,15cR)-1-(3,5-dichlorophenyl)-8-(((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
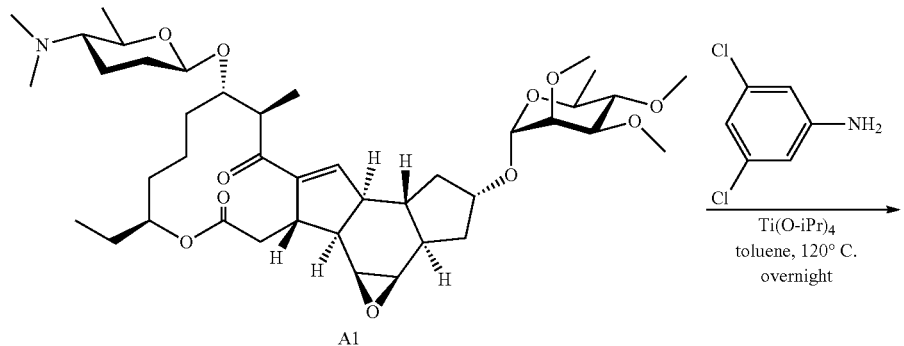
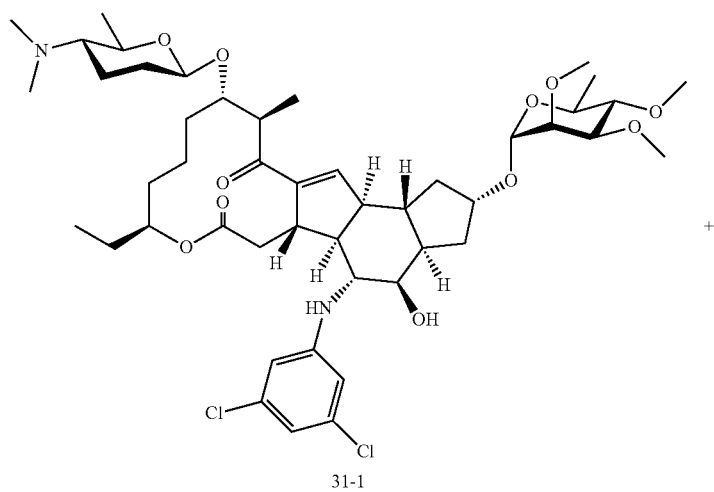
31-1

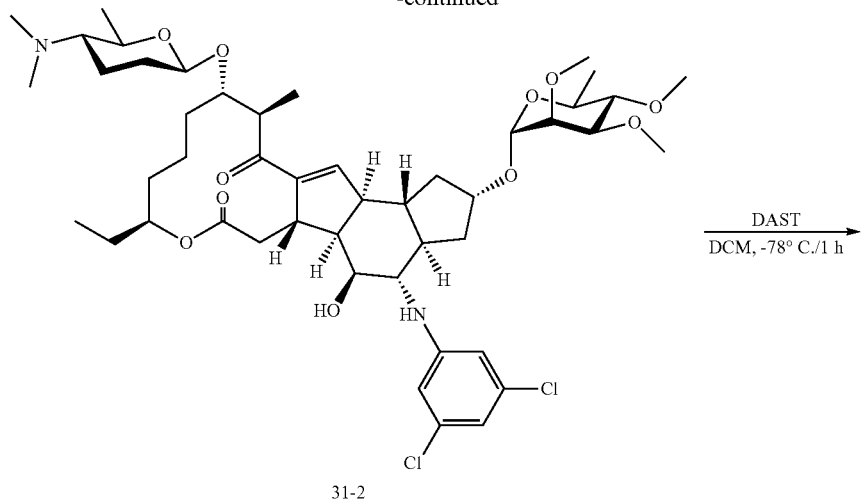

31-2

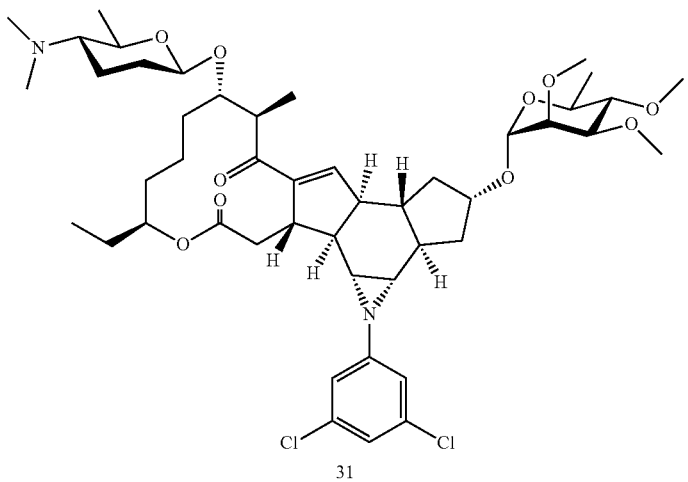

31

To a solution of compound A1 (0.4 g, 0.53 mmol) and 3,5-dichloroaniline (171.7 mg, 1.06 mmol) in toluene (10 mL) was added Ti(O-iPr)$_4$ (150.5 mg, 0.53 mmol). The mixture was stirred at 120° C. over night under N$_2$. The mixture was quenched with H$_2$O (30 mL) and extracted with EA (30 mL×3). The combined organic layer was dried over potassium carbonate, filtered and concentrated. The residue was purified by prep-HPLC to afford the crude products 31-1 and 31-2 (100 mg) as a yellow solid. LC-MS: m/z 909.1 [M+H]$^+$.

To a solution of compounds 31-1 and 31-2 (75 mg, 0.08 mmol) in DCM (5 mL) was added DAST (13.3 mg, 0.08 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 31 (18 mg, yield 25%) as white solid. Partial $^1$H NMR (CDCl$_3$, 400 MHz): δ 6.95 (s, 1H), 6.88 (s, 2H), 6.74 (s, 1H), 4.89 (s, 1H), 4.71-4.65 (m, 1H), 4.43 (d, J=7.6 Hz, 1H), 4.38-4.32 (m, 1H), 3.65 (m, 1H), 3.31-3.25 (m, 2H), 3.14-3.09 (m, 2H), 2.54-2.39 (m, 3H), 2.00-1.84 (m, 3H); LC-MS: m/z 891.1 [M+H]$^+$.

32. Synthesis of Compound 32
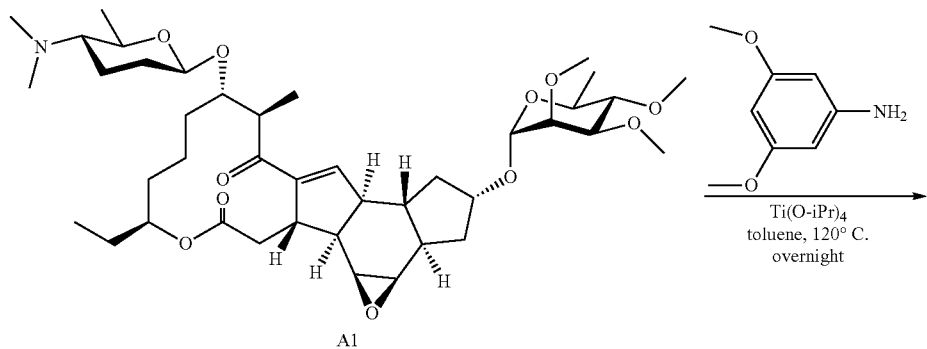
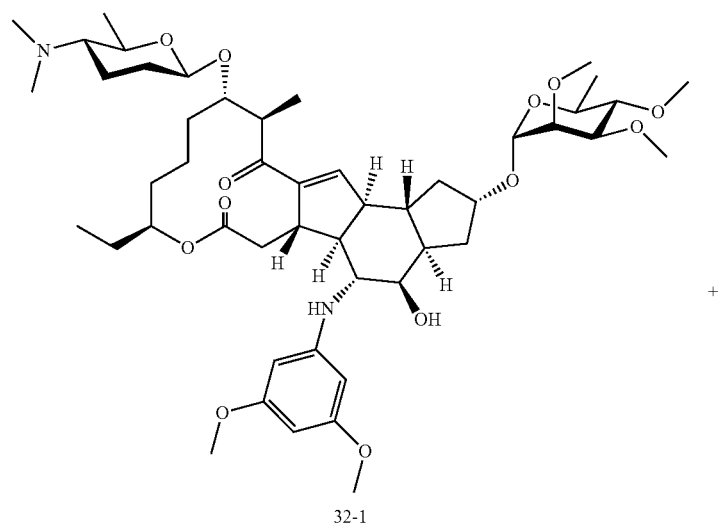
32-1

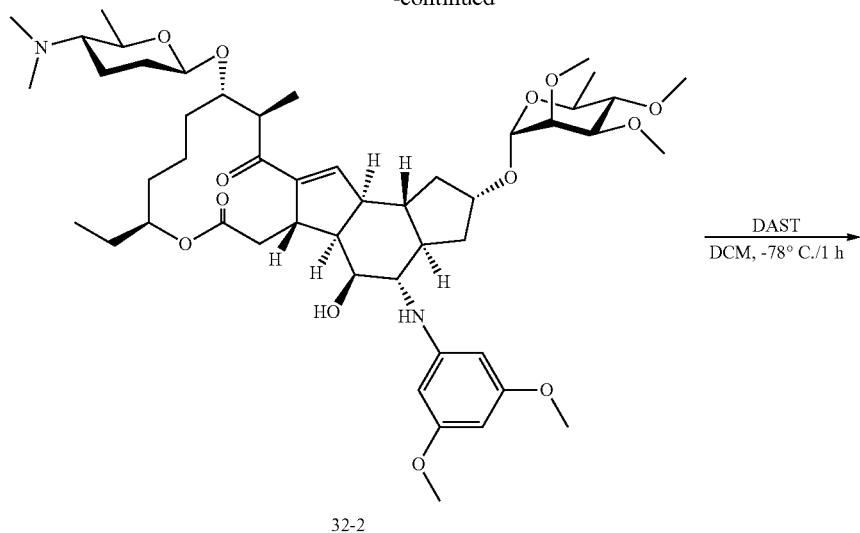

32-2

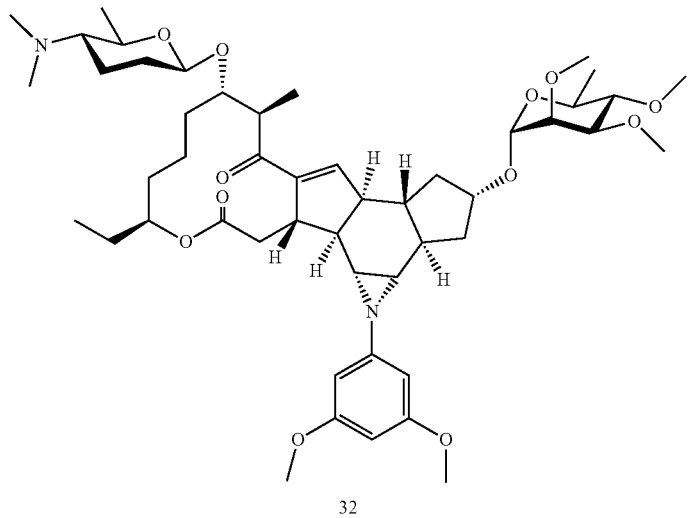

32

To a solution of compound A1 (0.5 g, 0.65 mmol) and 3,5-dimethoxyaniline (205 mg, 1.34 mmol) in toluene (10 mL) was added Ti(O-iPr)$_4$ (190 mg, 0.67 mmol). The mixture was stirred at 120° C. overnight. The mixture was quenched with H$_2$O (30 mL) and extracted with EA (30 mL×3). The combined organic layer was dried over potassium carbonate, filtered and concentrated. The residue was purified by prep-HPLC to afford the crude products 32-1 and 32-2 (110 mg) as a yellow solid. LC-MS: m/z 901.5 [M+H]$^+$.

To a solution of compounds 32-1 and 32-2 (110 mg, 0.12 mmol) in DCM (10 mL) was added DAST (19.1 mg, 0.12 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 32 (12 mg, yield 11%) as yellow solid. Partial $^1$H NMR (CDCl$_3$, 400 MHz): δ 6.74 (s, 1H), 6.22 (d, J=2.0 Hz, 2H), 6.10 (t, J=2.0 Hz, 1H), 4.88 (s, 1H), 4.42 (d, J=7.2 Hz, 1H), 4.31 (m, 1H), 3.78 (s, 6H), 3.66-3.61 (m, 1H), 3.27 (dd, J=12.8, 4.8 Hz, 2H), 3.11 (t, J=9.6 Hz, 2H), 2.52-2.46 (m, 2H), 2.39-2.37 (m, 1H), 0.84 (t, J=7.2 Hz, 3H); LC-MS: m/z 883.5 [M+H]$^+$.

33. Synthesis of Compound 33
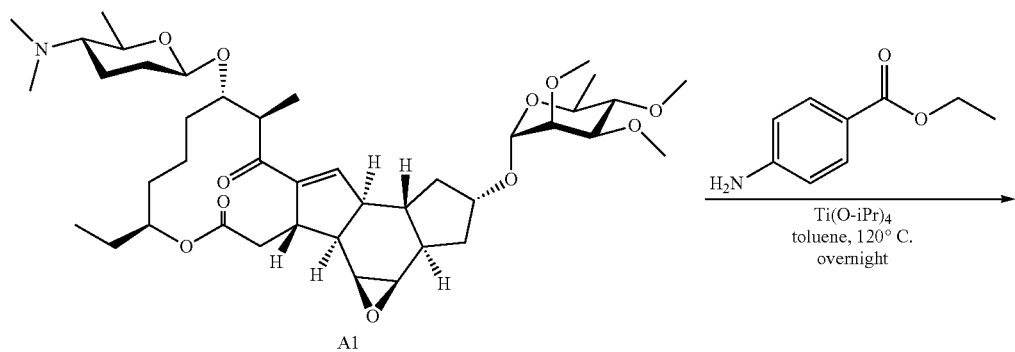

-continued

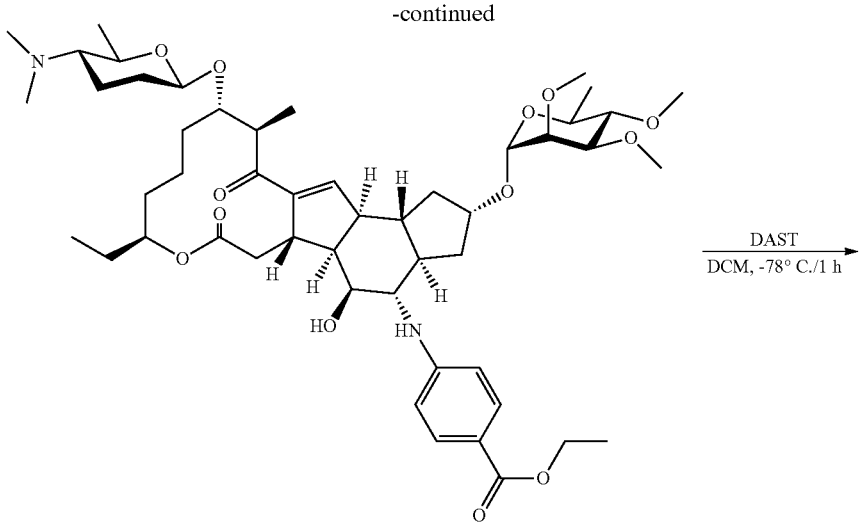

33-2

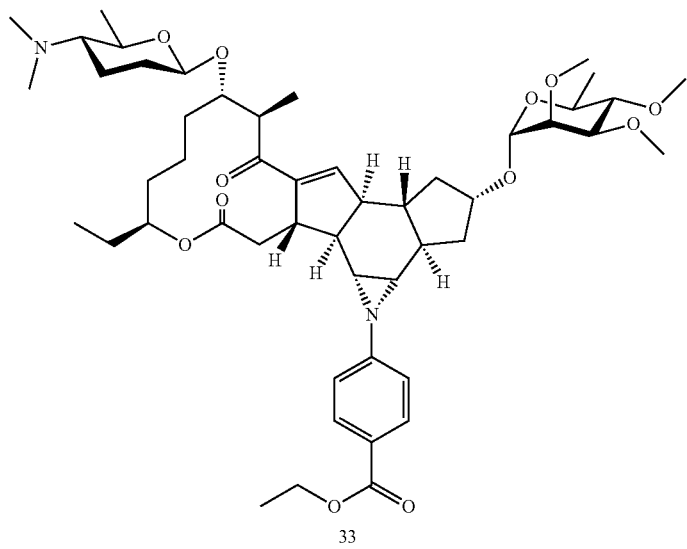

33

To a solution of compound A1 (0.4 g, 0.53 mmol) and ethyl 4-aminobenzoate (176.5 mg, 1.07 mmol) in toluene (10 mL) was added Ti(O-iPr)$_4$ (152 mg, 0.535 mmol). The mixture was stirred at 120° C. for overnight. The mixture was quenched with H$_2$O (30 mL) and extracted with EA (30 mL×3). The combined organic layer was dried over potassium carbonate, filtered and concentrated. The residue was purified by prep-HPLC to afford the crude products 33-1 and 33-2 (240 mg) as a yellow solid. LC-MS: m/z 913.2 [M+H]+.

To a solution of compounds 33-1 and 33-2 (240 mg, 0.26 mmol) in DCM (10 mL) was added DAST (42.3 mg, 0.26 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 33 (34 mg, yield 14%) as yellow solid. Partial $^1$H NMR (CDCl$_3$, 300 MHz): δ 7.93 (d, J=8.4 Hz, 2H), 7.05 (d, J=8.4 Hz, 2H), 6.76 (s, 1H), 4.90 (s, 1H), 4.74-4.68 (m, 1H), 4.46-4.31 (m, 4H), 3.35-3.29 (m, 2H), 3.16-3.09 (m, 2H), 2.61-2.45 (m, 3H), 0.87 (t, J=19.2 Hz, 3H); LC-MS: m/z 895.2 [M+H]$^+$.

34. Synthesis of Compound 34: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl)oxy)-12-ethyl-1-(2-fluorophenyl)-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
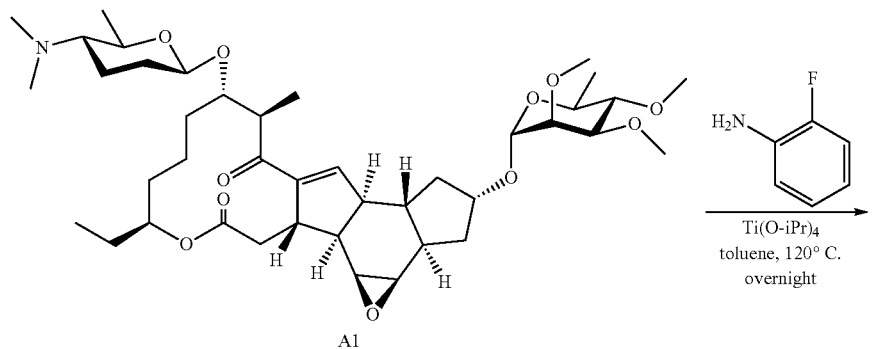
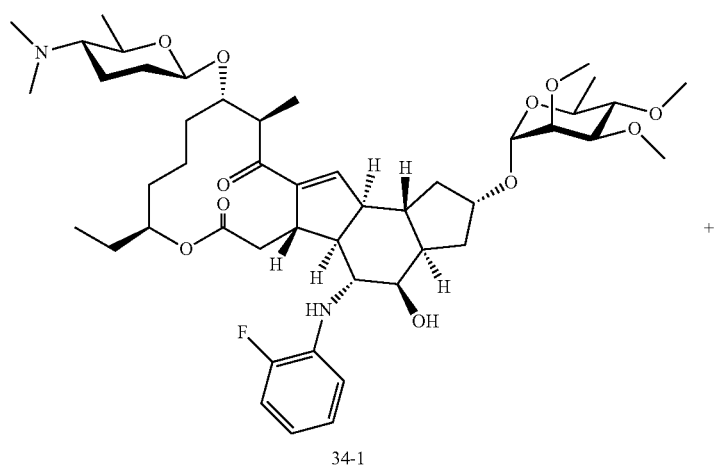
34-1

-continued

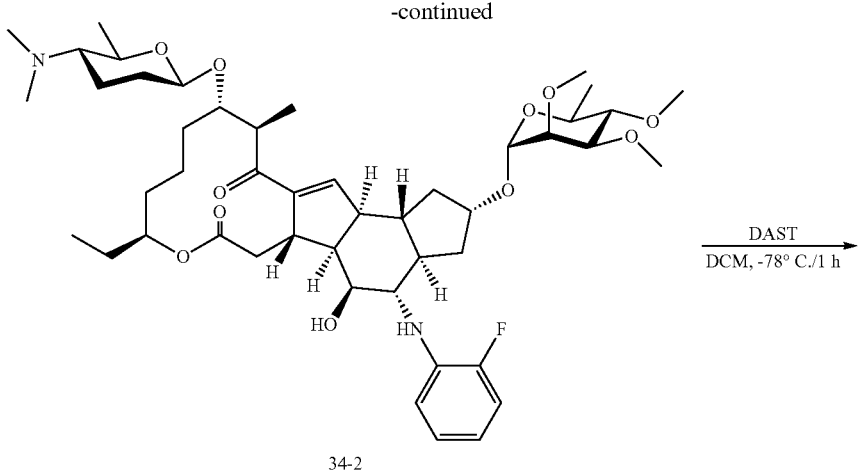

34-2

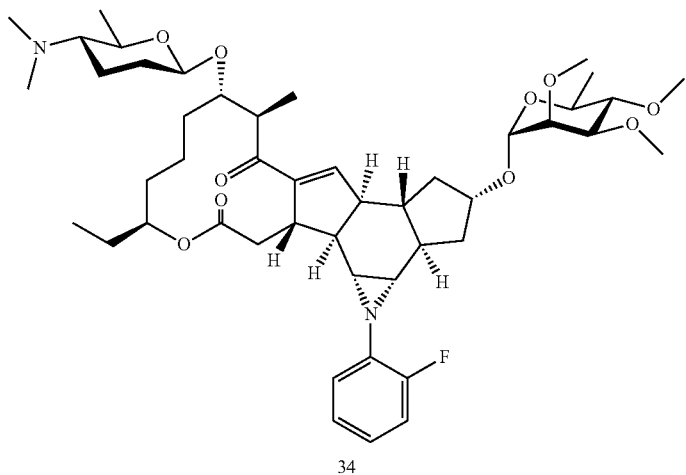

34

To a solution of compound A1 (0.5 g, 0.65 mmol) and 2-fluoroaniline (148 mg, 1.33 mmol) in toluene (10 mL) was added Ti(O-iPr)$_4$ (190 mg, 0.66 mmol). The mixture was stirred at 120° C. for overnight. The mixture was quenched with H$_2$O (30 mL) and extracted with EA (30 mL×3). The combined organic layer was dried over potassium carbonate, filtered and concentrated. The residue was purified by prep-HPLC to afford the crude products 34-1 and 34-2 (240 mg) as a yellow solid. LC-MS: m/z 859.2 [M+H]$^+$.

To a solution of compounds 34-1 and 34-2 (235 mg, 0.27 mmol) in DCM (10 mL) was added DAST (44.1 mg, 0.27 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 34 (30 mg, yield 13%) as yellow solid. Partial $^1$H NMR (CDCl$_3$, 400 MHz): δ 7.34-6.99 (m, 4H), 6.75 (s, 1H), 4.89 (s, 1H), 4.71 (m, 1H), 4.44 (d, J=7.2 Hz, 1H), 4.33 (m, 1H), 3.28-3.23 (m, 2H), 3.15-3.09 (m, 2H), 2.61-2.53 (m, 2H), 2.43 (m, 1H), 2.21-2.17 (m, 10H), 0.85 (t, J=7.2 Hz, 3H); LC-MS: m/z 841.2 [M+H]$^+$.

35. Synthesis of Compound 35
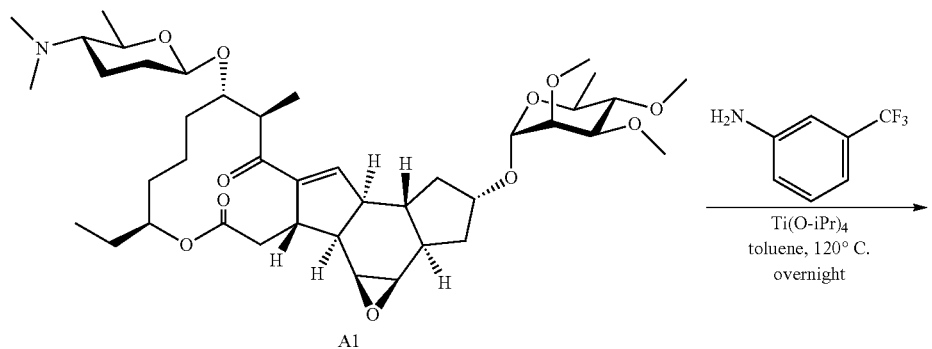
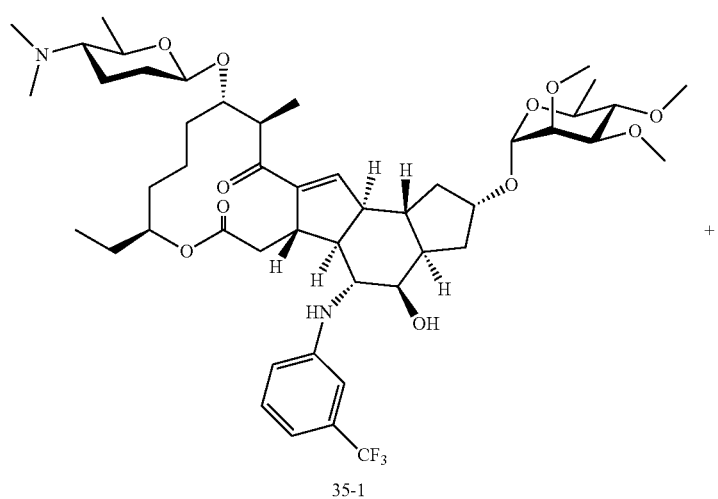

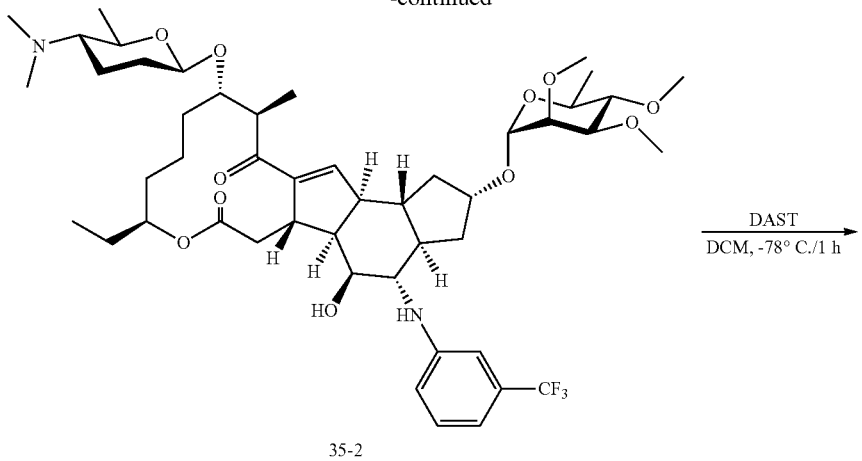

35-2

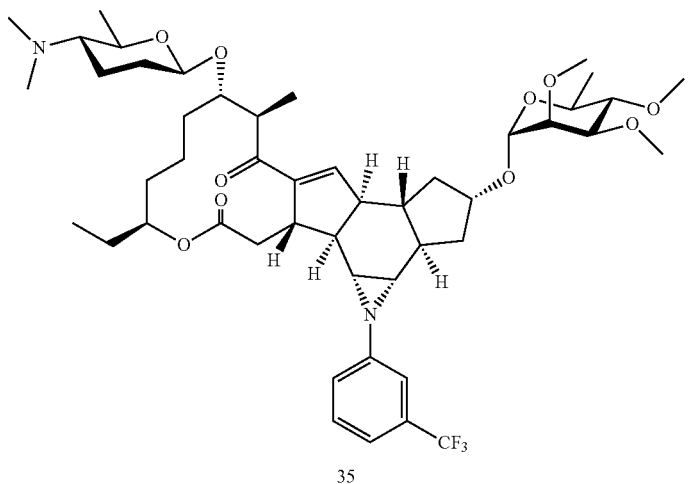

35

To a solution of compound A1 (0.4 g, 0.53 mmol) and 3-(trifluoromethyl)aniline (172 mg, 1.07 mmol) in toluene (10 mL) was added Ti(O-iPr)$_4$ (152 mg, 0.53 mmol). The mixture was stirred at 120° C. for overnight. The mixture was quenched with H$_2$O (30 mL) and extracted with EA (30 mL×3). The combined organic layer was dried over potassium carbonate, filtered and concentrated. The residue was purified by prep-HPLC to afford the crude products 35-1 and 35-2 (160 mg) as a yellow solid. LC-MS: m/z 909.2 [M+H]$^+$.

To a solution of compounds 35-1 and 35-2 (160 mg, 0.18 mmol) in DCM (10 mL) was added DAST (28.3 mg, 0.18 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 35 (70 mg, yield 45%) as yellow solid. Partial $^1$H NMR (CDCl$_3$, 400 MHz): δ 7.36-7.33 (m, 1H), 7.22-7.18 (m, 3H), 6.75 (s, 1H), 4.90 (s, 1H), 4.69 (m, 1H), 4.43 (d, J=8.4 Hz, 1H), 4.34 (m, 1H), 3.33-3.28 (m, 2H), 3.14-3.10 (m, 2H), 2.56-2.43 (m, 2H), 0.86 (t, J=7.6 Hz, 3H); LC-MS: m/z 891.2 [M+H]$^+$.

36. Synthesis of Compound 36
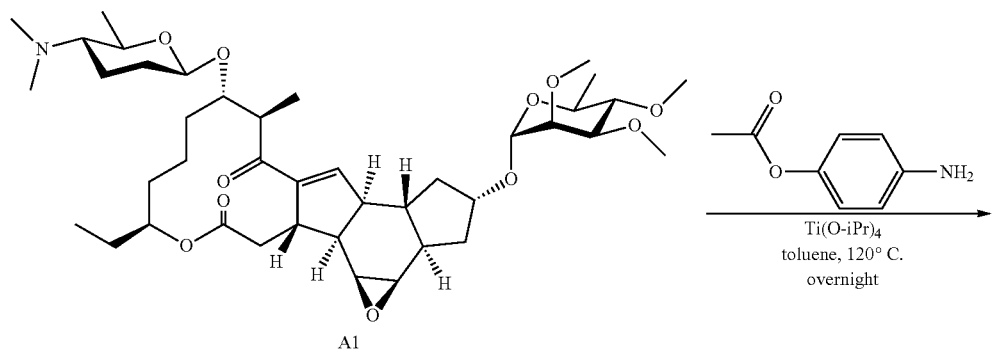

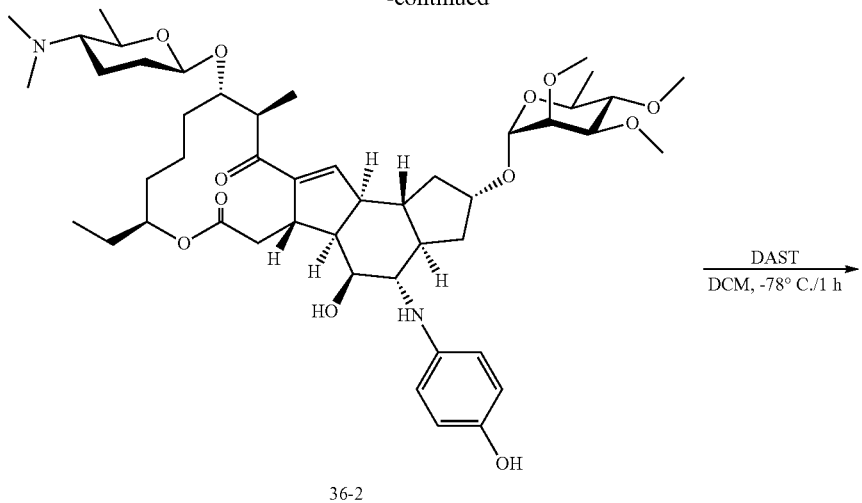

36-2

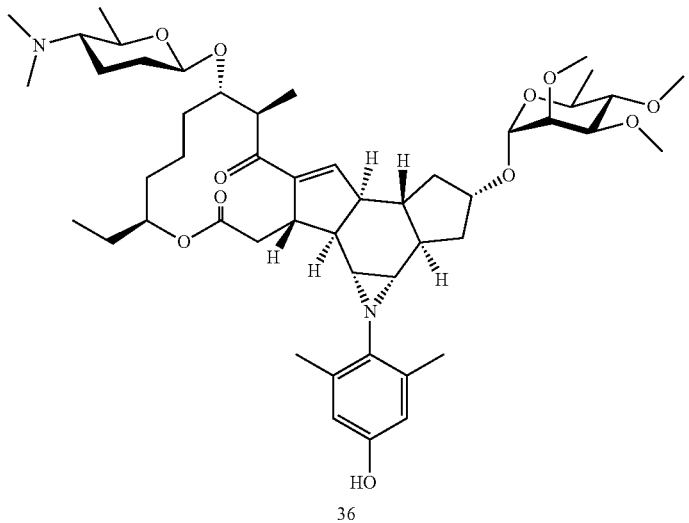

36

To a solution of compound A1 (0.5 g, 0.65 mmol) and 4-aminophenyl acetate (172 mg, 1.07 mmol) in toluene (10 mL) was added Ti(O-iPr)$_4$ (190 mg, 0.66 mmol). The mixture was stirred at 120° C. for overnight. The mixture was quenched with H$_2$O (30 mL) and extracted with EA (30 mL×3). The combined organic layer was dried over potassium carbonate, filtered and concentrated. The residue was purified by prep-HPLC to afford the crude products 36-1 and 36-2 (210 mg) as a yellow solid. LC-MS: m/z 857.2 [M+H]$^+$.

To a solution of compounds 36-1 and 36-2 (210 mg, 0.24 mmol) in DCM (10 mL) was added DAST (51.5 mg, 0.31 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 36 (80 mg, yield 39%) as yellow solid. Partial $^1$H NMR (CDCl$_3$, 400 MHz): δ 6.91 (d, J=8.4 Hz, 2H), 6.75 (s, 1H), 6.71 (d, J=8.4 Hz, 2H), 4.88 (s, 1H), 4.69 (m, 1H), 4.43 (d, J=7.2 Hz, 1H), 4.31 (m, 1H), 3.31-3.26 (m, 2H), 3.14-3.09 (m, 2H), 0.85 (t, J=7.2 Hz, 3H); LC-MS: m/z 839.2 [M+H]$^+$.

37. Synthesis of Compound 37
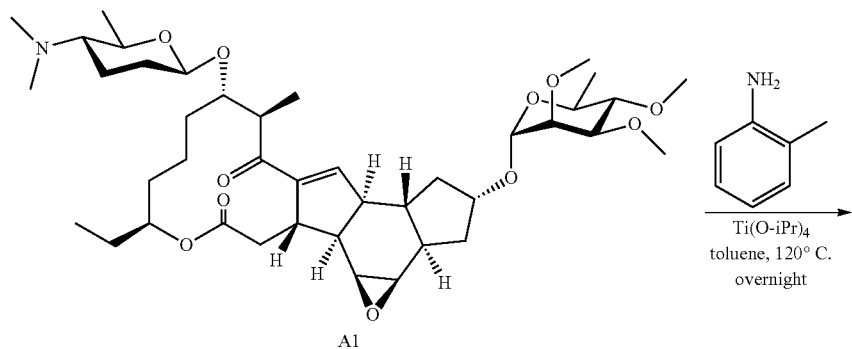
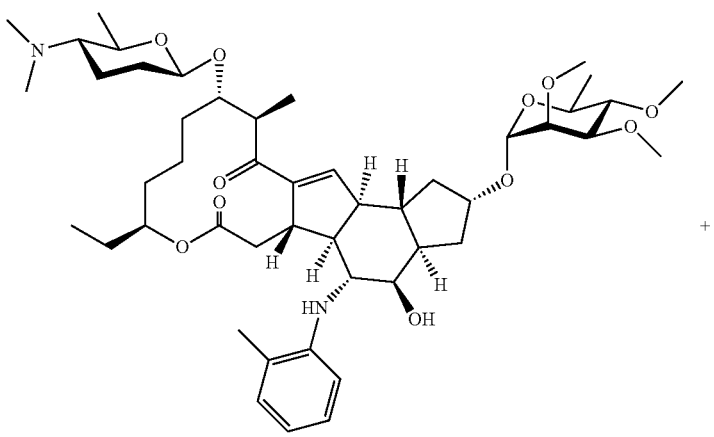

-continued

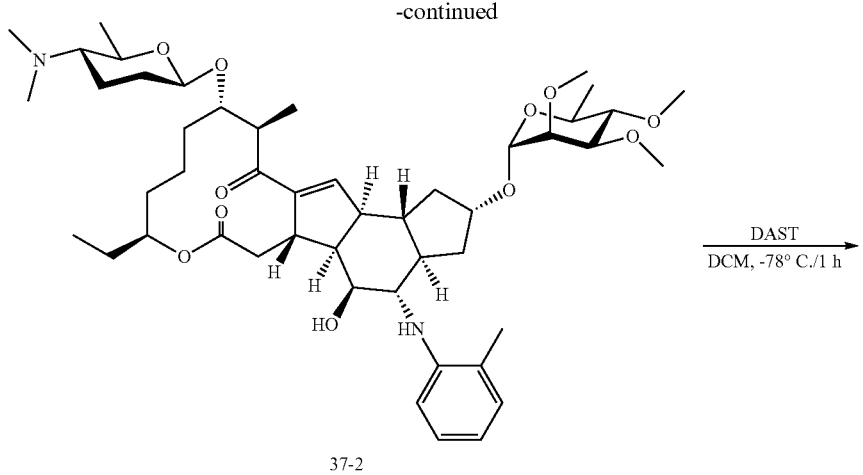

37-2

DAST
―――――→
DCM, -78° C./1 h

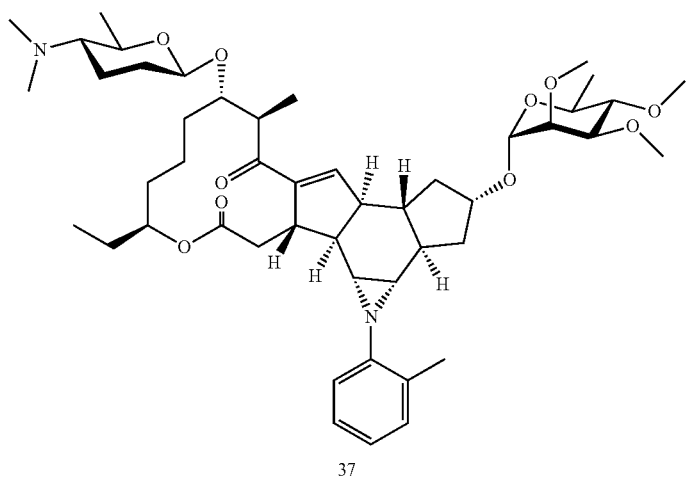

37

To a solution of compound A1 (0.5 g, 0.65 mmol) and o-toluidine (143 mg, 1.07 mmol) in toluene (10 mL) was added Ti(O-iPr)$_4$ (190 mg, 0.66 mmol). After stirred at 120° C. overnight, the mixture was quenched with H$_2$O (30 mL) and extracted with EA (30 mL×3). The combined organic layer was dried over potassium carbonate, filtered and concentrated. The residue was purified by prep-HPLC to afford the crude products 37-1 and 37-2 (140 mg) as a yellow solid. LC-MS: m/z 855.5 [M+H]$^+$.

To a solution of compounds 37-1 and 37-2 (140 mg, 0.16 mmol) in DCM (10 mL) was added DAST (26.4 mg, 0.16 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 37 (14 mg, yield 10%) as yellow solid. Partial $^1$H NMR (CDCl$_3$, 400 MHz): δ 7.12-7.08 (m, 2H), 6.92-6.85 (m, 2H), 6.77 (s, 1H), 4.88 (s, 1H), 4.69 (m, 1H), 4.43 (d, J=7.6 Hz, 1H), 4.33 (m, 1H), 3.30-3.24 (m, 2H), 3.16-3.09 (m, 2H), 0.84 (t, J=7.2 Hz, 3H); LC-MS: m/z 837.5 [M+H]$^+$.

38. Synthesis of Compound 38: (1aS,1bR,3S,4aS, 4bR,7R,8S,12S,15aS,15bR,15cR)-1-(3,4-difluorophenyl)-8-((((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
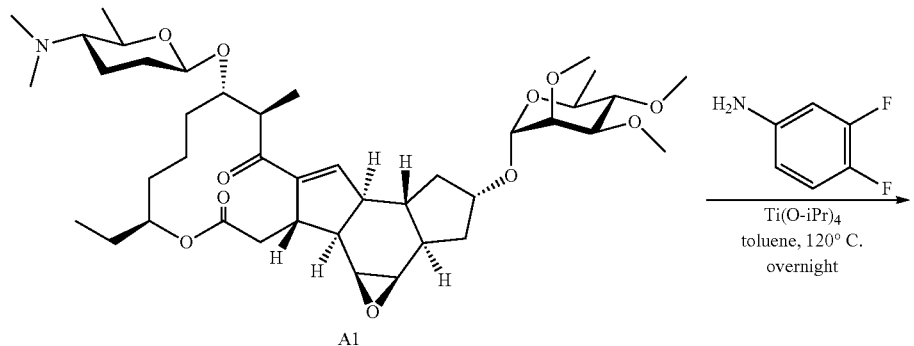
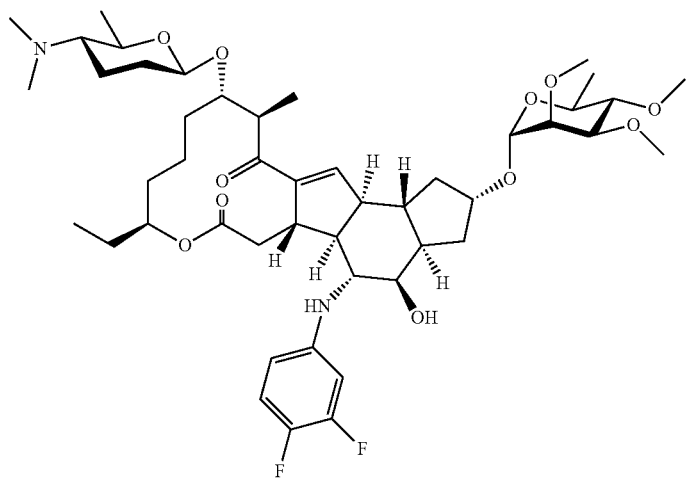
38-1

-continued

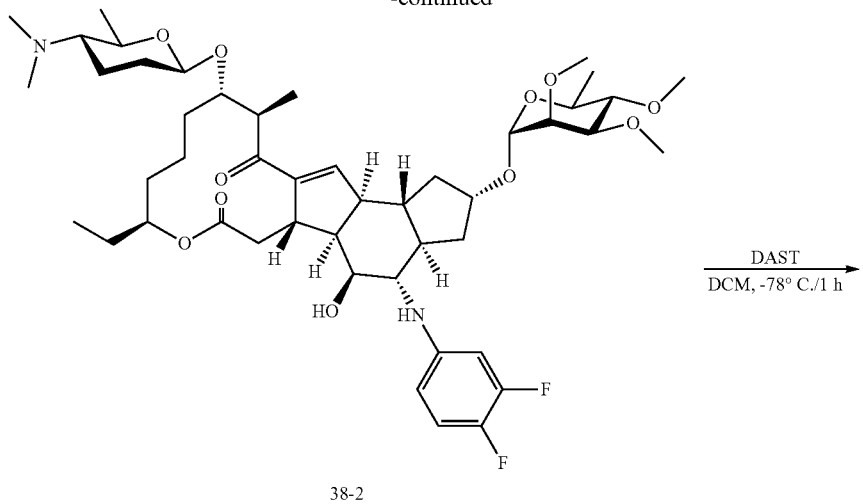

38-2

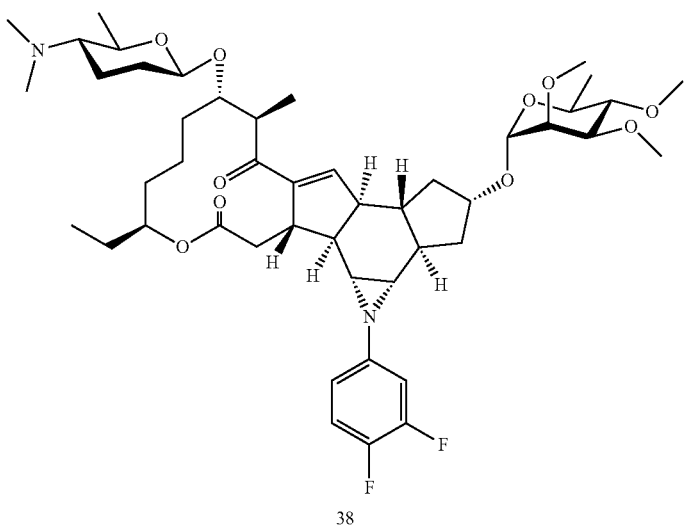

38

To a solution of compound A1 (0.5 g, 0.65 mmol) and 3,4-difluoroanline (172.0 mg, 1.34 mmol) in toluene (10 mL) was added Ti(O-iPr)$_4$ (190 mg, 0.66 mmol). After stirred at 120° C. overnight, the mixture was quenched with H$_2$O (30 mL) and extracted with EA (30 mL×3). The combined organic layer was dried over potassium carbonate, filtered and concentrated. The residue was purified by prep-HPLC to afford the crude products 38-1 and 38-2 (240 mg) as a brown solid. LC-MS: m/z 877.2 [M+H]$^+$.

To a solution of compounds 38-1 and 38-2 (240 mg, 0.27 mmol) in DCM (10 mL) was added DAST (44.5 mg, 0.27 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 38 (40 mg, yield 28%) as yellow solid. Partial $^1$H NMR (CDCl$_3$, 400 MHz): δ 7.03-6.99 (m, 1H), 6.85-6.78 (m, 1H), 6.75-6.72 (m, 2H), 4.90 (s, 1H), 4.68 (m, 1H), 4.47 (d, J=8.8 Hz, 1H), 4.32 (m, 1H), 3.66-3.62 (m, 1H), 3.33-3.22 (m, 2H), 3.15-3.11 (m, 2H), 2.37 (m, 1H), 0.85 (t, J=7.6 Hz, 3H); LC-MS: m/z 859.2 [M+H]$^+$.

39. Synthesis of Compound 39: (1aS,1bR,3S,4aS, 4bR,7R,8S,12S,15aS,15bR,15cR)-1-(2,3-difluorophenyl)-8-((((2R,5S,6R)-5-(dimethylamino)-6-methyltetrahydro-2H-pyran-2-yl)oxy)-12-ethyl-7-methyl-3-((((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
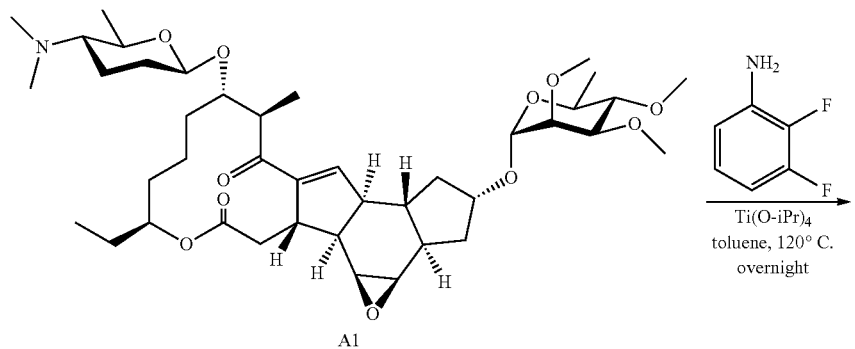
A1
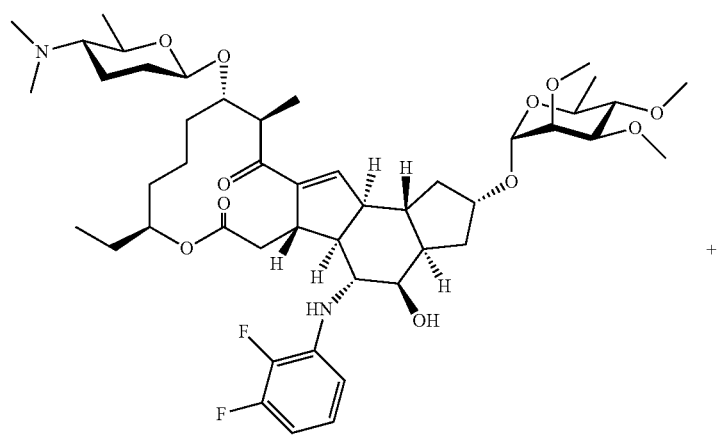
39-1

-continued

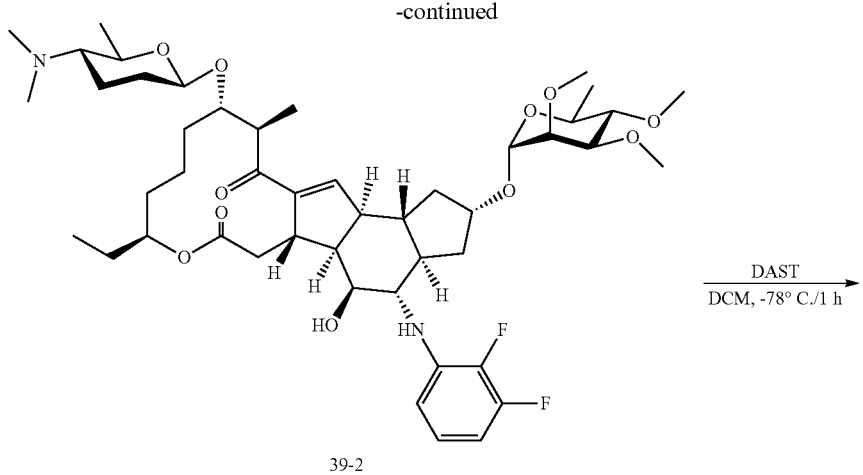

39-2

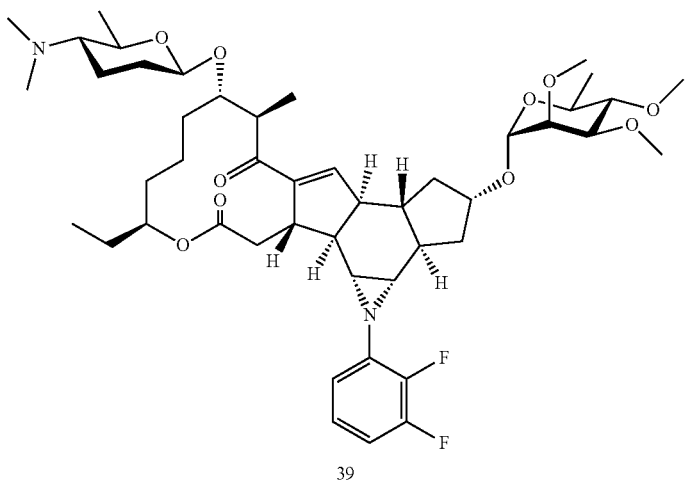

39

To a solution of compound A1 (0.5 g, 0.65 mmol) and 2,3-difluoroanline (172.0 mg, 1.34 mmol) in toluene (10 mL) was added Ti(O-iPr)$_4$ (190 mg, 0.66 mmol). After stirred at 120° C. overnight, the mixture was quenched with H$_2$O (30 mL) and extracted with EA (30 mL×3). The combined organic layer was dried over potassium carbonate, filtered and concentrated. The residue was purified by prep-HPLC to afford the crude products 39-1 and 39-2 (150 mg) as a brown solid. LC-MS: m/z 877.2 [M+H]$^+$.

To a solution of compounds 39-1 and 39-2 (150 mg, 0.17 mmol) in DCM (10 mL) was added DAST (28 mg, 0.17 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 39 (20 mg, yield 14%) as yellow solid. Partial $^1$H NMR (CDCl$_3$, 400 MHz): δ 6.95-6.91 (m, 1H) 6.79-6.75 (m, 3H), 4.88 (s, 1H), 4.70 (m, 1H), 4.43 (d, J=7.6 Hz, 1H), 4.33 (m, 1H), 3.30-3.23 (m, 2H), 3.16-3.09 (m, 2H), 2.62-2.50 (m, 2H), 2.47-2.44 (m, 1H), 0.85 (t, J=7.2 Hz, 3H); LC-MS: m/z 859.2 [M+H]$^+$.

40. Synthesis of Compound 40: (1aS,1bR,3S,4aS,4bR,7R,8S,12S,15aS,15bR,15cR)-1-(2,4-difluorophenyl)-8-((((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
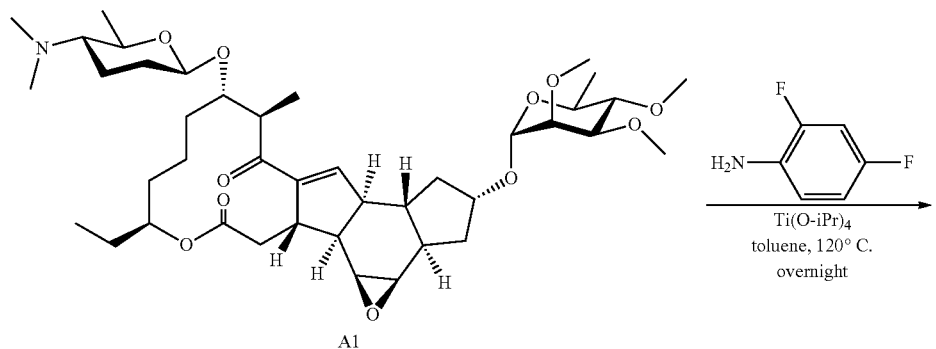
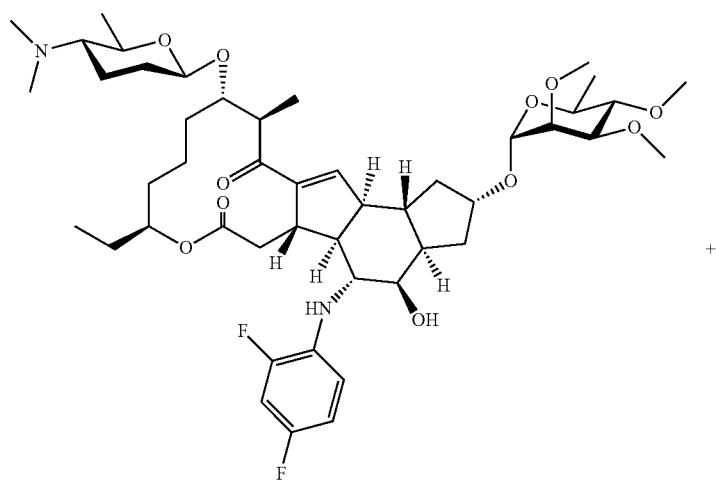
40-1

-continued

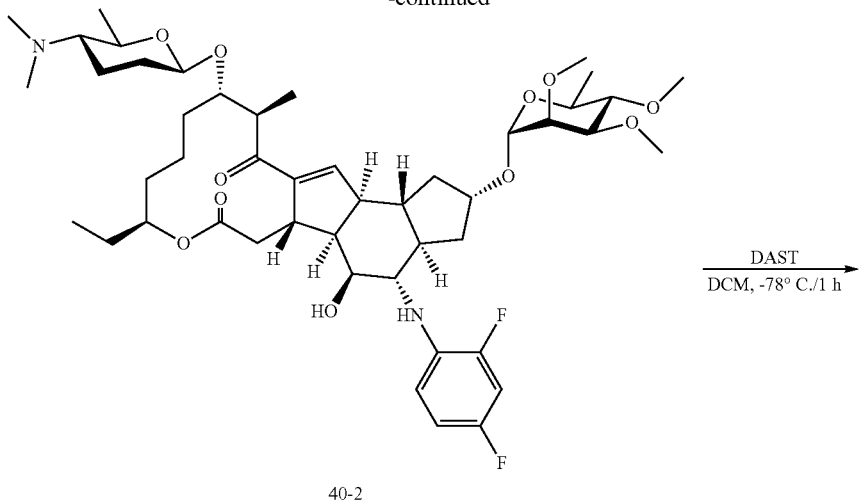

40-2

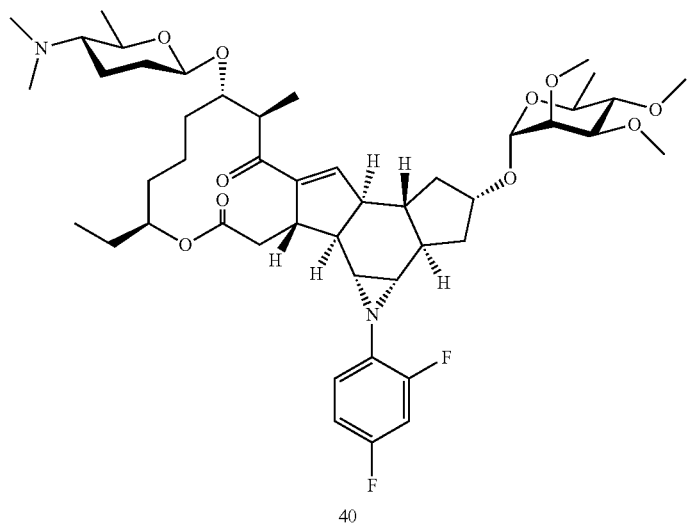

40

To a solution of compound A1 (0.5 g, 0.65 mmol) and 2,4-difluoroanline (172.0 mg, 1.34 mmol) in toluene (10 mL) was added Ti(O-iPr)₄ (190 mg, 0.66 mmol). After stirred at 120° C. overnight, the mixture was quenched with H₂O (30 mL) and extracted with EA (30 mL×3). The combined organic layer was dried over potassium carbonate, filtered and concentrated. The residue was purified by prep-HPLC to afford the crude products 40-1 and 40-2 (210 mg) as a brown solid. LC-MS: m/z 877.2 [M+H]⁺.

To a solution of compounds 40-1 and 40-2 (210 mg, 0.24 mmol) in DCM (10 mL) was added DAST (38 mg, 0.24 mmol) at −78 HC under N₂. After stirred at −78° C. for 1 h, the mixture was quenched with aqueous NaHC₃ and H₂O and then extracted with DCM (30 m L×3). The combined organic layer was dried over potassium carbonate, filtered and concentrated. The residue was purified by prep-HPLC to afford compound 40 (40 mg, yield 20.5%) as yellow solid. Partial ¹H NMR (CDCl₃, 400 MHz): δ 6.94-6.93 (m, 1H), 6.81-6.74 (m, 3H), 4.88 (s, 1H), 4.69 (m, 1H), 4.44 (d, J=6.8 Hz, 1H), 4.32 (m, 1H), 3.30-3.24 (m, 2H), 3.18-3.09 (m, 2H); LC-MS: m/z 859.2 [M+H]⁺.

41. Synthesis of Compound 41
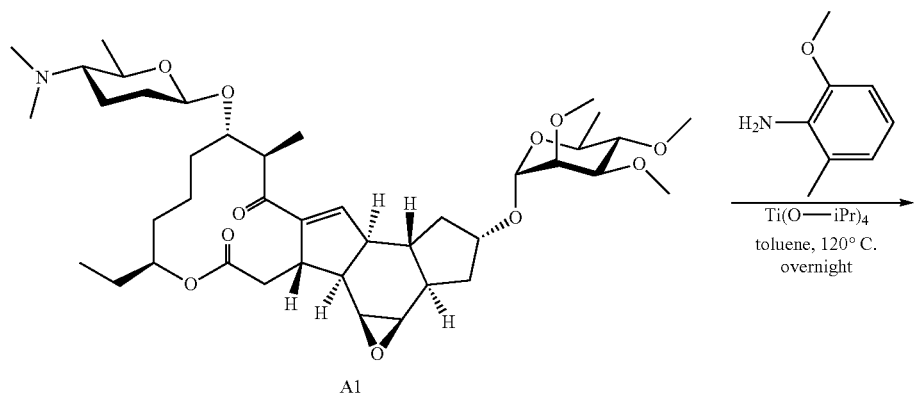
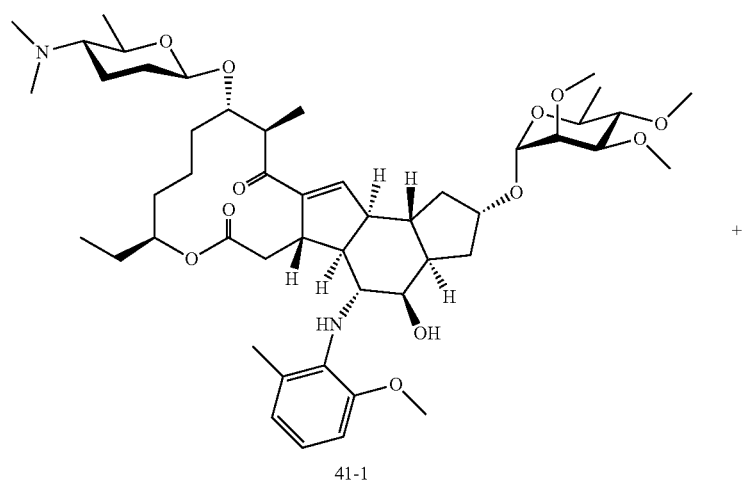

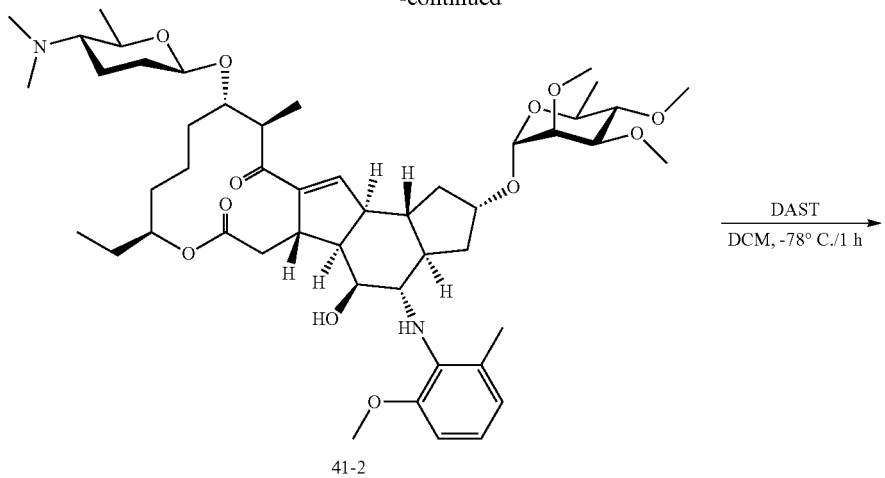

41-2

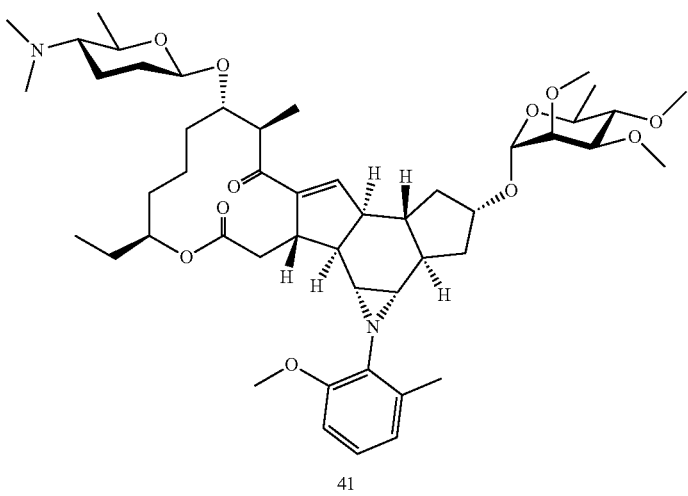

41

To a solution of compound A1 (0.5 g, 0.65 mmol) in toluene (10 mL) were added Ti(O-iPr)$_4$ (190 mg, 0.66 mmol) and 2-methoxy-6-methylaniline (188 mg, 1.33 mmol). After stirred at 120° C. overnight, the mixture was quenched with H$_2$O (30 mL) and extracted with EA (30 mL×3). The combined organic layer was dried over potassium carbonate, filtered and concentrated. The residue was purified by flash to afford the crude products 41-1 and 41-2 (300 mg, yield 51%) as yellow solid which was used for next step without further purification. LC-MS: m/z 886.4 [M+H]$^+$.

To a solution of compounds 41-1 and 41-2 (300 mg, 033 mmol) in DCM (10 mL) was added DAST (54 mg, 0.33 mmol) at −78° C. under N$_2$. After stirred at −78° C. for 1 h, the mixture was quenched with aqueous NaHCO$_3$ and H$_2$O and then extracted with DCM (30 mL×3). The combined organic layer was dried over potassium carbonate, filtered and concentrated. The residue was purified by prep-HPLC to afford compound 41 (20 mg, yield 7%) as yellow solid. Partial $^1$H NMR (CDCl$_3$, 400 MHz): δ 6.84 (t, J=7.6 Hz, 1H), 6.77 (s, 1H), 6.72 (d, J=7.6 Hz, 2H), 4.88 (s, 1H), 4.76-4.73 (m, 1H), 4.43 (d, J=9.6 Hz, 1H), 4.32-4.30 (m, 1H), 3.85 (s, 3H), 3.30-3.20 (m, 2H), 3.14-3.09 (m, 2H), 2.62-2.56 (m, 2H), 2.36 (s, 3H); LC-MS: m/z 868.4 [M+H]$^+$.

42. Synthesis of Compound 42
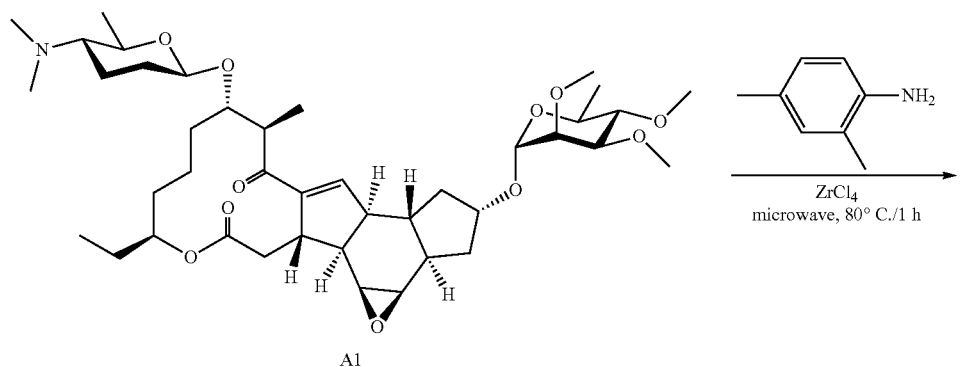
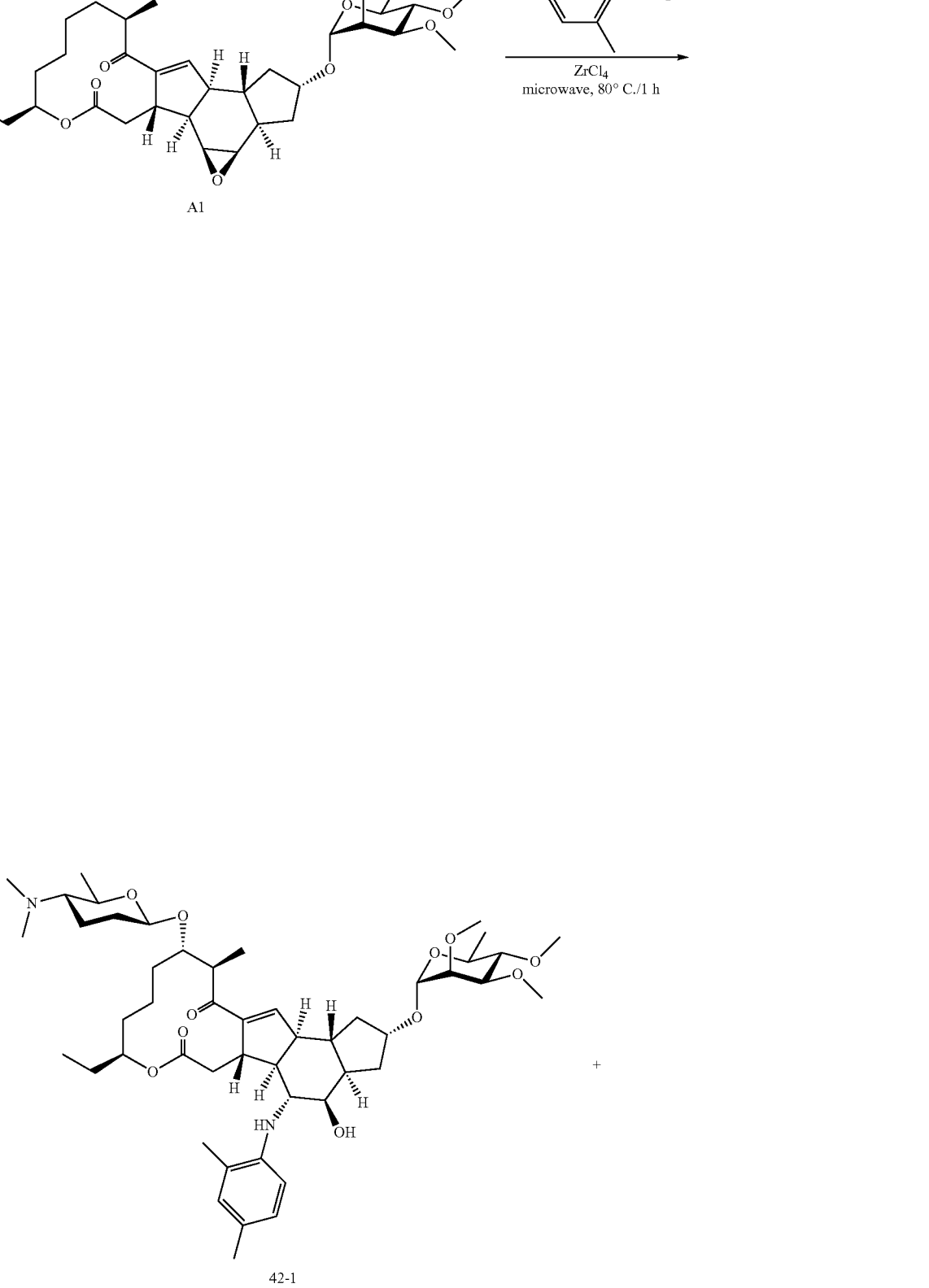

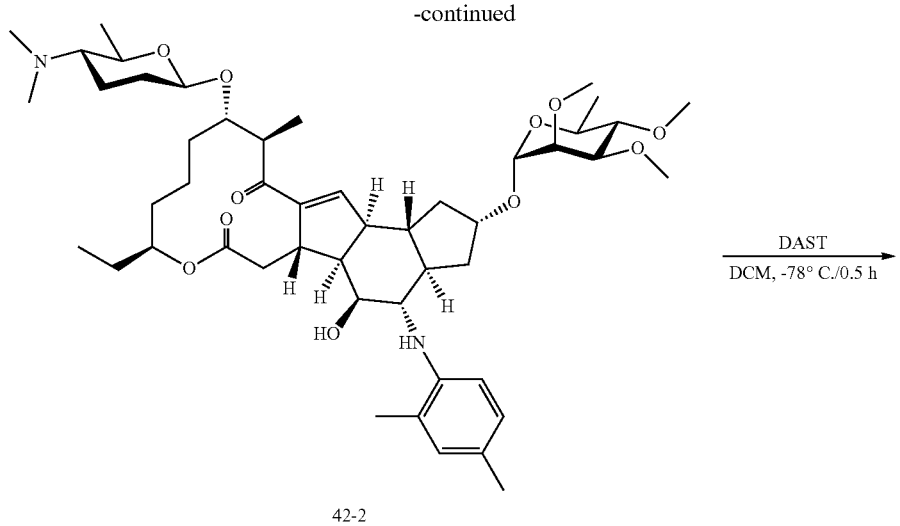

42-2

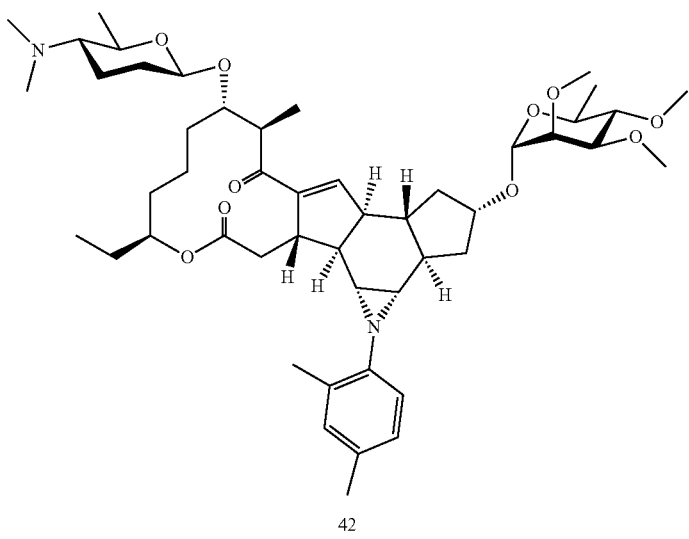

42

To a solution of compound A1 (400 mg, 0.53 mmol) in 2,4-dimethylaniline (5 mL) was added ZrCl$_4$ (6.0 mg, 0.026 mmol). The mixture was stirred at 80° C. under microwave for 1 h. The mixture was purified by silica gel column (DCM:MeOH=20:1-10:1) and then prep-HPLC to give a mixture of compound 42-1 and 42-2 (180 mg) as white solid. LCMS: m/z 869.2 [M+H]$^+$.

To a solution of a mixture of compounds 42-1 and 42-2 (173 mg, 0.2 mmol) in DCM (5 mL) was added DAST (99 mg, 0.6 mmol) at −78° C. under N$_2$ pressure. The mixture was stirred at −78° C. under N$_2$ pressure for 0.5 h. The reaction mixture was quenched with saturated NaHCO$_3$ solution (10 mL) and extracted with DCM (15 mL×2). The combined organic phase was dried over anhydrous Na$_2$SO$_4$, filtered and concentrated. The residue was purified by Prep-HPLC to afford compound 42 (20 mg, yield 11.7%) as a white solid. Partial $^1$H NMR (CDCl$_3$, 400 MHz): δ6.94 (s, 1H), 6.88 (d, J=9.2 Hz, 1H), 6.77-6.73 (m, 2H), 4.88 (s, 1H), 4.69 (s, 1H), 4.42 (d, J=11.2 Hz, 1H), 4.31 (s, 1H), 2.36 (s, 3H), 0.84 (t, J=7.6 Hz, 3H), LCMS: m/z 851.2 [M+H]$^+$ Synthesis of Compounds A3, A4 and 43
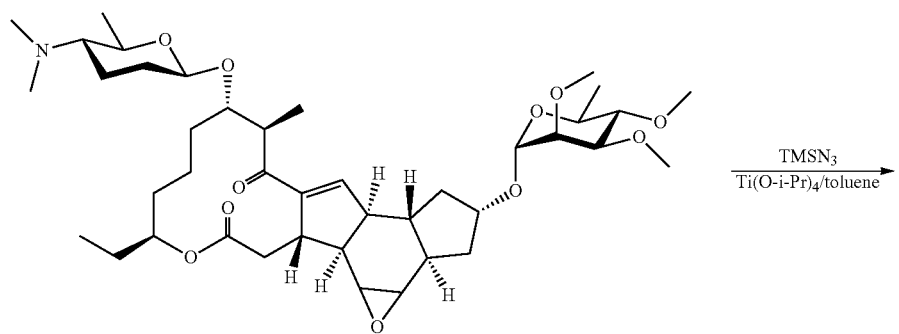
A
(A1/A2 = 5/1)
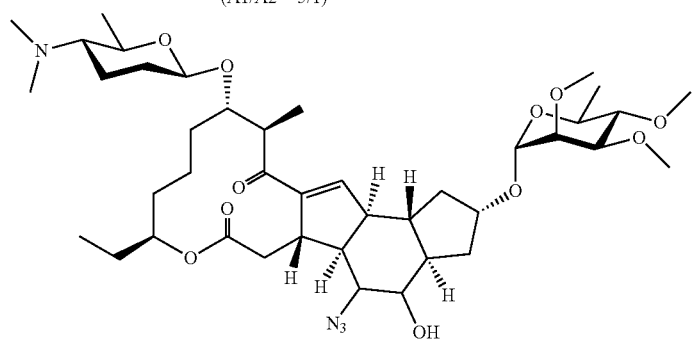
N1
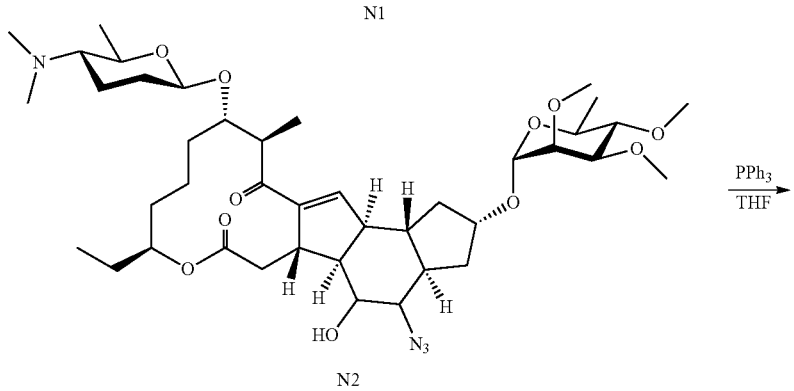
N2
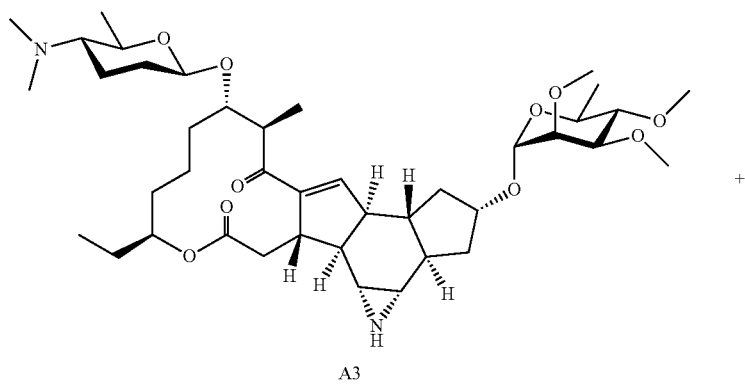
A3

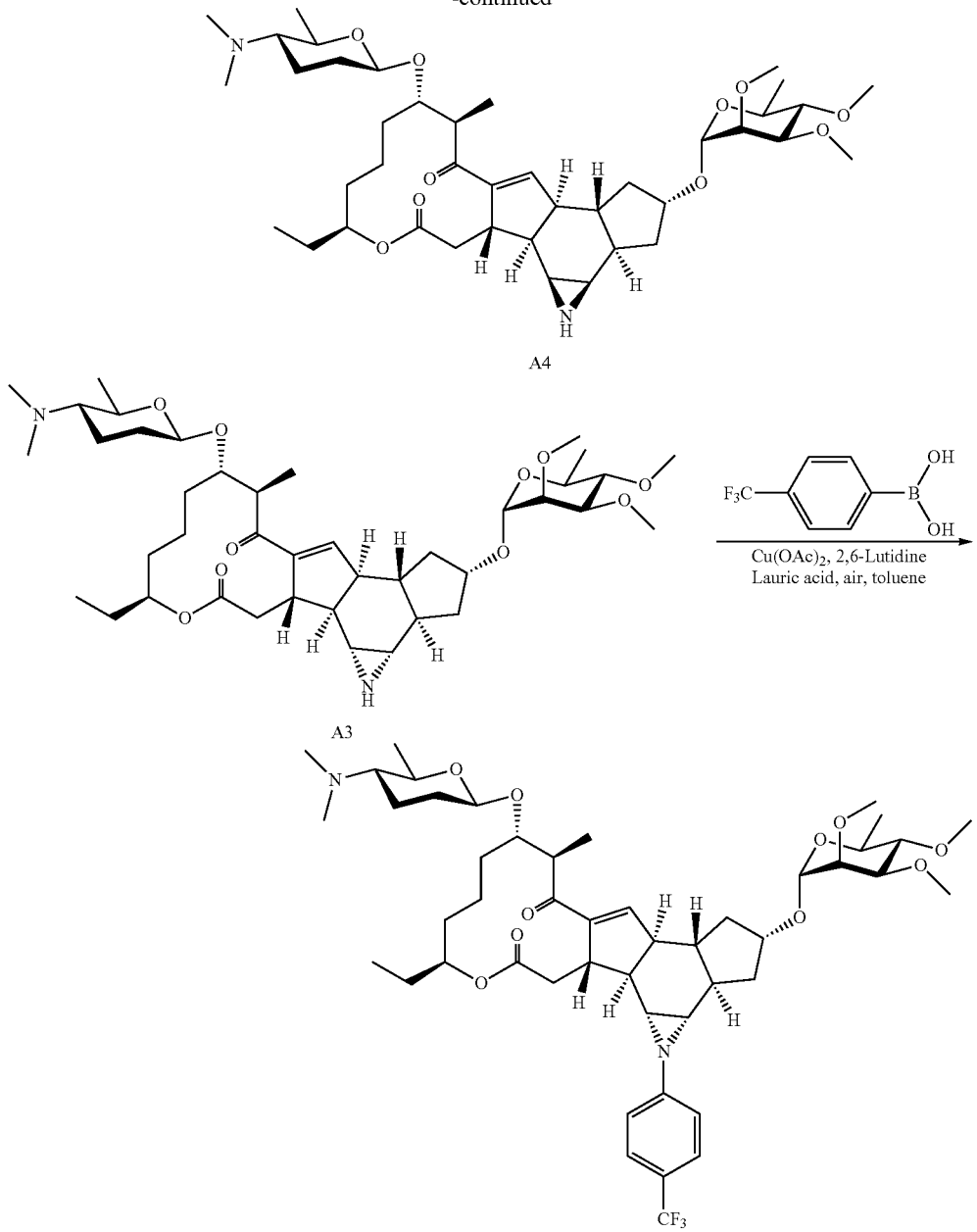

To a solution of epoxide compound A (A1/A2=5/1, 3.0 g, 4.0 mmol) and Trimethylsilyl azide (923 mg, 8.0 mmol) in toluene (30 mL) was added Ti(O-iPr)$_4$ (1.14 g, 4.0 mmol). The mixture was stirred at 120° C. overnight. After cooled to r.t, the mixture was quenched with H$_2$O and extracted with DCM (30 mL×3). The combined organic layer was dried over potassium carbonate, filtered and concentrated to give a mixture of compound N$_1$ and N$_2$ (2.9 g) which was used for next step without further purification.

To a solution of compounds N$_1$ and N$_2$ (2.9 g, 3.6 mmol) in THF (30 mL) was added PPh3 (961 mg, 3.6 mmol). The mixture was heated to reflux for 3 h. The mixture was concentrated and the residue was purified by column chromatography on silica gel (DCM/MeOH=15/1) to give the crude product which was further purified by prep-HPLC to afford compound A3 (930 mg) and A4 (116 mg) as white solid.

A3 (AG-733): Partial $^1$H NMR (CDCl$_3$, 400 MHz): δ6.72 (s, 1H), 4.85 (s, 1H), 4.70-4.66 (m, 1H), 4.43-4.41 (m, 1H), 4.29-4.25 (m, 1H), 3.29-3.18 (m, 3H), 3.14-3.07 (m, 2H), 2.49-2.45 (m, 2H), 2.16-2.07 (m, 3H), 1.99-1.97 (m, 1H), 0.82 (t, J=7.2 Hz, 3H). LCMS: m/z 747.2 [M+H]$^+$ A4: Partial $^1$H NMR (CDCl$_3$, 300 MHz): δ6.57 (s, 1H), 4.86 (s, 1H), 4.67-4.62 (m, 1H), 4.40-4.41 (m, 1H), 4.25-4.18 (m, 1H), 3.67-3.63 (m, 3H), 3.36-3.08 (m, 4H), 2.57-2.49 (m, 2H), 2.43-2.37 (m, 1H, 0.82 (t, J=7.8 Hz, 3H). LCMS: m/z 747.2 [M+H]$^+$.

To a solution of 4-Trifluoromethylphenylboronic acid (151 mg, 0.79 mmol) and Cu(OAc)$_2$ (10 mg, 0.05 mmol) in toluene (20 mL) were added 2,6-Lutidine (57.4 mg, 0.53 mmol), Lauric acid (21.2 mg, 0.1 mmol) and compound A3 (400 mg, 0.53 mmol). The mixture was stirred under air atmosphere for two days at room temperature. The mixture was concentrated and the residue was purified by column chromatography on silica gel (MeOH/DCM=1/20) and prep-HPLC to afford compound 43 (40 mg, yield 8.5%) as a white solid. Partial $^1$H NMR (CDCl$_3$, 400 MHz): δ7.47 (d, J=8.4 Hz, 2H), 7.08 (d, J=8.4 Hz, 2H), 6.95 (s, 1H), 4.89 (s, 1H), 4.74-4.65 (m, 1H), 4.47-4.41 (m, 1H), 4.38-4.28 (m, 1H), 3.69-3.61 (m, 1H), 3.35-3.23 (m, 2H), 3.17-3.07 (m, 2H), 2.60-2.41 (m, 3H), 2.28-2.13 (m, 10H), 2.04-1.94 (m, 1H), 0.90-0.74 (m, 4H). LCMS: m/z 891.4 [M+H]$^+$.

43. Synthesis of Compound 44

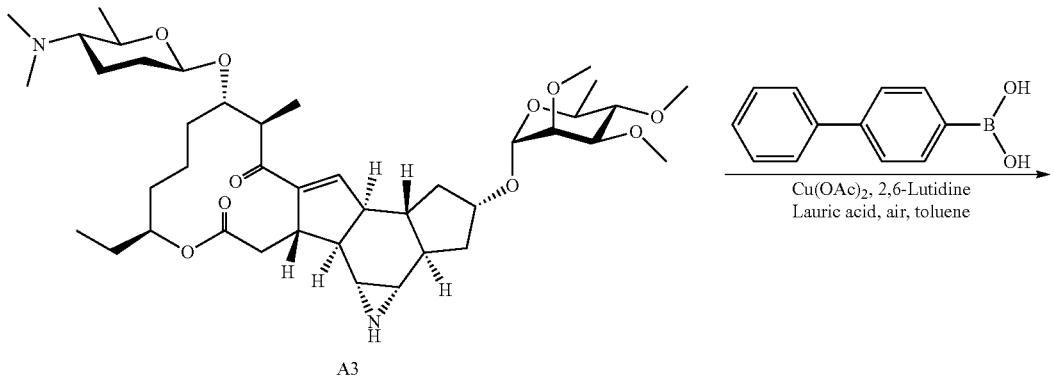

A3

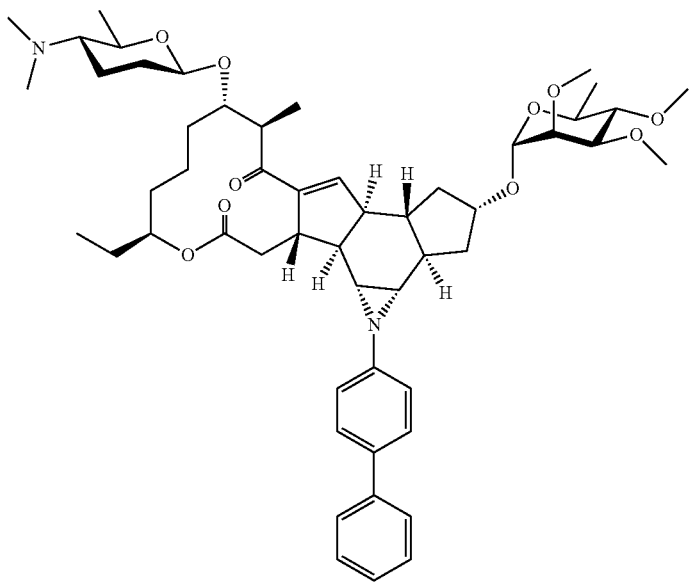

44

To a solution of 4-Biphenylboronic acid (119 mg, 0.6 mmol) and Cu(OAc)$_2$ (15.9 mg, 0.08 mmol) in toluene (20 mL) were added 2,6-Lutidine (42.8 mg, 0.4 mmol), Lauric acid (8.0 mg, 0.04 mmol) and compound A3 (300 mg, 0.4 mmol). The mixture was stirred under air atmosphere for two days at room temperature. The mixture was concentrated and the residue was purified by column chromatography on silica gel (MeOH/DCM=1/20) and prep-HPLC to afford compound 44 (30 mg, yield 8.3%) as white solid.

Partial $^1$H NMR (CDCl$_3$, 400 MHz): δ7.54 (d, J=8.8 Hz, 2H), 7.47 (d, J=8.8 Hz, 2H), 7.41 (t, J=8.0 Hz, 2H), 7.29-7.26 (m, 1H), 7.09 (d, J=8.4 Hz, 2H), 6.76 (s, 1H), 4.89 (s, 1H), 4.75-4.66 (m, 1H), 4.46-4.40 (m, 1H), 3.37-3.30 (m, 1H), 3.69-3.61 (m, 1H), 3.34-3.25 (m, 2H), 3.18-3.08 (m, 2H), 2.61-2.50 (m, 2H), 2.45-2.41 (m, 1H), 2.26-2.16 (m, 9H), 0.90-0.79 (m, 4H). LCMS: m/z 899.4 [M+H]$^+$.

44. Synthesis of Compound 45

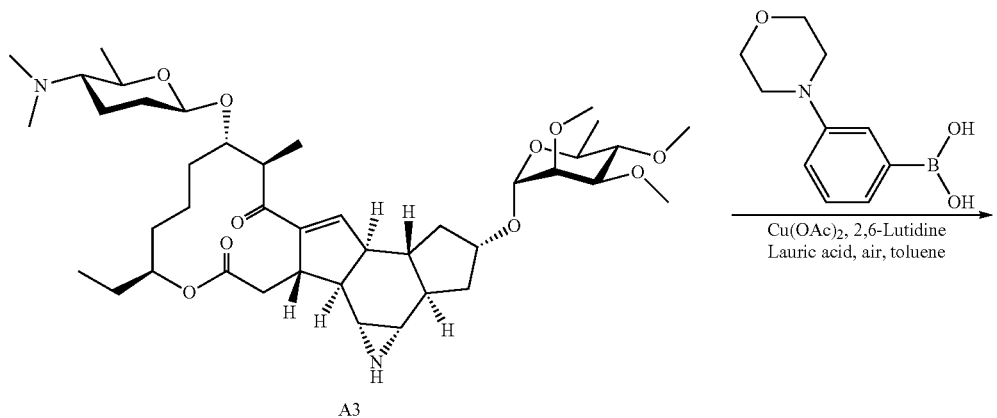

A3

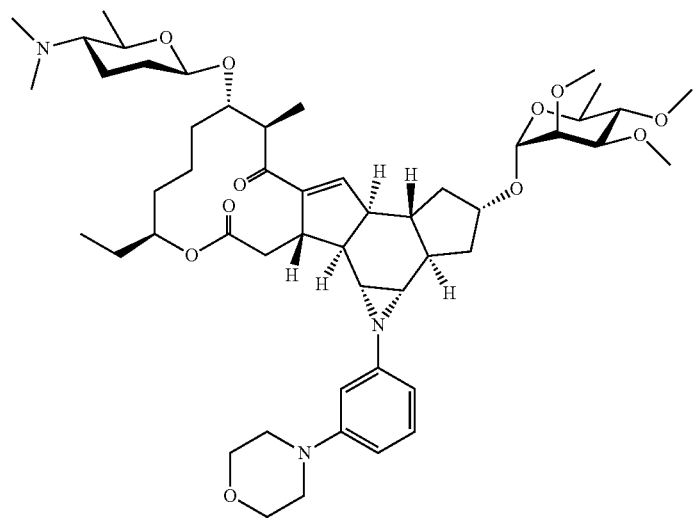

45

To a solution of 3-(Morpholino)phenylboronic acid (124 mg, 0.6 mmol) and Cu(OAc)$_2$ (15.6 mg, 0.08 mmol) in toluene (10 mL) were added 2,6-Lutidine (42.8 mg, 0.4 mmol), Lauric acid (8.0 mg, 0.04 mmol) and compound A3 (300 mg, 0.4 mmol) The mixture was stirred under air atmosphere for two days at room temperature. The mixture was concentrated and the residue was purified by column chromatography on silica gel (MeOH/DCM=1/20) and prep-HPLC to afford compound 45 (40 mg, yield 11.2%) as white solid. Partial $^1$H NMR (CDCl$_3$, 400 MHz): δ7.94-7.89 (m, 2H), 7.48 (dd, J=8.8 Hz, 2H) 7.27-7.20 (m, 2H), 6.78 (s, 1H), 4.91 (s, 1H), 4.76-4.67 (m, 1H), 4.47-4.42 (m, 1H), 4.39-4.31 (m, 1H), 3.69-3.62 (m, 1H), 3.58-3.44 (m, 15H), 3.36-3.25 (m, 2H), 3.21-3.09 (m, 2H), 2.70 (s, 3H), 2.64-2.49 (m, 3H), 2.34-2.17 (m, 11H), 1.33-1.16 (m, 2H), 0.91-0.80 (m, 4H). LCMS: m/z 888.4 [M+H]$^+$.

46. Synthesis of Compound 46

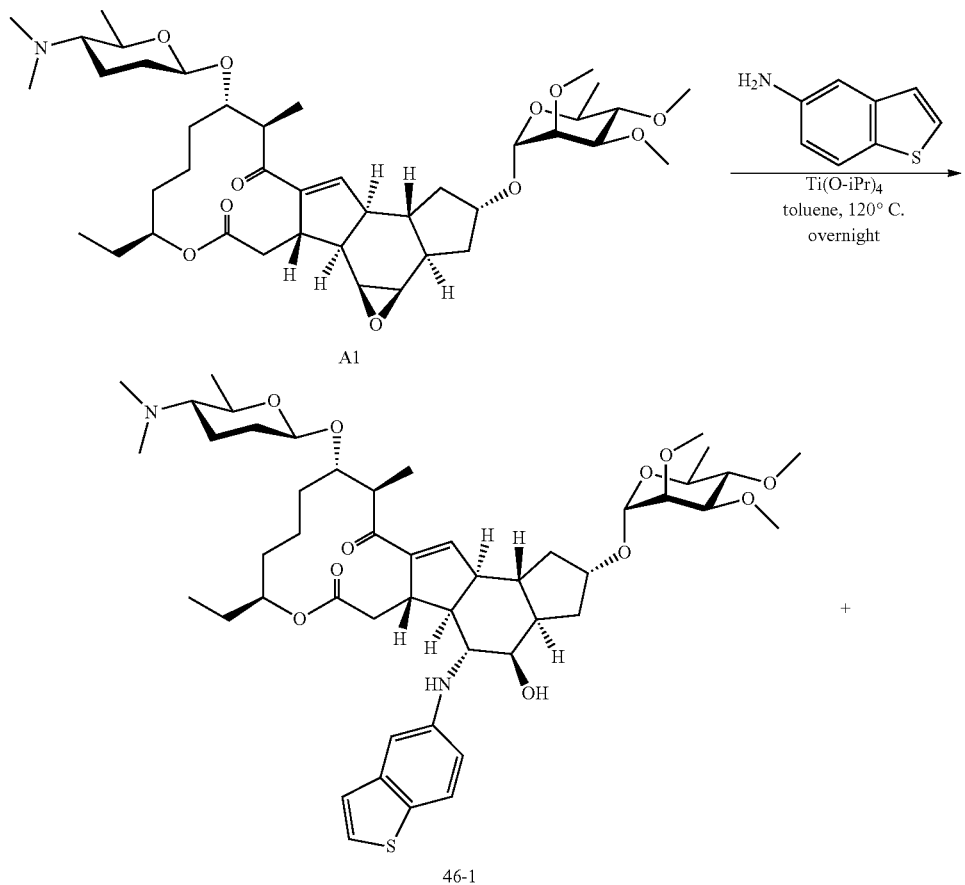

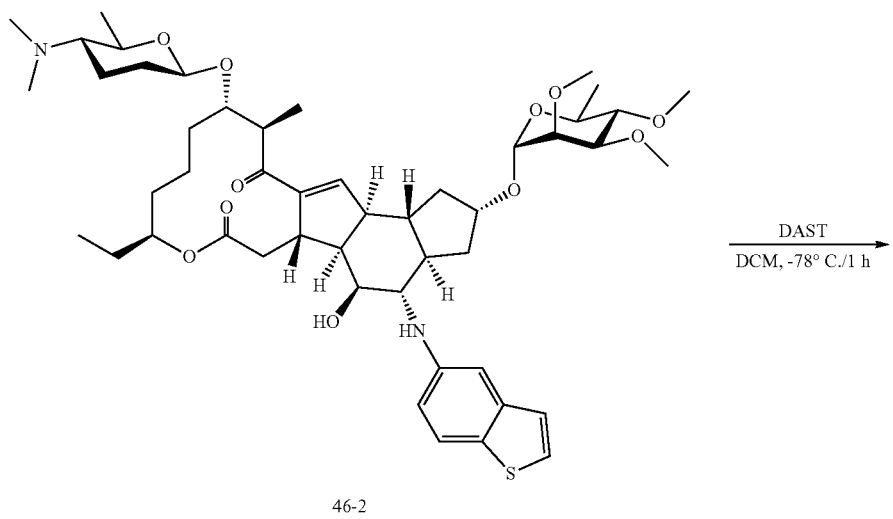

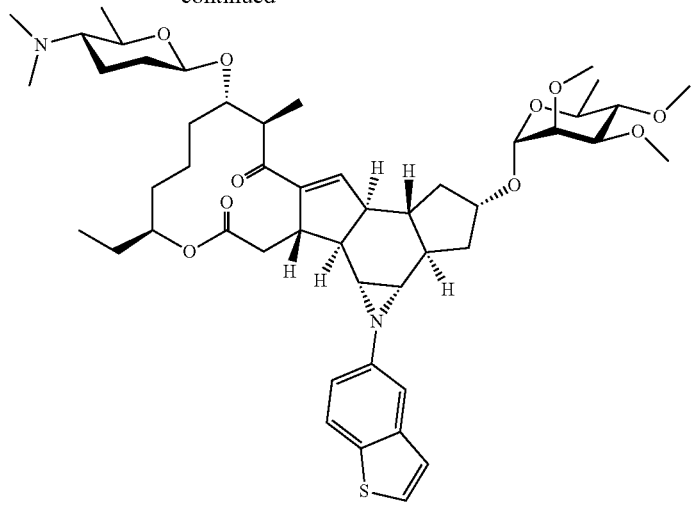

46

To a solution of compound A1 (0.5 g, 0.65 mmol) in toluene (15 mL) were added Ti(O-iPr)$_4$ (190 mg, 0.67 mmol) and benzo[b]thiophen-5-amine (200 mg, 1.34 mmol). After stirred at 120° C. for overnight, the mixture was concentrated and the residue was diluted with EA (30 ml) and washed with water. The organic layer was dried over Na$_2$SO$_4$, filtered and concentrated. The residue was purified by flash to give the crude compounds 46-1 and 46-2 (236 mg, yield 39%) as brown solid which used in next step without further purification. LC-MS: m/z 897.4 [M+H]$^+$.

To a solution of a mixture of compounds 46-1 and 46-2 (225 mg, 0.25 mmol) in DCM (5 mL) was added DAST (82 mg, 0.5 mmol) at −78° C. under N$_2$ pressure. The mixture was stirred at −78° C. under N$_2$ pressure for 1 h. The reaction mixture was quenched with saturated NaHCO$_3$ solution (10 mL) and extracted with DCM (15 mL×2). The combined organic phase was dried over anhydrous Na$_2$SO$_4$, filtered and concentrated. The residue was purified by Prep-HPLC to afford compound 46 (18 mg, yield 8.1%) as yellow solid. Partial $^1$H NMR (CDCl$_3$, 400 MHz): δ 7.71 (d, J=8.8 Hz, 1H), 7.42 (d, J=5.2 Hz, 1H), 7.38 (s, 1H), 7.24 (d, J=5.2 Hz, 1H), 7.12 (d, J=8.8 Hz, 1H), 6.77 (s, 1H), 4.90 (s, 1H), 4.72-4.70 (m, 1H), 4.43 (d, J=7.2 Hz, 1H), 4.35-4.33 (m, 1H), 3.33-3.27 (m, 2H), 3.16-3.10 (m, 2H), 2.58-2.53 (m, 2H), 2.22-2.18 (m, 10H), 0.87 (t, J=7.2 Hz, 3H); LC-MS: m/z 879.4 [M+H]$^+$.

47. Synthesis of Compound 47

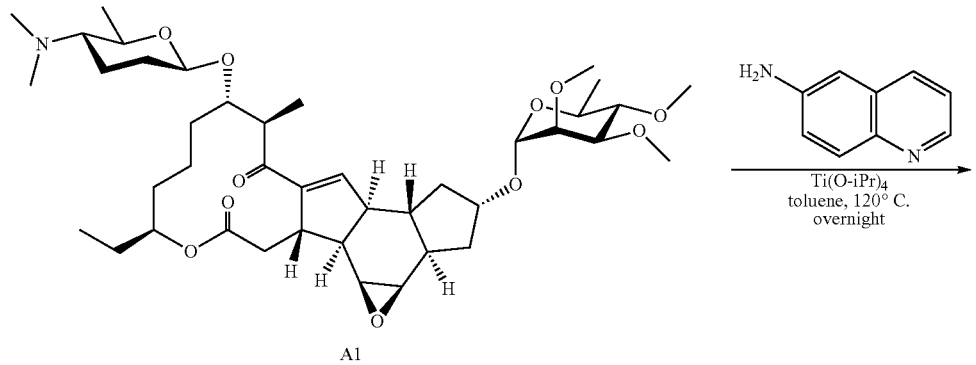

-continued
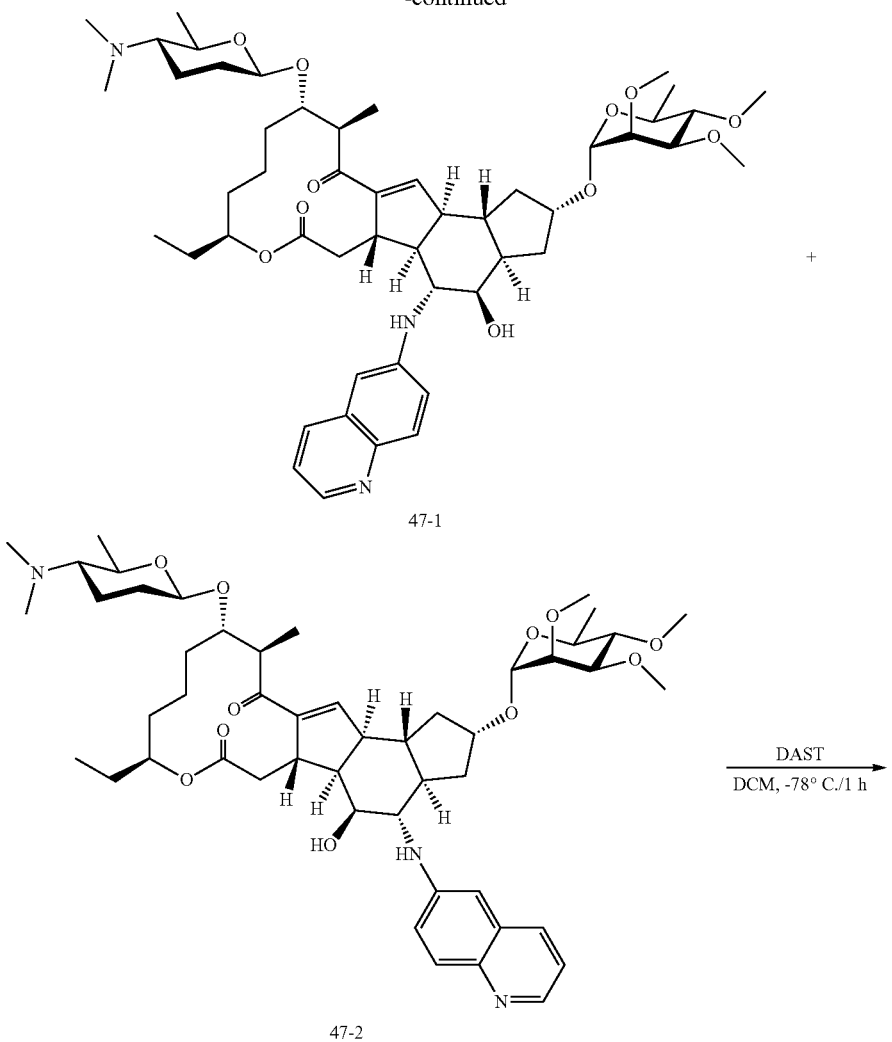
47-1
47-2
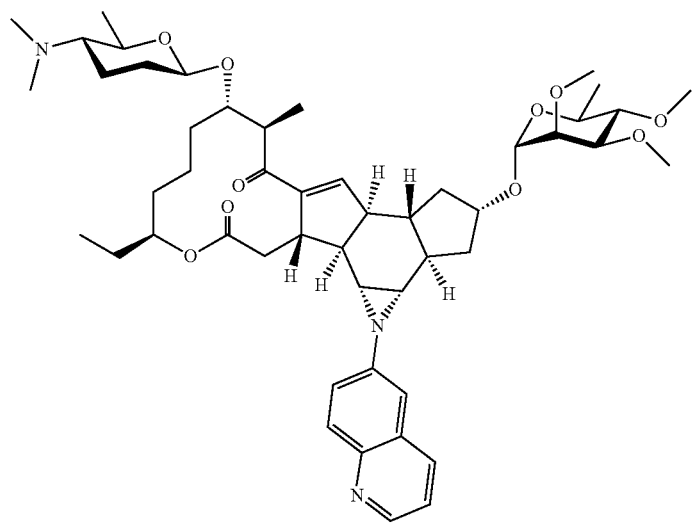
47

To a solution of compound A1 (0.2 g, 0.26 mmol) in toluene (10 mL) was added Ti(O-iPr)$_4$ (76 mg, 0.26 mmol) and quinolin-6-amine (77 mg, 0.53 mmol). After stirred at 120° C. for overnight, the mixture was concentrated and the residue was diluted with EA (30 ml) and washed with water. The organic layer was dried over Na$_2$SO$_4$, filtered and concentrated. The residue was purified by flash to give the crude compounds 47-1 and 47-2 (90 mg, yield 38%) as brown solid which used in next step without further purification. LC-MS: m/z 899.2 [M+H]$^+$.

To a solution of a mixture of compounds 47-1 and 47-2 (90 mg, 0.1 mmol) in DCM (5 mL) was added DAST (33 mg, 0.2 mmol) at −78° C. under N$_2$ pressure. The mixture was stirred at −78° C. under N$_2$ pressure for 1 h. The reaction mixture was quenched with saturated NaHCO$_3$ solution (10 mL) and extracted with DCM (15 mL×2). The combined organic phase was dried over anhydrous Na$_2$SO$_4$, filtered and concentrated. The residue was purified by Prep-HPLC to afford compound 47 (10 mg, yield 11%) as white solid. Partial $^1$H NMR (CDCl$_3$, 400 MHz): δ 8.77-8.75 (m, 1H), 8.04-7.89 (m, 2H), 7.53-7.51 (m, 1H), 7.35-7.33 (m, 1H), 7.24 (m, 1H), 6.77 (s, 1H), 4.91 (s, 1H), 4.71 (s, 1H), 4.44 (d, J=8.0 Hz, 1H), 4.37-4.34 (m, 1H), 3.35-3.32 (m, 2H), 3.15-3.13 (m, 2H), 2.58-2.54 (m, 3H), 2.34-2.19 (m, 12H); LC-MS: m/z 881.2 [M+H]$^+$.

48. Synthesis of Compound 48

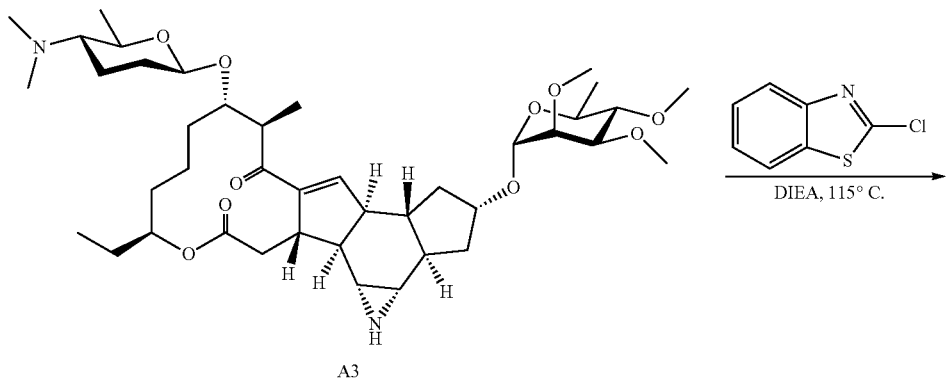

A3

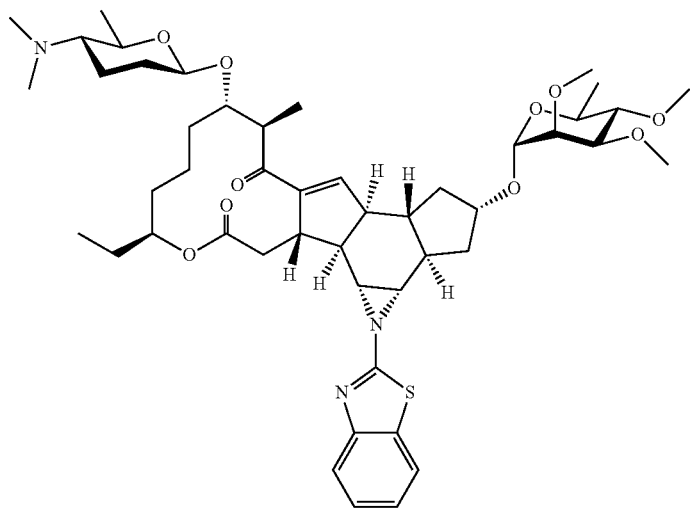

48

To a solution of compound A3 (100 mg, 0.13 mmol) in DIEA (5 mL) was added 2-Chloro-benzothiazole (45.3 mg, 0.27 mmol). The resulting mixture was stirred at 115° C. for 3 h under $N_2$. The mixture was quenched with water (50 mL) and extracted with DCM (30 mL×3). The combined organic layer was dried over potassium carbonate, filtered and concentrated. The residue was purified by prep-HPLC to afford compound 48 (20 mg, yield 17.5%) as white solid.

Partial $^1$H NMR (CDCl$_3$, 400 MHz): δ 7.74 (d, J=8.0 Hz, 1H), 7.69 (d, J=7.6 Hz, 1H), 7.41-7.36 (m, 1H), 7.26-7.22 (m, 1H), 6.75 (s, 1H), 4.88 (s, 1H), 4.75-4.68 (m, 1H), 3.31-3.22 (m, 2H), 3.19-3.08 (m, 3H), 2.75 (d, J=6.4 Hz, 1H), 2.67-2.59 (m, 1H), 2.56-2.50 (m, 1H), 0.92-0.78 (m, 5H); LC-MS: m/z 880.2 [M+H]$^+$.

49. Synthesis of Compound 49

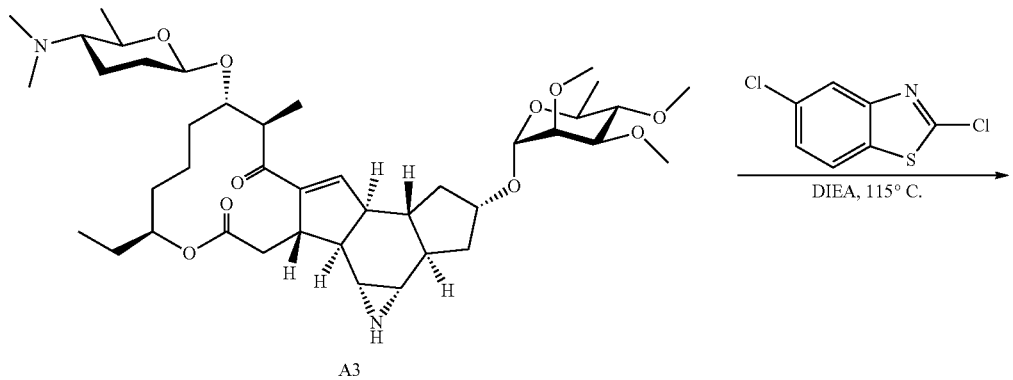

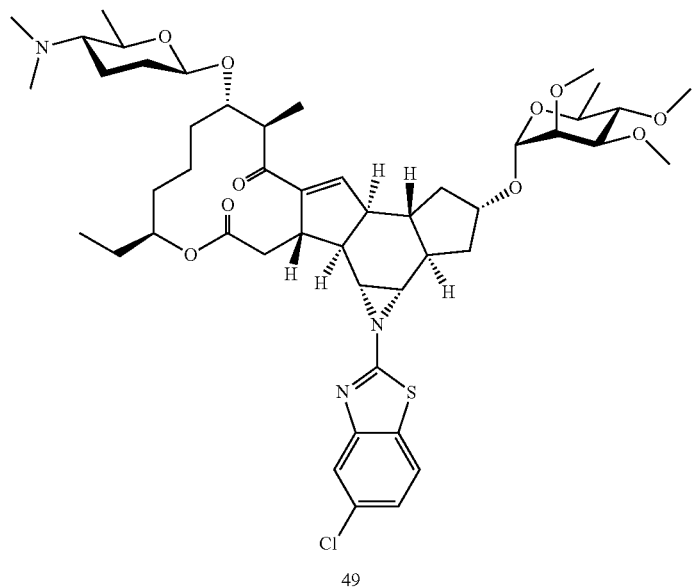

49

To a solution of compound A3 (200 mg, 0.26 mmol) in DIEA (5 mL) was added 2,5-Dichloro-benzothiazole (110 mg, 0.54 mmol). The resulting mixture was stirred at 115° C. for 3 h under $N_2$. The reaction was quenched with water (50 mL) and extracted with DCM (20 mL×3). The combined organic layer was dried over potassium carbonate, filtered and concentrated. The residue was purified by prep-HPLC to afford compound 49 (17 mg, yield 7.1%) as a yellow solid. Partial $^1$H NMR (CDCl$_3$, 400 MHz): δ 7.65-7.63 (m, 2H), 7.33 (dd, J=2.4, 2.0 Hz, 1H), 6.74 (s, 1H), 5.36-5.33 (m, 1H), 4.88 (s, 1H), 4.75-4.67 (m, 1H), 4.44-4.41 (m, 1H), 4.36-4.31 (m, 1H), 3.68-3.60 (m, 1H), 3.29-3.22 (m, 2H), 3.18-3.09 (m, 3H), 2.77 (d, J=6.0 Hz, 1H), 2.65-2.49 (m, 2H), 2.04-1.96 (m, 3H), 0.89-0.78 (m, 5H); LC-MS: m/z 914.4 [M+H]$^+$.

50. Synthesis of Compound 50

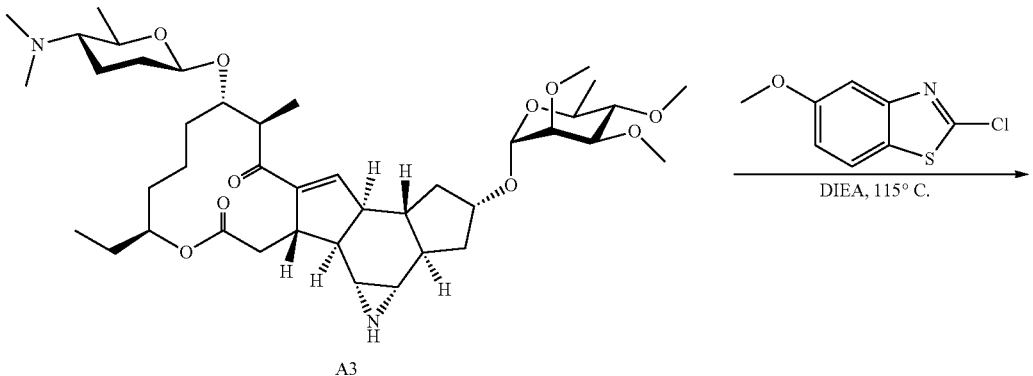

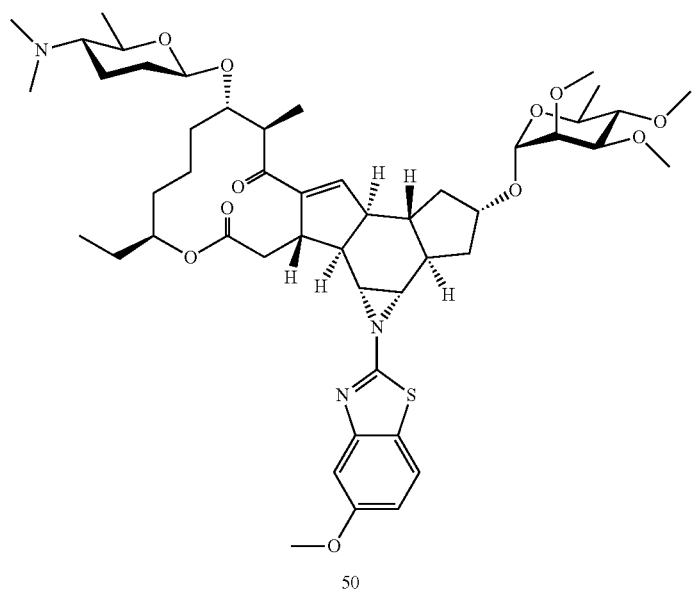

To a solution of compound A3 (200 mg, 0.27 mmol) in DIEA (5 mL) was added 2-Chloro-5-methoxy-benzothiazole (107 mg, 0.53 mmol). The resulting mixture was stirred at 115° C. for 4 h under nitrogen. The reaction was quenched with water (50 mL) and extracted with DCM (20 mL×3). The combined organic layer was dried over potassium carbonate, filtered and concentrated. The residue was purified by prep-HPLC to afford compound 50 (10 mg, yield 4.0%) as a yellow solid. Partial $^1$H NMR (CDCl$_3$, 400 MHz): 7.63 (d, J=7.2 Hz, 1H), 7.17 (d, J=2.4 Hz, 1H), 6.98-6.96 (m, 1H), 6.74 (s, 1H), 4.88 (s, 1H), 4.73-4.68 (m, 1H), 4.45-4.40 (m, 1H), 4.35-4.32 (m, 1H), 3.84 (s, 3H), 3.66-3.61 (m, 2H), 3.57-3.42 (m, 29H), 3.29-3.22 (m, 3H), 3.18-3.08 (m, 3H), 2.75-2.72 (m, 1H); LC-MS: m/z 910.4 [M+H]$^+$.

51. Synthesis of Compound 51

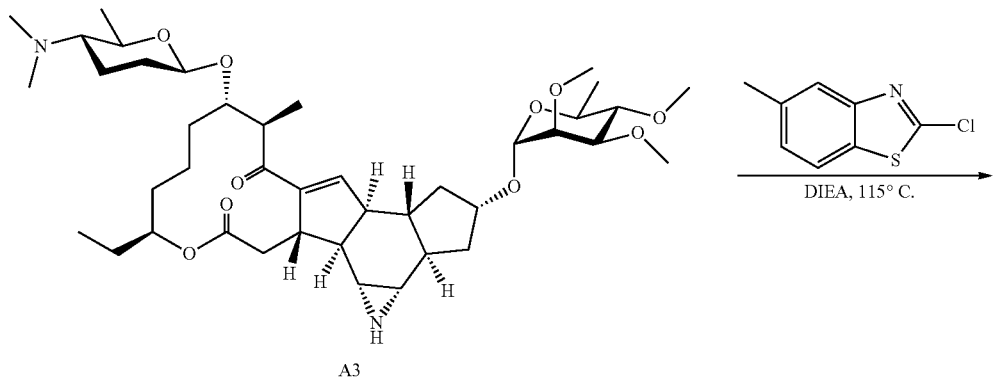

A3

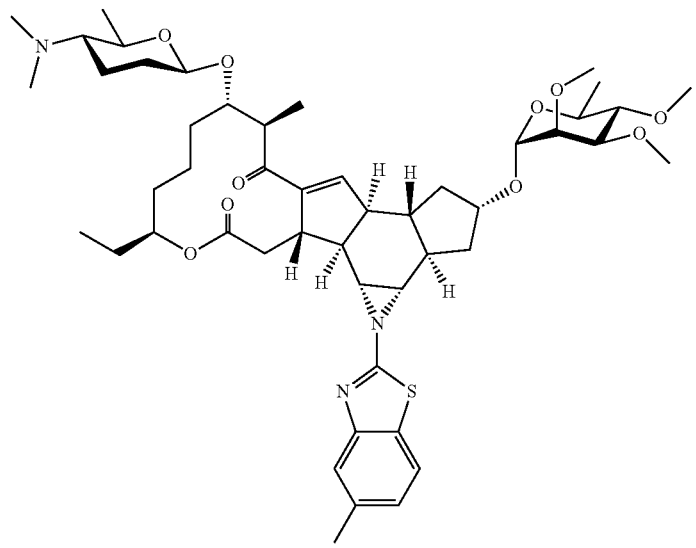

51

To a solution of compound A3 (200 mg, 0.26 mmol) in DIEA (5 mL) was added 2-Chloro-5-methyl-benzothiazole (99.4 mg, 0.54 mmol). The resulting mixture was stirred at 115° C. for 3 h under $N_2$. The reaction was quenched with water (50 mL) and extracted with DCM (20 mL×3). The combined organic layer was dried over potassium carbonate, filtered and concentrated. The residue was purified by prep-HPLC to afford compound 51 (15 mg, yield 6.0%) as a yellow solid. Partial $^1$H NMR (CDCl$_3$, 400 MHz): δ 7.50 (d, J=5.6 Hz, 1H), 7.20-7.12 (m, 2H), 6.75 (s, 1H), 4.89 (s, 1H), 4.75-4.68 (m, 1H), 4.45-4.41 (m, 1H), 4.37-4.30 (m, 1H), 3.67-3.42 (m, 20H), 3.31-3.08 (m, 6H), 2.75 (d, J=6.8 Hz, 1H), 2.62 (s, 3H), 2.55-2.49 (m, 1H), 0.89-0.82 (m, 6H); LC-MS: m/z 895.4 [M+H]$^+$.

52. Synthesis of Compound 52

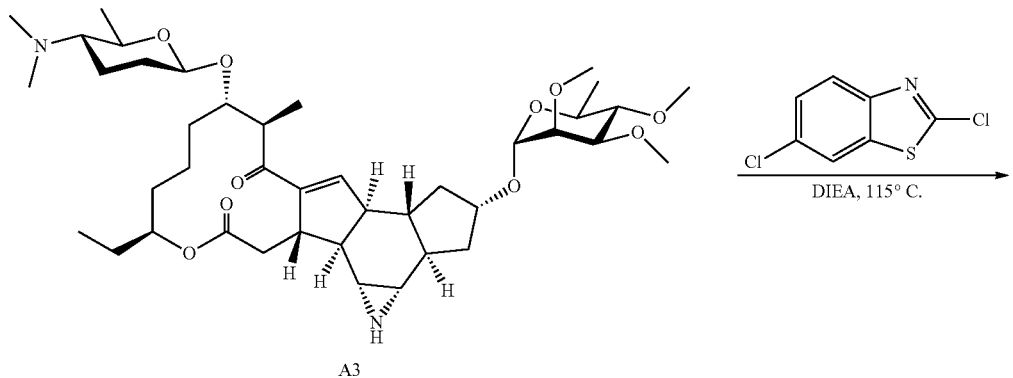

A3

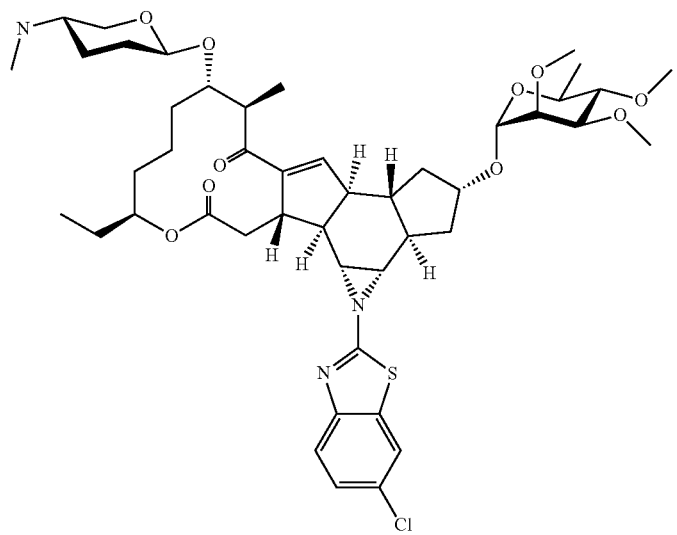

52

To a solution of compound A3 (200 mg, 0.26 mmol) in DIEA (10 mL) was added 2,5-Dichloro-benzothiazole (110 mg, 0.54 mmol). The resulting mixture was stirred at 115° C. for 3 h under $N_2$. The reaction was quenched with water (50 mL) and extracted with DCM (20 mL×3). The combined organic layer was dried over potassium carbonate, filtered and concentrated. The residue was purified by prep-HPLC to afford compound 52 (17 mg, yield 7.1%) as a yellow solid.

Partial $^1$H NMR (CDCl$_3$, 400 MHz): δ 7.72 (s, 1H) 7.57 (d, J=9.6 Hz, 1H), 7.22 (d, J=6.8 Hz, 1H), 6.74 (s, 1H), 4.88 (s, 1H), 4.71 (m, 1H), 4.42 (d, J=7.6 Hz, 1H), 4.33 (m, 1H), 3.27-3.24 (m, 2H), 2.76 (d, J=6.4 Hz, 1H), 0.85 (t, J=7.6 Hz, 3H); LC-MS: m/z 916.3 [M+H]$^+$.

53. Synthesis of Compound 53

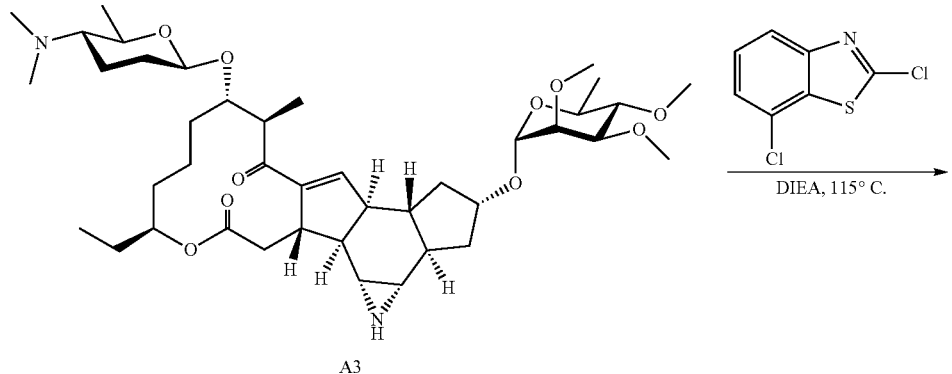

A3

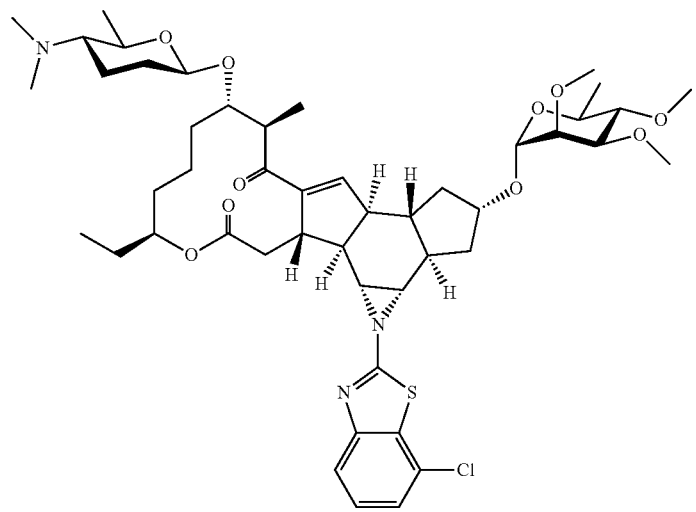

53

To a solution of compound A3 (200 mg, 0.26 mmol) in DIEA (10 mL) was added 2,7-Dichloro-benzothiazole (110 mg, 0.54 mmol). The resulting mixture was stirred at 115° C. for 3 h under $N_2$. The reaction was quenched with water (50 mL) and extracted with DCM (20 mL×3). The combined organic layer was dried over potassium carbonate, filtered and concentrated. The residue was purified by prep-HPLC to afford compound 53 (20 mg, yield 8.3%) as a yellow solid.

Partial $^1$H NMR (CDCl$_3$, 400 MHz): δ 7.63 (d, J=8.0 Hz, 1H), 7.32-7.23 (m, 2H), 6.74 (s, 1H), 4.88 (s, 1H), 4.75-4.70 (m, 1H), 4.45-4.38 (m, 1H), 4.36-4.31 (m, 1H), 3.68-3.41 (m, 17H), 3.30-3.09 (m, 6H), 2.80 (d, J=6.0 Hz, 1H), 2.67-2.51 (m, 2H), 2.32-2.13 (m, 10H), 0.85 (t, J=7.2 Hz, 3H); LC-MS: m/z 914.3 [M+H]$^+$.

54. Synthesis of Compound 54

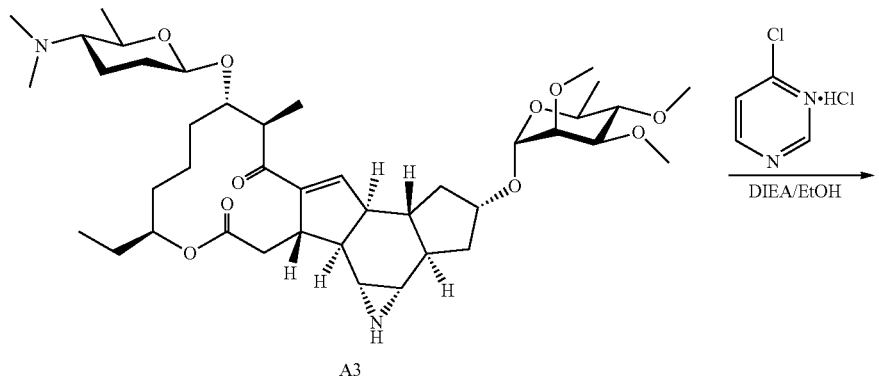

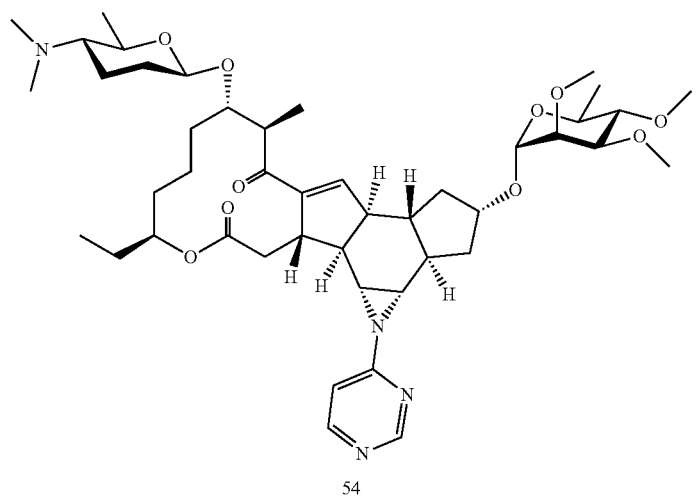

To a solution of compound A3 (100 mg, 0.13 mmol) and DIEA (86 mg, 0.67 mmol) in EtOH (2 mL) was added 4-chloropyrimidine hydrochloride (40 mg, 0.26 mmol). The mixture was heated to 85° C. for 20 h. The mixture was purified by Prep-HPLC to afford compound 54 (26 mg, 23.6% yield). Partial $^1$H NMR (CDCl$_3$, 300 MHz): δ7.73 (s, 1H), 7.33 (d, J=8.1 Hz, 1H), 6.67 (s, 1H), 6.23 (d, J=7.2 Hz, 1H), 4.86 (s, 1H), 4.65-4.61 (m, 1H), 4.43-4.35 (m, 2H), 4.01-3.96 (m, 1H), 3.89-3.85 (m, 1H), 3.81-3.68 (m, 1H), 2.93-2.86 (m, 1H), 2.60-2.46 (m, 3H).
LC-MS: m/z 825.5 [M+H]$^+$.
55. Synthesis of Compound 55
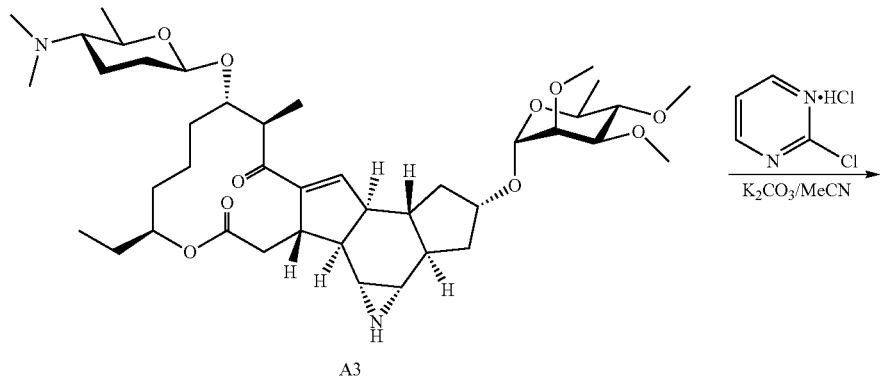
A3
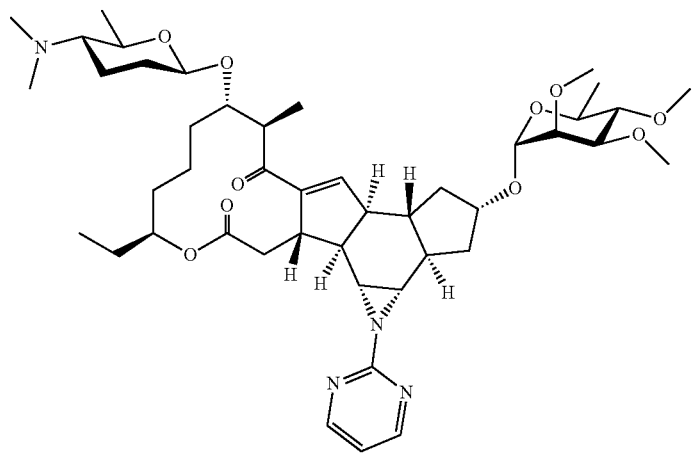
55

To a solution of compound A3 (250 mg, 0.33 mmol) and 2-chloropyrimidine hydrochloride (77 mg, 0.67 mmol) in MeCN (10 mL) was added $K_2CO_3$ (138 mg, 1.0 mmol). The mixture was heated to 85° C. for 20 h. The reaction mixture was concentrated and the residue was diluted with in EA (60 mL). The mixture was washed with water (30 mL), dried over anhydrous $Na_2SO_4$, filtered and concentrated. The residue was purified by prep-HPLC to afford compound 55 (50 mg, 18% yield) Partial $^1$H NMR (CDCl$_3$, 400 MHz): δ8.51 (d, J=4.8 Hz, 2H), 6.90 (t, J=4.8 Hz, 1H), 6.76 (s, 1H), 4.88 (s, 1H), 4.76-4.70 (m, 1H), 4.43-4.41 (m, 1H), 4.35-4.30 (m, 1H), 3.66-3.62 (m, 1H), 3.30-3.19 (m, 3H), 3.11 (t, J=9.6 Hz, 1H), 2.83-2.80 (m, 1H), 2.72 (d, J=6.4 Hz, 1H), 2.70-2.61 (m, 2H), 2.34-2.29 (m, 1H), 0.81 (t, J=7.6 Hz, 3H). LCMS: m/z 825.5 [M+H]$^+$.

56. Synthesis of Compound 56: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl)oxy)-12-ethyl-1-(1H-indol-6-yl)-7-methyl-3-(((2R,3R,4R,5S,6S)-3,4,5-trimethoxy-6-methyltetrahydro-2H-pyran-2-yl)oxy)-1,1a,1b,2,3,4,4a,4b,7,8,9,10,11,12,15,15a,15b,15c-octadecahydro-[1]oxacyclododecino[5',4':2,3]-as-indaceno[4,5-b]azirine-6,14-dione

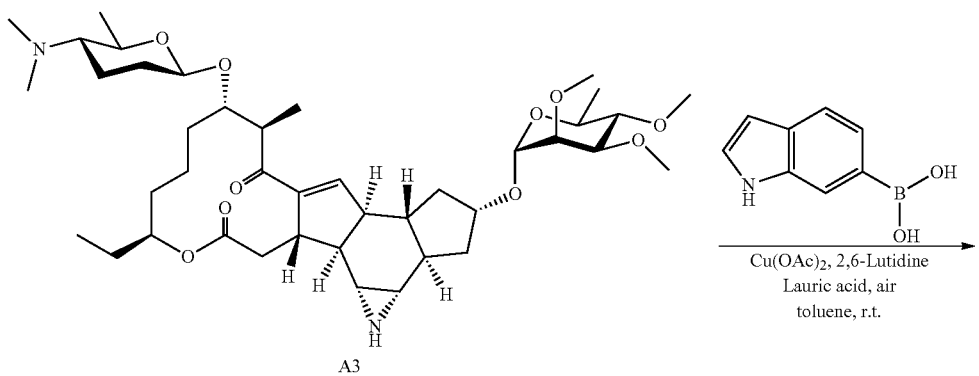

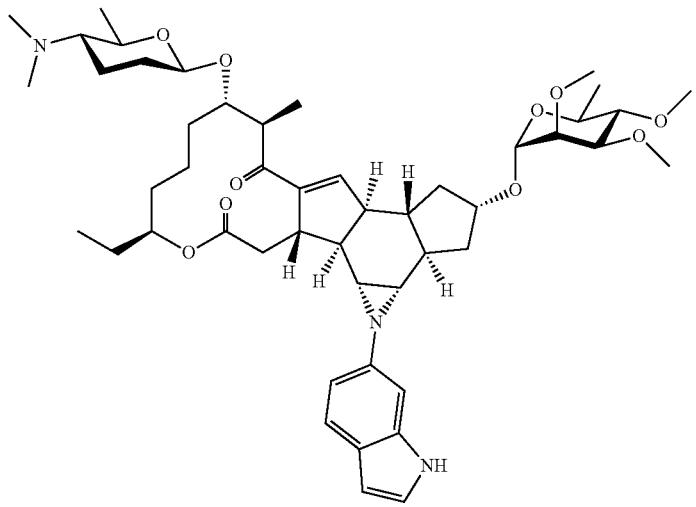

56

To a solution of Indole-6-boronic acid (96 mg, 0.6 mmol) and Cu(OAc)$_2$ (15.6 mg, 0.08 mmol) in toluene (10 mL) were added 2,6-Lutidine (42.8 mg, 0.4 mmol), Lauric acid (8.0 mg, 0.04 mmol) and compound A3 (300 mg, 0.4 mmol). The mixture was stirred under air atmosphere for two days at room temperature. The mixture was concentrated and the residue was purified by column chromatography on silica gel (MeOH/DCM=1/20) and prep-HPLC to afford compound 56 (40 mg, yield 11.6%) as white solid. Partial $^1$H NMR (CDCl$_3$, 400 MHz): δ8.05 (s, 1H), 7.47 (d, J=8.4 Hz, 1H), 7.11 (s, 1H), 7.03 (s, 1H), 6.89 (d, J=4.0 Hz, 1H), 6.77 (s, 1H), 6.46 (s, 1H), 4.90 (s, 1H), 4.75-4.67 (m, 1H), 4.46-4.41 (m, 1H), 3.37-3.29 (m, 1H), 3.70-3.42 (m, 19H), 3.36-3.25 (m, 2H), 3.18-3.07 (m, 2H), 2.62-2.52 (m, 2H), 2.46-2.41 (m, 1H), 2.30-2.13 (m, 12H), 2.03-1.95 (m, 1H), 0.91-0.77 (m, 5H). LCMS: m/z 862.4 [M+H]$^+$.

57. Synthesis of Compound 57

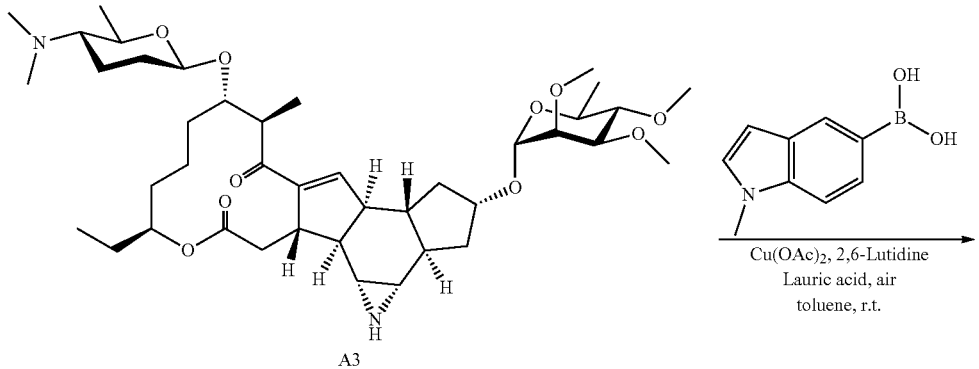

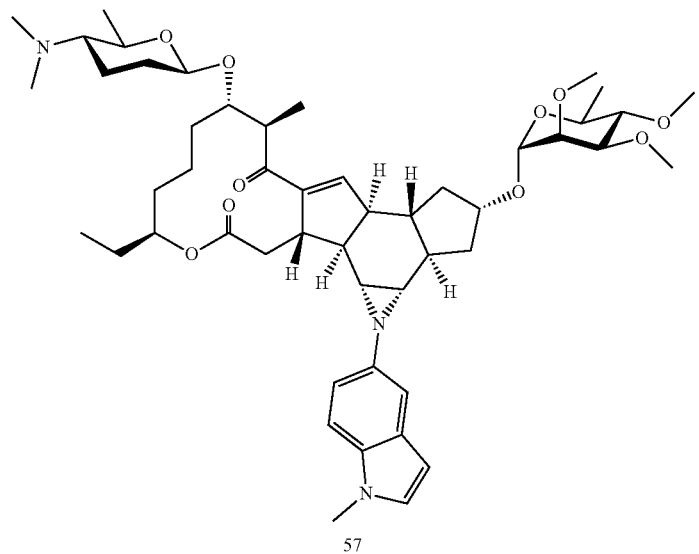

To a solution of N-Methylindole-5-boronic acid (105 mg, 0.6 mmol) and Cu(OAc)$_2$ (15.6 mg, 0.08 mmol) in toluene (10 mL) were added 2,6-Lutidine (42.8 mg, 0.4 mmol), Lauric acid (8.0 mg, 0.04 mmol) and compound A3 (300 mg, 0.4 mmol). The mixture was stirred under air atmosphere for two days at room temperature. The mixture was concentrated and the residue was purified by column chromatography on silica gel (MeOH/DCM=1/20) and prep-HPLC to afford compound 57 (15 mg, yield 4.2%) as white solid.

Partial $^1$H NMR (CDCl$_3$, 400 MHz): δ7.85 (s, 1H), 7.25-7.21 (m, 2H), 6.77 (s, 1H), 4.90 (s, 1H), 4.76-4.67 (m, 1H), 4.46-4.41 (m, 1H), 4.03 (s, 3H), 3.69-3.62 (m, 1H), 3.59-3.43 (m, 15H), 3.35-3.25 (m, 2H), 3.19-3.08 (m, 2H), 2.63-2.52 (m, 2H), 2.46-2.42 (m, 1H), 2.30-2.16 (m, 10H), 2.03-1.95 (m, 1H), 1.32-1.16 (m, 16H), 0.91-0.79 (m, 6H). LCMS: m/z 877.4 [M+H]$^+$.

58. Synthesis of Compound 58

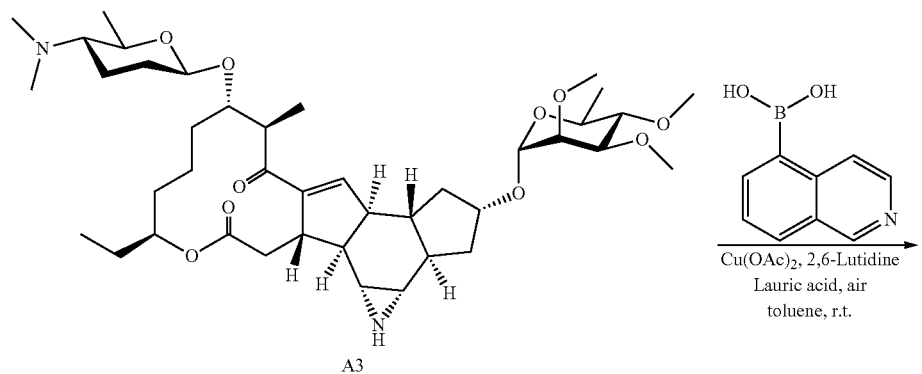

A3

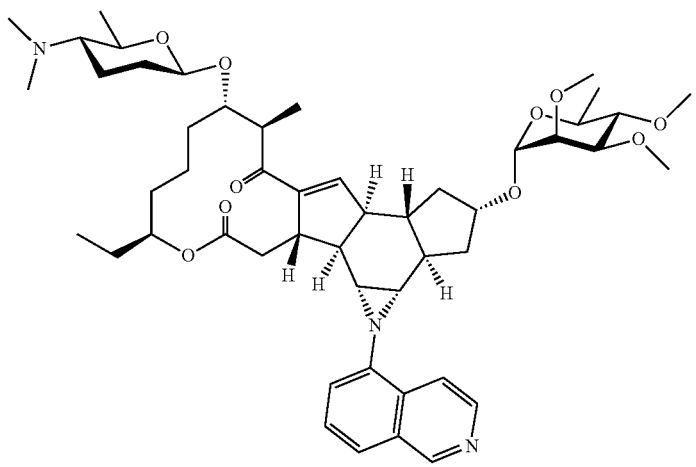

58

To a solution of Isoquinoline-5-boronic acid (103.8 mg, 0.6 mmol) and Cu(OAc)$_2$ (15.6 mg, 0.08 mmol) in toluene (10 mL) were added 2,6-Lutidine (42.8 mg, 0.4 mmol), Lauric acid (8.0 mg, 0.04 mmol) and compound A3 (300 mg, 0.4 mmol). The mixture was stirred under air atmosphere for two days at room temperature. The mixture was concentrated and the residue was purified by column chromatography on silica gel (MeOH/DCM=1/20) and prep-HPLC to afford compound 58 (40 mg, yield 11.5%) as white solid. Partial $^1$H NMR (CDCl$_3$, 400 MHz): δ9.22 (s, 1H), 8.56 (dd, J=6.0 Hz, 1H), 8.17 (d, J=6.0 Hz, 1H), 7.61 (d, J=8.0 Hz, 1H), 7.46 (t, J=7.6 Hz, 1H), 7.16 (d, J=7.6 Hz, 1H), 6.79 (s, 1H), 4.92 (s, 1H), 4.81-4.72 (m, 1H), 4.47-4.43 (m, 1H), 4.42-4.34 (m, 1H), 3.67-3.79 (m, 1H), 3.70-3.44 (m, 16H), 3.35-3.23 (m, 2H), 3.19-3.10 (m, 2H), 2.73-2.65 (m, 1H), 2.61-2.55 (s, 1H), 2.52-2.45 (m, 1H), 2.33-2.45 (m, 1H), 2.33-2.21 (m, 10H), 0.98-0.85 (m, 4H). LCMS: m/z 874.4 [M+H]$^+$.

59. Synthesis of Compound 59

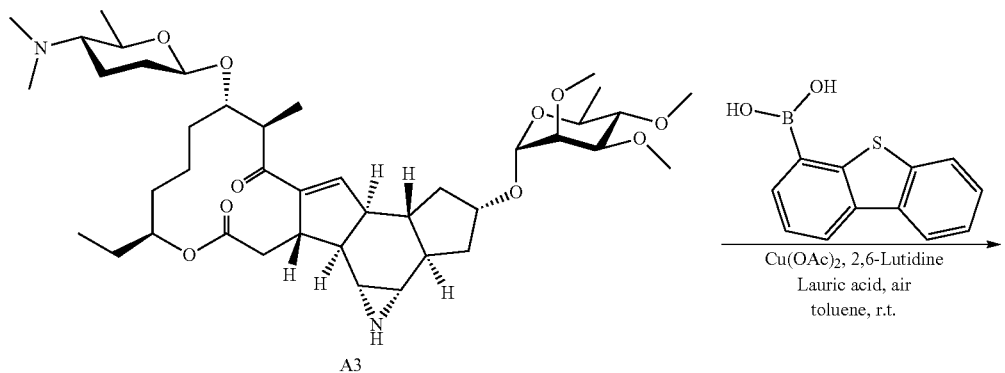

A3

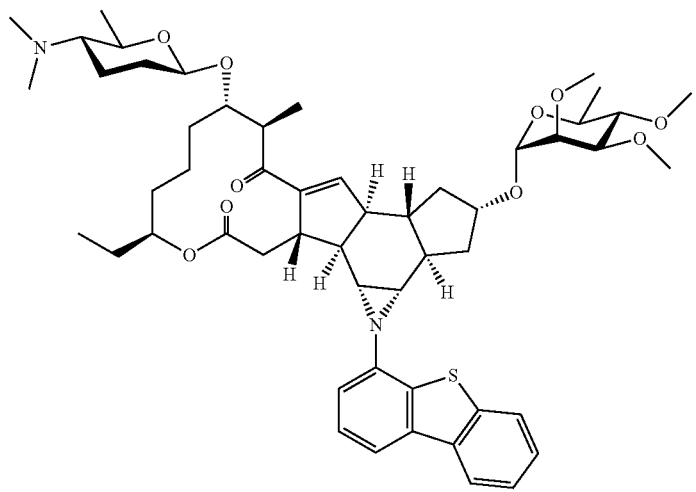

59

To a solution of Dibenzothiophene-4-boronic acid (136.8 mg, 0.6 mmol) and Cu(OAc)$_2$ (15.6 mg, 0.08 mmol) in toluene (10 mL) were added 2,6-Lutidine (42.8 mg, 0.4 mmol), Lauric acid (8.0 mg, 0.04 mmol) and compound A3 (300 mg, 0.4 mmol). The mixture was stirred under air atmosphere for two days at room temperature. The mixture was concentrated and the residue was purified by column chromatography on silica gel (MeOH/DCM=1/20) and prep-HPLC to afford compound 59 (45 mg, yield 10.9%) as white solid. Partial $^1$H NMR (CDCl$_3$, 400 MHz): δ8.17-8.11 (m, 1H), 7.88-7.80 (m, 2H), 7.48-7.41 (m, 2H), 7.37 (t, J=7.6 Hz, 2H), 7.02 (d, J=7.6 Hz, 1H), 6.80 (s, 1H), 4.94 (s, 1H), 4.83-4.76 (m, 1H), 4.46-4.34 (m, 2H), 3.79-3.73 (m, 1H), 3.68-3.47 (m, 17H), 3.34-3.10 (m, 4H), 2.78-2.60 (m, 3H), 2.42-2.18 (m, 13H), 2.04-1.96 (m, 3H), 0.94-0.85 (m, 5H). LCMS: m/z 930.4 [M+H]$^+$.

60. Synthesis of Compound 60

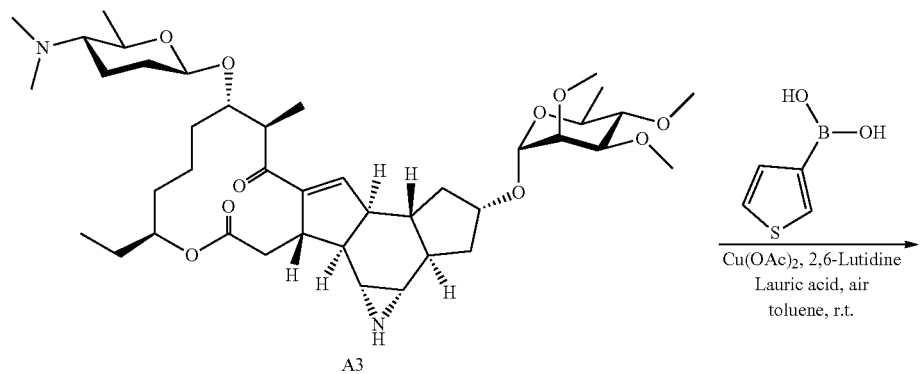

A3

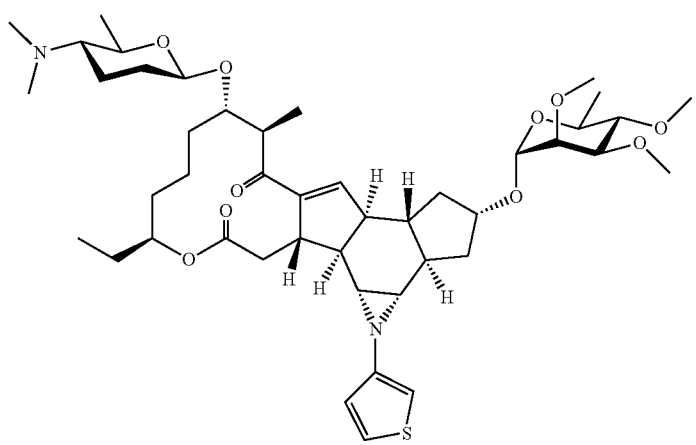

60

To a solution of 3-Thiopheneboronic acid (134 mg, 1.05 mmol) and Cu(OAc)$_2$ (28 mg, 0.14 mmol) in toluene (10 mL) were added 2,6-Lutidine (75 mg, 0.7 mmol), Lauric acid (14 mg, 0.07 mmol) and compound A3 (500 mg, 0.7 mmol). The mixture was stirred under air atmosphere for two days at room temperature. The mixture was concentrated and purified by column chromatography on silica gel (MeOH/DCM=1/20) followed by prep-HPLC to afford compound 60 (35 mg, yield 6%) as white solid. Partial $^1$H NMR (CDCl$_3$, 400 MHz): δ7.17 (dd, J=5.2, 2.8 Hz, 1H), 6.92 (dd, J=5.2, 1.2 Hz, 1H), 6.74 (s, 1H), 6.53 (dd, J=2.8, 1.2 Hz, 1H), 4.87 (s, 1H), 4.72-4.63 (m, 1H), 4.45-4.40 (m, 1H), 3.31-3.21 (m, 2H), 3.16-3.08 (m, 2H), 2.60-2.35 (m, 6H), 2.28-2.11 (m, 11H), 2.01-1.94 (m, 1H), 1.32-1.16 (m, 4H). LCMS: m/z 829.4 [M+H]$^+$.

61. Synthesis of Compound 61

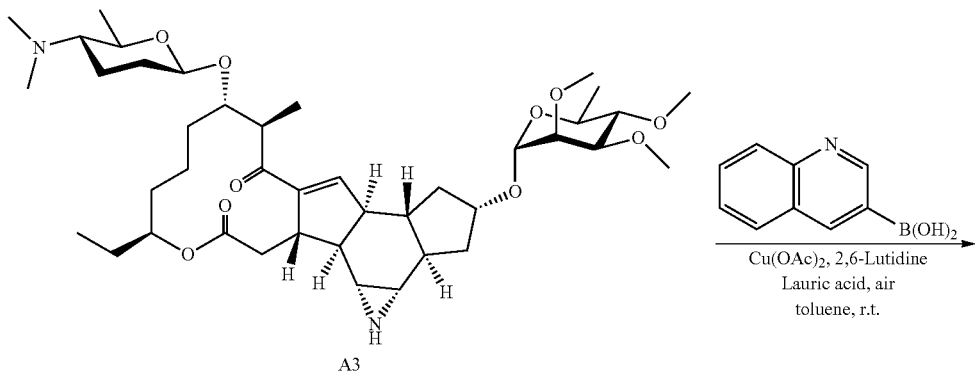

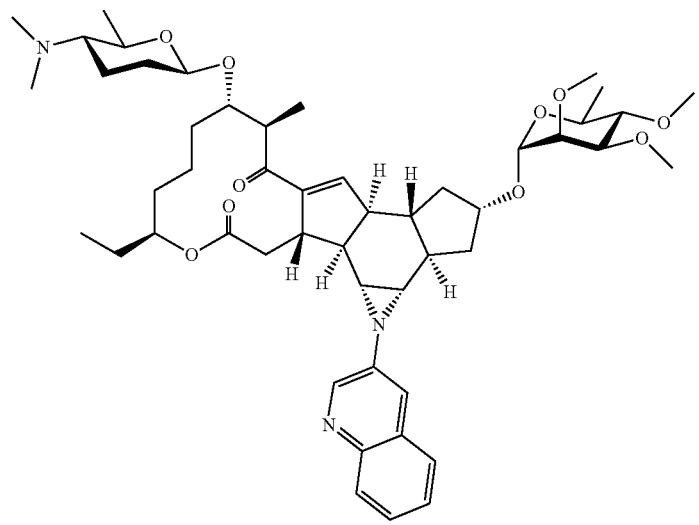

To a solution of quinolin-3-ylboronic acid (103.8 mg, 0.6 mmol) and Cu(OAc)$_2$ (15.6 mg, 0.08 mmol) in toluene (10 mL) were added 2,6-Lutidine (42 mg, 0.4 mmol), Lauric acid (7.8 mg, 0.04 mmol) and compound A3 (300 mg, 0.4 mmol). The mixture was stirred under air atmosphere for two days at room temperature. The mixture was concentrated and purified by column chromatography on silica gel (MeOH/DCM=1/20) followed by prep-HPLC to afford compound 61 (30 mg, yield 8.6%) as white solid. Partial $^1$H NMR (CDCl$_3$, 400 MHz): δ 8.80 (d, J=2.4 Hz, 1H), 8.03 (d, J=8.4 Hz, 1H), 7.71 (d, J=8.0 Hz, 1H), 7.57-7.26 (m, 3H), 6.77 (s, 1H), 4.91 (s, 1H), 4.76-4.67 (m, 1H), 4.46-4.41 (m, 1H), 4.40-4.32 (m, 1H), 3.36-3.26 (m, 2H), 3.22-3.08 (m, 2H), 2.66-2.50 (m, 3H), 2.35-2.18 (m, 10H), 2.02-1.95 (m, 1H); LCMS: m/z 874.3 [M+H]$^+$.

62. Synthesis of Compound 62

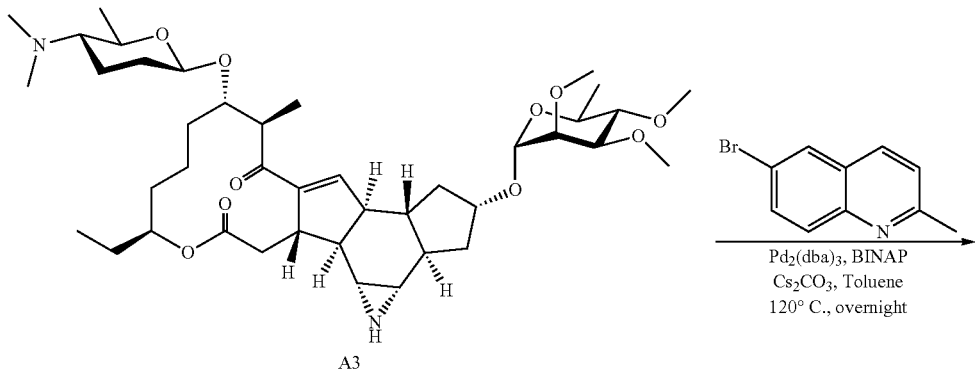

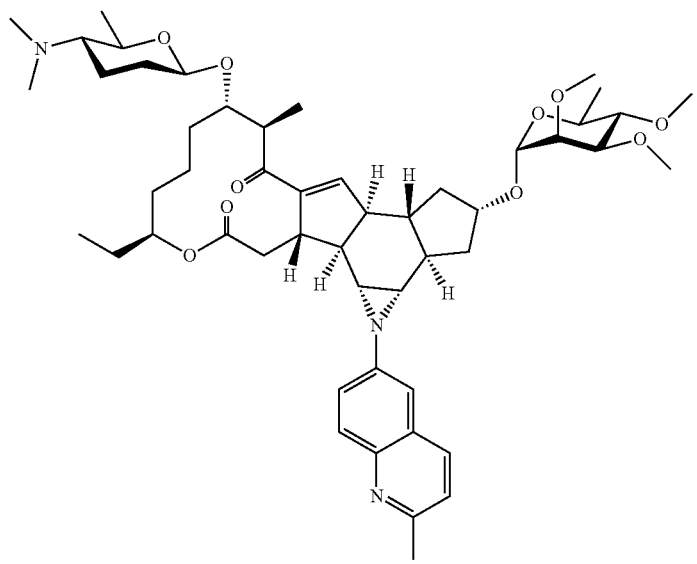

To a solution of 6-Bromo-2-methyl-quinoline (89 mg, 0.4 mmol) and compound A3 (300 mg, 0.4 mmol) in toluene (30 mL) were added $Pd_2(dba)_3$ (14.1 mg, 0.02 mmol), BINAP (17.3 mg, 0.03 mmol) and $Cs_2CO_3$ (190.5 mg, 0.6 mmol) under $N_2$. The reaction was stirred at 120° C. for overnight. The reaction was quenched with water (50 mL) and extracted with DCM (30 mL×3). The combined organic layer was dried over $Na_2SO_4$, filtered and concentrated. The residue was purified by column chromatography on silica gel (MeOH/DCM=1/20) and prep-HPLC to afford compound 62 (40 mg, yield 11.3%) as a white solid. Partial $^1H$ NMR ($CDCl_3$, 400 MHz): δ7.94-7.89 (m, 2H), 7.51-7.45 (m, 1H), 7.26-7.18 (m, 2H), 6.77 (s, 1H), 4.91 (s, 1H), 4.76-4.67 (m, 1H), 4.46-4.41 (m, 1H), 4.38-4.31 (m, 1H), 3.69-3.63 (m, 1H), 3.36-3.26 (m, 3H), 2.70 (s, 3H), 2.03-1.96 (m, 1H). LCMS: m/z 888.4 $[M+H]^+$.

63. Synthesis of Compound 63

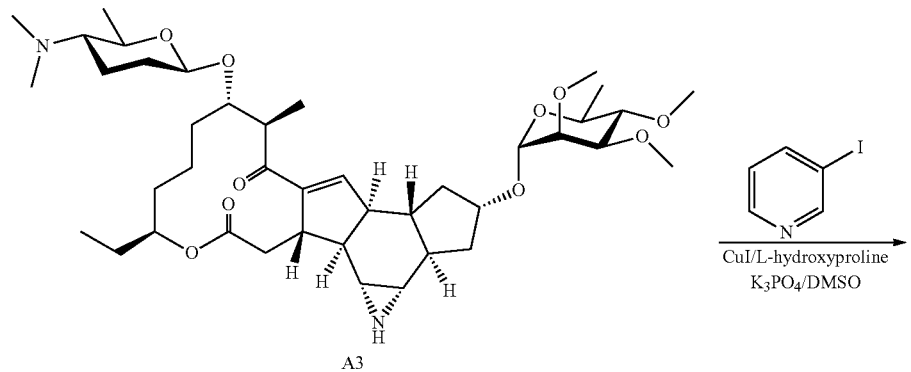

A3

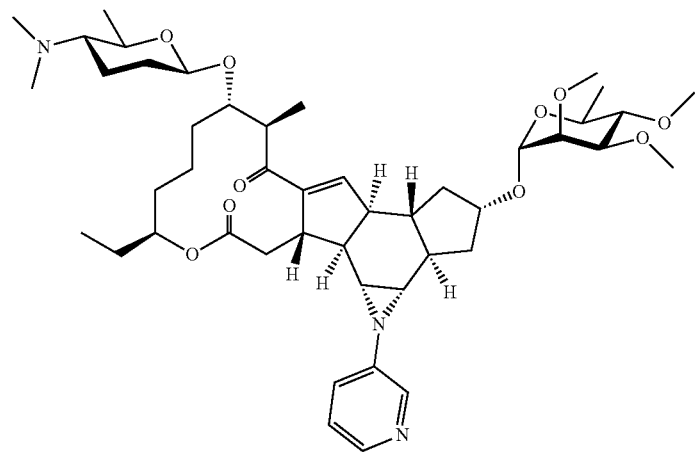

63

A 25 mL round-bottomed flask containing a magnetic stir bar was charged with CuI (15 mg, 0.08 mmol) followed by L-hydroxyproline (21 mg, 0.16 mmol), 3-iodopyridine (165 mg, 0.80 mmol) and $K_3PO_4$ (256 mg, 1.2 mmol). The flask was flushed with $N_2$ and a solution of the compound A3 (300 mg, 0.40 mmol) in anhydrous DMSO (10 mL) was then added. The mixture was stirred under $N_2$ at 60° C. for 24 h. After cooled to r.t, the mixture was partitioned between EA and 5% aqueous $NH_3 \cdot H_2O$ (100 mL/50 mL). The organic layer was washed with water (30 mL×2), and brine, dried over anhydrous $Na_2SO_4$, filtered and concentrated. The residue was purified by Prep-TLC (MeOH/DCM=1/15) to afford compound 63 (19 mg, 5.7% yield) as a white solid. Partial $^1H$ NMR (CDCl$_3$, 300 MHz): δ 8.39-8.37 (m, 1H), 8.26-8.22 (m, 1H), 7.35-7.33 (m, 1H), 7.19-7.14 (m, 1H), 6.76 (s, 1H), 4.90 (s, 1H), 4.72-4.67 (m, 1H), 4.47-4.44 (m, 1H), 4.374-4.32 (m, 1H), 3.33-3.26 (m, 2H), 3.17-3.10 (m, 2H), 2.59-2.44 (m, 3H), 2.24-2.18 (m, 3H), 0.86 (t, J=7.5 Hz, 3H). LCMS: m/z 824.3 $[M+H]^+$.

64. Synthesis of Compound 64

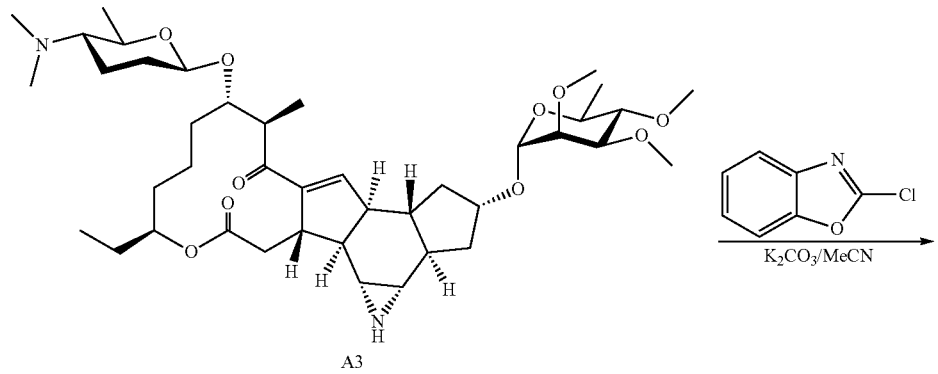

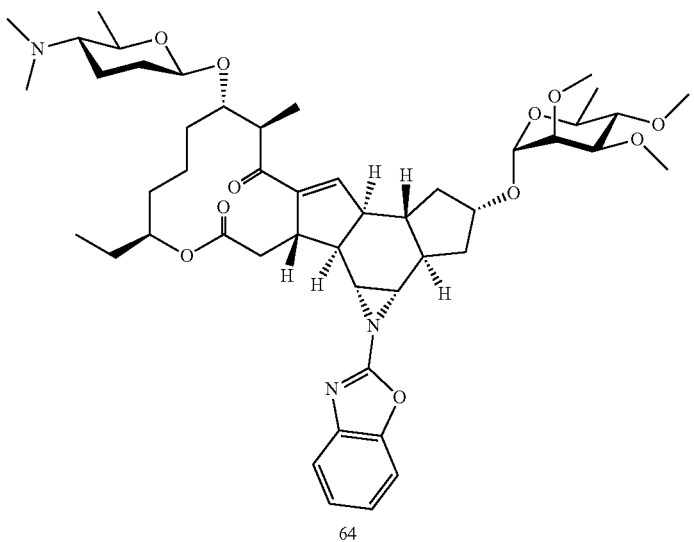

To a solution of compounds A3 (300 mg, 0.4 mmol) and 2-chlorobenzo[d]oxazole (62 mg, 0.4 mmol) in MeCN (5 mL) was added K₂CO₃ (111 mg, 0.8 mmol). The mixture was then stirred at r.t overnight. The mixture was filtered and the filtrate was purified by silica gel column chromatography (DCM/MeOH=20/1) to give compound 64 (125 mg, 36.0% yield) as a white solid. Partial ¹H NMR (CDCl₃, 400 MHz): δ7.52-7.50 (m, 1H), 7.40-7.38 (m, 1H), 7.25-7.19 (m, 2H), 6.74 (s, 1H), 4.88 (s, 1H), 4.77-4.71 (m, 1H), 4.43-4.41 (m, 1H), 4.36-4.30 (m, 1H), 3.66-3.61 (m, 2H), 3.31-3.21 (m, 4H), 3.11 (t, J=9.6 Hz, 2H), 2.84 (d, J=6.8 Hz, 1H), 2.67-2.62 (m, 2H), 0.84 (t, J=7.6 Hz, 3H); LCMS: m/z 864.4 [M+H]⁺.

65. Synthesis of Compound 65

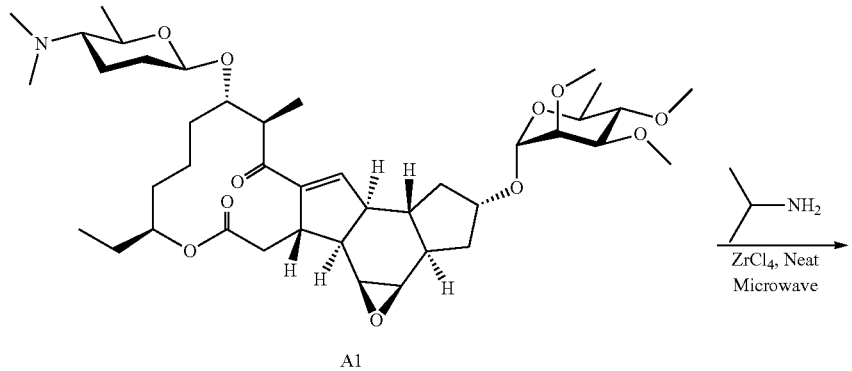

A1

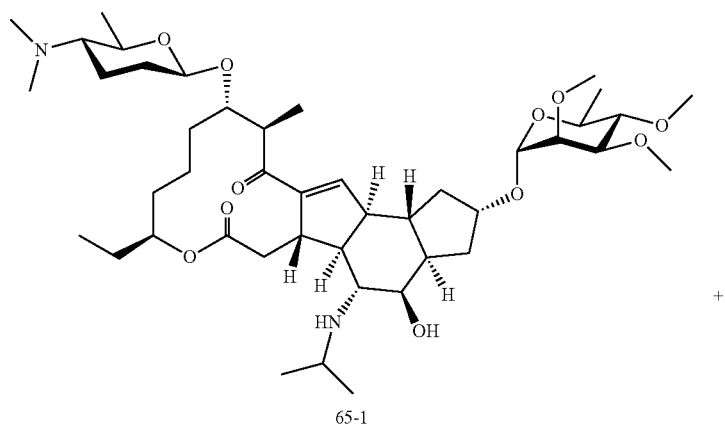

65-1

+

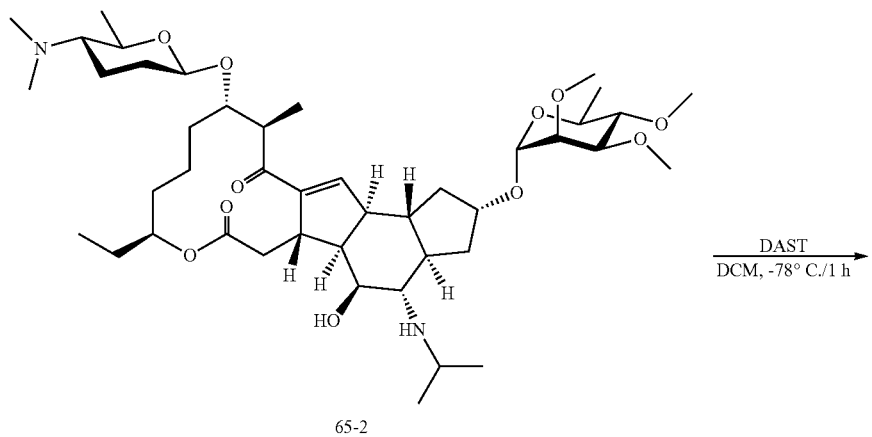

65-2

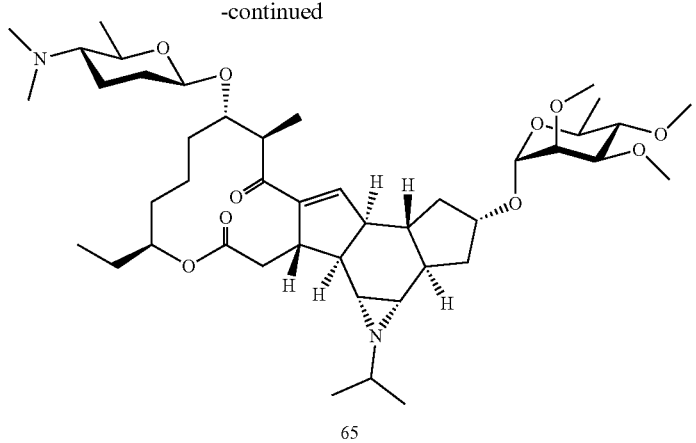

65

To a solution of compound A1 (400 mg, 0.53 mmol) in propan-2-amine (10 mL) was added ZrCl$_4$ (6.0 mg, 0.026 mmol). The mixture was stirred at 80° C. under microwave for 1 h. The mixture was purified by silica gel column (DCM/MeOH=100:1-10:1) and then prep-HPLC to give a mixture of compounds 65-1 and 65-2 (210 mg, 45.3% yield) as white solid. LCMS: m/z 807.2 [M+H]+.

To a solution of a mixture of compounds 65-1 and 65-2 (200 mg, 0.25 mmol) in DCM (5 mL) was added DAST (50.0 mg, 0.3 mmol) at −78° C. under N$_2$ pressure. The mixture was stirred at −78° C. under N$_2$ pressure for 1 h. The reaction mixture was quenched with saturated NaHCO$_3$ solution (10 mL) and extracted with DCM (15 mL×2). The combined organic phase was dried over anhydrous Na$_2$SO$_4$, filtered and concentrated. The residue was purified by Prep-HPLC to afford compound 65 (20 mg, yield 10.2%) as a white solid. Partial $^1$H NMR (CDCl$_3$, 400 MHz): δ6.70 (s, 1H), 4.83 (s, 1H), 4.64 (s, 1H), 4.42 (d, J=7.2 Hz, 1H), 4.26 (s, 1H), 3.27-3.03 (m, 6H), 2.48-2.40 (m, 2H), 0.82 (t, J=7.6 Hz, 3H); LCMS: m/z 789.2 [M+H]$^+$.

66. Synthesis of Compound 66

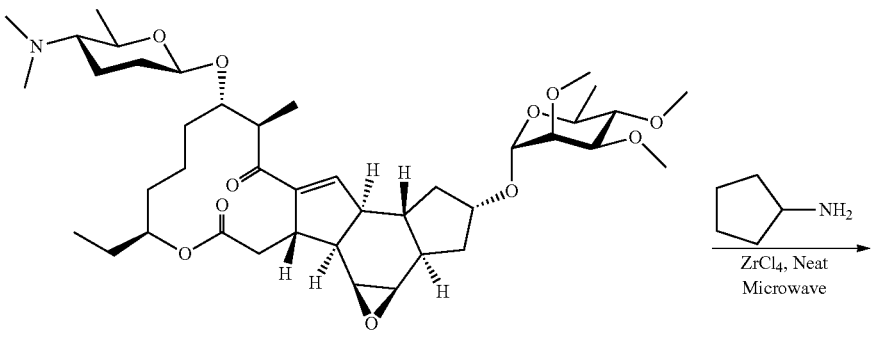

A1

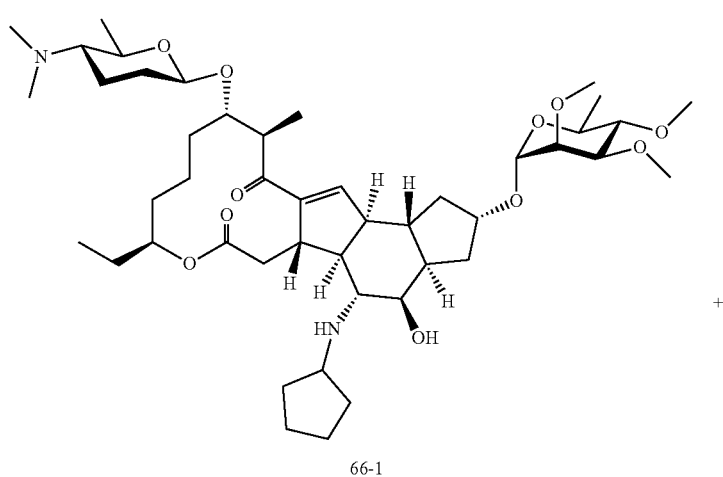

66-1

-continued

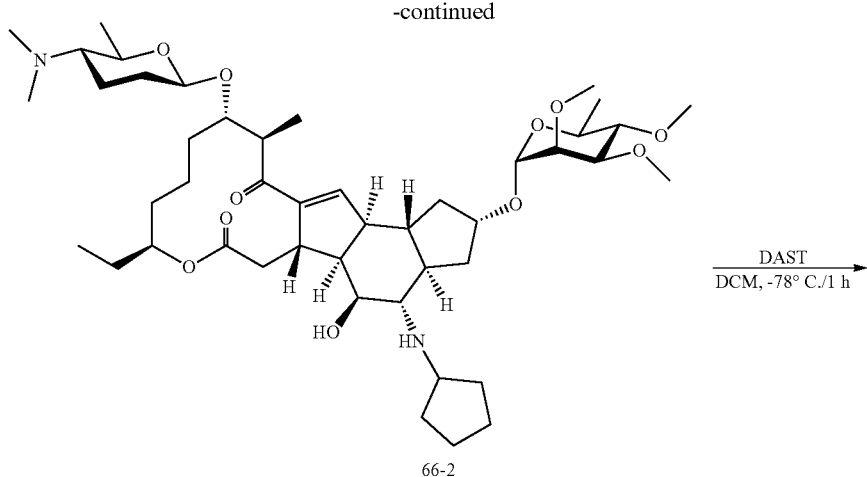

66-2

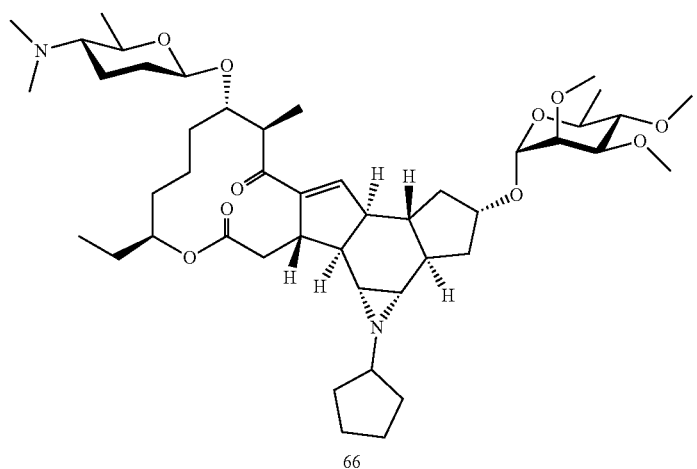

66

To a solution of compound A1 (1.0 g, 1.3 mmol) in cyclopentanamine (10 mL) was added ZrCl$_4$ (16 mg, 0.07 mmol). The mixture was stirred at 80° C. under microwave for 1 h. The mixture was purified by silica gel column (DCM/MeOH=100:1-10:1) and then prep-HPLC to give a mixture of compounds 66-1 and 66-2 (250 mg, 23% yield) as white solid. LCMS: m/z 833.2 [M+H]$^+$.

To a solution of a mixture of compounds 66-1 and 66-2 (167 mg, 0.2 mmol) in DCM (5 mL) was added DAST (50.0 mg, 0.3 mmol) at −78° C. under N$_2$ pressure. The mixture was stirred at −78° C. under N$_2$ for 1 h. The reaction mixture was quenched with saturated NaHCO$_3$ solution (10 mL) and extracted with DCM (15 mL×2). The combined organic phase was dried over anhydrous Na$_2$SO$_4$, filtered and concentrated. The residue was purified by Prep-HPLC to afford compound 66 (55 mg, yield 34%) as a white solid. Partial $^1$H NMR (CDCl$_3$, 400 MHz): δ6.67 (s, 1H), 4.81 (s, 1H), 4.63 (s, 1H), 4.39 (d, J=7.2 Hz, 1H), 4.24 (s, 1H), 3.28-3.01 (m, 5H), 2.23 (s, 6H), 2.48-2.43 (m, 2H), 0.79 (t, J=7.6 Hz, 3H), 0.65 (m, 1H); LCMS: m/z 815.2 [M+H]$^+$.

67. Synthesis of Compound 67

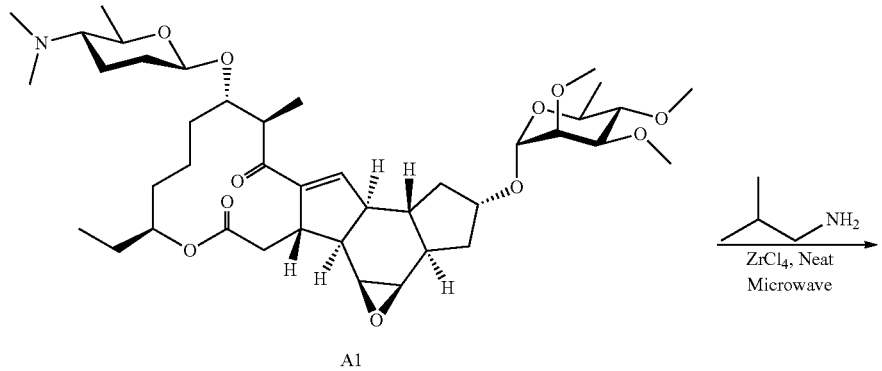

A1

-continued

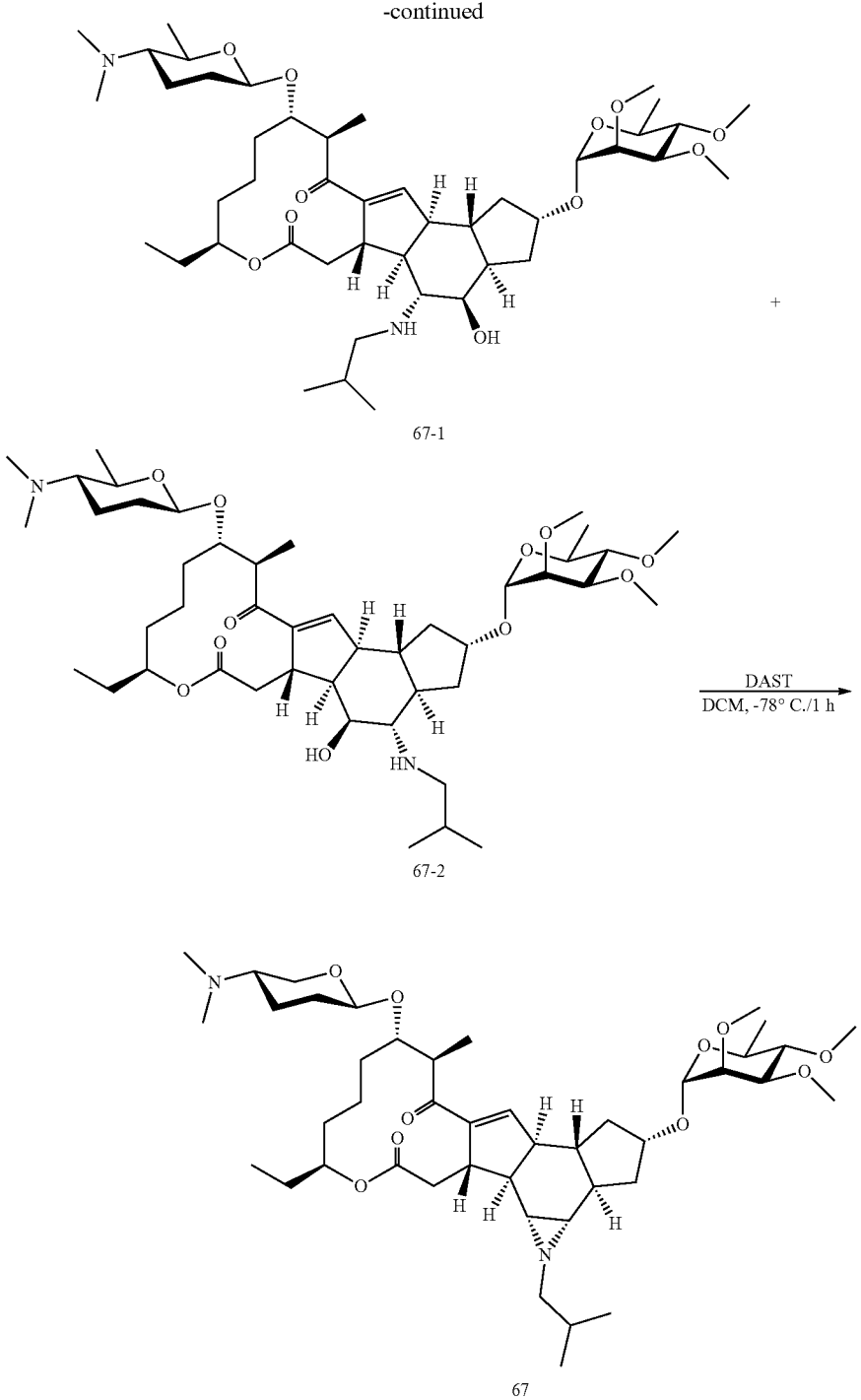

To a solution of compound A1 (1.0 g, 1.3 mmol) in 2-methylpropan-1-amine (10 mL) was added ZrCl$_4$ (63 mg, 0.26 mmol). The mixture was stirred at 80° C. under microwave under N$_2$ pressure for 1 h. The mixture was purified by silica gel column (DCM/MeOH=100:1-10:1) to give a mixture of compounds 63-1 and 63-2 (410 mg, 38% yield) as white solid. LCMS: m/z 821.2 [M+H]$^+$.

To a solution of compounds 63-1 and 63-2 (350 mg, 0.42 mmol) in DCM (20 mL) was was added DAST (99 mg, 0.6 mmol) at −78° C. under N$_2$. After stirred at −78° C. for 1 h, the mixture was quenched with aqueous NaHCO$_3$ (30 mL). After stirred for 15 min, the mixture was extracted with DCM (20 mL×3). The combined organic layer was washed with brine, dried over Na$_2$SO$_4$, filtered and concentrated. The residue was purified by prep-HPLC to afford compound 63 (80 mg, yield 24%) as a white solid. Partial $^1$H NMR (CDCl$_3$, 400 MHz): δ6.70 (s, 1H), 4.83 (s, 1H), 4.67 (m, 1H), 4.39 (d, J=8.8 Hz, 1H), 4.26 (m, 1H), 3.64 (m, 1H), 3.26-3.04 (m, 6H), 0.98-0.94 (m, 6H), 0.79 (t, J=7.2 Hz, 3H), LCMS: m/z 803.2 [M+H]$^+$

68. Synthesis of Compound 68
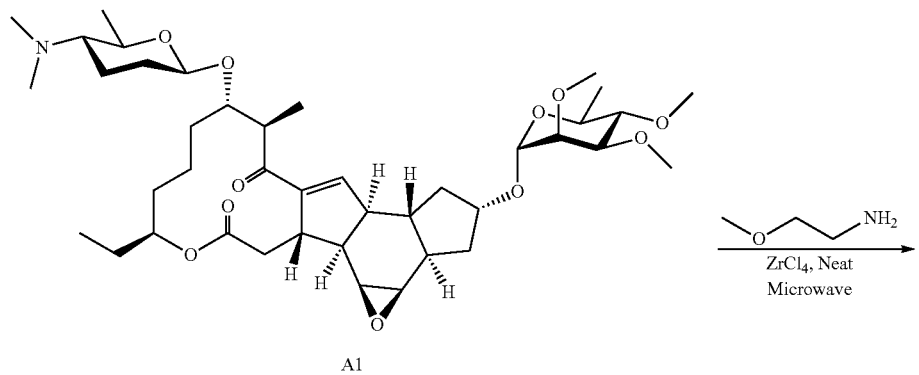

-continued

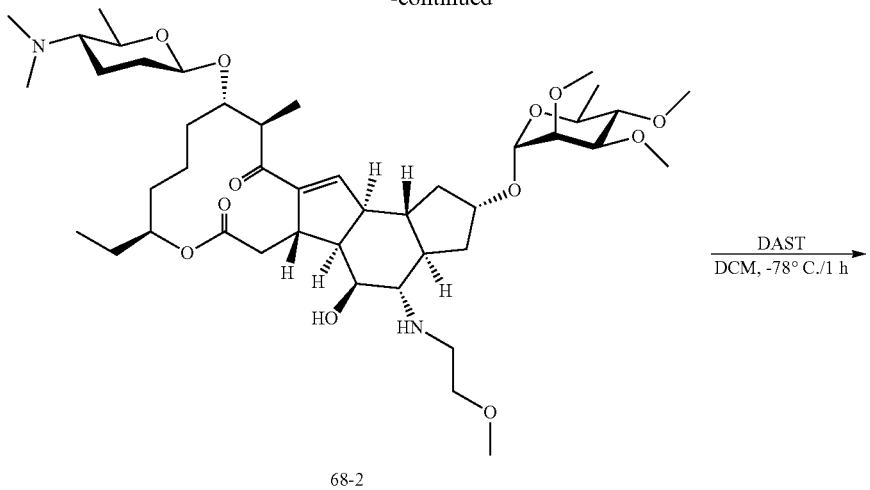

68-2

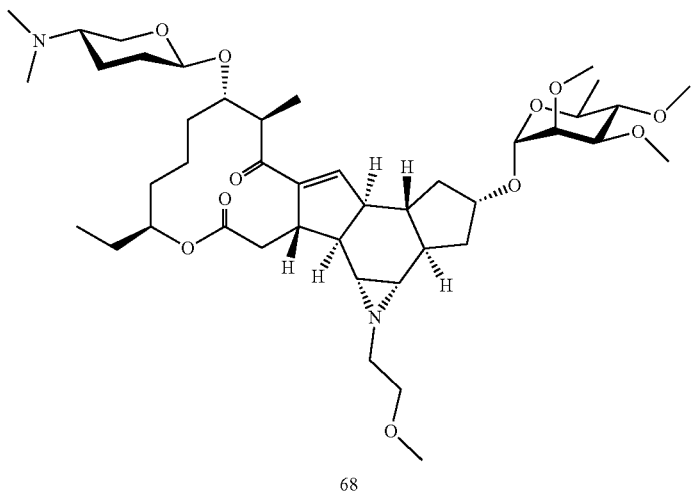

68

To a solution of compound A1 (0.5 g, 0.65 mmol) in 2-methoxyethanamine (5 mL) was added ZrCl$_4$ (16 mg, 0.07 mmol). The mixture was stirred at 80° C. under microwave under N$_2$ pressure for 1 h. The mixture was purified by silica gel column chromatography (DCM/MeOH=100:1-10:1) and prep-HPLC to give a mixture of compounds 68-1 and 68-2 (100 mg, 18.6% yield) as white solid. LCMS: m/z 823.2 [M+H]$^+$.

To a solution of compounds 68-1 and 68-2 (50 mg, 0.06 mmol) in DCM (5 mL) was added DAST (20 mg, 0.12 mmol) at −78° C. under N$_2$. After stirred at −78° C. for 1 h, the mixture was warmed to room temperature and was quenched with aqueous NaHCO$_3$ (30 mL). After stirred for 15 min, the mixture was extracted with DCM (20 mL×3). The combined organic layer was washed with brine, dried over Na$_2$SO$_4$, filtered and concentrated. The residue was purified by prep-HPLC to afford compound 68 (20 mg, yield 40%) as a white solid. Partial $^1$H NMR (CDCl$_3$, 400 MHz): 6.70 (s, 1H), 4.84 (s, 1H), 4.69 (m, 1H), 4.43 (d, J=7.2 Hz, 1H), 4.24 (m, 1H), 3.39 (s, 3H), 2.76-2.72 (m, 1H), 2.48-2.42 (m, 2H), 0.82 (t, J=7.6 Hz, 3H), LCMS: m/z 805.1 [M+H]$^+$.

69. Synthesis of Compound 69
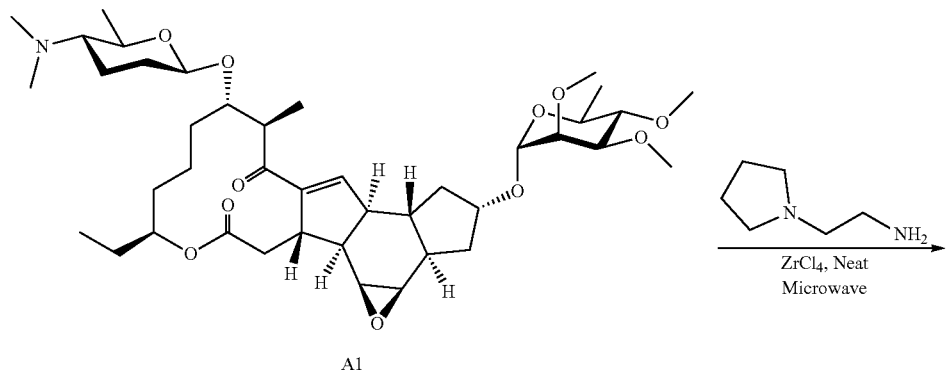

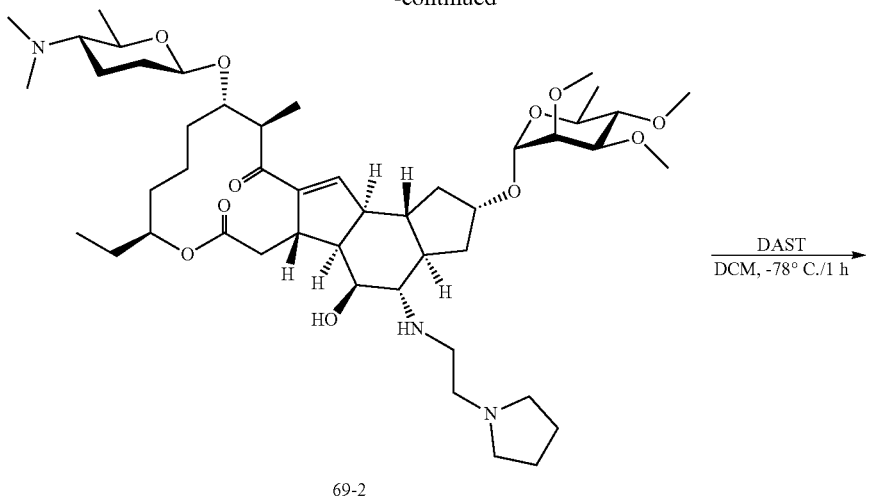

69-2

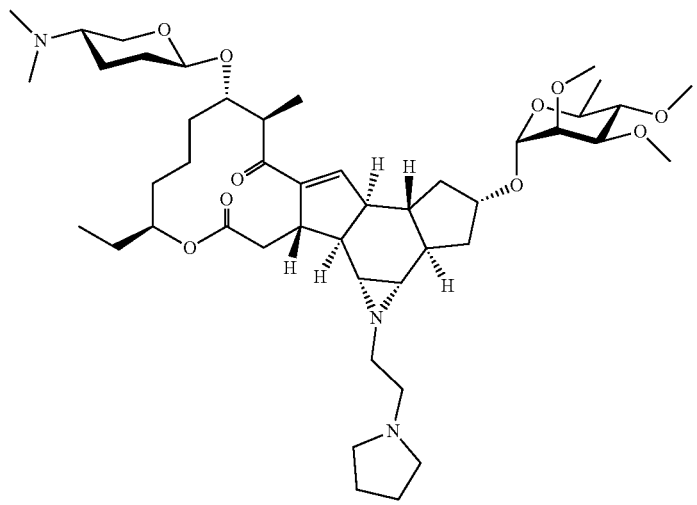

69

To a solution of compound A1 (0.5 g, 0.65 mmol) in 2-(pyrrolidin-1-yl)ethanamine (5 mL) was added $ZrCl_4$ (63 mg, 0.26 mmol). The mixture was stirred at 80° C. under microwave under $N_2$ pressure for 1 h. The mixture was purified by flash (MeCN/$H_2O$=50:50-95:5) to afford a mixture of compounds 69-1 and 69-2 (200 mg, yield 35%). LCMS: m/z 863.2 [M+H]$^+$ To a solution of compounds 69-1 and 69-2 (200 mg, 0.23 mmol) in DCM (20 mL) was was added DAST (5 mL) at −78° C. under $N_2$. After stirred at −78° C. for 30 min, the mixture was warmed to room temperature and quenched with aqueous $NaHCO_3$ (30 mL). After stirred for 15 min, the mixture was extracted with DCM (20 mL×3). The combined organic layer was washed with brine, dried over $Na_2SO_4$, filtered and concentrated. The residue was purified by prep-HPLC to afford compound 69 (15 mg, yield 7.7%) as a white solid. Partial $^1$H NMR ($CDCl_3$, 400 MHz): 36.70 (s, 1H), 4.84 (s, 1H), 4.67 (m, 1H), 4.41 (d, J=7.6 Hz, 1H), 4.25 (m, 1H), 0.83 (t, J=7.2 Hz, 3H); LCMS: m/z 845.2 [M+H]$^+$

70. Synthesis of Compound 70
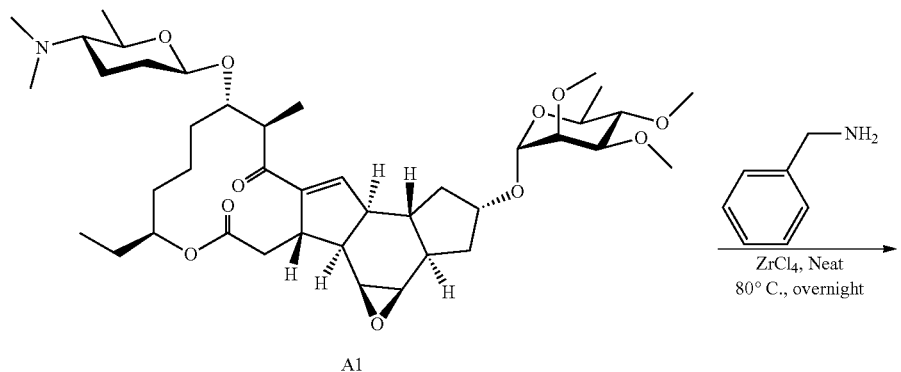

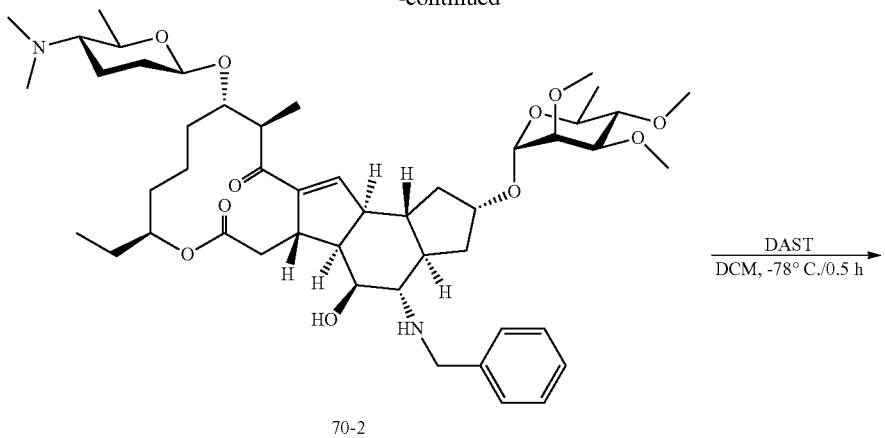

70-2

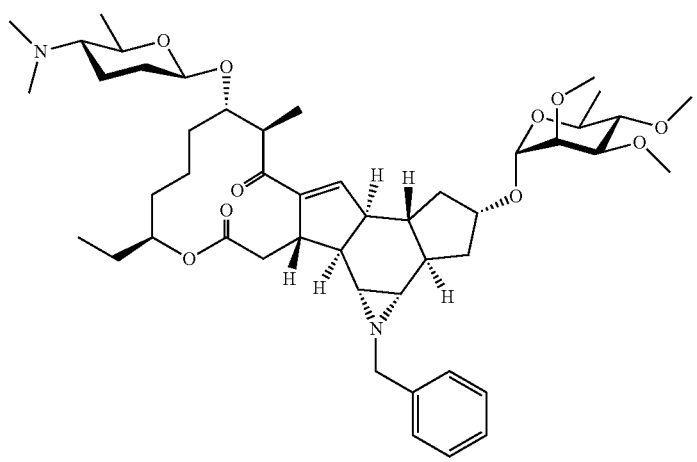

70

To a solution of compound A1 (0.6 g, 0.8 mmol) in phenylmethanamine (4 mL) was added $ZrCl_4$ (93.2 mg, 0.4 mmol). The mixture was stirred at 80° C. under $N_2$ pressure for overnight. The mixture was quenched with water and extracted with DCM. The organic layer was washed with water and dried over $Na_2SO_4$, filtered and concentrated. The residue was purified by flash ($MeCN/H_2O$=50:50-95:5) to afford the crude compounds 70-1 and 70-2 (487 mg, yield 71%). LCMS: m/z 855.2 $[M+H]^+$ To a stirred solution of compounds 70-1 and 70-2 (487 mg, 0.57 mmol) in DCM (10 mL) was added DAST (184 mg, 1.14 mmol) at −78° C. under $N_2$ atmosphere. The resulting mixture was stirred at −78° C. for 30 min. The reaction mixture was warmed to the room temperature and was quenched with aqueous $NaHCO_3$ (10 mL). The mixture was extracted with DCM (10 mL×3). The combined organic layer was dried over anhydrous $Na_2SO_4$, filtered and concentrated. The residue was purified by Prep-HPLC to give the compound 70 (58 mg, 12.2% yield) as white solid. Partial $^1H$ NMR ($CDCl_3$, 400 MHz): δ7.39-7.32 (m, 4H), 7.26-7.23 (m, 1H), 6.71 (s, 1H), 4.84 (s, 1H), 4.72-4.66 (m, 1H), 4.42 (d, J=8.8 Hz, 1H), 4.30-4.23 (m, 1H), 3.54 (s, 2H), 3.39-3.32 (m, 1H), 2.53-2.48 (m, 1H), 2.38-2.34 (m, 1H), 2.24 (s, 6H), 2.17-2.10 (m, 1H), 0.83 (t, J=7.2 Hz, 3H), 0.78-0.68 (m, 1H). LCMS: m/z 837.2 $[M+H]^+$.

71. Synthesis of Compound 71
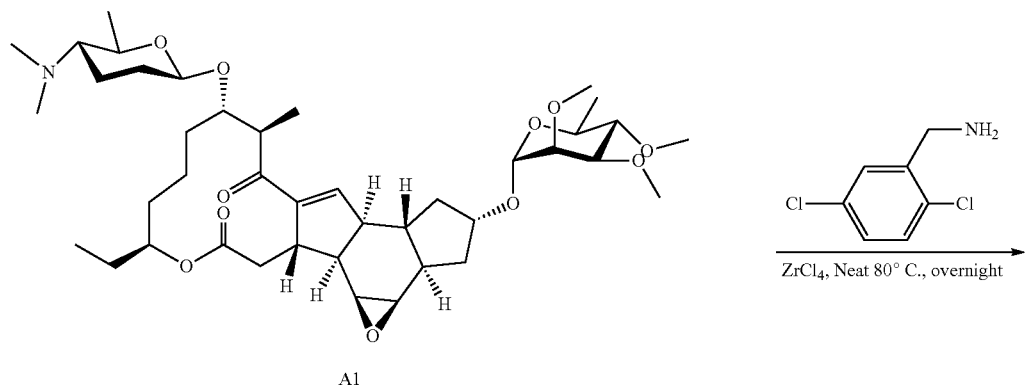
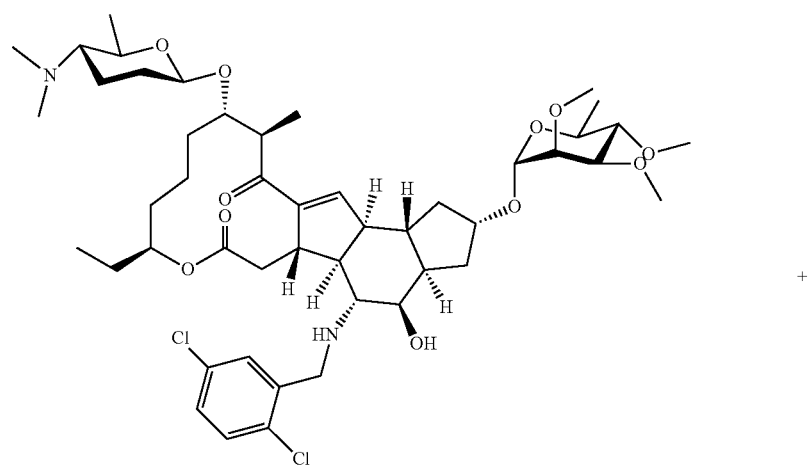
71-1

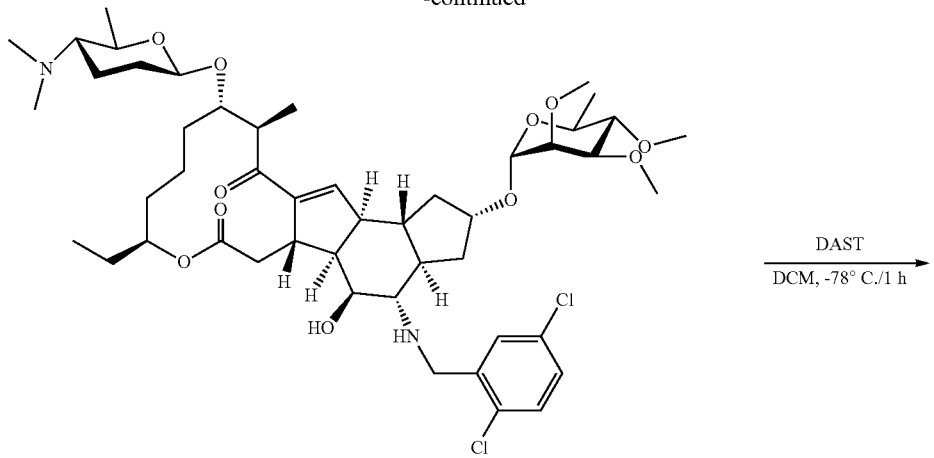

71-2

DAST
DCM, -78° C./1 h

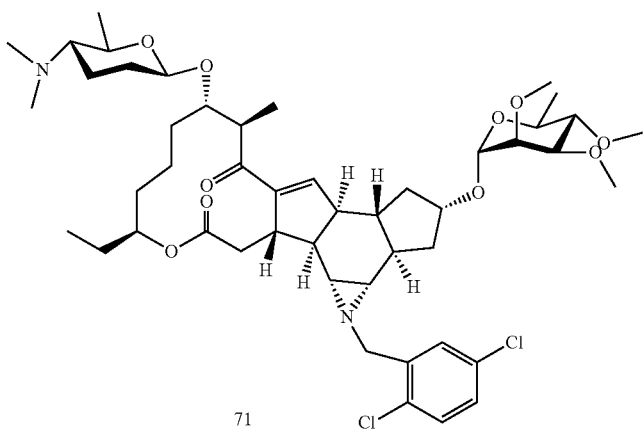

71 a solution of compound A1 (500 mg, 0.65 mmol) and 2,5-Dichloro-benzylamine (467.3 mg, 2.67 mmol) in 1,4-Dioxane (5 mL) was added ZrCl$_4$ (155 mg, 0.67 mmol). The mixture was stirred at 80° C. for overnight. The mixture was quenched with water and extracted with DCM. The organic layer was washed with water and dried over Na$_2$SO$_4$, filtered and concentrated. The residue was purified by flash (MeCN/H$_2$O=50:50-95:5) to afford the crude compounds 71-1 and 71-2 (250 mg, 41.5% yield) as yellow solid. LC-MS: m/z 925.5 [M+H]$^+$.

To a solution of compounds 71-1 and 71-2 (250 mg, 0.27 mmol) in DCM (10 mL) was added DAST (87.3 mg, 0.54 mmol) at −78° C. under N$_2$ pressure. The mixture was stirred at −78° C. under N$_2$ pressure for 1 h. The mixture was quenched with aqueous NaHCO$_3$ (10 mL) and extracted with DCM (30 mL×3). The combined organic layer was dried over Na$_2$SO$_4$, filtered and concentrated. The residue was purified by Prep-HPLC to afford compound 71 (50 mg, yield 20.4%) as yellow solid. Partial $^1$H NMR (CDCl$_3$, 300 MHz): δ 7.71 (d, J=8.1 Hz, 1H), 7.37-7.30 (m, 2H), 6.73 (s, 1H), 4.86 (s, 1H), 4.75-4.65 (m, 1H), 4.47-4.40 (m, 1H), 4.34-4.24 (m, 1H), 3.85 (d, J=16.2 Hz, 1H), 3.67-3.06 (m, 22H), 2.57-2.46 (m, 1H), 0.85 (t, J=7.5 Hz, 3H); LC-MS: m/z 907.5 [M+H]$^+$.

72. Synthesis of Compound 72
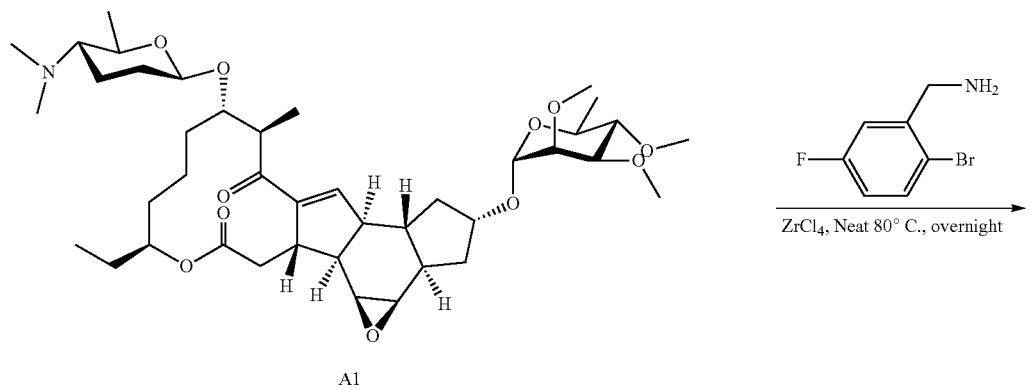
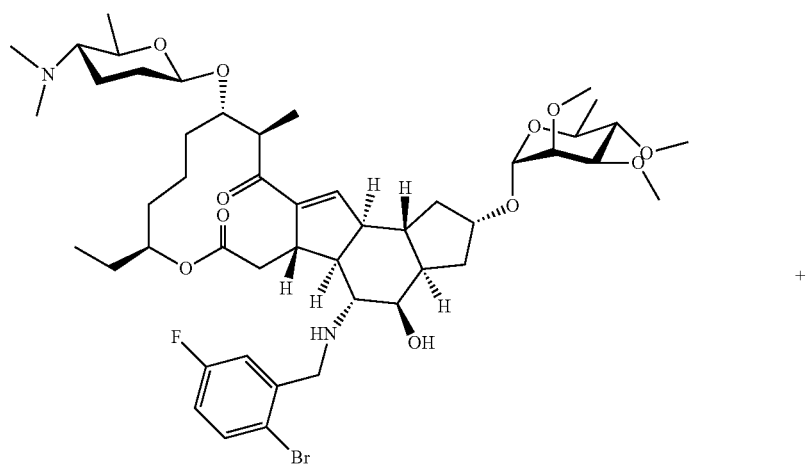

-continued

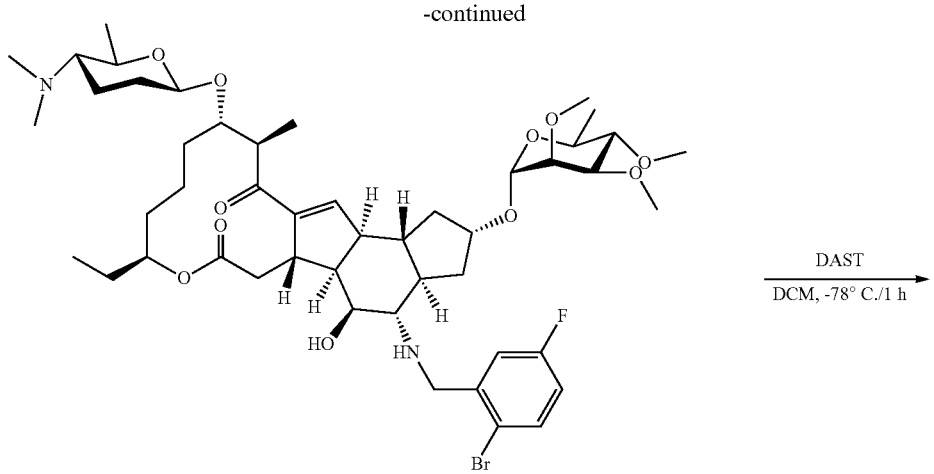

72-2

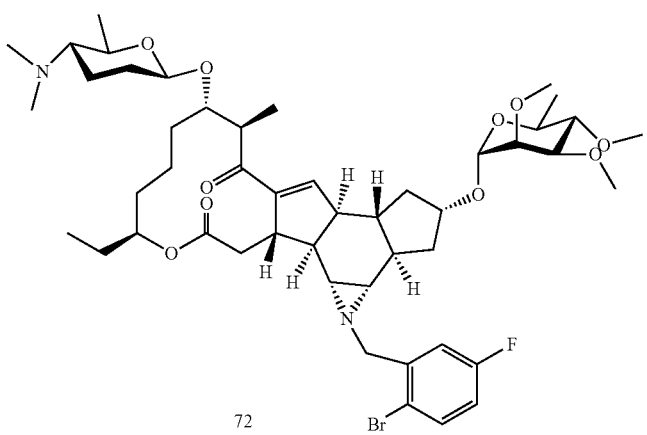

72

To a solution of compound A1 (300 mg, 0.4 mmol) and 2-Bromo-5-fluoro-benzylamine (245 mg, 1.2 mmol) in 1,4-Dioxane (2 mL) was added ZrCl₄ (155 mg, 0.67 mmol). The mixture was stirred at 80° C. for overnight. The mixture was quenched with water and extracted with DCM. The organic layer was washed with water and dried over Na₂SO₄, filtered and concentrated. The residue was purified by flash (MeCN/H₂O=50:50-95:5) to afford the crude compounds 72-1 and 72-2 (250 mg, 65% yield) as yellow solid.

To a solution of compounds 72-1 and 72-2 (250 mg, 0.26 mmol) in DCM (10 mL) was added DAST (87.3 mg, 0.54 mmol) at −78° C. under N₂ pressure. The mixture was stirred at −78° C. under N₂ pressure for 1 h. The mixture was quenched with aqueous NaHCO₃ (10 mL) and extracted with DCM (30 mL×3). The combined organic layer was dried over Na₂SO₄, filtered and concentrated. The residue was purified by Prep-HPLC to afford compound 72 (25 mg, yield 10.3%) as yellow solid. Partial $^1$H NMR (CDCl₃, 300 MHz): δ 7.48-7.43 (m, 2H), 6.90-6.83 (m, 1H), 6.73 (s, 1H), 4.87 (s, 1H), 4.75-4.65 (m, 1H), 4.43 (d, J=7.8 Hz, 1H), 4.34-4.28 (m, 1H), 3.32-3.06 (m, 4H), 2.60-2.50 (m, 1H), 2.45-2.40 (m, 1H), 0.85 (t, J=7.5 Hz, 3H); LC-MS: m/z 907.5 [M+H]⁺.

73. Synthesis of Compound 73
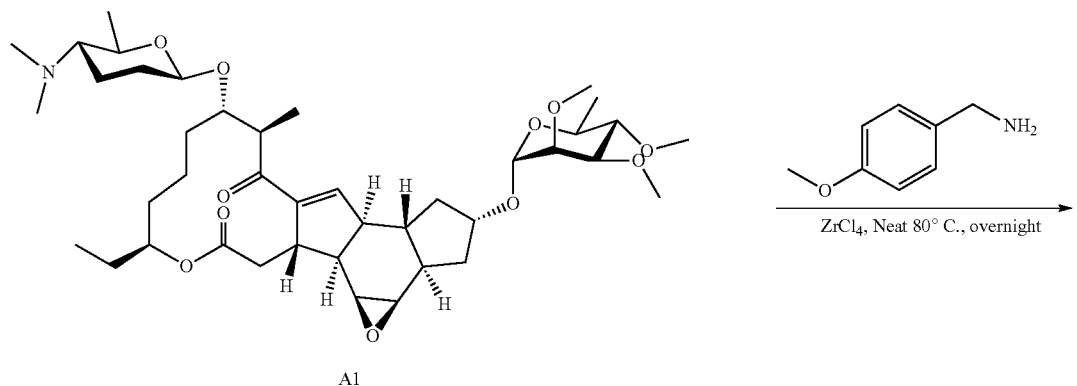
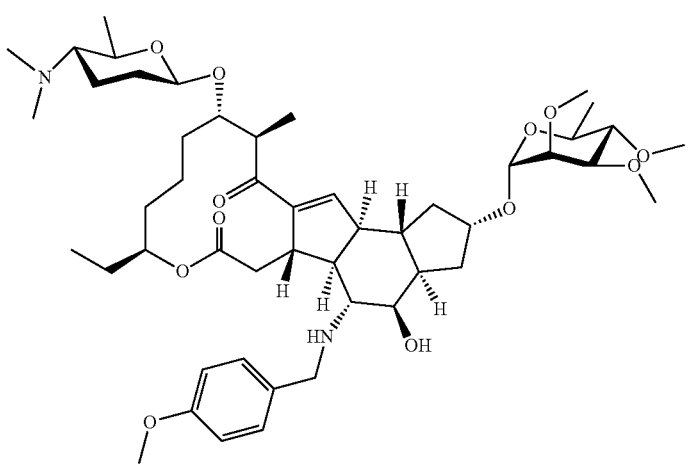

-continued

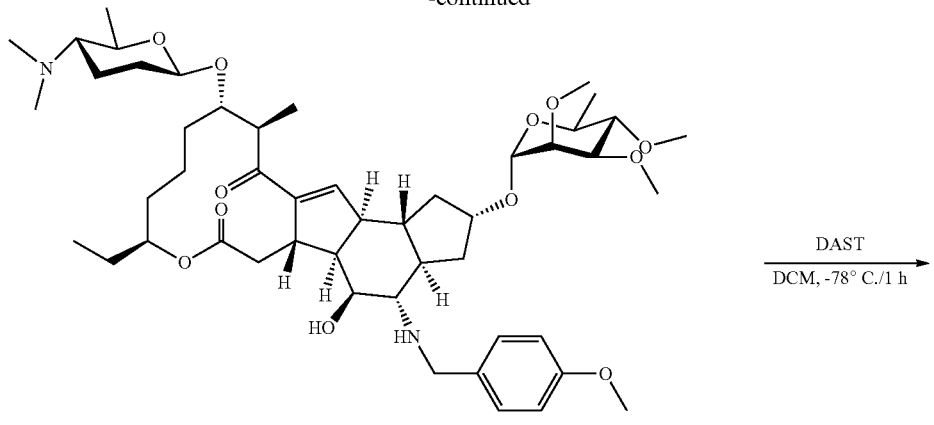

73-2

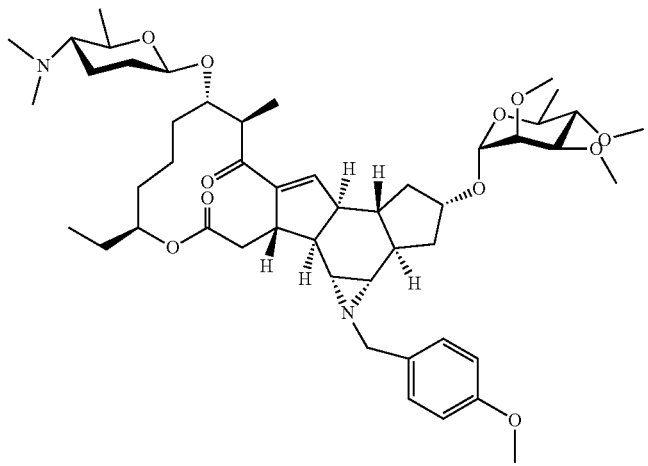

73

To a solution of compound A1 (300 mg, 0.40 mmol) and 2-Methoxy-4-methyl-phenylamine (164.6 mg, 1.2 mmol) in 1,4-Dioxane (5 mL) was added ZrCl$_4$ (93.2 mg, 0.4 mmol). The mixture was stirred at 80° C. for overnight. The mixture was quenched with water and extracted with DCM. The organic layer was washed with water and dried over Na$_2$SO$_4$, filtered and concentrated. The residue was purified by flash (MeCN/H$_2$O=50:50-95:5) to afford the crude compounds 73-1 and 73-2 (100 mg, 28.2% yield) as yellow solid. LC-MS: m/z 885.2 [M+H]$^+$.

To a solution of compounds 73-1 and 73-2 (100 mg, 0.11 mmol) in DCM (10 mL) was added DAST (145.5 mg, 0.9 mmol) at −78° C. under N$_2$ pressure. The mixture was stirred at −78° C. under N$_2$ pressure for 1 h. The mixture was quenched with aqueous NaHCO$_3$ (10 mL) and extracted with DCM (30 mL×3). The combined organic layer was dried over Na$_2$SO$_4$, filtered and concentrated. The residue was purified by Prep-HPLC to afford compound 73 (16 mg, yield 8.4%) as yellow solid. Partial $^1$H NMR (CDCl$_3$, 300 MHz): δ 7.31 (d, J=8.7 Hz, 2H), 6.88 (d, J=8.7 Hz, 2H), 6.72 (s, 1H), 4.85 (s, 1H), 4.75-4.65 (m, 1H), 4.45-4.38 (m, 1H), 4.31-4.24 (m, 1H), 3.80 (s, 3H), 3.68-3.03 (m, 21H), 2.54-2.45 (m, 1H), 2.41-2.33 (m, 1H), 0.84 (t, J=7.2 Hz, 3H); LC-MS: m/z 867.2 [M+H]$^+$.

74. Synthesis of Compound 74
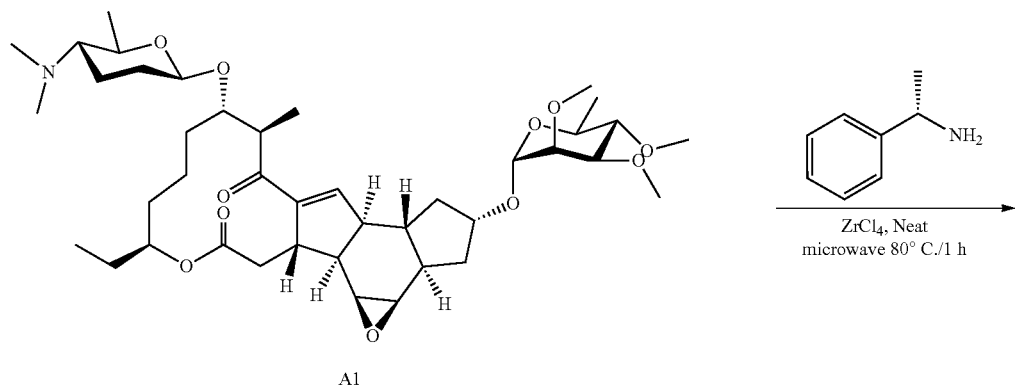

-continued

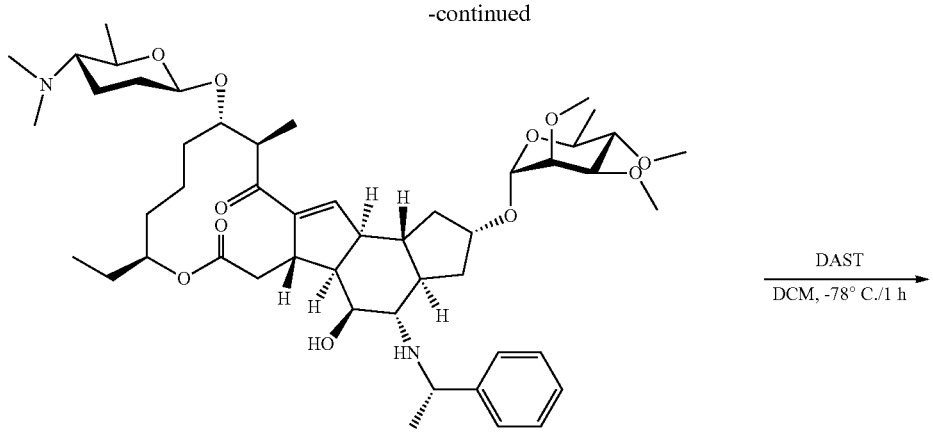

74-2

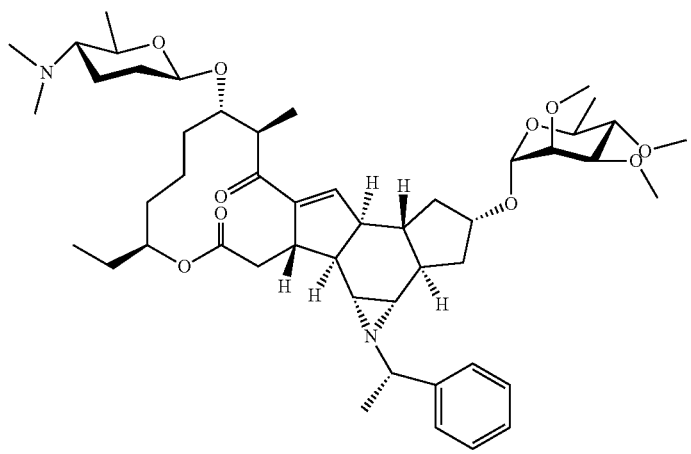

74

To a solution of compound A1 (1.0 g, 1.3 mmol) in (S)-1-phenylethanamine (3 mL) was added ZrCl$_4$ (311 mg, 1.3 mmol). The mixture was stirred at 80° C. under microwave under N$_2$ pressure for 1 h. The mixture was purified by flash (MeCN/H$_2$O=50:50-95:5) to afford the crude compounds 74-1 and 74-2 (600 mg, yield 53%) as yellow solid. LC-MS: m/z 869.2 [M+H]$^+$.

To a solution of compounds 74-1 and 74-2 (200 mg, 0.23 mmol) in DCM (10 mL) was added DAST (111.1 mg, 0.7 mmol) at −78° C. under N$_2$ pressure. The mixture was stirred at −78° C. under N$_2$ pressure for 1 h. The mixture was quenched with aqueous NaHCO$_3$ (10 mL) and extracted with DCM (30 mL×3). The combined organic layer was dried over Na$_2$SO$_4$, filtered and concentrated. The residue was purified by Prep-HPLC to afford compound 74 (30 mg, yield 15.3%) as yellow solid. Partial $^1$H NMR (CDCl$_3$, 300 MHz): δ 7.42-7.31 (m, 5H), 6.74 (s, 1H), 4.78 (s, 1H), 4.72-4.64 (m, 1H), 4.47-4.41 (m, 1H), 4.25-4.20 (m, 1H), 3.69-3.62 (m, 1H), 3.57-3.41 (m, 4H), 3.34-3.24 (m, 3H), 3.16-3.06 (m, 2H), 2.59-2.42 (m, 3H), 2.15-1.81 (m, 5H), 1.31-1.17 (m, 12H), 0.85 (t, J=7.8 Hz, 3H); LC-MS: m/z 851.2 [M+H]$^+$.

75. Synthesis of Compound 75
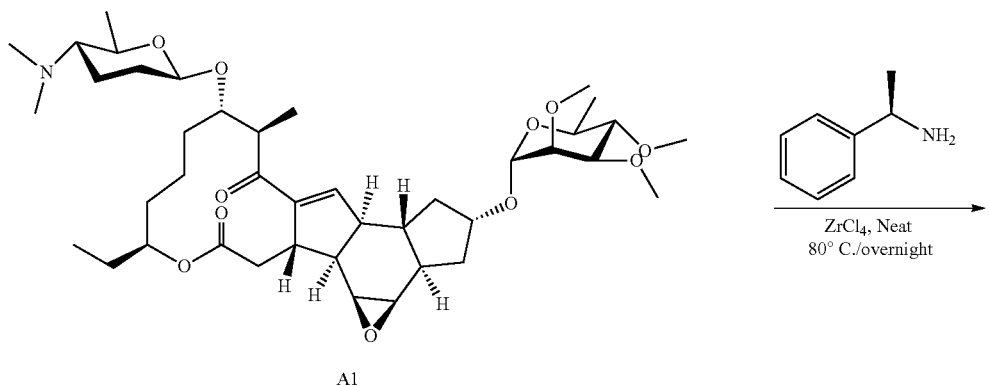
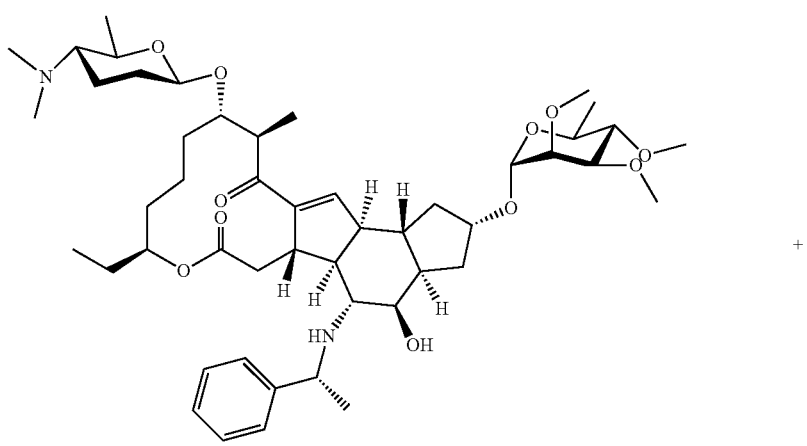

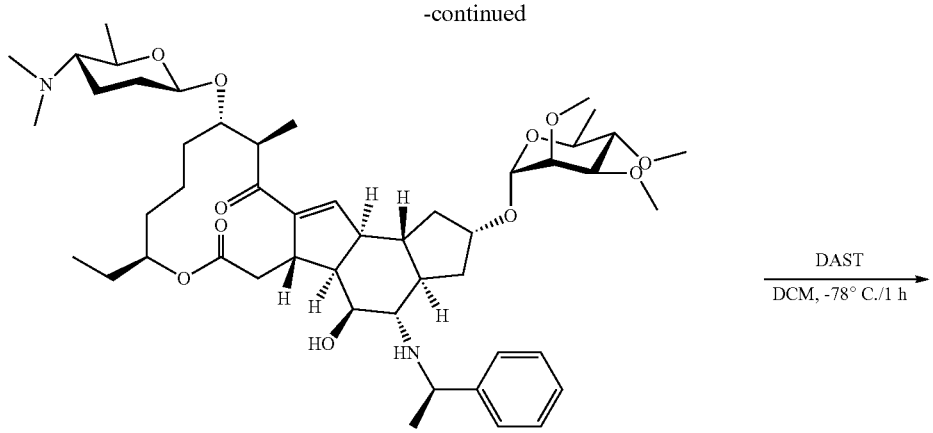

75-2

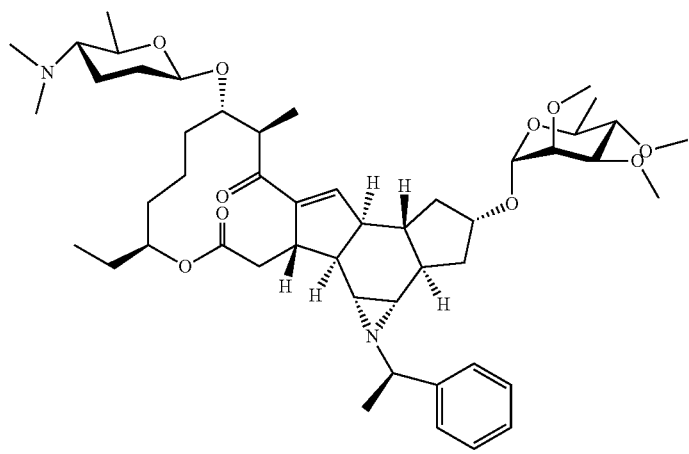

75

To a solution of compound A1 (0.5 g, 0.65 mmol) in (R)-1-phenylethanamine (4 mL) was added ZrCl₄ (153.1 mg, 0.65 mmol). The mixture was stirred at 80° C. under N₂ for overnight. The mixture was purified by flash (MeCN/H₂O=50:50-95:5) to afford the crude compounds 75-1 and 75-2 (250 mg, yield 44%) as yellow solid. LC-MS: m/z 869.2 [M+H]⁺.

To a solution of compounds 75-1 and 75-2 (250 mg, 0.28 mmol) in DCM (10 mL) was added DAST (138.9 mg, 0.86 mmol) at −78° C. under N₂ pressure. The mixture was stirred at −78° C. under N₂ pressure for 1 h. The mixture was quenched with aqueous NaHCO₃ (10 mL) and extracted with DCM (30 mL×3). The combined organic layer was dried over Na₂SO₄, filtered and concentrated. The residue was purified by Prep-HPLC to afford compound 75 (40 mg, yield 16.7%) as yellow solid. Partial ¹H NMR (CDCl₃, 300 MHz): δ 7.44-7.30 (m, 4H), 7.25-7.18 (m, 1H), 6.68 (s, 1H), 4.88 (s, 1H), 4.73-4.64 (m, 1H), 4.44-4.37 (m, 1H), 4.37-4.27 (m, 1H), 3.35-3.09 (m, 3H), 3.00-2.90 (m, 2H), 2.62-2.52 (m, 2H), 2.28-2.11 (m, 8H), 0.81 (t, J=7.2 Hz, 3H); LC-MS: m/z 851.2 [M+H]⁺.

76. Synthesis of Compound 76
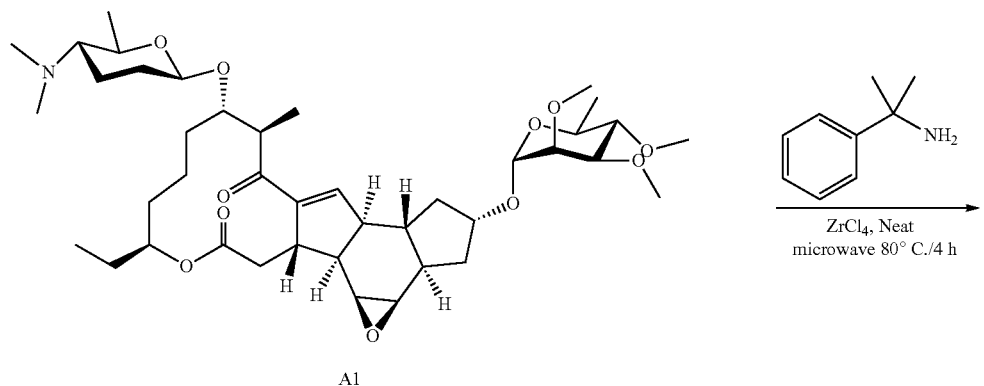
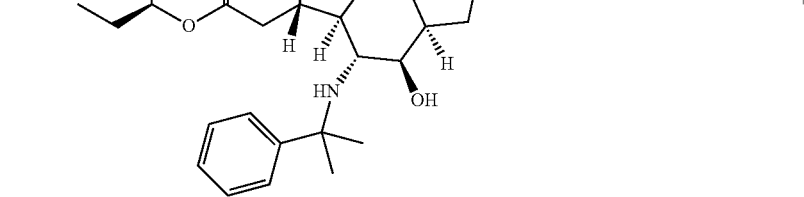
76-1

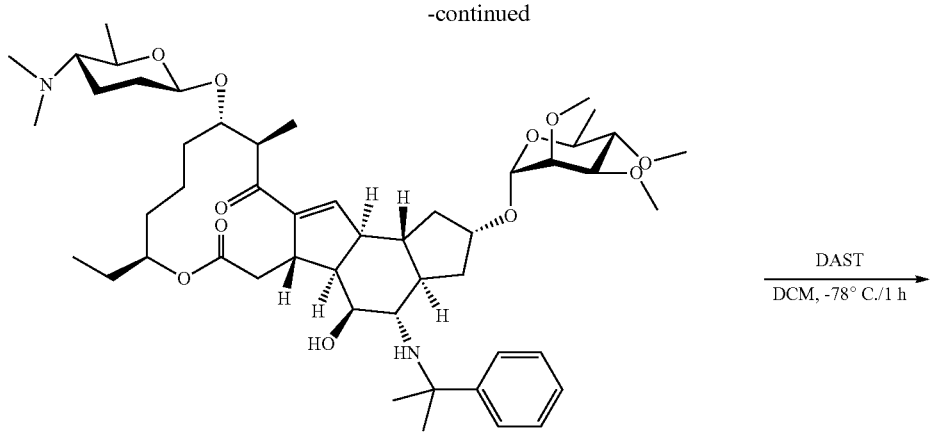

76-2

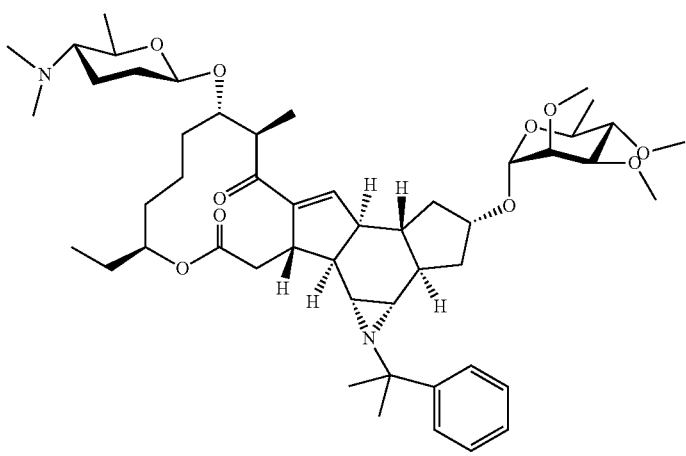

76

To a solution of compound A1 (0.5 g, 0.65 mmol) in 2-phenylpropan-2-amine (5 mL) was added $ZrCl_4$ (153.1 mg, 0.65 mmol). The mixture was stirred at 80° C. under $N_2$ under microwave for 4 h. The mixture was purified by flash (MeCN/$H_2O$=50:50-95:5) to afford the crude compounds 76-1 and 76-2 (300 mg, yield 52%) as yellow solid. LC-MS: m/z 883.2 [M+H]$^+$.

To a solution of compounds 76-1 and 76-2 (300 mg, 0.34 mmol) in DCM (10 mL) was added DAST (164.0 mg, 1.0 mmol) at −78° C. under $N_2$ pressure. The mixture was stirred at −78° C. under $N_2$ pressure for 1 h. The mixture was quenched with aqueous $NaHCO_3$ (10 mL) and extracted with DCM (30 mL×3). The combined organic layer was dried over $Na_2SO_4$, filtered and concentrated. The residue was purified by Prep-HPLC to afford compound 76 (40 mg, yield 13.6%) as yellow solid. Partial $^1$H NMR (CDCl$_3$, 300 MHz): δ 7.52-7.46 (m, 2H), 7.39-7.31 (m, 2H), 6.73 (s, 1H), 4.70 (s, 1H), 4.72-4.64 (m, 1H), 4.46-4.39 (m, 1H), 4.31-4.23 (m, 1H), 3.31-2.97 (m, 5H), 2.59-2.50 (m, 1H), 0.85 (t, J=7.8 Hz, 3H); LC-MS: m/z 865.2 [M+H]$^+$.

77. Synthesis of Compound 77

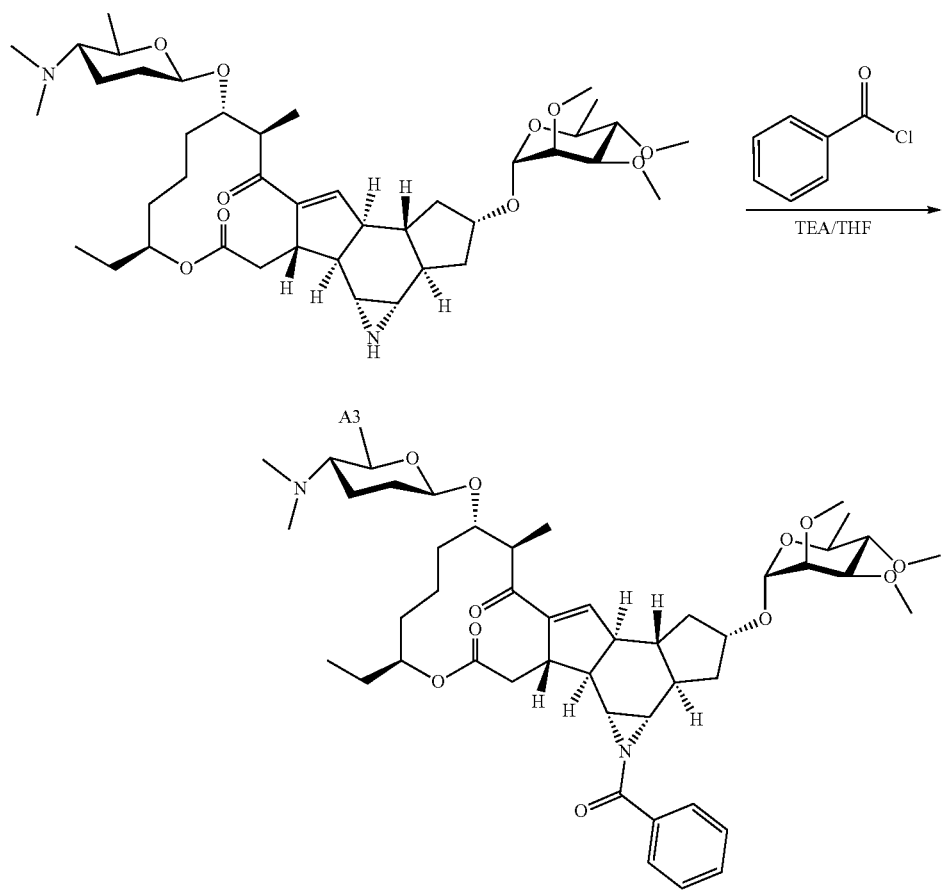

To a solution of compound A3 (180 mg, 0.24 mmol) and TEA (73 mg, 0.72 mmol) in THF (13 mL) was added benzoyl chloride (50 mg, 0.36 mmol) at 0° C. The mixture was stirred at r.t for 2 h. The reaction mixture was diluted with saturated NaHCO$_3$ solution (30 mL) and extracted with DCM (50 mL×2). The combined organic phase was dried over anhydrous Na$_2$SO$_4$, filtered and concentrated. The residue was purified by Prep-HPLC to afford compound 77 (43 mg, 21% yield) as white solid. Partial $^1$H NMR (CDCl$_3$, 400 MHz): δ8.12 (d, J=7.2 Hz, 2H), 7.55 (t, J=7.6 Hz, 1H), 7.46 (t, J=7.6 Hz, 2H), 6.74 (s, 1H), 4.88 (s, 1H), 4.75-4.71 (m, 1H), 4.43-4.41 (m, 1H), 4.36-4.31 (m, 1H), 3.76-3.71 (m, 1H), 3.66-3.62 (m, 1H), 3.32-3.25 (m, 1H), 3.18-3.12 (m, 3H), 2.95-2.93 (m, 1H), 2.69-2.64 (m, 1H), 2.52 (d, J=6.0 Hz, 1H), 0.85 (t, J=7.2 Hz, 3H); LCMS: m/z 851.2 [M+H]$^+$.

78. Synthesis of Compound 78

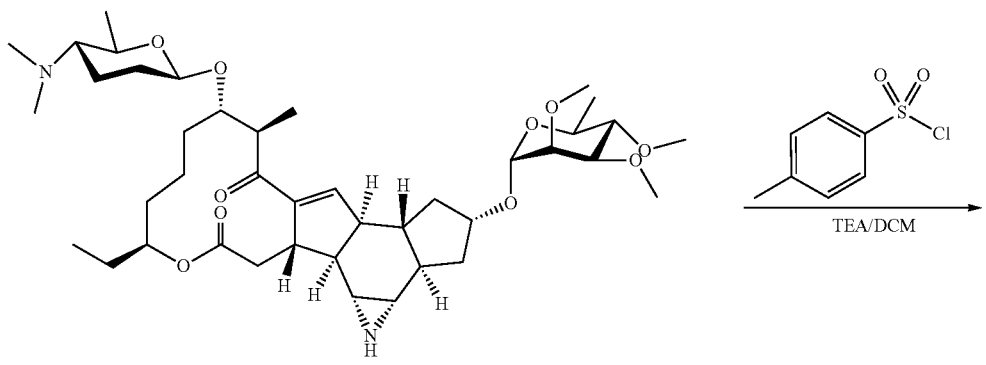

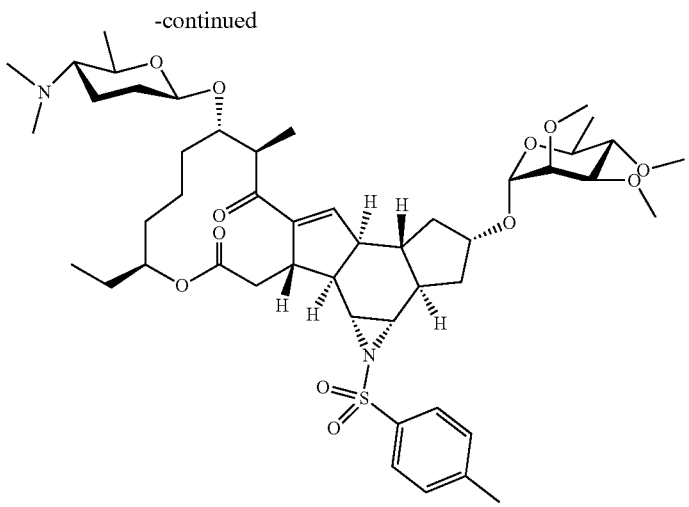

78

To a solution of compound A3 (100 mg, 0.13 mmol) and TEA (68 mg, 0.67 mmol) in DCM (2 mL) was added Tosyl chloride (51 mg, 0.26 mmol) at 0° C. The mixture was stirred at r.t for 2 h. The reaction mixture was diluted with saturated NaHCO$_3$ solution (20 mL) and extracted with DCM (20 mL×2). The combined organic phase was dried over anhydrous Na$_2$SO$_4$, filtered and concentrated. The residue was purified by Prep-HPLC to afford compound 78 (79 mg, 65.5% yield). Partial $^1$H NMR (CDCl$_3$, 300 MHz): δ7.84 (d, J=8.4 Hz, 2H), 7.35 (d, J=7.5 Hz, 2H), 6.62 (s, 1H), 4.84 (s, 1H), 4.65-4.60 (m, 1H), 4.42-4.39 (m, 1H), 4.32-4.26 (m, 1H), 3.23-3.08 (m, 6H), 2.70 (d, J=7.8 Hz, 1H), 2.49-2.43 (m, 4H); LCMS: m/z 901.5 [M+H]$^+$.

79. Synthesis of Compound 79

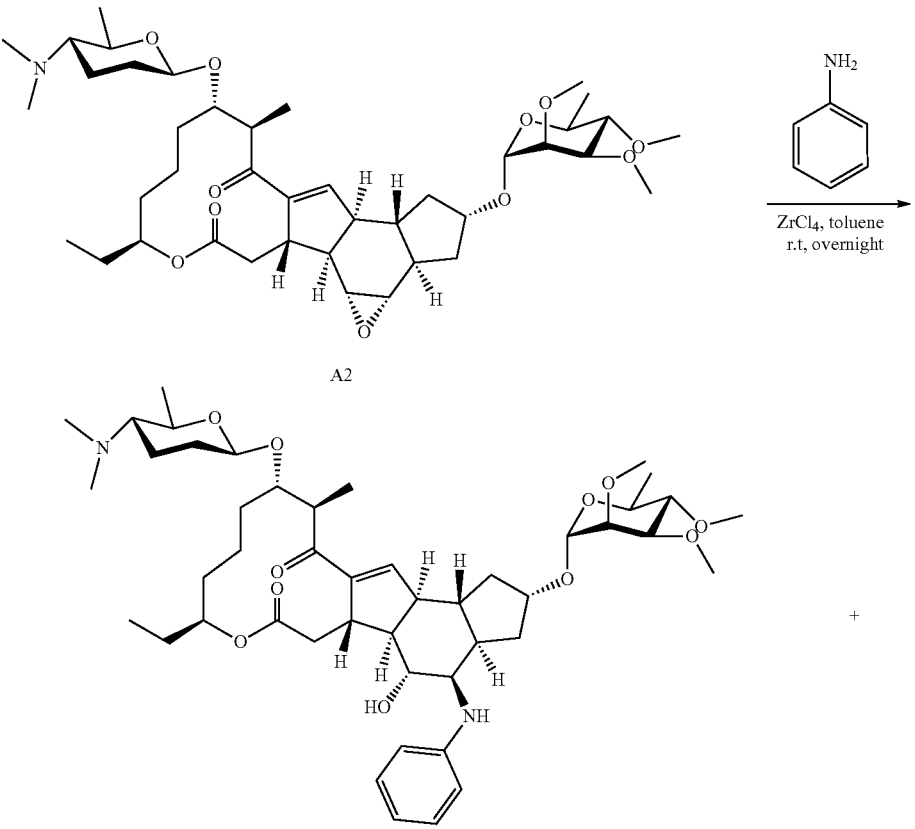

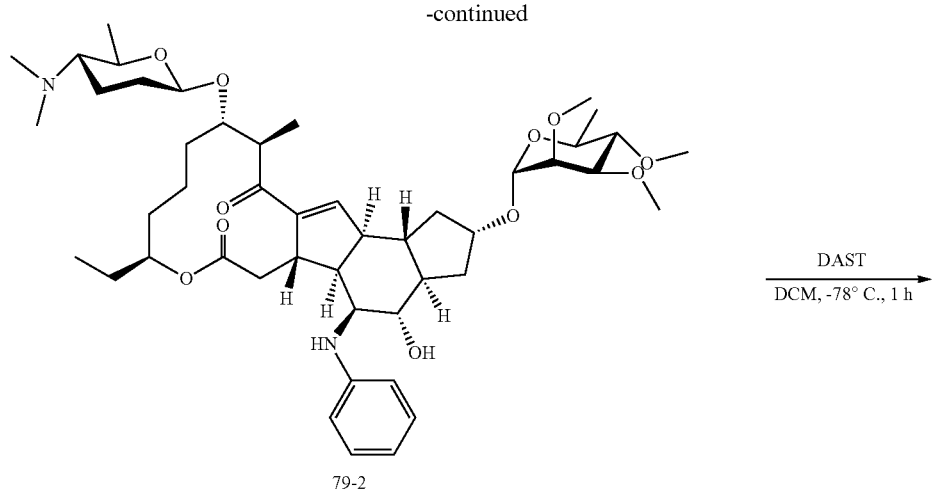

79-2

DAST
―――――――――
DCM, -78° C., 1 h

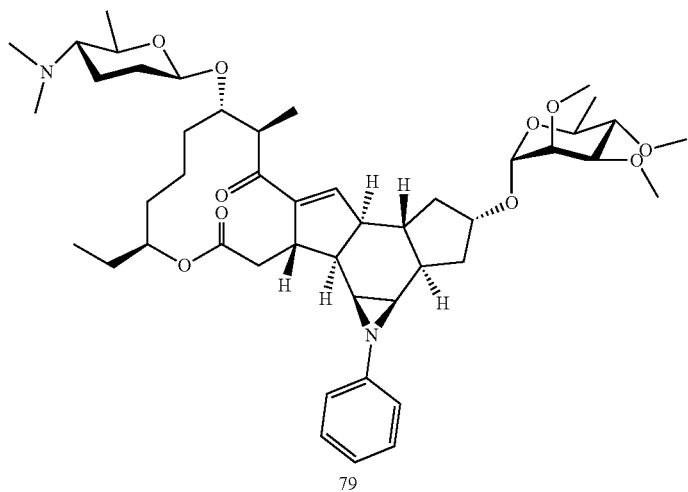

79

To a solution of compound A2 (310 mg, 0.4 mmol) and aniline (77 mg, 0.83 mmol) in toluene (5 mL) was added ZrCl$_4$ (578 mg, 2.5 mmol). The mixture was stirred at r.t overnight. The mixture was quenched with aqueous NaHCO$_3$ (30 mL) and extracted with EA (20 ml). The organic layer was washed with water, dried over Na$_2$SO$_4$, filtered and concentrated. The residue was purified by silica gel column chromatography (DCM/MeOH=100:1-10:1) to give a mixture of compounds 79-1 and 79-2 (170 mg, yield 49%) as brown solid. LC-MS: m/z 841.2 [M+H]$^+$.

To a solution of compounds 79-1 and 79-2 (170 mg, 0.2 mmol) in DCM (10 mL) was added DAST (33 mg, 0.2 mmol) at −78° C. under N$_2$. The mixture was stirred at −78° C. under N$_2$ pressure for 1 h. The reaction mixture was diluted with saturated NaHCO$_3$ solution (10 mL) and extracted with DCM (15 mL×2). The combined organic phase was dried over anhydrous Na$_2$SO$_4$, filtered and concentrated. The residue was purified by Prep-HPLC to afford compound 79 (20 mg, yield 12.1%) as yellow solid. Partial $^1$H NMR (CDCl$_3$, 400 MHz): δ 7.21 (t, J=7.6 Hz, 2H), 6.93 (t, J=7.6 Hz, 1H), 6.83 (d, J=7.2 Hz, 2H), 6.62 (s, 1H), 4.90 (s, 1H), 4.71-4.66 (m, 1H), 4.47 (d, J=7.2 Hz, 1H), 4.32-4.26 (m, 1H), 3.36-3.31 (m, 1H), 3.28-3.22 m, 1H), 3.12 (t, J=9.2 Hz, 1H), 2.67-2.59 (m, 6H), 2.50 (s, 6H); LC-MS: m/z 823.2 [M+H]$^+$.

80. Synthesis of Compound 80

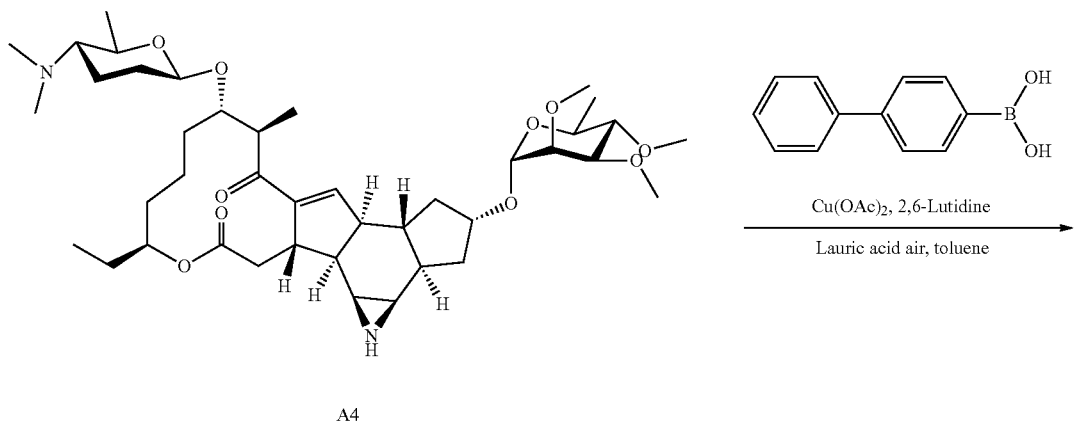

A4

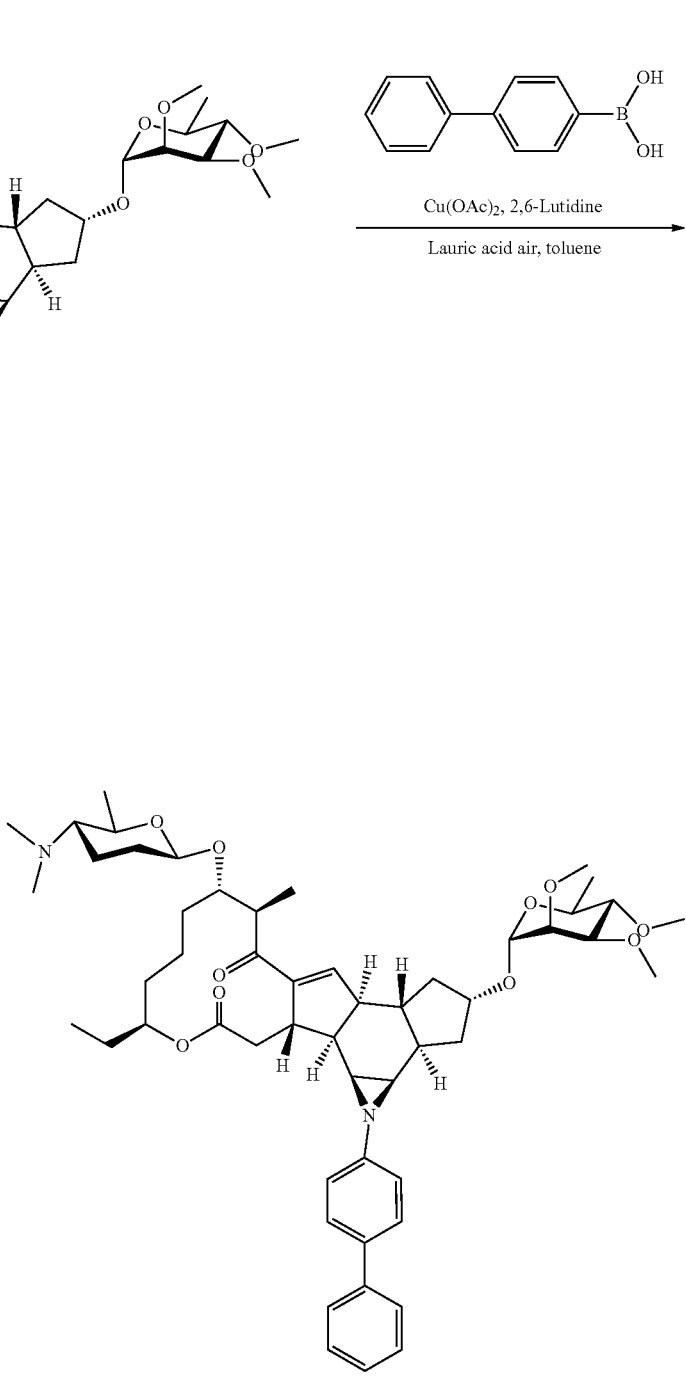

80

To a solution of 4-Biphenylboronic acid (60 mg, 0.3 mmol) and Cu(OAc)$_2$ (8.0 mg, 0.04 mmol) in toluene (10 mL) were added 2,6-Lutidine (21.4 mg, 0.2 mmol), Lauric acid (4.0 mg, 0.02 mmol) and compound A4 (150 mg, 0.2 mmol). The mixture was stirred under air atmosphere for two days at room temperature. The mixture was concentrated and the residue was purified by column chromatography on silica gel (MeOH/DCM=1/20) and prep-HPLC to afford compound 80 (12 mg, yield 6.7%) as white solid.

Partial $^1$H NMR (CDCl$_3$, 400 MHz): δ 7.52 (d, J=7.2 Hz, 2H), 7.46-7.38 (m, 4H), 7.32-7.26 (m, 1H), 6.90 (d, J=8.4 Hz, 2H), 6.63 (s, 1H), 4.91 (s, 1H), 4.75-4.68 (m, 1H), 4.44-4.40 (m, 1H), 4.34-4.26 (m, 1H), 3.68-3.62 (m, 1H), 3.41-3.34 (m, 2H), 3.29-3.21 (m, 1H), 3.16-3.11 (m, 1H), 2.74-2.57 (m, 4H), 2.27-2.17 (m, 9H), 2.12-2.05 (m, 1H), 2.02-1.92 (m, 2H), 1.87-1.70 (m, 3H), 0.85 (t, J=7.6 Hz, 3H), LCMS: m/z 900.4 [M+H]$^+$.

81. Synthesis of Compound 81

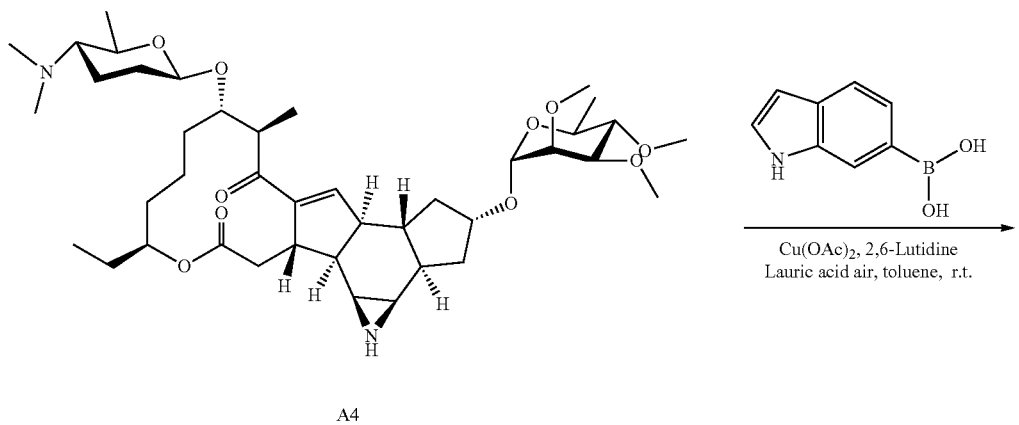

A4

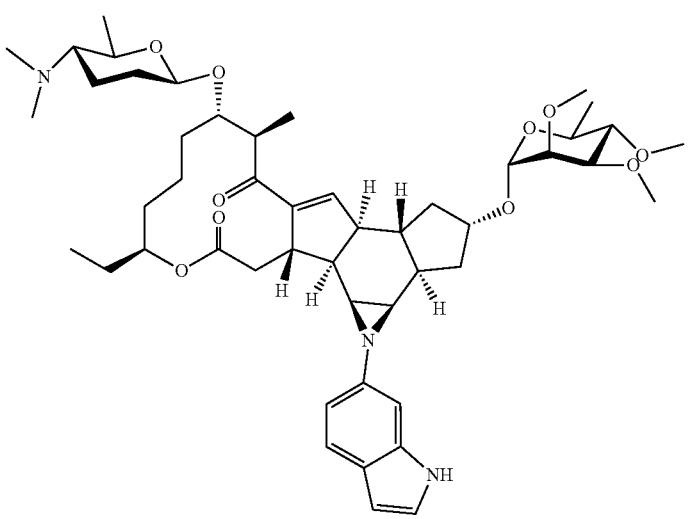

81

To a solution of Indole-6-boronic acid (32 mg, 0.2 mmol) and Cu(OAc)$_2$ (5.2 mg, 0.027 mmol) in toluene (10 mL) were added 2,6-Lutidine (13.3 mg, 0.013 mmol), Lauric acid (2.7 mg, 0.013 mmol) and compound A4 (100 mg, 0.13 mmol). The mixture was stirred under air atmosphere for two days at room temperature. The mixture was concentrated and the residue was purified by column chromatography on silica gel (MeOH/DCM=1/20) and prep-HPLC to afford compound 81 (10 mg, yield 8.9%) as white solid.

Partial $^1$H NMR (CDCl$_3$, 400 MHz): δ7.58 (d, J=2.0 Hz, 1H), 7.35 (d, J=8.8 Hz, 1H), 7.18 (d, J=2.4 Hz, 1H), 7.03 (dd, J=8.8, 2.4 Hz, 1H), 6.77 (s, 1H), 6.68 (d, J=2.4 Hz, 1H), 4.90 (s, 1H), 4.76-4.66 (m, 1H), 4.45-4.41 (m, 1H), 4.37-4.28 (m, 1H), 3.68-3.62 (m, 1H), 3.34-3.25 (m, 2H), 3.17-3.06 (m, 2H), 2.62-2.51 (m, 2H), 2.44-2.39 (m, 1H), 2.02-1.96 (m, 1H), 1.31-1.17 (m, 13H), 0.90-0.79 (m, 4H). LCMS: m/z 863.4 [M+H]$^+$.

82. Synthesis of Compound 82

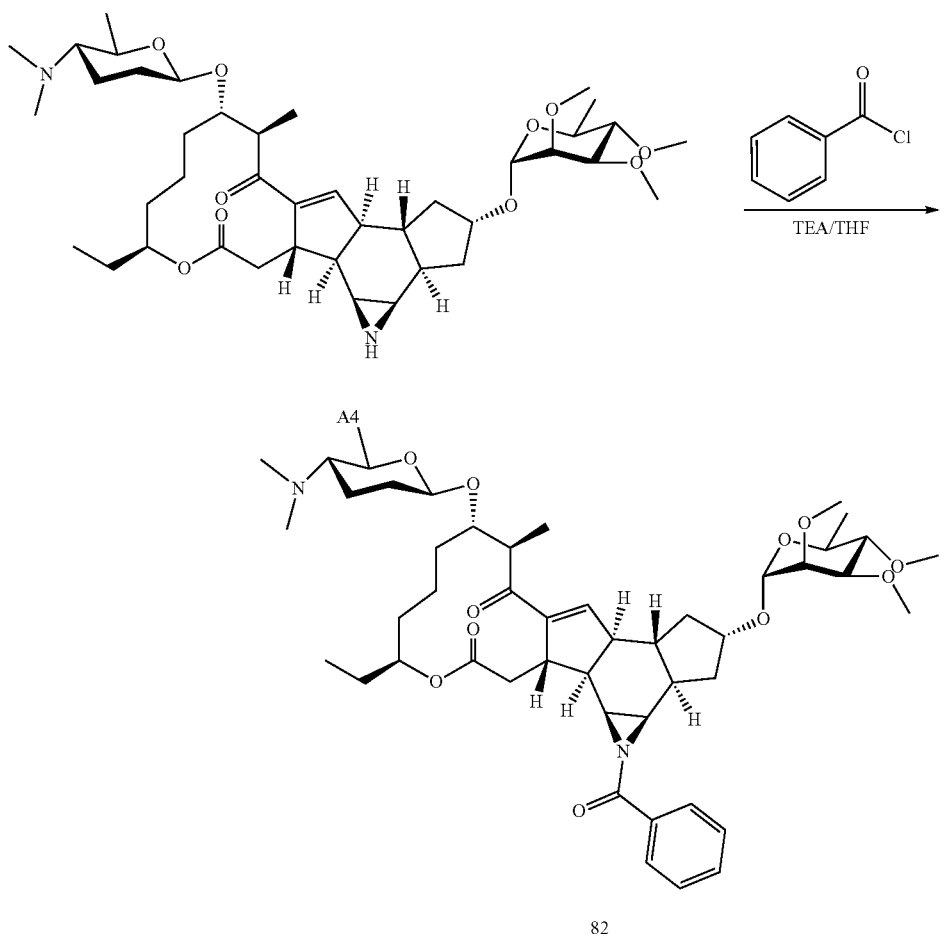

To a solution of compound A4 (45 mg, 0.06 mmol) and TEA (18 mg, 0.18 mmol) in THF (5 mL) was added benzoyl chloride (12.5 mg, 0.09 mmol) at 0° C. The mixture was stirred at r.t for 2 h. The reaction mixture was diluted with saturated NaHCO₃ solution (10 mL) and extracted with DCM (20 mL×2). The combined organic phase was dried over anhydrous Na₂SO₄, filtered and concentrated. The residue was purified by Prep-HPLC to afford compound 82 (15 mg, 29% yield) as white solid. Partial ¹H NMR (CDCl₃, 400 MHz): δ7.89 (d, J=7.2 Hz, 2H), 7.54 (t, J=7.2 Hz, 1H), 7.42 (t, J=7.2 Hz, 2H), 6.62 (s, 1H), 4.87 (s, 1H), 4.70-4.65 (m, 1H), 4.43-4.41 (m, 1H), 4.37-4.32 (m, 1H), 3.67-3.62 (m, 1H), 3.31-3.29 (m, 1H), 3.29-3.12 (m, 3H), 3.02 (d, J=6.8 Hz, 1H), 2.71-2.66 (m, 1H), 2.54 (d, J=13.2 Hz, 1H), 2.07-1.92 (m, 3H), 1.87-1.74 (m, 3H), 0.82 (t, J=7.2 Hz, 3H); LCMS: m/z 851.2 [M+H]⁺.

83. Synthesis of Compound 83

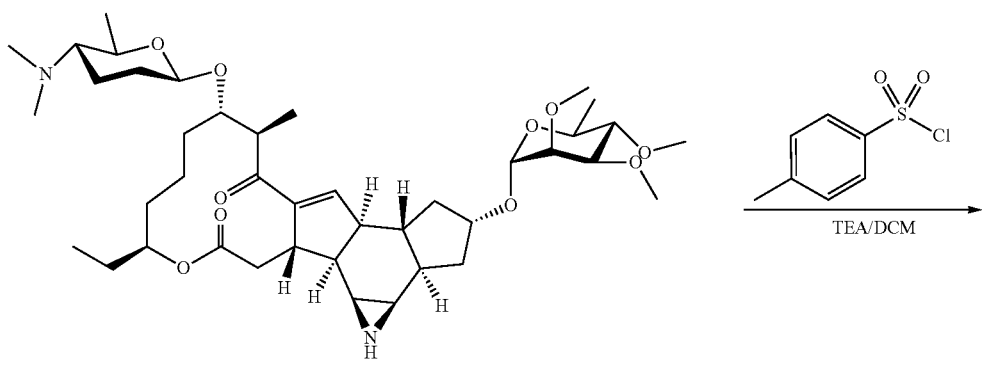

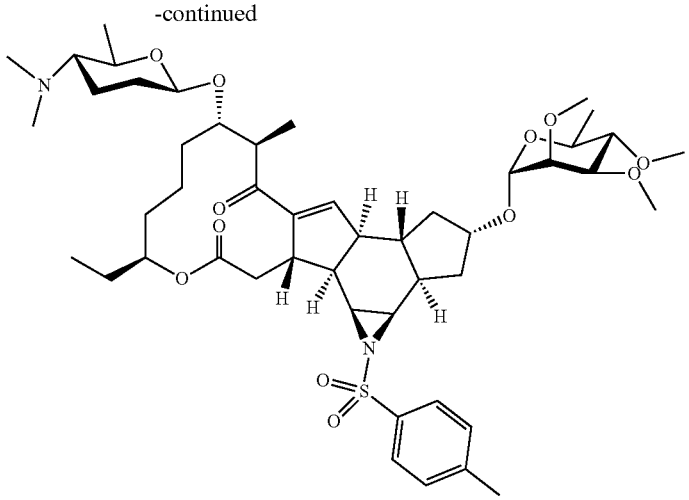

83

To a solution of compound A4 (80 mg, 0.10 mmol) and TEA (54 mg, 0.53 mmol) in DCM (3 mL) was added Tosyl chloride (41 mg, 0.21 mmol). The mixture was stirred at r.t for 2 h. The reaction mixture was diluted with saturated NaHCO$_3$ solution (20 mL) and extracted with DCM (20 mL×2). The combined organic phase was dried over anhydrous Na$_2$SO$_4$, filtered and concentrated. The residue was purified by Prep-HPLC to afford compound 83 (70 mg, 72.5% yield) as white solid. Partial $^1$H NMR (CDCl$_3$, 300 MHz): δ7.80 (d, J=8.4 Hz, 2H), 7.35 (d, J=8.1 Hz, 2H), 6.50 (s, 1H), 4.80 (s, 1H), 4.67-4.61 (m, 1H), 4.43-4.39 (m, 1H), 4.19-4.12 (m, 1H), 3.22-2.98 (m, 4H), 2.87-2.81 (m, 1H), 2.13-2.10 (m, 1H), 2.06-1.96 (m, 3H), 0.80 (t, J=8.4 Hz, 3H); LCMS: m/z 901.5 [M+H]$^+$.

84. Synthesis of Compound 84

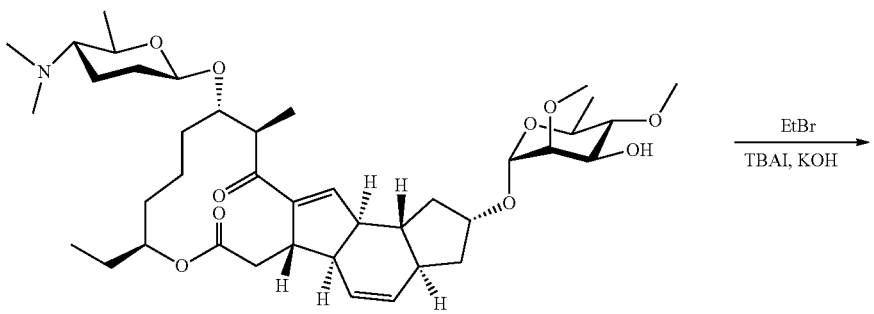

Spinosyn J

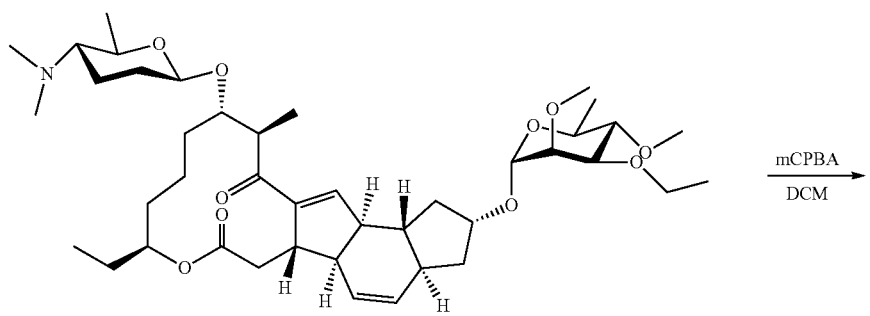

J-1

-continued
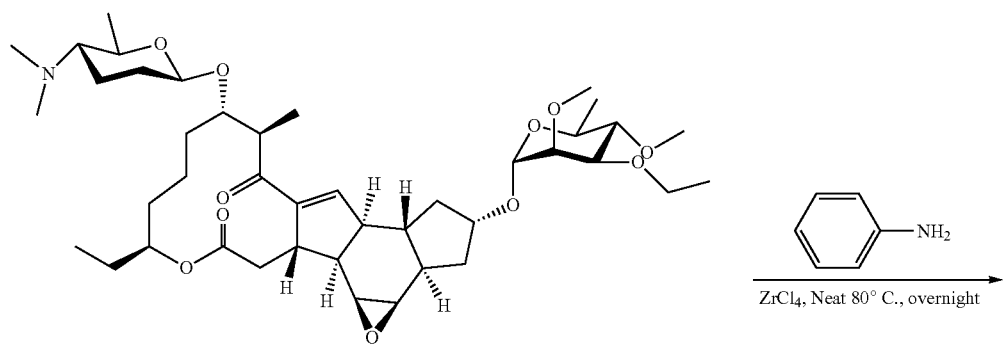
J-2
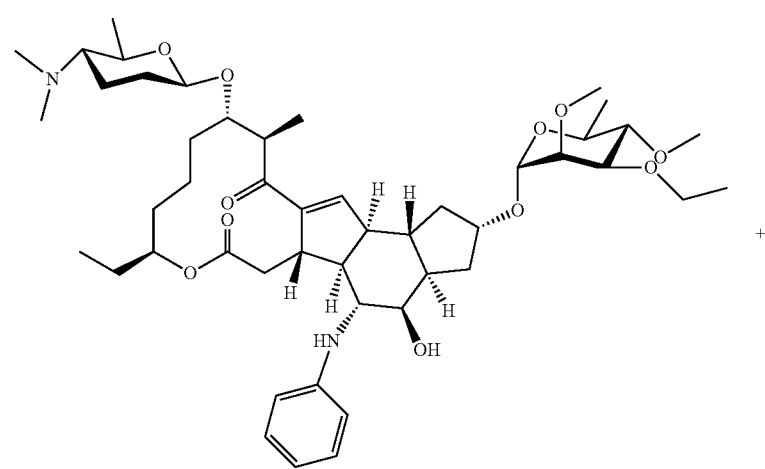
84-1

-continued

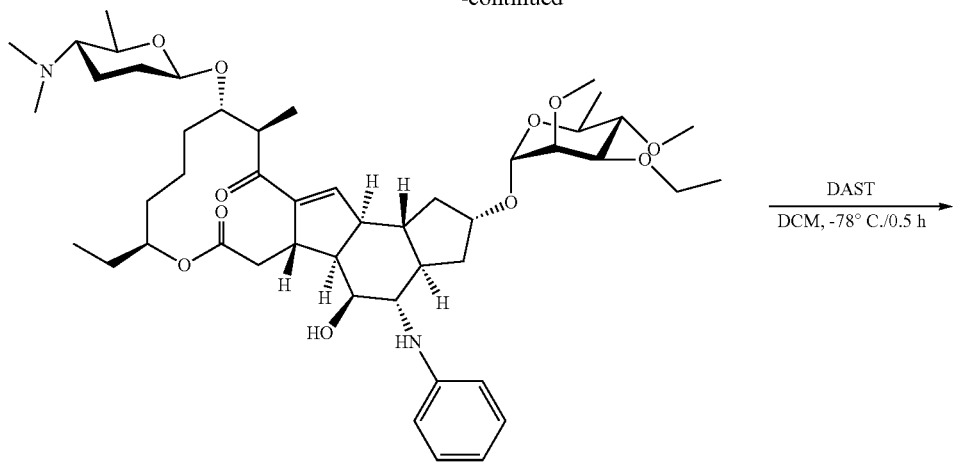

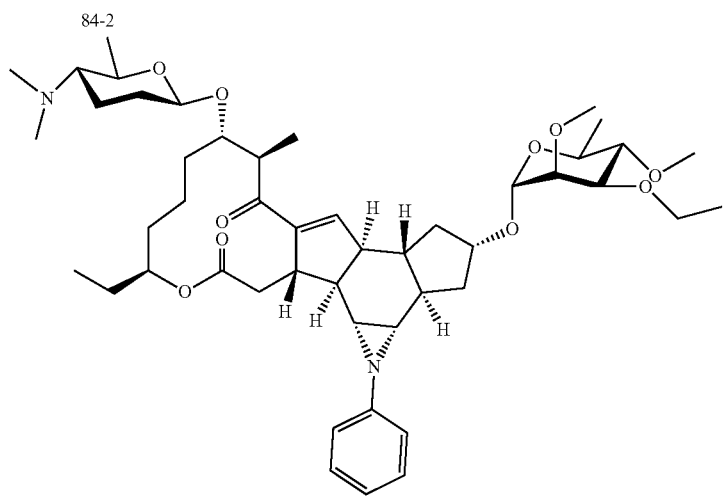

84

To a solution of Spinosyn J (2.15 g, 3.0 mmol) in ethyl bromide (15 mL) was added powered potassium hydroxide/tetra-n-buthyl ammonium iodide (10:1, 1.0 g/0.1 g). The mixture was stirred at ambient temperature for 2 h and then evaporated under reduced pressure. The residue was dissolved with water (60 mL) and extracted with EA (50 mL×2). The combined organic layer was washed with brine, dried over $Na_2SO_4$, filtered and concentrated in vacuo to give an oil which was purified by column chromatography on silica gel (DCM/MeOH=50/1-20/1) to give compound J-1 (2.0 g, 90% yield) as a white solid. LCMS: m/z 746.2 $[M+H]^+$.

To a solution of compound J-1 (2.9 g, 3.8 mmol) in DCM (50 mL) was added m-CPBA (2.0 g, 11.6 mmol) at 0° C. The mixture was stirred at room temperature overnight. The reaction was quenched with saturated $Na_2SO_3$ (30 mL). After stirred for another 5 h, the organic solvent was removed under reduced pressure. The aqueous residue was extracted with EA (50 mL×3). The combined organic layer was washed with saturated $NaHCO_3$ (30 mL×2), water (30 mL) and brine, dried over anhydrous $Na_2SO_4$, filtered and concentrated. The residue was purified by column chromatography on silica gel (DCM/MeOH=50/1-20/1) to give compound J-2 (2.5 g, 86% yield) as yellow solid. LCMS: m/z 761.2 $[M+H]^+$.

To a solution of compound J-2 (200 mg, 0.26 mmol) in aniline (2 mL) was added $ZrCl_4$ (31 mg, 0.13 mmol). The mixture was stirred at 80° C. for overnight. The mixture was purified by column chromatography on silica gel (DCM/MeOH=20/1-10/1) to give compounds 84-1 and 84-2 (88 mg, 40% yield). LCMS: m/z 855.2 $[M+H]^+$.

To a solution of the mixture of compounds 84-1 and 84-2 (86 mg, 0.1 mmol) in DCM (3 mL) was added DAST (82 mg, 0.5 mmol) at −78° C. under $N_2$. The mixture was stirred at −78° C. under $N_2$ pressure for 0.5 h. The reaction mixture was diluted with saturated $NaHCO_3$ solution (50 mL) and extracted with EA (30 mL×2). The combined organic phase was dried over anhydrous $Na_2SO_4$, filtered and concentrated. The residue was purified by Prep-HPLC to afford compound 84 (24 mg, yield 28%) as a white solid. Partial $^1H$ NMR ($CDCl_3$, 300 MHz): δ7.23 (d, J=8.1 Hz, 2H), 7.04 (d, J=7.5 Hz, 2H), 6.97 (t, J=6.9 Hz, 1H), 6.76 (s, 1H), 4.87 (s, 1H), 4.72-4.67 (m, 1H), 4.45-4.43 (m, 1H), 4.35-4.30 (m, 1H), 3.76-3.71 (m, 1H), 3.67-3.62 (m, 1H), 3.33-3.27 (m, 2H), 3.19-3.09 (m, 2H), 2.60-2.51 (m, 2H), 2.41-2.40 (m, 1H), 0.86 (t, J=7.8 Hz, 3H). LCMS: m/z 837.2 $[M+H]^+$.

85. Synthesis of Compound 85: (1aS,1bR,3S,4aS, 4bR,7R,8S,12S,15aS,15bR,15cR)-8-(((2R,5S,6R)-5-(dimethylamino)-6-methyltetrahydro-2H-pyran-2-yl)oxy)-3-(((2R,3R,4R,5S,6S)-4-ethoxy-3,5-dimethoxy-6-methyltetrahydro-2H-pyran-2-yl)oxy)-12-ethyl-1-(4-fluorophenyl)-7-methyl-1,1a, 1b,2,3,4,4a,4b,7,8,9,10,11,12,15,15a,15b,15c-octadecahydro-[1]oxacyclododecino[5',4':2,3]-as-indaceno[4,5-b]azirine-6,14-dione
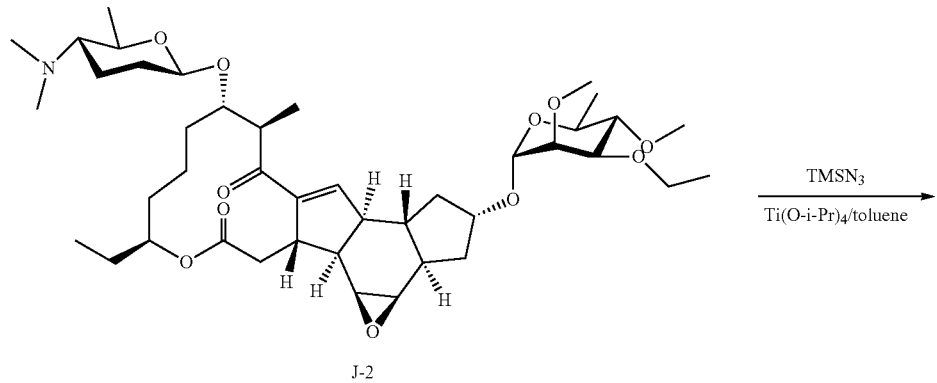
J-2
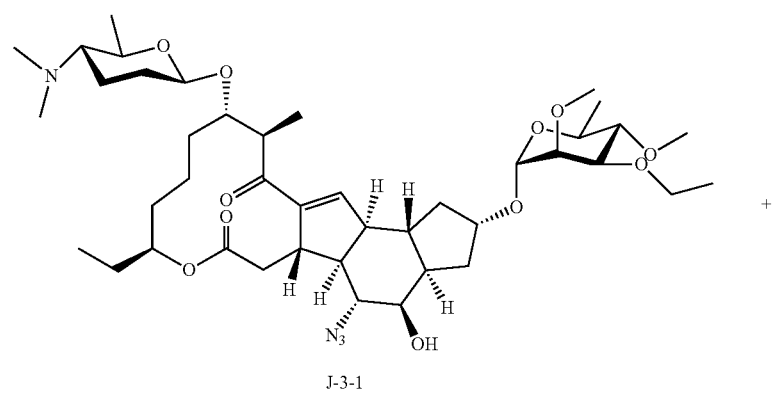
J-3-1
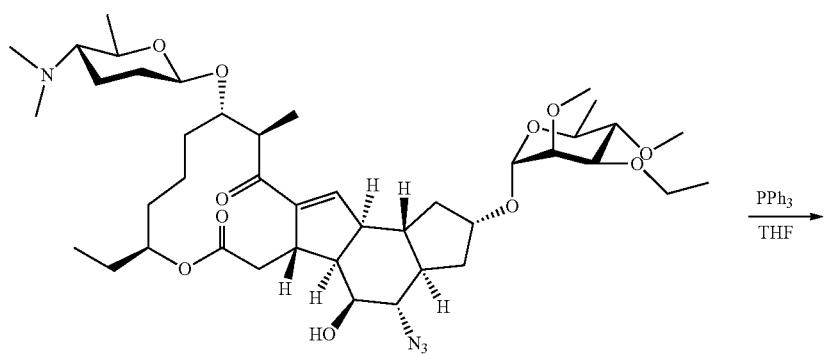
J-3-2

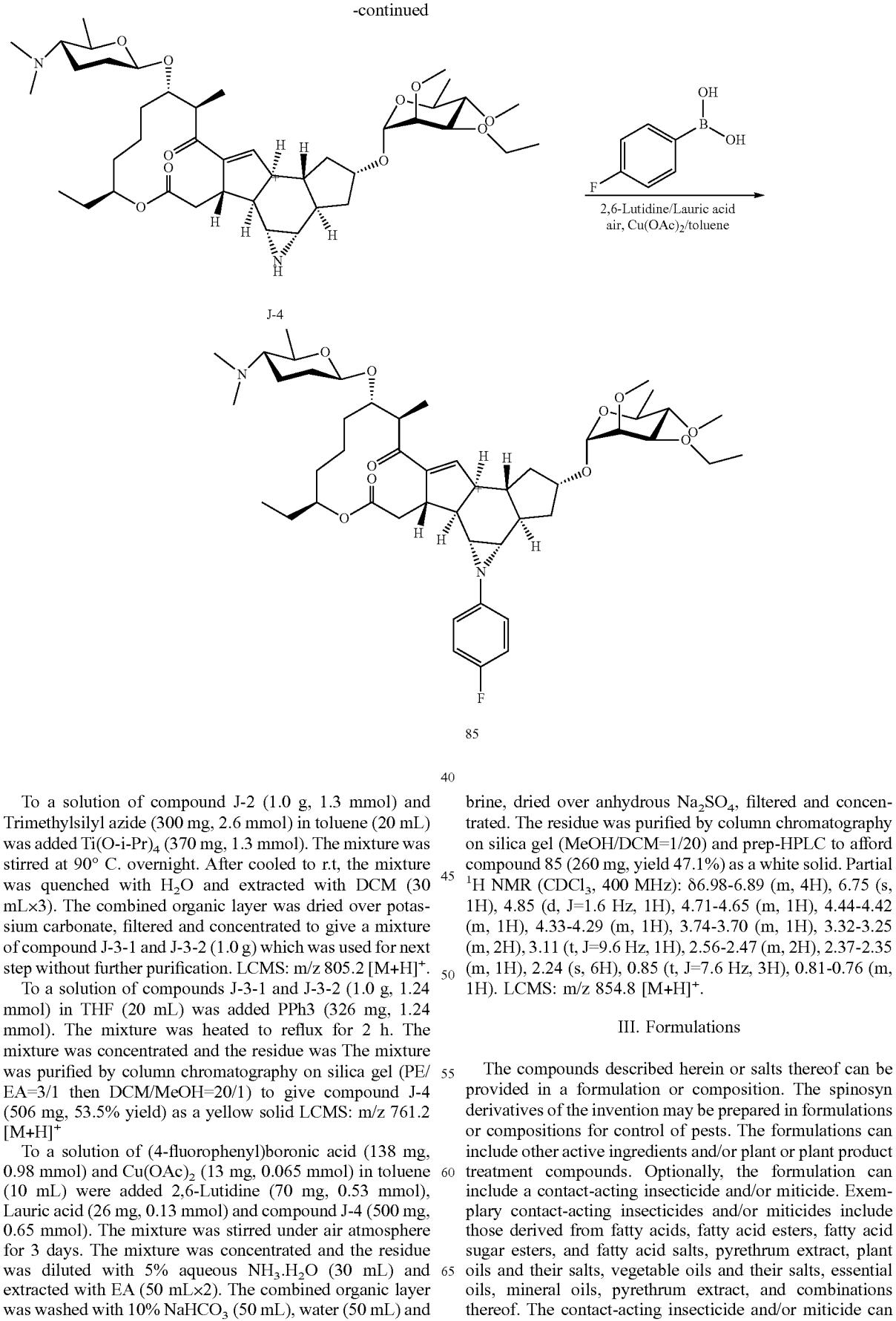

To a solution of compound J-2 (1.0 g, 1.3 mmol) and Trimethylsilyl azide (300 mg, 2.6 mmol) in toluene (20 mL) was added Ti(O-i-Pr)$_4$ (370 mg, 1.3 mmol). The mixture was stirred at 90° C. overnight. After cooled to r.t, the mixture was quenched with H$_2$O and extracted with DCM (30 mL×3). The combined organic layer was dried over potassium carbonate, filtered and concentrated to give a mixture of compound J-3-1 and J-3-2 (1.0 g) which was used for next step without further purification. LCMS: m/z 805.2 [M+H]$^+$.

To a solution of compounds J-3-1 and J-3-2 (1.0 g, 1.24 mmol) in THF (20 mL) was added PPh3 (326 mg, 1.24 mmol). The mixture was heated to reflux for 2 h. The mixture was concentrated and the residue was The mixture was purified by column chromatography on silica gel (PE/EA=3/1 then DCM/MeOH=20/1) to give compound J-4 (506 mg, 53.5% yield) as a yellow solid LCMS: m/z 761.2 [M+H]$^+$ To a solution of (4-fluorophenyl)boronic acid (138 mg, 0.98 mmol) and Cu(OAc)$_2$ (13 mg, 0.065 mmol) in toluene (10 mL) were added 2,6-Lutidine (70 mg, 0.53 mmol), Lauric acid (26 mg, 0.13 mmol) and compound J-4 (500 mg, 0.65 mmol). The mixture was stirred under air atmosphere for 3 days. The mixture was concentrated and the residue was diluted with 5% aqueous NH$_3$.H$_2$O (30 mL) and extracted with EA (50 mL×2). The combined organic layer was washed with 10% NaHCO$_3$ (50 mL), water (50 mL) and brine, dried over anhydrous Na$_2$SO$_4$, filtered and concentrated. The residue was purified by column chromatography on silica gel (MeOH/DCM=1/20) and prep-HPLC to afford compound 85 (260 mg, yield 47.1%) as a white solid. Partial $^1$H NMR (CDCl$_3$, 400 MHz): δ6.98-6.89 (m, 4H), 6.75 (s, 1H), 4.85 (d, J=1.6 Hz, 1H), 4.71-4.65 (m, 1H), 4.44-4.42 (m, 1H), 4.33-4.29 (m, 1H), 3.74-3.70 (m, 1H), 3.32-3.25 (m, 2H), 3.11 (t, J=9.6 Hz, 1H), 2.56-2.47 (m, 2H), 2.37-2.35 (m, 1H), 2.24 (s, 6H), 0.85 (t, J=7.6 Hz, 3H), 0.81-0.76 (m, 1H). LCMS: m/z 854.8 [M+H]$^+$.

III. Formulations

The compounds described herein or salts thereof can be provided in a formulation or composition. The spinosyn derivatives of the invention may be prepared in formulations or compositions for control of pests. The formulations can include other active ingredients and/or plant or plant product treatment compounds. Optionally, the formulation can include a contact-acting insecticide and/or miticide. Exemplary contact-acting insecticides and/or miticides include those derived from fatty acids, fatty acid esters, fatty acid sugar esters, and fatty acid salts, pyrethrum extract, plant oils and their salts, vegetable oils and their salts, essential oils, mineral oils, pyrethrum extract, and combinations thereof. The contact-acting insecticide and/or miticide can also include avermectins. One skilled in the art will appreciate that the resulting spinosyn-containing compositions and formulations disclosed herein are not only pesticidally effective, but also environmentally sound and safe for human use. Further, some of the compositions and formulations can be residual in that they do not leach out of baits or easily wash off of the leaves during rain, and thus can protect against insect and mite pests during and after rainy weather. Optionally, the compositions and formulations can exhibit synergy, and result in better than expected results than just the spinosyn or the insecticide or miticide treatment alone.

Optionally, the present compounds are usefully combined with ectoparasiticides (agents that control arthropod pests that typically attack their hosts on the external ("ecto") surface). The spinosyn compounds are formulated for use as ectoparasiticides in manners known to those skilled in the art. Representative ectoparasiticides include, but are not limited to, the following: Abamectin, Alphamethrin, Amitraz, Avermectin, Coumaphos, Cycloprothrin, Cyfluthrin, Cyhalothrin, Cypermethrin, Cyromazine, Deltamethrin, Diazinon, Diflubenzuron, Dioxathion, Doramectin, Famphur, Fenthion, Fenvalerate, Flucythrinate, Flumethrin, Hexaflumuron, Ivermectin, Lindane, Lufenuron, Malathion, Methoprene, Metriphonate, Moxidectin, Permethrin, Phosme, Pirimiphos, Propetamphos, Propoxur, Rotenone, Temephos, Tetrachlorvinphos, Trichlorfon, Zetacypermethrin, B.t. Biotoxins and Boric Acid.

Optionally, the present compounds are usefully combined with other ectoparasiticides or with anthelmentics, the latter also known as endoparasiticides ("endo"=internal, controlling internal parasites which are typically platyhelminthes and nemathelminthes). Representative such endoparasiticides include, but are not limited to, the following: Abamectin, Albendazole, Avermectin, Bunamidine, Coumaphos, Dichlorvos, Doramectin, Epsiprantel, Febantel, Fenbendazole, Flubendazole, Ivermectin, Levamisole, Mebendazole, Milbemycin, Morantel, Moxidectin, Netobimin, Niclosamide, Nitroscanate, Oxfendazole, Oxibendazole, Piperazine, Praziquantel, Pyrantel, Ricombendazole, Tetramisole, Thiabendazole, Clorsulon, Closantel, Diamphenethide, Nitroxynil, Oxyclozanide, Rafoxanide, Triclabendazole.

The formulations described herein can further include, in combination with the spinosyn component, one or more other compounds that have activity against the specific ectoparasite or endoparasite to be controlled, such as, for example, synthetic pyrethroids, natural pyrethins, organophosphates, organochlorines, carbamates, foramidines, avermectins, milbemycins, insect growth regulators (including chitin synthesis inhibitors, juvenile hormone analogs, and juvenile hormones), nitromethylenes, pyridines and pyrazoles. In an exemplary embodiment, the composition can include an additional contact-acting insecticide and/or miticide. The compositions can be utilized as liquid concentrates, Ready-To-Use (RTU) liquid sprays, dusts, or solids, depending upon the needs of the user. In use, the composition can be applied to the pests themselves, in the vicinity of the pests, and/or in the vicinity of plants and plant products that are to be protected.

In general, a formulation will include a compound as described herein and one or more physiologically acceptable adjuvants. Formulations include concentrated versions, in which the present active agent is present in a concentration of from 0.001 to 98.0 percent, with the remaining content being physiologically acceptable carriers. Such formulations, especially those with less than 50 percent of the present compound, can sometimes be used directly, but these formulations can also be diluted with other physiologically acceptable carriers to form more dilute treating formulations. These latter formulations can include the active agent in lesser concentrations of from 0.001 to 0.1 percent.

Compositions are prepared according to the procedures and formulas which are conventional in the agricultural or pest control art. The compositions may be concentrated and dispersed in water or may be used in the form of a dust, bait or granular formulation. The dispersions are typically aqueous suspensions or emulsions prepared from concentrated formulations of the compounds. The water-soluble or water-suspension or emulsifiable formulations are either solids, wettable powders, or liquids, known as emulsifiable concentrates or aqueous suspensions. Wettable powders may be agglomerated or compacted to form water dispersible granules. These granules comprise mixtures of compound, inert carriers and surfactants. The concentration of the compound is typically between about 0.1% to about 90% by weight. The inert carrier is typically attapulgite clays, montmorillonite clays and the diatomaceous earths or purified silicates.

Surfactants comprise typically about 0.5% to about 10% of the wettable powder. Surfactants include sulfonated lignins, condensed napthalene-sulfonates, the napthalene-sulfonates, alkyl-benenesulfonates, alkysulfonates or non-ionic surfactants such as ethylene oxide adducts of alkylphenols or mixtures thereof. Emulsifiable concentrates of the derivatives of the invention typically range from about 50 to about 500 grams of spinosyn derivative per liter of liquid, equivalent to about 10% to about 50%, dissolved in an inert carrier which is a mixture of a water immiscible solvent and emulsifiers. Organic solvents include organics such as xylenes, and petroleum fractions such as high-boiling naphthlenic and olefinic portions of petroleum which include heavy and aromatic naphtha. Other organics may also be used such as terpenic solvents-rosin derivatives, aliphatic ketones such as cyclohexanone and complex alcohols. Emulsifiers for emulsifiable concentrates are typically mixed ionic and/or nonionic surfactants such as those mentioned herein or their equivalents.

Aqueous suspensions may be prepared containing water-insoluble spinosyn derivatives, where the compounds are dispersed in an aqueous vehicle at a concentration typically in the range of between about 5% to about 50% by weight. The suspensions are prepared by finely grinding the compound and vigorously mixing it into a vehicle of water, surfactants, and dispersants. Inert ingredients such as inorganic salts and synthetic or natural gums may also be employed to increase the density and/or viscosity of the aqueous vehicle as is desired.

Precipitated flowables may be prepared by dissolving at least one spinosyn derivative of the invention in a water-miscible solvent and surfactants or surface active polymers. When these formulations are mixed with water, the active spinosyn derivative precipitates with the surfactant controlling the size of the resulting micro-crystalline precipitate. The size of the crystal can be controlled through the selection of specific polymer and surfactant mixtures.

The spinosyn derivatives may also be applied as a granular composition that is applied to the soil. The granular composition typically contains from about 0.5% to about 10% by weight of the derivative. The spinosyn derivative is dispersed in an inert carrier which is typically clay or an equivalent substance. Generally, granular compositions are prepared by dissolving the compounds of the invention in a suitable solvent and applying it to a granular carrier which has been pre-formed to the desirable particle size. The particle size is typically between about 0.5 mm to 3 mm. The granular compositions may also be prepared by forming a dough or paste of the carrier and compound, drying the combined mixture, and crushing the dough or paste to the desired particle size.

The spinosyn derivative may also be combined with an appropriate organic solvent. The organic solvent is typically a bland petroleum oil that is widely used in the agricultural industry. These combinations are typically used as a spray. More typically, the spinosyn compounds are applied as a dispersion in a liquid carrier, where the liquid carrier is water. The compounds may also be applied in the form of an aerosol composition. The compound is dissolved in an inert carrier, which is a pressure-generating propellant mixture. The aerosol composition is packaged in a container, where the mixture is dispersed through an atomizing valve. Propellant mixtures contain either low-boiling halocarbons, which may be mixed with organic solvents or aqueous suspensions pressurized with inert gases or gaseous hydrocarbons.

The compounds may be applied to any locus inhabited by an insect or mite. Such locus typically is cotton, soybean and vegetable crops, fruit and nut trees, grape vines, houses and ornamental plants. The amount of the spinosyn derivative applied to the loci of insects and mites can be determined by those skilled in the art. Generally, the concentrations of from about 10 ppm to about 5,000 ppm provide the desired control. For crops such as soybeans and cotton, the rate of application is about 0.01 to about 1 kilograms per hectare (kg/ha), where the spinosyn derivative is applied in a 5 to 50 gallons per acre (gal/A) spray formulation.

The composition can be formulated in a liquid concentrate, ready-to-use (RTU) liquid spray, dust, or solid form. The formulation chosen will depend on the use of the product.

The following general treatment methods are preferably suitable for carrying out the seed treatment, or plant propagation material treatment, according to the invention: dry treatments (preferably with addition of adhesion promoters such as, for example, liquid paraffin or talc), and, if appropriate, colorants, slurry treatments (preferably with addition of wetters, dispersants, emulsifiers, adhesives, inert fillers and colorants), aqueous liquid treatments (preferably with addition of emulsifiers, dispersants, thickeners, antifreeze agents, polymers, adhesives and colorants), solvent-based liquid treatments (with addition of solvents and colorants), emulsion treatments (with addition of emulsifiers, solvents and colorants).

The total active spinosyn derivative in the treatment formulations preferably amounts to 0.01% to 80% by weight. For example, the total active spinosyn compound can amount to 0.01% by weight, 0.05% by weight, 0.1% by weight, 0.5% by weight, 1% by weight, 5% by weight, 10% by weight, 20% by weight, 30% by weight, 40% by weight, 50% by weight, 60% by weight, 70% by weight, or 80% by weight. Generally, about 1 to about 300 g of spinosyn derivative are applied to every 100 kg of seed or plant propagation material in the form of a treatment.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex, and diet of the subject, the mode and time of administration, rate of excretion, drug combination, and severity of the particular condition. The precise dose to be employed in the formulation will also depend on the route of administration, and the seriousness of the infection, and should be decided according to the judgment of the practitioner and each subject's circumstances.

IV. Methods of Use

The spinosyn compounds described herein have insecticidal and pesticidal activity against pests, including insects, arachnids and nematodes. Therefore, the compounds and formulations as described herein can be used for controlling, inhibiting, and/or inactivating a pest of interest. The spinosyn compounds and formulations described herein provide a key source of agrichemicals with activities against crop pest species. In some instances, the compounds and formulations can be used in animal health. The spinosyn compounds and formulations described herein can be provided in agricultural and/or pharmaceutical compositions in effective amounts to control or inhibit the pest or condition being treated. The spinosyn compounds and formulations described herein may possess one or more the following characteristics as compared to natural spinosyns: increased potency; reduced risk to non-target species; lower potential for environmental damage; minimal cross-resistance to other pesticides; and may overcome existing pest resistance to currently available spinosyn products.

The compounds and formulations described herein are useful in controlling or containing pests populations. The compounds and formulations exhibit potent and broad-spectrum activity against numerous commercially important insect pests. The spectrum of target insects include many species of Lepidoptera and Diptera along with some members of several other insect orders, including planthoppers, leafhoppers, spider mites and cockroaches. The compounds and formulations have potent and broad activity against many problematic larval species of Lepidoptera. Insecticidal activity is generally observed after administration of the spinosyns by a variety of delivery methods, including contact and oral feeding assays.

One skilled the art will appreciate that the compounds, formulations, and methods disclosed herein can be used to treat a variety of home and garden insect and mite pests such as, by way of non-limiting example, members of the insect order Lepidoptera including Southern armyworm, codling moth, cutworms, clothes moths, Indian meal moth, leaf rollers, corn earworm, cotton bollworm (also called Tomato fruit worm), European corn borer, imported cabbageworm, cabbage looper, pink bollworm, American bolloworm, tomato hornworm, bagworms, Eastern tent caterpillar, sod webworm, diamondback moth, tomato pinworm, grape berry moth, cotton leafworm, beet armyworm, and fall armyworm; members of the order Homoptera including cotton aphid leafhoppers, plant hoppers, pear *psylla*, scale insects, whiteflies, and spittle bugs; and members of the insect order Diptera including house flies, stable flies, blow flies and mosquitoes; mites; and ants. The compounds and formulations described herein can also be used to treat members of the order Thysanoptera including melon *thrips* and Western flower *thrips*; members of the order Coleoptera, including Colorado potato beetles; members of the order Orthoptera; and Leaf miners of the orders Lepidoptera (moths and butterflies), Hymenoptera (leaf mining sawflies), Coleoptera (beetles), and Diptera (true flies). The compounds and formulations can be used to control and/or treat ants, green peach aphids, adult house flies, western tent caterpillar larvae, and two-spotted spider mites. Generally, the spinosyn compounds and formulations described herein can be active against a number of ectoparasites in a number of animals by a variety of routes. The present compounds and formulations can be used to control a wide variety of arthropod pests.

Representative pests which can be controlled by the present compounds and formulations additionally include: Arachnids, *Amblyomma americanum* (Lone-star tick), *Amblyomma maculatum* (Gulf Coast tick), *Argas persicus* (fowl tick), *Boophilus microplus* (cattle tick), *Chorioptes* spp. (mange mite), *Demodex bovis* (cattle follicle mite), *Demodex canis* (dog follicle mite), *Dermacentor andersoni* (Rocky Mountain spotted fever tick), *Dermacentor variabilis* (American dog tick), *Dermanyssus gallinae* (chicken mite), *Ixodes ricinus* (common sheep tick), *Knemidokoptes gallinae* (deplumming mite), *Knemidokoptes mutans* (scaly-leg mite), *Otobius megnini* (ear tick), *Psoroptes equi* (scab mite), *Psoroptes ovis* (scab mite), *Rhipicephalus sanguineus* (brown dog tick), *Sarcoptes scabiei* (mange mite), Insects— *Aedes* (mosquitoes), *Anopheles* (mosquitoes), *Culex* (mosquitoes), *Culiseta, Bovicola bovis* (cattle biting louse), *Callitroga homnivorax* (blowfly), *Chrysops* spp. (deer fly), *Cimex lectularius* (bed bug), *Cochliomyia* spp. (screwworm), *Ctenocephalides canis* (dog flea), *Ctenocephalides felis* (cat flea), *Culicoides* spp. (midges, sandflies, punkies, or no-see-ums), *Damalinia ovis* (sheep biting louse), *Dermatobia* spp. (warble fly), *Gasterophilus haemorrhoidalis* (nose bot fly), *Gasterophilus intestinalis* (common horse bot fly), *Gasterophilus* nasalis (chin fly), *Glossina* spp. (tsetse fly), *Haematobia irritans* (horn fly, buffalo fly), *Haematopinus asini* (horse sucking louse), *Haematopinus eurysternus* (short nosed cattle louse), *Haematopinus ovillus* (body louse), *Haematopinus suis* (hog louse), *Hydrotaea irritans* (head fly), *Hypoderma bovis* (bomb fly), *Hypoderma lineatum* (heel fly), *Linognathus ovillus* (body louse), *Linognathus pedalis* (foot louse), *Linognathus vituli* (long nosed cattle louse), *Lucilia* spp. (maggot fly), *Melophagus ovinus* (sheep ked), *Musca* spp. (house fly, face fly), *Oestrus ovis* (nose bot fly), *Pediculus* spp. (lice), *Phlebotomus* spp. (sandfly), *Phormia regina* (blowfly), *Psorophora* spp. (mosquito), *Pthirus* spp. (lice), *Reduvius* spp. (assassin bug), *Simulium* spp. (black fly), *Solenopotes capillatus* (little blue cattle louse), *Stomoxys calcitrans* (stable fly), *Tabanus* spp. (horse fly), *Tenebrio* spp. (mealworms), *Triatoma* spp. (kissing bugs). Likewise, the spinosyn derivatives are useful against pests including: from the order of the Isopoda, for example, *Oniscus asellus, Armadillidium vulgare, Porcellio scaber*; from the order of the Diplopoda, for example, *Blaniulus guttulatus*; from the order of the Chilopoda, for example, *Geophilus carpophagus, Scutigera* spp; from the order of the Symphyla, for example, *Scutigerella immaculata*; from the order of the Thysanura, for example, *Lepisma saccharina*; from the order of the Collembola, for example, *Onychiurus armatus*; from the order of the Orthoptera, for example, *Blatta orientalis, Periplaneta americana, Leucophaea maderae, Blattella germanica, Acheta domesticus, Gryllotalpa* spp., *Locusta migratoria* migratorioides, *Melanoplus differentialis, Schistocerca gregaria*; from the order of the Dermaptera, for example, *Forficula auricularia*; from the order of the Isoptera, for example, *Reticulitermes* spp.; from the order of the Anoplura, for example, *Phylloxera vastatrix, Pemphigus* spp., *Pediculus humanus corporis, Haematopinus* spp., *Linognathus* spp; from the order of the Mallophaga, for example, *Trichodectes* spp., *Damalinea* spp.; from the order of the Thysanoptera, for example, *Frankliniella occidentalis, Hercinothrips femoralis, Thrips palmi, Thrips tabaci*; from the order of the Heteroptera, for example, *Eurygaster* spp., *Dysdercus intermedius, Piesma quadrata, Cimex lectularius, Rhodnius prolixus, Triatoma* spp.; from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp.; from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Antho nomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Oulema oryzae, Lissorhoptrus oryzophilus*; from the order of the Hymenoptera, for example, *Diprion* spp., *Hoplocampa* spp., *Lasius* spp., *Monomorium pharaonis, Vespa* spp.; from the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Liriomyza* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipulapaludosa*; from the order of the Siphonaptera, for example, *Xenopsylla cheopis, Ceratophyllus* spp.; from the order of the Arachnida, for example, *Scorpio maurus, Latrodectus mactans*; from the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp.

Insects that can be controlled with the aid of the compounds and formulations described herein include those of the following orders: soil-dwelling insects: Diptera (for example the frit-fly, wheat-bulb fly), Coleoptera (for example Diabrotica (wire worm), Lepidoptera (for example dart moth), Blattophtheroidea, Myriopoda. Leaf insects: Aphidina, Coleoptera, Brachycera, Lepidotera, Homoptera, Tysanoptera, Aleurodina, Cicadina, Acasi, Cossina, Heteroptera.

Methods for controlling insect and mite pests as described herein can include providing a formulation that has an effective amount of at least one spinosyn compound as described herein, at least one of an additional insecticide and miticide, and at least one of a solvent or an acceptable carrier, and administering an effective amount of the formulation to control pests. Where the formulation is a liquid, the method can further include administering an effective amount of the formulation such that an effective amount of the formulation contacts pests, plants and plant products, the vicinity of the pests, and/or the vicinity of the plants and plant products. Where the formulation is a dust or a solid, administering an effective amount of the formulation can include placing an effective amount of the composition in a vicinity of pests and/or placing an effective amount of the composition in a vicinity of plants and plant products to be protected.

An effective amount of the spinosyn compound or formulation as described herein is an amount to control or kill the target pest. The use rates vary widely and are highly impacted by the target pest, target pest size and number, host crop and crop age, climate and economic threshold or acceptable damage. In general, a typical use rate is set at about 1 ppm (1 mg active ingredient (a.i.)/kg of grain). For use on crops, between about 25 and about 200 grams per hectare (0.023 and 0.184 lbs per acre) of active ingredient is used. Turf rates are 88-450 g a.i./ha (0.078-0.4 lb ai/acre). Ornamental rates are 0.046-0.17 lb ai/100 gallons or 55-204 ppm. There is typically a positive temperature correlation that results in better activity with higher temperatures. Performance against some pests, such as leafminers and *thrips*, are positively impacted by the addition of nominal rates of penetrating surfactants such as crop oils.

All animals are subject to attack by such pests, though the problems are most severe among vertebrate hosts. Accordingly, the spinosyn compounds and formulations described herein can be used on humans, livestock animals, (cattle, sheep, pigs, goats, buffalo, water buffalo, deer, rabbits, chickens, turkeys, ducks, geese, ostriches, and the like), horses and other pleasure animals, mink and other animals grown for their fur, rats, mice, other animals used in laboratory and research settings, companion animals such as dogs and cats, fish, crustacea, and other aquatic animals. In short, the spinosyn compounds and formulations described herein are useful for treatment of the whole range of animals.

Arthropod pests are inhibited or killed on a host animal by contacting the pest with an effective amount of a spinosyn compound as described herein.

Techniques for delivering the compounds and formulations described herein are well known to those skilled in the art. In general, a present formulation comprising at least one spinosyn compound is applied to the exterior surface of an animal, whereby it contacts pests already present on the host as well as those which arrive on the host's body within the efficacy period. Typically, the spinosyn compound is formulated in a liquid formulation which is sprayed onto the animal's surface or poured onto the animal's surface. Another conventional treatment is a "dip", whereby cattle are treated by being substantially immersed in a dilute solution containing the spinosyn compound. For some hosts and pests, the formulation can be a dust, which is sprinkled onto the host, or a shampoo or cream which is employed in bathing the animal. Collars on cats and dogs can also be employed as a way of delivering the derivatives directly to the animal's surface.

The compounds and formulations described herein can also be applied to locations frequented by animals, so that pests are thereby contacted by the compound even as in direct application to the host. Application to pet bedding can be used, as well as application to carpeting. For cattle, dusting bags can be used. These are positioned in a doorway where the cattle inevitably rub against the bag and pests are contacted by the present compound.

Optionally, the present compounds and formulations can be used to control insects and arachnids which are pests in the feces of cattle and other animals. The compounds and formulations can be administered orally and the compounds travel through the intestinal tract and emerge in the feces. Control of pests in the feces indirectly protects the animals from the pests.

The compounds and formulations described herein may be applied to the foliage of a plant which a pest might feed on. Additionally, the compounds may be used orally or topically to control pests on animals.

Oral administration may be carried out using tablets and animal feeds. For some animals, such as certain cats, administration is best accomplished by using an acceptable liquid formulation that is administered directly or added to their food ration. Especially useful methods of orally administering the spinosyn derivatives are by administering it in chewable tablets or treats and animal feeds.

The spinosyn compounds and formulations described herein are also useful for the treatment of animals to control arthropods, i.e., insects and arachnids, which are pests on animals. These arthropod pests typically attack their hosts on the external ("ecto") surface; agents which control such pests are referred to as "ectoparasiticides".

The spinosyn compounds and formulations can be used for treating the soil, for treating seed or plant propagation material, and for drenching and irrigating plants. The following exemplary types of seed and plant propagation material can be treated: maize, cereals (such as, for example, wheat, barley, oats, rye), rice, seed potatoes, cotton, oilseed rape, sunflower, beet (such as, for example, sugar beet), vegetable seed (such as, for example, onion, cabbage, tomato), (fodder) legumes, peanuts, soya, sorghum, and the like.

It is advantageous to apply granules comprising the active compound described herein into or onto the soil. Examples of suitable applications include broadcast, band, furrow and planting-hole application.

It is particularly advantageous to emulsify or dissolve the spinosyns or their salts in water and to use this for irrigating the plants. Examples of suitable applications are spraying onto the soil, drenching, i.e. irrigating the plants with active-compound-containing solutions, and drip irrigation, and also use in hydroponic systems, in particular in the production of vegetables and ornamentals.

Seed treatments are suitable for controlling animal pests, preferably arthropods and nematodes, in particular insects and arachnids, which are found in agriculture and in forests. They are effective against normally-sensitive and resistant species and against all or individual developmental stages.

In some embodiments, the spinosyn compounds and formulations described herein can be used for promoting or accelerating wound healing in a mammal comprising administering at least one spinosyn compound or a physiologically acceptable derivative or salt thereof, to a mammal in need thereof. In this manner, the spinosyn compounds and formulations can be used for the manufacture of a medicament for promoting or accelerating wound healing in animals, including humans (see, for example, U.S. Pat. No. 8,536, 142) or in the treatment of head lice in humans.

As used herein the terms treatment, treat, or treating refer to a method of reducing one or more symptoms of a disease, infection, or condition. Such methods include controlling, inhibiting, and/or inactivating a pest. Thus in the disclosed method, treatment can refer to a 10%, 20%, 30%, 40%, 50%, 60%, 70%, 80%, 90%, or 100% reduction in pests found in crops or animals and/or the severity of one or more symptoms of the disease, infection, or condition associated with such pests. For example, a method for controlling a pest is considered to be a treatment if there is a 10% reduction in one or more pests in a crop or in a subject as compared to a control. Similarly, a method for treating an infection is considered to be a treatment if there is a 10% reduction in one or more symptoms or signs of an infection in a subject as compared to a control. As used herein, control refers to the untreated condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a complete elimination of pests, or a cure or complete ablation of the disease, infection, condition, or symptoms of the disease, infection, or condition.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Non-limiting embodiments include:
1. A spinosyn compound of the following formula:

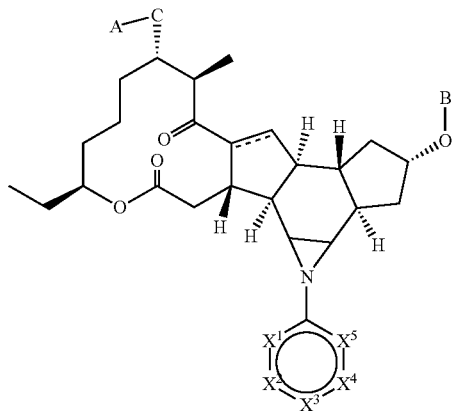

or a salt thereof, wherein:
═══ is a single bond or a double bond;
A is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl;
B is selected from the group consisting of substituted or unsubstituted cycloalkyl, substituted or unsubstituted heterocycloalkyl, substituted or unsubstituted aryl, and substituted or unsubstituted heteroaryl;
C is O or NH;
$X^1$, $X^2$, $X^3$, $X^4$ and $X^5$ are each independently selected from N, NR, CR, and $CR_2$, wherein $X^5$ may alternatively be a direct bond and when $X^5$ is a direct bond, one of $X^1$, $X^2$, $X^3$, and $X^4$ may be further selected from O or S, wherein each R is selected from hydrogen, hydroxyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl.

2. The embodiment of paragraph 1, wherein when $X^1$ and $X^2$ are selected from NR, CR, and $CR_2$, the R groups of $X^1$ and $X^2$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

3. The embodiment of paragraph 1, wherein when $X^2$ and $X^3$ are selected from NR, CR, and $CR_2$, the R groups of $X^2$ and $X^3$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

4. The embodiment of any of paragraphs 1-3, wherein A comprises forosamine.

5. The embodiment of any of paragraphs 1-4, wherein B comprises rhamnose or a (2R,5S)-4-ethoxy-3,5-dimethoxy-6-methyloxan-2-yl group.

6. The embodiment of any of paragraphs 1-5, wherein A is forosamine, B is rhamnose, C is O, $X_1$ is N, $X_2$ is $C(CH_3)$, and $X_3$ is S.

7. The embodiment of any of paragraphs 1-6, wherein the spinosyn compound is (1 S,2R,8R,10S,12S,13R,17R,18S,22S)-18-{[(2R,5S,6R)-5-(dimethylamino)-6-methyloxan-2-yl]oxy}-22-ethyl-5,17-dimethyl-10-{[(2R,3R,4R,5S,6S)-3,4,5-trimethoxy-6-methyloxan-2-yl]oxy}-23-oxa-6-thia-4-azapentacyclo[13.10.0.0$^2$,$^{13}$0.0$^3$,$^7$0.0$^8$,$^{12}$]pentacosa-3 (7),4,14-triene-16,24-dione.

8. The embodiment of any of paragraphs 1-5, wherein A is forosamine, B is rhamnose, C is O, $X_1$ is N, $X_2$ is $C(NH_2)$, and $X_3$ is S.

9. The embodiment of any of paragraphs 1-5 or 8, wherein the spinosyn compound is (1 S,2R,8R,10S,12S,13R,17R,18S,22S)-5-amino-18-{[(2R,5S,6R)-5-(dimethylamino)-6-methyloxan-2-yl]oxy}-22-ethyl-17-methyl-10-{[(2R,3R,4R,5S,6S)-3,4,5-trimethoxy-6-methyloxan-2-yl]oxy}-23-oxa-6-thia-4-azapentacyclo[13.10.0.0$^2$,$^{13}$0.0$^3$,$^7$.0$^8$,$^{12}$] pentacosa-3(7),4,14-triene-16,24-dione.

10. A formulation, comprising at least one spinosyn compound of any of paragraphs 1-9 and an acceptable carrier.

11. The embodiment of paragraph 10, further comprising at least one additional active ingredient.

12. The embodiment of paragraph 10 or 11, further comprising at least one plant or plant product treatment compound.

13. The embodiment of paragraph 11, wherein the at least one additional active ingredient comprises an insecticide or a miticide.

14. The embodiment of paragraph 13, wherein the insecticide is a contact-acting insecticide.

15. The embodiment of paragraph 13, wherein the miticide is a contact-acting miticide.

16. A method for controlling pests, comprising contacting a pest with an effective amount of a spinosyn compound of any of paragraphs 1-9 or a formulation of any of paragraphs 10-15.

17. The embodiment of paragraph 16, wherein the pest is an insect.

18. The embodiment of paragraph 16, wherein the pest is an arachnid.

19. The embodiment of paragraph 16, wherein the pest is a nematode.

20. A method for making a spinosyn compound, comprising reacting the C-5,6 double bond of Spinosyn A to form a spinosyn compound according to paragraph 1, wherein the spinosyn compound forms via an α-halo ketone intermediate.

The examples below are intended to further illustrate certain aspects of the methods and compounds described herein, and are not intended to limit the scope of the claims.

Intermediate 1

(1aR,1bR,3S,4aS,4bR,7R,8S,12S,15aS,15bR,15cS)-8-(((2R,5S,6R)-5-(dimethylamino)-6-methyltetrahydro-2H-pyran-2-yl)oxy)-12-ethyl-7-methyl-3-(((2R,3R,4R,5S,6S)-3,4,5-trimethoxy-6-methyltetrahydro-2H-pyran-2-yl)oxy)-2,3,4,4a,7,8,9,10,11,12,15,15a,15b,15c-tetradecahydro-1aH-oxireno[2',3':4,5]-as-indaceno[3,2-d][1]oxacyclododecine-6,14(1bH,4bH)-dione (1)

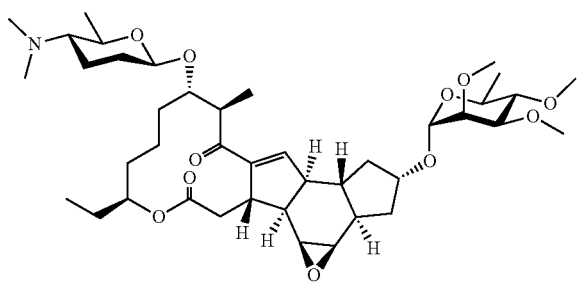

To a solution of Spinosyn A (3.0 g, 4.1 mmol) in DCM (100 mL) was added m-CPBA (2.18 g, 12.3 mmol) at 0° C. The mixture was stirred at 0° C. for 1 h and at r.t. for 1.5 h. To the mixture was added saturated aqueous $NaHSO_3$ (100 mL) and the resulted mixture was stirred at r.t. for 2 h. The organic layer was separated and the aqueous layer was extracted with DCM (100 mL×2). The combined organic phases were washed with brine (300 mL), dried over anhydrous $Na_2SO_4$, filtered and concentrated to give a residue which was purified by column chromatography on silica gel (DCM/methanol=40/1) to give the title compound 1 (2.35 g, 76%) as white solid. Partial $^1$H NMR (400 MHz, $CDCl_3$,): δ6.58 (s, 1H), 4.85 (1H, s), 4.67-4.65 (m, 1H), 4.43-4.41 (m, 1H), 4.26-4.21 (m, 1H), 3.64-3.52 (m, 1H), 3.27-3.18 (m, 2H), 3.12 (t, J=9.6 Hz, 1H), 2.61-2.56 (m, 1H), 2.43 (dd, J=13.6, 2.4 Hz, 1H), 0.82 (t, J=7.2 Hz, 3H). LCMS: m/z 748.5 [M+H]$^+$.

Intermediates 2a and 2b (2S,3aR,4R,5R,5aR,5bS,9S,13S,14R,16aR,16bS)-13-(((2R,5S,6R)-5-(dimethylamino)-6-methyltetrahydro-2H-pyran-2-yl)oxy)-9-ethyl-4-hydroxy-14-methyl-5-(phenylamino)-2-(((2R,3R,4R,5S,6 S)-3,4,5-trimethoxy-6-methyltetrahydro-2H-pyran-2-yl)oxy)-2,3,3a,4,5,5a,5b,6,9,10,11,12,13,14-tetradecahydro-1H-as-indaceno[3,2-d][1]oxacyclododecine-7,15(16aH,16bH)-dione (2a)

and (2S,3aR,4S,5S,5aR,5bS,9S,13S,14R,16aR,16bS)-13-(((2R,5S,6R)-5-(dimethylamino)-6-methyltetrahydro-2H-pyran-2-yl)oxy)-9-ethyl-5-hydroxy-14-methyl-4-(phenylamino)-2-(((2R,3R,4R,5S,6 S)-3,4,5-trimethoxy-6-methyltetrahydro-2H-pyran-2-yl)oxy)-2,3,3a,4,5,5a,5b,6,9,10,11,12,13,14-tetradecahydro-1H-as-indaceno[3,2-d][1]oxacyclododecine-7,15(16aH,16bH)-dione (2b)

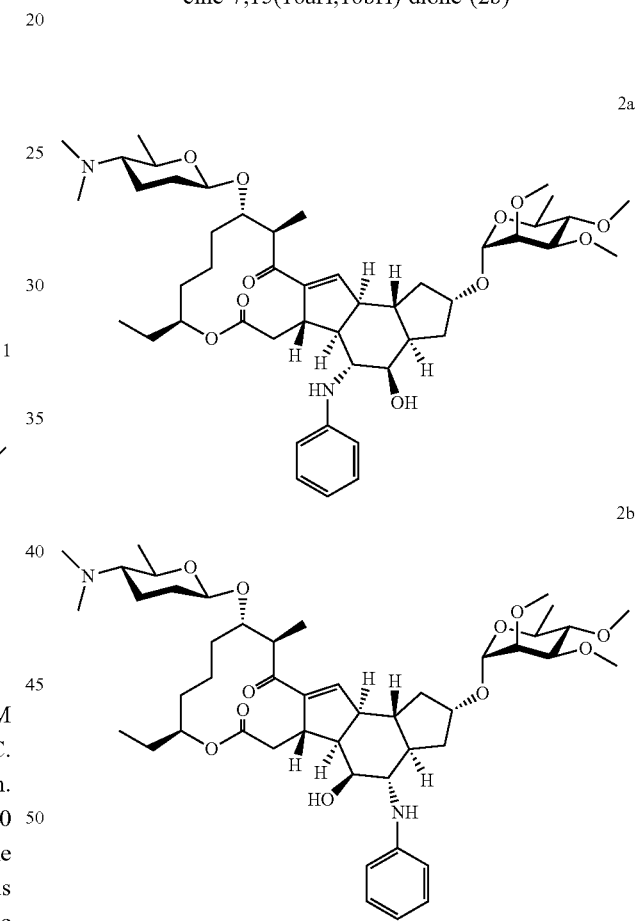

To a solution of compound 1 (1.0 g, 1.3 mmol) in aniline (3 mL) in a microwave tube was added $ZrCl_4$ (15 mg, 0.066 mmol) under $N_2$. The reaction mixture was stirred at 80° C. under microwave irradiation for 1 h. After cooling to room temperature, the mixture was purified by silica gel column (DCM:MeOH=20:1-10:1) to give the mixture of 2a and 2b which were further purified by Chiral-prep-HPLC to afford the title compounds 2a (110 mg, yield 10.1%) and 2b (65 mg, yield 6.0%) as white solid.

Partial $^1$H NMR ($CDCl_3$, 400 MHz) for 2a: δ7.17 (t, J=7.6 Hz, 2H), 6.78 (s, 1H), 6.70 (t, J=7.6 Hz, 1H), 6.66 (d, J=7.6 Hz, 2H), 4.83 (d, J=0.8 Hz, 1H), 4.64-4.62 (m, 1H), 4.42-

4.40 (m, 1H), 4.27-4.25 (m, 1H), 4.10 (s, 1H), 3.66-3.61 (m, 2H), 3.56-3.44 (m, 16H), 3.31-3.27 (m, 1H), 3.11 (t, J=9.6 Hz, 1H), 3.04 (dd, $J_1$=4.8 Hz, $J_2$=13.6 Hz, 1H), 2.90-2.87 (m, 2H), 2.23 (s, 7H), 0.79 (t, J=7.6 Hz, 3H). LCMS: m/z 841.2 [M+H]$^+$.

Partial $^1$H NMR (CDCl$_3$, 400 MHz) for 2b: δ7.18 (t, J=7.2 Hz, 2H), 6.82 (s, 1H), 6.76-6.70 (m, 3H), 4.73 (s, 1H), 4.70-4.66 (m, 1H), 4.43-4.42 (m, 1H), 4.20-4.18 (m, 1H), 3.87 (t, J=6.4 Hz, 1H), 3.65-3.63 (m, 1H), 3.54-3.38 (m, 17H), 3.31-3.23 (m, 2H), 3.13-3.07 (m, 2H), 2.90 (dd, $J_1$=3.2 Hz, $J_2$=14.0 Hz, 1H), 2.26 (s, 9H), 1.40-1.17 (m, 15H), 0.81 (t, J=7.2 Hz, 3H).

LCMS: m/z 841.2 [M+H]$^+$.

Example 1

(1aS,1bR,3S,4aS,4bR,7R,8S,12S,15aS,15bR,15cR)-8-(((2R,5S,6R)-5-(dimethylamino)-6-methyltetrahydro-2H-pyran-2-yl)oxy)-12-ethyl-7-methyl-1-phenyl-3-(((2R,3R,4R,5S,6S)-3,4,5-trimethoxy-6-methyltetrahydro-2H-pyran-2-yl)oxy)-1,2,3,4,4a,4b,7,8,9,10,11,12,15,15a,15b,15c-hexadecahydro-[1]oxacyclododecino[5',4':2,3]-as-indaceno[4,5-b]azirine-6,14(1aH,1bH)-dione (3)

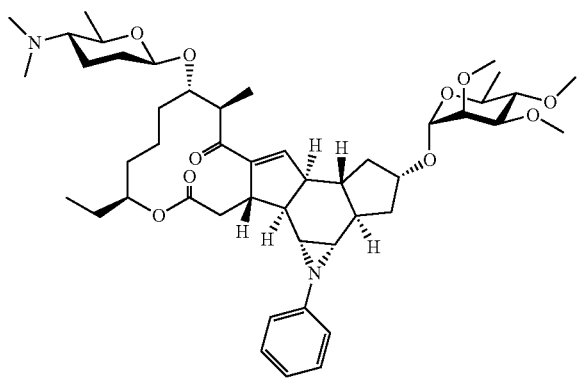

3

To a solution of a mixture of compounds 2a and 2b (150 mg, 0.18 mmol) in DCM (10 mL) was added Diethylaminosulfurtrifluoride (86.1 mg, 0.54 mmol) at −78° C. under N$_2$. The mixture was stirred at −78° C. for 0.5 h. The reaction mixture was quenched with saturated NaHCO$_3$ solution (5 mL) and extracted with DCM (5 mL×3). The combined organic phase was dried over anhydrous Na$_2$SO$_4$, filtered and concentrated. The residue was purified by prep-HPLC to afford the title compound 3 (30 mg, yield 21%) as a white solid. Partial $^1$H NMR (CDCl$_3$, 400 MHz): 37.23 (d, J=7.6 Hz, 2H), 7.03 (d, J=7.2 Hz, 2H), 6.96 (t, J=7.2 Hz, 1H), 6.76 (s, 1H), 4.89 (s, 1H), 4.73-4.68 (m, 1H), 4.44-4.42 (m, 1H), 4.34-4.32 (m, 1H), 3.67-3.62 (m, 1H), 3.32-3.26 (m, 2H), 3.14-3.10 (m, 2H), 2.58-2.50 (m, 2H), 2.41-2.39 (m, 1H), 0.81 (t, J=7.2 Hz, 3H).

LCMS: m/z 823.2 [M+H]$^+$.

Example 2: Testing Compounds for Insecticide and Miticide Utility

The compounds produced by the methods described above are tested for activity against a number of insects and mites. More specifically, the compounds are tested against melon aphid, which is a member of the insect order Homoptera. Other members of the Homoptera include leafhoppers, planthoppers, pear pyslla, apple sucker, scale insects, whiteflies, spittle bugs, as well as numerous other host specific aphid species. Activity is also tested against greenhouse thrips, which are members of the order Thysanoptera. The compounds are also tested against Southern armyworm, which is a member of the insect order Lepidoptera. Other typical members of this order include codling moth, cutworm, clothes moth, Indianmeal moth, leaf rollers, corn earworm, European corn borer, cabbage worm, cabbage looper, cotton bollworm, bagworm, eastern tent caterpillar, sod webworm and fall armyworm.

Successful compounds are useful for reducing populations of insects and mites, and are used in a method of inhibiting an insect or mite population after application to a locus of the insect or mite an effective insect- or mite-inactivating amount of a compound.

In conducting evaluations of insecticidal activity, each test compound is formulated as a 400 ppm solution, and this solution is then diluted with water to give lower concentrations. The 400 ppm solution is prepared by combining 19.2 mL of 0.05% solution of Tween 20 (polyoxyethylene 5 (20) sorbitan monolaurate) in water with a solution of 8 mg of the compound in 0.8 mL of acetone/ethanol (9/1).

Activity against aster leafhopper (*Macrosteles tascifrons*) is tested as follows. The test is run using test compounds at concentrations of 400 ppm and 50 ppm. One ounce plastic cups containing a cotton wick are sprayed with 0.4 mL of formulated material using a flat-fan nozzle. The excess moisture is allowed to evaporate. Then, five to ten carbon dioxide anesthetized adult leafhoppers are added to each cup. The cups are capped and held at room temperature for 24 hours. Percent mortality is then determined.

Activity against beet armyworm (*Spodoptera exiqua*) is evaluated as follows. The test is run using test compounds at concentrations of 400 ppm and 50 ppm. A general purpose Lepidoptera artificial diet material is diluted to half strength with a 5% non-nutritive agar. This diet material (8 mL) is dispensed into one ounce diet cups. One hour prior to treatment, 35 to 40 eggs are dispensed onto the diet surface. The cups are then sprayed with formulated material through a flat-fan nozzle. Treated cups are air dried prior to sealing with plastic caps. The cups are held for 6 days at room temperature. Activity is then rated based on the total number of live and dead larvae, and on the size of live larvae.

Activity against cotton aphid (*Aphis gossypii*) and two-spotted spider mite (*Tetranychus urticae*) is evaluated as follows. Golden crookneck squash plants are grown to the expanded cotyledon stage (about 6 to 8 days). The plants are infested with cotton aphids and two-spotted spider mites 16 to 24 hours before application of the test material by transfer of infested foliage cut from a stock colony. Immediately prior to the spray application of the test material, the transfer foliage is removed from the squash plants. The test is run using test compounds at concentrations of 400 ppm and 50 ppm. The plants are sprayed with test solution using an atomizing sprayer at 17 psi. Both surfaces of the leaves are covered until runoff, and then allowed to dry. Activity of each compound is determined three days after treatment. Activity is rated as a percent based on the mites/aphids present in plants sprayed with solvent alone.

Activity against peanut root knot nematode (*Meloidogyne arenaria*) is evaluated as follows. Five untreated cucumber seeds are placed into the bottom of a clear one ounce cup, 20 g of clean white sand is added, and the cups are sprayed while rotating on a pedestal allowing 1.0 mL of a 400 ppm solution to be deposited on the sand. To each cup is dispensed 2.5 mL to 3.0 mL of deionized water containing 300 to 500 nematodes. The cups are held for 10 to 12 days in an environmental growth chamber at a temperature of from 76 to 85° F. and at ambient humidity of 50% to 60%. After 10 to 12 days, the cups are evaluated by inverting each cup and observing nematode mortality and feeding damage to the cucumber plants.

Activity on Southern corn rootworm (*Diabrocica undecimpuccaca bowardi* Barber) is evaluated by adding one mL of test solution containing a predetermined concentration of test compound to a cup containing a kernel of corn in 16 g of sterile soil. This produces a soil concentration of 24 ppm. After 1.5 to 2 hours of drying, five fourth instar corn rootworm larvae are added to the individual cups. Mortality is measured at 3-4 days by emptying the cup onto a pan and inspecting the soil for live rootworms.

Activity against tobacco budworm (*Heliotbis virescens*) is evaluated as follows. A general purpose lepidoptera artificial diet material is diluted to half strength with a 5% non-nutritive agar. This diet material (8 mL) is dispensed into each one ounce diet cup. One hour prior to treatment, 18 to 20 eggs are dispensed onto the diet surface. The cups are then sprayed with formulated material through a flat-fan nozzle. The test is run using test compounds at concentrations of 400 ppm and 50 ppm. Treated cups are air dried prior to sealing with plastic caps. The cups are held for 6 days at room temperature. Activity is then rated based on the total number of live and dead larvae, and on the size of live larvae.

Activity against German cockroach (*Blattella germanicus*) is evaluated as follows. Alfalfa based green insect diet material (8 mL) is dispensed into a one ounce diet cup. The cups are then sprayed with formulated material through a flat-fan nozzle. The test is run using test compounds at concentrations of 400 ppm and 50 ppm. Treated cups are air dried for 24 hours and infested with five late third or early fourth instar German cockroaches. The cups are capped and held for ten days in an environmental growth chamber at a temperature of from 76 to 85° F. Activity is then rated based on the total number of live and dead insects.

It is understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

What is claimed is:
1. A spinosyn compound of the following formulas:

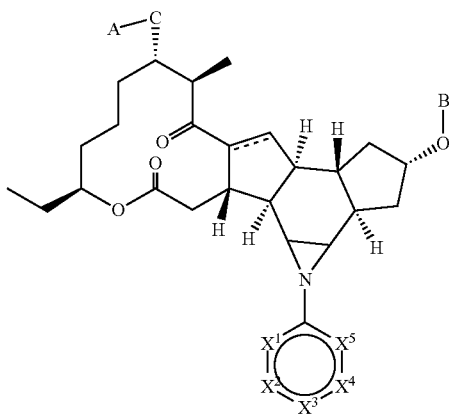

-continued

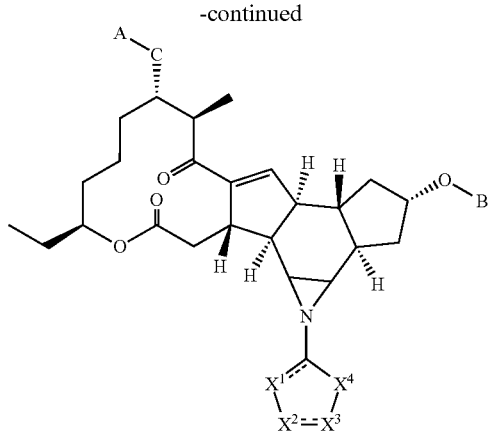

or a salt thereof, wherein:
≡≡≡ is a single bond or a double bond;
A is forosamine;
B is rhamnose, a (2R,5S)-4-ethoxy-3,5-dimethoxy-6-methyloxan-2-yl group, or a (2R,5S)-3,4,5-trimethoxy-6-methyloxan-2-yl group;
C is O or NH; and
$X^1$, $X^2$, $X^3$, $X^4$ and $X^5$ are each independently selected from N, NR, CR, and $CR_2$, wherein $X^5$ may alternatively be a direct bond and when $X^5$ is a direct bond, one of $X^1$, $X^2$, $X^3$, and $X^4$ may be further selected from O or S, wherein each R is selected from hydrogen, hydroxyl, halogen, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;
wherein when $X^1$ and $X^2$ are selected from NR, CR, and $CR_2$, the R groups of $X^1$ and $X^2$ optionally combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl; and
wherein when $X^2$ and $X^3$ are selected from NR, CR, and $CR_2$, the R groups of $X^2$ and $X^3$ optionally combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

2. The spinosyn compound of claim 1, wherein when $X^1$ and $X^2$ are selected from NR, CR, and $CR_2$, the R groups of $X^1$ and $X^2$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

3. The spinosyn compound of claim 1, wherein when $X^2$ and $X^3$ are selected from NR, CR, and $CR_2$, the R groups of $X^2$ and $X^3$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

4. The spinosyn compound of claim 1, wherein B comprises rhamnose or a (2R,5S)-4-ethoxy-3,5-dimethoxy-6-methyl oxan-2-yl group.

5. The spinosyn compound of claim 1, wherein A is forosamine, B is rhamnose, C is O, $X_1$ is N, $X_2$ is $C(CH_3)$, and $X_3$ is S.

6. The spinosyn compound of claim 1, wherein A is forosamine, B is rhamnose, C is O, $X_1$ is N, $X_2$ is $C(NH_2)$, and $X_3$ is S.

7. The spinosyn compound of claim 1, wherein when R is halogen, R is fluorine or chlorine.

8. The spinosyn compound of claim 1, wherein the compound has the following formula:

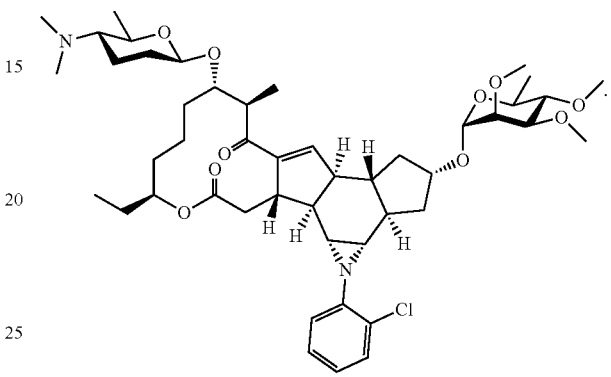

9. The spinosyn compound of claim 1, wherein the compound has the following formula:

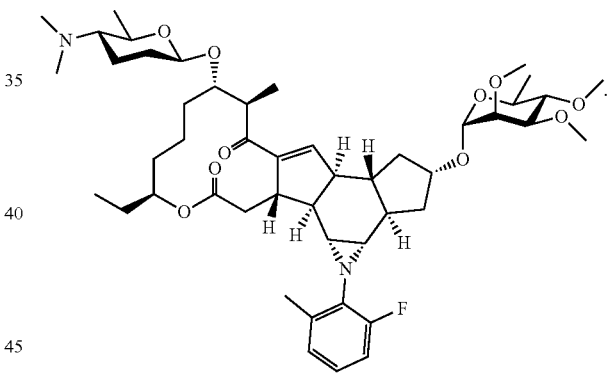

10. The spinosyn compound of claim 1, wherein the compound has the following formula:

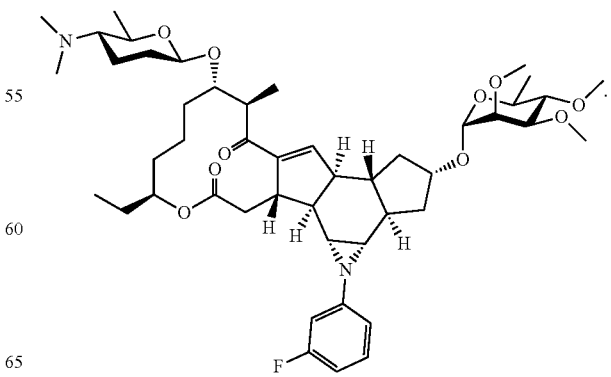

11. The spinosyn compound of claim 1, wherein the compound has the following formula:

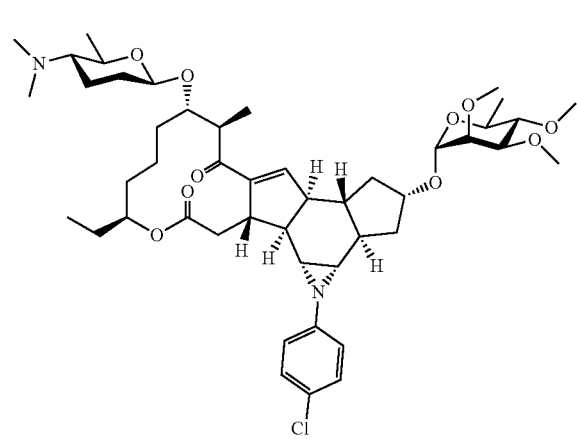

12. The spinosyn compound of claim 1, wherein the compound has the following formula:

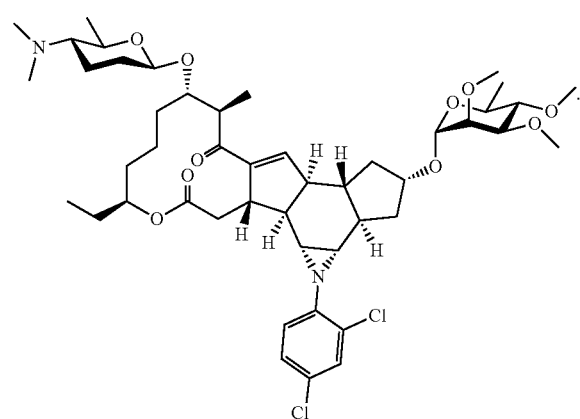

13. The spinosyn compound of claim 1, wherein the compound has the following formula:

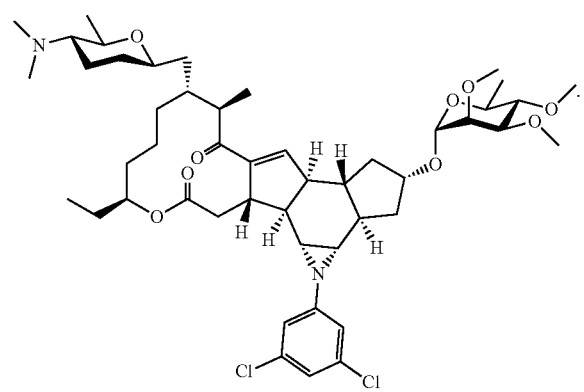

14. The spinosyn compound of claim 1, wherein the compound has the following formula:

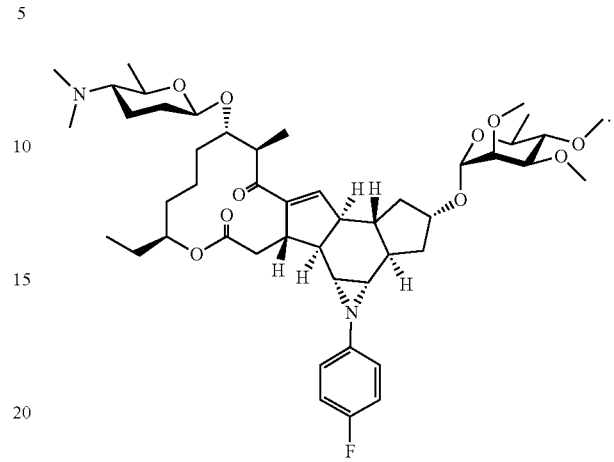

15. The spinosyn compound of claim 1, wherein the compound has the following formula:

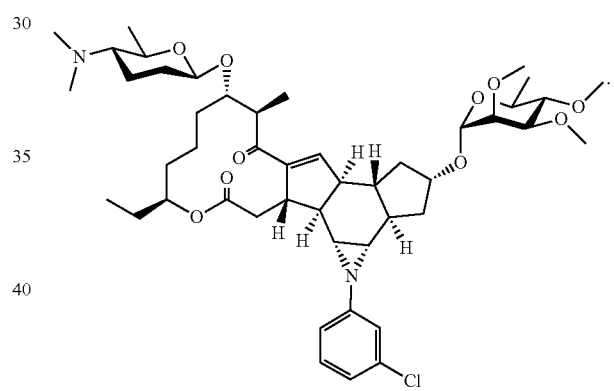

16. The spinosyn compound of claim 1, wherein the compound has the following formula:

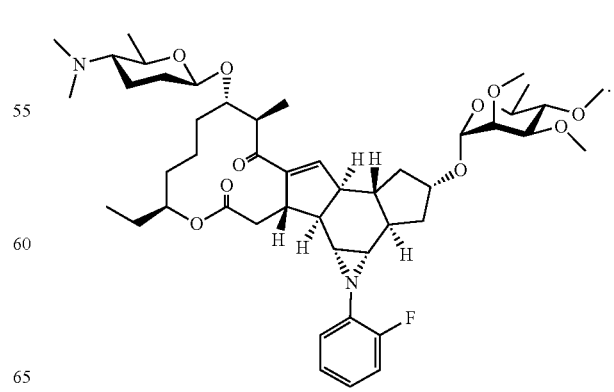

17. The spinosyn compound of claim 1, wherein the compound has the following formula:

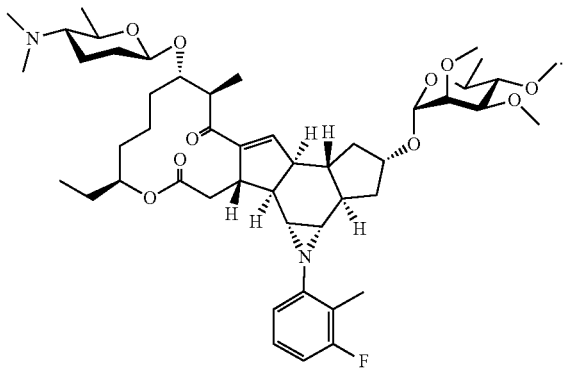

18. The spinosyn compound of claim 1, wherein the compound has the following formula:

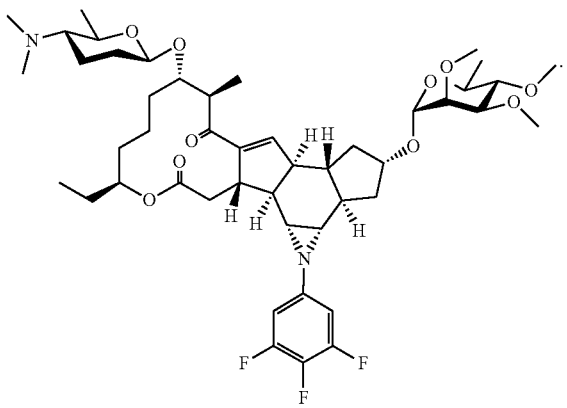

19. The spinosyn compound of claim 1, wherein the compound has the following formula:

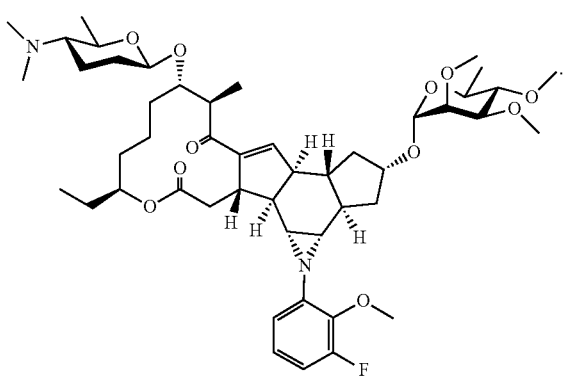

20. The spinosyn compound of claim 1, wherein the compound has the following formula:

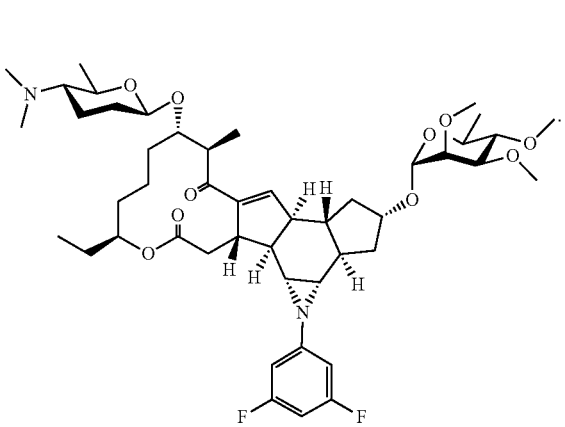

21. The spinosyn compound of claim 1, wherein the compound has the following formula:

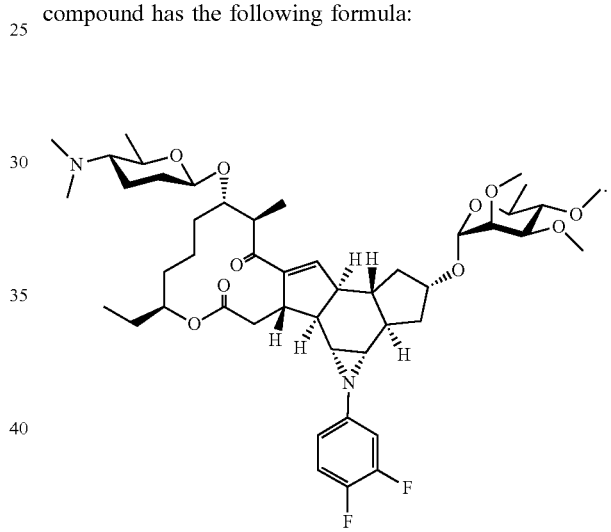

22. The spinosyn compound of claim 1, wherein the compound has the following formula:

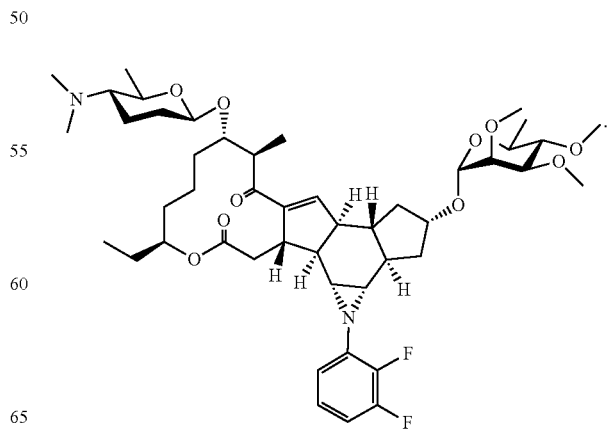

23. The spinosyn compound of claim 1, wherein the compound has the following formula:

24. The spinosyn compound of claim 1, wherein the compound has the following formula:

25. The spinosyn compound of claim 1, wherein the compound has the following formula:

26. The spinosyn compound of claim 1, wherein the compound has the following formula:

27. The spinosyn compound of claim 1, wherein the compound has the following formula.

28. The spinosyn compound of claim 1, wherein the compound has the following formula:

29. A formulation, comprising at least one spinosyn compound of claim 1 and an acceptable carrier.

30. The formulation of claim 29, further comprising at least one additional active ingredient.

31. The formulation of claim 30, wherein the at least one additional active ingredient comprises an insecticide or a miticide.

32. The formulation of claim 31, wherein the insecticide is a contact-acting insecticide.

33. The formulation of claim 31, wherein the miticide is a contact-acting miticide.

34. A method for controlling pests, comprising contacting a pest with an effective amount of a spinosyn compound of claim 1.

35. The method of claim 34, wherein the pest is an insect.

36. The method of claim 34, wherein the pest is an arachnid.

37. The method of claim 34, wherein the pest is a nematode.

38. A method for making a spinosyn compound of claim 1, comprising reacting the C-5,6 double bond of Spinosyn A to form the spinosyn compound according to claim 1, wherein the spinosyn compound forms via either an epoxide or an 1,2-dihalo intermediate or directly via nitrene insertion into the double bond.

* * * * *